(12) United States Patent
Derouazi et al.

(10) Patent No.: US 12,220,450 B2
(45) Date of Patent: *Feb. 11, 2025

(54) COMPLEX COMPRISING A CELL PENETRATING PEPTIDE, A CARGO AND A TLR PEPTIDE AGONIST FOR TREATMENT OF COLORECTAL CANCER

(71) Applicant: Amal Therapeutics SA, Geneva (CH)

(72) Inventors: Madiha Derouazi, Grand-Saconnex (CH); Elodie Belnoue, Geneva (CH)

(73) Assignee: Amal Therapeutics SA, Geneva (CH)

( * ) Notice: Subject to any disclaimer, the term of this patent is extended or adjusted under 35 U.S.C. 154(b) by 95 days.

This patent is subject to a terminal disclaimer.

(21) Appl. No.: 17/397,447

(22) Filed: Aug. 9, 2021

(65) Prior Publication Data

US 2022/0031850 A1    Feb. 3, 2022

Related U.S. Application Data

(63) Continuation of application No. 15/557,649, filed as application No. PCT/EP2016/000473 on Mar. 16, 2016, now abandoned.

(30) Foreign Application Priority Data

Mar. 16, 2015 (WO) ................ PCT/EP2015/000580
Nov. 9, 2015 (WO) ................ PCT/EP2015/002244

(51) Int. Cl.
| | | |
|---|---|---|
| *C07K 7/06* | (2006.01) | |
| *A61K 38/10* | (2006.01) | |
| *A61K 38/17* | (2006.01) | |
| *A61K 38/18* | (2006.01) | |
| *A61K 39/00* | (2006.01) | |
| *A61K 47/42* | (2017.01) | |
| *A61K 47/64* | (2017.01) | |
| *A61K 47/68* | (2017.01) | |
| *A61P 1/00* | (2006.01) | |
| *A61P 35/00* | (2006.01) | |
| *C07K 7/08* | (2006.01) | |
| *C07K 14/47* | (2006.01) | |
| *C07K 14/475* | (2006.01) | |
| *C07K 19/00* | (2006.01) | |
| *C12N 5/10* | (2006.01) | |

(52) U.S. Cl.
CPC .......... *A61K 39/0011* (2013.01); *A61K 38/10* (2013.01); *A61K 38/17* (2013.01); *A61K 38/177* (2013.01); *A61K 38/18* (2013.01); *A61K 47/42* (2013.01); *A61K 47/64* (2017.08); *A61K 47/6425* (2017.08); *A61K 47/6803* (2017.08); *A61K 47/6811* (2017.08); *A61K 47/6865* (2017.08); *A61P 1/00* (2018.01); *A61P 35/00* (2018.01); *C07K 7/06* (2013.01); *C07K 7/08* (2013.01); *C07K 14/47* (2013.01); *C07K 14/475* (2013.01); *C07K 19/00* (2013.01); *C12N 5/10* (2013.01); *A61K 2039/5154* (2013.01); *A61K 2039/6031* (2013.01); *C07K 2319/02* (2013.01); *C07K 2319/03* (2013.01); *C07K 2319/10* (2013.01); *C07K 2319/33* (2013.01); *C07K 2319/40* (2013.01); *C12N 2710/16233* (2013.01); *Y02A 50/30* (2018.01)

(58) Field of Classification Search
CPC ........ A61K 38/18; A61K 38/10; A61K 38/17; A61K 38/1709; A61K 47/64; A61K 39/00; A61K 39/35; C07K 19/00; C07K 2319/10; C07K 7/08; C07K 2319/01; C07K 7/06; C07K 14/47; C07K 14/475
See application file for complete search history.

(56) References Cited

U.S. PATENT DOCUMENTS

| | | | |
|---|---|---|---|
| 5,811,097 A | 9/1998 | Allison et al. | |
| 5,855,887 A | 1/1999 | Allison et al. | |
| 5,977,318 A | 11/1999 | Linsley et al. | |
| 6,051,227 A | 4/2000 | Allison et al. | |
| 6,093,794 A | 7/2000 | Barney et al. | |
| 6,207,156 B1 | 3/2001 | Kuchroo et al. | |
| 6,337,180 B1 | 1/2002 | Drouet et al. | |
| 6,682,736 B1 | 1/2004 | Hanson et al. | |
| 6,984,720 B1 | 1/2006 | Korman et al. | |
| 7,109,003 B2 | 9/2006 | Hanson et al. | |
| 7,132,281 B2 | 11/2006 | Hanson et al. | |
| 8,119,775 B2 | 2/2012 | Moretta et al. | |
| 8,217,149 B2 | 7/2012 | Irving et al. | |

(Continued)

FOREIGN PATENT DOCUMENTS

| | | |
|---|---|---|
| EP | 1212422 A2 | 6/2002 |
| EP | 2320940 A2 | 5/2011 |

(Continued)

OTHER PUBLICATIONS

Sayegh, E.T., et al., "Vaccine therapies for patients with glioblastoma," J Neurooncol, 119: 531-546 (2014).

(Continued)

*Primary Examiner* — Bridget E Bunner
(74) *Attorney, Agent, or Firm* — Harness Dickey & Pierce P.L.C.

(57) ABSTRACT

The present invention provides a novel complex for use in the prevention and/or treatment of colorectal cancer, the complex comprising a) a cell penetrating peptide, b) at least one antigen or antigenic epitope, and c) at least one TLR peptide agonist, wherein the components a)-c) are covalently linked. In particular, compositions for use in the prevention and/or treatment of colorectal cancer, such as a pharmaceutical compositions and vaccines are provided.

26 Claims, 56 Drawing Sheets
Specification includes a Sequence Listing.

(56) References Cited

U.S. PATENT DOCUMENTS

| | | | |
|---|---|---|---|
| 8,795,678 | B2 | 8/2014 | Liang et al. |
| 9,187,534 | B2 | 11/2015 | Derouazi et al. |
| 9,657,064 | B2 | 5/2017 | Derouazi et al. |
| 10,206,986 | B2 | 2/2019 | Ohlfest et al. |
| 11,338,027 | B2 | 5/2022 | Derouazi et al. |
| 2002/0039581 | A1 | 4/2002 | Carreno et al. |
| 2002/0086014 | A1 | 7/2002 | Korman et al. |
| 2003/0105000 | A1 | 6/2003 | Pero et al. |
| 2005/0019344 | A1 | 1/2005 | Khanna et al. |
| 2005/0201994 | A1 | 9/2005 | Korman et al. |
| 2006/0051372 | A1 | 3/2006 | Vande Velde |
| 2007/0148184 | A1 | 6/2007 | Straten et al. |
| 2008/0044407 | A1 | 2/2008 | Strome et al. |
| 2009/0220532 | A1 | 9/2009 | Leclerc et al. |
| 2009/0297552 | A1 | 12/2009 | Aderem et al. |
| 2010/0029571 | A1 | 2/2010 | Rammensee et al. |
| 2010/0133338 | A1 | 6/2010 | Brown et al. |
| 2011/0236406 | A1 | 9/2011 | Messmer et al. |
| 2012/0052080 | A1 | 3/2012 | Okada |
| 2012/0070491 | A1 | 3/2012 | Blais et al. |
| 2012/0177645 | A1 | 7/2012 | Langermann et al. |
| 2012/0214744 | A1 | 8/2012 | Bourdoulous et al. |
| 2012/0231030 | A1 | 9/2012 | Derouazi et al. |
| 2012/0294796 | A1 | 11/2012 | Johnson et al. |
| 2013/0116201 | A1 | 5/2013 | Lenormand et al. |
| 2013/0183377 | A1 | 7/2013 | Agrewala et al. |
| 2013/0331546 | A1 | 12/2013 | Ohlfest et al. |
| 2016/0279212 | A1 | 9/2016 | Ohlfest et al. |
| 2017/0313775 | A1 | 11/2017 | Diaz et al. |
| 2018/0133205 | A1 | 5/2018 | Gelormini |
| 2018/0133295 | A1 | 5/2018 | Derouazi et al. |
| 2018/0133327 | A1 | 5/2018 | Derouazi |
| 2018/0133338 | A1 | 5/2018 | Derouazi et al. |
| 2018/0133339 | A1 | 5/2018 | Derouazi et al. |
| 2019/0022203 | A1 | 1/2019 | Lichty et al. |
| 2019/0175748 | A1 | 6/2019 | Derouazi et al. |
| 2019/0255165 | A1 | 8/2019 | Derouazi et al. |
| 2020/0000898 | A1 | 1/2020 | Yee et al. |
| 2020/0031825 | A1 | 1/2020 | Slassi et al. |
| 2020/0061097 | A1 | 2/2020 | Iwasaki et al. |
| 2021/0085768 | A1 | 3/2021 | Derouazi et al. |
| 2022/0031850 | A1 | 2/2022 | Derouazi et al. |
| 2022/0040314 | A1 | 2/2022 | Derouazi et al. |
| 2022/0088162 | A1 | 3/2022 | Wollmann et al. |
| 2022/0111028 | A1 | 4/2022 | Rossi et al. |
| 2022/0118102 | A1 | 4/2022 | Derouazi et al. |
| 2022/0175933 | A1 | 6/2022 | Derouazi et al. |

FOREIGN PATENT DOCUMENTS

| | | | |
|---|---|---|---|
| EP | 2476440 | A1 | 7/2012 |
| EP | 1 913 954 | B1 | 8/2012 |
| EP | 3270955 | A1 | 1/2018 |
| JP | 2006500358 | A | 1/2006 |
| JP | 2007519612 | A | 7/2007 |
| JP | 2008528643 | A | 7/2008 |
| JP | 2011519834 | A | 7/2011 |
| JP | 2015527313 | A | 9/2015 |
| KR | 1020020079887 | | 10/2002 |
| KR | 101040281 | B1 | 6/2011 |
| WO | 1998/042752 | A1 | 10/1998 |
| WO | 1999/059615 | A1 | 11/1999 |
| WO | 2000/037504 | A2 | 6/2000 |
| WO | 2001/014424 | A2 | 3/2001 |
| WO | 2001/051673 | A1 | 7/2001 |
| WO | 2004016241 | A1 | 2/2004 |
| WO | 2004/035607 | A2 | 4/2004 |
| WO | 2005/039632 | A1 | 5/2005 |
| WO | 2006/081826 | A2 | 8/2006 |
| WO | 2008083174 | A2 | 7/2008 |
| WO | 2008/132601 | A1 | 11/2008 |
| WO | 2008/156712 | A1 | 12/2008 |
| WO | 2009/015843 | A1 | 2/2009 |
| WO | 2009018500 | A1 | 2/2009 |
| WO | 2009/044273 | A2 | 4/2009 |
| WO | 2009155535 | A2 | 12/2009 |
| WO | 2010105347 | A1 | 9/2010 |
| WO | 2011/014438 | A1 | 2/2011 |
| WO | 2011/036211 | A1 | 3/2011 |
| WO | 2011/066389 | A1 | 6/2011 |
| WO | 2011/101332 | A1 | 8/2011 |
| WO | 2011/135222 | A2 | 11/2011 |
| WO | 2012/013326 | A1 | 2/2012 |
| WO | 2012/048190 | A1 | 4/2012 |
| WO | 2012/050365 | A2 | 4/2012 |
| WO | 2012097012 | A1 | 7/2012 |
| WO | 2013/006490 | A2 | 1/2013 |
| WO | 2013/025779 | A1 | 2/2013 |
| WO | 2013/067492 | A1 | 5/2013 |
| WO | 2013/075048 | A1 | 5/2013 |
| WO | 2013/113501 | A1 | 8/2013 |
| WO | 2013/120073 | A1 | 8/2013 |
| WO | 2014009209 | A2 | 1/2014 |
| WO | 2014/041505 | A1 | 3/2014 |
| WO | 2014046983 | A1 | 3/2014 |
| WO | 2014/070663 | A1 | 5/2014 |
| WO | 2014/165101 | A1 | 10/2014 |
| WO | 2015/069932 | A1 | 5/2015 |
| WO | 2015/103037 | A2 | 7/2015 |
| WO | 2015/188197 | A2 | 12/2015 |
| WO | 2016070136 | A1 | 5/2016 |
| WO | 2016146143 | A1 | 9/2016 |
| WO | 2016146261 | A1 | 9/2016 |
| WO | WO-2016146260 | A1 | 9/2016 |
| WO | 201702345 | A1 | 1/2017 |
| WO | 2017089779 | A1 | 6/2017 |
| WO | 2017118864 | A1 | 7/2017 |
| WO | 2017195032 | A1 | 11/2017 |
| WO | 201815845 | A1 | 1/2018 |
| WO | WO-2018053508 | A1 | 3/2018 |
| WO | WO-2018055060 | A1 | 3/2018 |
| WO | 2018187356 | A2 | 10/2018 |
| WO | 2019150310 | A1 | 8/2019 |

OTHER PUBLICATIONS

Black, M., et al., "Advances in the design and delivery of peptide subunit vaccines with a focus on Toll-like receptor agonists," Expert Review of Vaccines, 9(2): 157-173 (2010).

Schirmbeck, R., et al., "Antigenic Epitopes Fused to Cationic Peptide Bound to Oligonucleotides Facilitate Toll-Like Receptor 9-Dependent, but CD4+ T Cell Help-Independent, Priming of CD8+ T Cells," Journal of Immunology, 171: 5198-5207 (2003).

National Cancer Institute, NCI Drug Dictionary, "glioblastoma multiforme multipeptide vaccine IMA950," (2019).

Woo, S.J., et al., "Co-administration of carcinoembryonic antigen and HIV TAT fusion protein with CpG-oligodeoxynucleotide induces potent antitumor immunity," Cancer Sci, 99(5): 1034-1039 (2008).

Office Action from corresponding U.S. Appl. No. 15/557,651 dated May 10, 2019.

Jones et al., 2008, J Exp Med. 205 (12): 2763-79.

Huang, Y.H., et al., CEACAM1 regulates TIM-3-mediated tolerance and exhaustion. Nature, 2015. 517(7534): p. 386-90.

Gray-Owen, S.D. and R.S. Blumberg, CEACAM1: contact-dependent control of immunity. Nat Rev Immunol, 2006. 6(6): p. 433-46.

Creelan, B.C., Update on immune checkpoint inhibitors in lung cancer. Cancer Control, 2014. 21(1): p. 80-9.

Yin, Y., et al., Phosphatidylserine-targeting antibody induces MI macrophage polarization and promotes myeloid-derived suppressor cell differentiation. Cancer Immunol Res, 2013. 1(4): p. 256-68.

Zhu, Y., et al., CSF1/CSF1R Blockade Reprograms Tumor-Infiltrating Macrophages and Improves Response to T-cell Checkpoint Immunotherapy in Pancreatic Cancer Models. Cancer Research, 2014. 74(18): p. 5057- 5069.

Sheu, B.C., et al., Up-regulation of inhibitory natural killer receptors CD94/NKG2A with suppressed intracellular perforin expression of tumor infiltrating CD8+ T lymphocytes in human cervical carcinoma. Cancer Res, 2005. 65(7): p. 2921-9.

(56) References Cited

OTHER PUBLICATIONS

Tanaka, J., et al., Cytolytic activity against primary leukemic cells by inhibitory NK cell receptor (CD94/NKG2A)-expressing T cells expanded from various sources of blood mononuclear cells. Leukemia, 2005. 19(3): p. 486-9.
Ball, H.J., et al., Indoleamine 2,3-dioxygenase-2; a new enzyme in the kynurenine pathway. Int J Biochem Cell Biol, 2009. 41(3): p. 467-71.
Liu, X., et al., Selective inhibition of ID01 effectively regulates mediators of antitumor immunity. Blood, 2010. 115(17): p. 3520-30.
Ino., K., et al., Inverse correlation between tumoral indoleamine 2,3-dioxygenase expression and tumor-infiltrating lymphocytes in endometrial cancer: its association with disease progression and survival. Clin Cancer Res, 2008. 14(8): p. 2310-7.
Muller, A.J., et al., Chronic inflammation that facilitates tumor progression creates local immune suppression by inducing indoleamine 2,3 dioxygenase. Proc Natl Acad Sci US A, 2008. 105( 44): p. 17073-8.
Sheridan C., 2015: IDO inhibitors move center stage in immune-oncology; Nature Biotechnology 33: 321-322.
Garber, K., Evading immunity: new enzyme implicated in cancer. J Natl Cancer Inst, 2012. 104(5): p. 349-52.
Platten, M., W. Wick, and B.J. Van den Eynde, Tryptophan catabolismin cancer: beyond !DO and tryptophan depletion. Cancer Res, 2012. 72(21): p. 5435-40.
Platten, M., et al., Cancer Immunotherapy by Targeting IDOI/TDO and Their Downstream Effectors. Front Immunol, 2014. 5: p. 673.
Robert D. Leone et al., 2015: A2aR antagonists: Next generation checkpoint blockade for cancer immunotherapy. Computational and Structural Biotechnology Journal 13: 265-272.
Woo et al ., 2012, Cancer Res. 72: 917-27.
Butler N. S. et al., 2011, Nat Immunol. 13: 188-95.
Fu et al., 2011, Cancer Res. 71: 5445-54.
Curran et al., 2011, PLoS One 6(4): el 9499.
Kryczek I, Zou L, Rodriguez P, Zhu G, Wei S, Mottram P, et al. B7-H4 expression identifies a novel suppressive macrophage population in human ovarian carcinoma. J Exp Med. 2006; 203:871-81.
Van Dijk, M. A., and van de Winkel, J. G., Curr. Opin. Chem. Biol. 5 (2001) 368-374.
Jakobovits, A., et al., Proc. Natl. Acad. Sci. USA 90 (1993) 2551-2555.
Jakobovits, A., et al., Nature 362 (1993) 255-258.
Bruggemann, M., et al., Year Immunol. 7 (1993) 3340).
Hoogenboom, H. R., and Winter, G., J. Mol. Biol. 227 (1992) 381-388.
Marks, J. D., et al., J. Mol. Biol. 222 (1991) 581-597.
Cole et al., Monoclonal Antibodies and Cancer Therapy, Alan R. Liss, p. 77 (1985).
Boerner, P., et al., J. Immunol. 147 (1991) 86-95.
Holliger and Hudson, 2005, Nature Biotechnology 9: 1126-1136.
Saikali, S., et al., Expression of nine tumour antigens in a series of human glioblastoma multiforme: interest of EGFRvIII, IL-13Ralpha2, gp100 and TRP-2 for immunotherapy. J Neurooncol, 2007. 81(2): p. 139-48.
Schuster, J., et al., A phase II, multicenter trial of rindopepimut (CDX-110) in newly diagnosed glioblastoma: the ACT III study. Neuro Oncol, 2015. 17(6): p. 854-61.
Nakada, M., Y. Hayashi, and J. Hamada, Role of Eph/ephrin tyrosine kinase in malignant glioma. Neuro Oncol, 2011. 13(11): p. 1163-70.
Phuphanich, S., et al., Phase I trial of a multi-epitope-pulsed dendritic cell vaccine for patients with newly diagnosed glioblastoma. Cancer Immunol Immunother, 2013. 62(1): p. 125-35.
Kyte and Doolittle, 1982, J. Mol. Biol. 157(1):105- 132.
Cobbs CS, Harkins L, Samanta M, et al. Human cytomegalovirus infection and expression human malignant glioma. Cancer Res. 2002;62:3347-3350.
Trivedi et al., Blood, 105:2793 (2005).

Shaw, E.G., et al., Recurrence following neurosurgeon-determined gross-total resection of adult supratentorial low- grade glioma: results of a prospective clinical trial. J Neurosurg, 2008. 109(5): p. 835-41.
Greenspan, N.S., & Cera, E.D., "Defining epitopes: It's not as easy as it seems," Nature Biotechnology, 17: 936-937 (1999).
Rudikoff, S., et al., "Single amino acid substitution altering antigen-binding specificity," Proc. Natl. Acad. Sci. USA, 79: 1979-1983 (1982).
Colman, P.M., "Effects of amino acid sequence changes on antibody-antigen interactions," Research in Immunology, 145(1): 33-36 (1994).
Wang, C.Y., et al., "Systematic analysis of the achaete-scute complex-like gene signature in clinical cancer patients". Mol Clin Oncol., 6(1):7-18 (2017).
Semakova A. P. et al., "Adjuvant Technologies in the Construction of Advanced Vaccines", Problems of Particularly Dangerous Infections, 2: 28-35 (2016).
Zhao, M., and Weissleder, R., "Intracellular Cargo Delivery Using Tat Peptide and Derivatives," Medicinal Research Reviews, 24(1): 1-12 (2004).
Heitz, F., et al., "Twenty years of cell-penetrating peptides: from molecular mechanisms to therapeutics," British Journal of Pharmacology, 157(2): 195-206 (2009).
Spencer, A.J., et al., "Fusion of the *Mycobacterium tuberculosis* Antigen 85A to an Oligomerization Domain Enhances Its Immunogenicity in Both Mice and Non-Human Primates," PLOS One, 7(3): p.e33555, (2012).
Shen, J., et al., "Single Variable Domain-IgG Fusion: A Novel Recombinant Approach to Fc Domain-Containing Bispecific Antibodies", The Journal of Biological Chemistry, 281(16), 10706-10714 (2006).
Swiech, K., et al., "Human cells: New platform for recombinant therapeutic protein production," Protein Expression and Purification, 84(1): 147-153 (2012).
Welniak, L.A., et al., "Immunobiology of Allogeneic Hematopoietic stem cell transplantation," Annu. Rev. Immunol., 25: 139-170 (2007).
Grupp, S.A., et al., "Chimeric Antigen Receptor-Modified T Cells for Acute Lymphoid Leukemia," New England Journal of Medicine, 368(16): 1509-1518 (2013).
Jones, H.L., et al., "Luminal Epithelial Antigen (LEA.135) Expression Correlates with Tumor Progression for Transitional Carcinoma of the Bladder," AntiCancer Research, 17: 685-688 (1997).
Beckett, M.L., and Wright Jr., G.L., "Characterization of a Prostate Carcinoma Mucin-Like Antigen (PMA)," Int. J. Cancer, 62: 703-710 (1995).
Antonia, Scott et al., 2016, Safety and antitumour activity of durvalumab plus tremelimumab in non-small cell lung cancer: a multicentre, phase 1b study; Lancet Oncol. Feb. 5, 2016. pii: S1470-2045(15)00544-6. doi: 10.1016/S1470-2045(15)00544-6.
Greenwald, R.J., G.J. Freeman, and A.H. Sharpe, The B7 family revisited. Annu Rev Immunol, 2005. 23: p. 515-48.
Zou, W. and L. Chen, Inhibitory B7-family molecules in the tumour microenvironment. Nat Rev Immunol, 2008. 8(6): p. 467-77.
Chapoval, A.I., et al., B7-H3: a costimulatory molecule for T cell activation and IFN-gamma production. Nat Immunol, 2001. 2(3): p. 269-74.
Sica, G.L., et al., B7-H4, a molecule of the B7 family, negatively regulates T cell immunity. Immunity, 2003. 18(6): p. 849-61.
Loos, M., et al., B7-h3 and its role in antitumor immunity. Clin Dev Immunol, 2010. 2010: p. 683875.
Hofmeyer, K.A., A. Ray, and X. Zang, The contrasting role of B7-H3. Proc Natl Acad Sci US A, 2008.105(30): p. 10277-8.
Sun, J., et al., Clinical significance and regulation of the costimulatory molecule B7-H3 in human colorectal carcinoma. Cancer Immunol Immunother, 2010. 59(8): p. 1163-71.
Dangaj, D. and N. Scholler, Blocking the B7-H4 pathway with novel recombinant antibodies enhances T cell-mediated antitumor responses. Oncoimmunology, 2013. 2(8): p. e25913.
Dangaj, D., et al., Novel recombinant human b7-h4 antibodies overcome tumoral immune escape to potentiate T-cell antitumor responses. Cancer Res, 2013. 73(15): p. 4820-9.

(56) References Cited

OTHER PUBLICATIONS

Wang, X., et al., B7-H4 Treatment o/T Cells Inhibits ERK,JNK, p38, and AKT Activation. PLoS One, 2012. 7(1): p. e28232.
Leong, S.R., et al., An anti-b7-h4 antibody-drug conjugate for the treatment of breast cancer. Mol Pharm, 2015.12(6): p. 1717-29.
Buchbinder E. I. and Desai A., 2016: CTLA-4 and PD-1 Pathways—Similarities, Differences and Implications of Their Inhibition; American Journal of Clinical Oncology, 39(1): 98-106.
Hurwitz et al., Proc. Natl. Acad. Sci. USA, 95(17): 10067-10071 (1998).
Camacho et al., J. Clin. Oncology, 22(14):Abstract No. 2505 (2004).
Mokyr et al., Cancer Res., 58:5301-5304 (1998).
Jenessa B. Smith et al., 2014: B7-H4 as a potential target for immunotherapy for gynecologic cancers: A closer look. Gynecol Oncol 134(1): 181-189.
Croft, M., C.A. Benedict, and C.F. Ware, Clinical targeting of the TNF and TNER superfamilies. Nat Rev Drug Discov, 2013.12(2): p. 147-68.
Aggarwal, B.B., Signalling pathways of the TNF superfamily: a double-edged sword. Nat Rev Immunol, 2003. 3(9): p. 745-56.
Avogadri, F., et al., Modulation of CTLA-4 and GITR/or cancer immunotherapy. Curr Top Microbiol Immunol, 2011. 344: p. 211-44.
Naidoo, J., D.B. Page, and J.D. Wolchok, Immune modulation for cancer therapy. Br J Cancer, 2014.111(12): p. 2214-9.
Bremer, E., Targeting of the tum or necrosis factor receptor superfamily for cancer immunotherapy. ISRN Oncol, 2013. 2013: p. 371854.
Sufia Butt Hassan, Jesper Freddie Sørensen, Barbara Nicola Olsen and Anders Elm Pedersen, 2014: Anti-CD40-mediated cancer immunotherapy: an update of recent and ongoing clinical trials, Immunopharmacology and Immunotoxicology, 36:2, 96-104.
Alison Crawford and E. John Wherry, 2009: Editorial: Therapeutic potential of targeting BTLA. Journal of Leukocyte Biology 86: 5-8.
Hemon, P., et al., MHC class II engagement by its ligand LAG-3 (CD223) contributes to melanoma resistance to apoptosis. J Immunol, 2011. 186(9): p. 5173-83.
Thielens, A., E. Vivier, and F. Romagne, NK cell MHC class I specific receptors (KIR): from biology to clinical intervention. Curr Opin Immunol, 2012. 24(2): p. 239-45.
Benson et al., 2012, Blood 120:4324-4333.
Ngiow, S.F., et al., Anti-TIM3 antibody promotes T cell IFN-gammamediated antitumor immunity and suppresses established tumors. Cancer Res, 2011. 71(10): p. 3540-51.
Rini, B., "Future Approaches in Immunotherapy," Seminars in Oncology, 41(5): S30-S40 (2014).
Mangsbo, S.M., et al., "Enhanced Tumor Eradication by Combining CTLA-4 or PD-1 Blockade With CpG Therapy," J. Immunother., 33(3): 225-235 (2010).
Deres, K., et al., "In vivo priming of virus-specific cytotoxic T lymphocytes with synthetic lipopeptide vaccine," Nature, 342: 561-564 (1989).
Fujita, Y., & Taguchi, H., "Current status of multiple antigen-presenting peptide vaccine systems: Application of organic and inorganic nanoparticles," Chemistry Central Journal, 5(48): 1-5 (2011).
Garaude, J., et al., "Simultaneous Targeting of Toll- and Nod-Like Receptors Induces Effective Tumor-Specific Immune Responses," Science Translational Medicine, 4(120): 1-13 (2012).
Khan, S., et al., "Chirality of TLR-2 ligand Pam$_3$CysSK$_4$ in fully synthetic peptide conjugates critically influences the induction of specific CD8$^+$ T-cells," Molecular Immunology, 46: 1084-1091 (2009).
Li, Q., & Guo, Z., "Recent Advances in Toll Like Receptor-Targeting Glycoconjugate Vaccines," Molecules, 23: 1-24 (2018).
Wilkinson, B.L., et al., "Self-Adjuvanting Multicomponent Cancer Vaccine Candidates Combining Per-Glycosylates MUC1 Glycopeptides and the Toll-like Receptor 2 Agonist Pam$_3$CysSer," Angew. Chem. Int. Ed., 50: 1635-1639 (2011).
Zhang, X., et al., "A Comparative Study of the Antigen-Specific Immune Response Induced by Co-Delivery of CpG ODN and Antigen Using Fusion Molecules or Biodegradable Microparticles," Journal of Pharmaceutical Sciences, 96(12): 3283-3292 (2007).
Aitken et al., "Taking a Stab at Cancer; Oncolytic Virus-Mediated Anti-Cancer Vaccination Strategies", Biomedicines, vol. 5, No. 1, 3, Jan. 4, 2017 (Jan. 4, 2017), XP055419683.
Belnoue et al., "Targeting self- and neoepitopes with a modular self-adjuvanting cancer vaccine", JCI Insight, vol. 4, No. 11, E127305, Jun. 6, 2019 (Jun. 6, 2019), XP055749546.
Das et al., "A modular self-adjuvanting cancer vaccine combined with an oncolytic vaccine induces potent antitumor immunity", Nature Communications, vol. 12, No. 1, 5195, Aug. 31, 2021 (Aug. 31, 2021), XP055879106.
Das et al., "Supplementary Materials: A modular self-adjuvanting cancer vaccine combined with an oncolytic vaccine induces potent antitumor immunity", Nature Communications, vol. 12, No. 1, 5195, Aug. 31, 2021 (Aug. 31, 2021), XP055879706.
Haq et al., "Evaluation of recombinant adenovirus vectors and adjuvanted protein as a heterologous prime-boost strategy using HER2 as a model antigen", Vaccine, vol. 37, No. 47, Sep. 7, 2019 (Sep. 7, 2019), pp. 7029-7040, XP085880235.
Hofer et al., "Heterologous Prime-Boost Vaccination with a Peptide-Based Vaccine and Viral Vector Reshapes Dendritic Cell, CD4+ and CDS+ T Cell Phenotypes to Improve the Antitumor Therapeutic Effect", Cancers, vol. 13, No. 23, Dec. 3, 2021 (Dec. 3, 2021), p. 6107, XP055879764.
Jung et al., "Heterologous prime-boost vaccination with adenoviral vector and protein nanoparticles induces both Th1 and Th2 responses against Middle East respiratory syndrome coronavirus", Vaccine, vol. 36, No. 24, Jun. 2018 (Jun. 2018), pp. 3468-3476, XP055879799.
Kim S-B et al., "A phase 1 study of a heterologous prime-boost vaccination involving a truncated HER2 sequence in patients with HER2-expressing breast cancer", Molecular Therapy, vol. 2, 15031, 2015, XP055879077.
Kim S-Y et al., "Prime-boost immunization by both DNA vaccine and oncolytic adenovirus expressing GM-CSF and shRNA of TGF-[beta]2 induces anti-tumor immune activation", Oncotarget, vol. 8, No. 9, Feb. 28, 2017 (Feb. 28, 2017), pp. 15858-15877, XP055879746.
Ortiz et al., "Immunization of cattle against Babesia bovis combining a multi-epitope modified vaccinia Ankara virus and a recombinant protein induce strong Th1 cell responses but fails to trigger neutralizing antibodies required for protection", Ticks and Ticks-Borne Diseases, vol. 10, 10270, Aug. 16, 2019 (Aug. 16, 2019), XP085809964.
Tober et al., "VSV-GP: a Potent Viral Vaccine Vector That Boosts the Immune Response upon Repeated Applications", Journal of Virology, vol. 88, No. 9, May 2014 (May 2014), pp. 4897-4907, XP055879082.
Rossi et al., "Combination treatment using KISIMA TM protein-based cancer vaccine and systemic STING agonist results in profound modulation of tumor microenvironment and improved tumor control", Journal for Immunotherapy of Cancer, vol. 8, No. Suppl 3, 452, Dec. 10, 2020 (Dec. 10, 2020), pp. A479-A479, XP055882322.
Rossi et al., "STING Agonist Combined to a Protein-Based Cancer Vaccine Potentiates Peripheral and Intra-Tumoral T Cell Immunity", Frontiers in Immunology, vol. 12, Jul. 1, 2021 (Jul. 1, 2021), XP55882273.
Sallets et al., "Enhancing immunotherapy of STING agonist for lymphoma in preclinical models", Blood Advances, vol. 2, No. 17, Sep. 11, 2018 (Sep. 11, 2018) f pp. 2230-2241, XP055764731.
Frankel, A.D. and C.O. Pabo, Cellular uptake of the tat protein from human immunodeficiency virus. Cell, 1988. 55(6): p. 1189-93.
Joliot, A., et al., Antennapedia homeobox peptide regulates neural morphogenesis. Proc Natl Acad Sci U S A, 1991. 88(5): p. 1864-8.
Derossi, D., et al., The third helix of the Antennapedia homeodomain translocates through biological membranes. J Biol Chem, 1994. 269(14): p. 10444-50.
Vives, E., P. Brodin, and B. Lebleu, A truncated HIV-1 Tat protein basic domain rapidly translocates through the plasma membrane and accumulates in the cell nucleus. J Biol Chem, 1997. 272(25): p. 16010-7.
Elliott, G. and P. O'Hare, Intercellular trafficking and protein delivery by a herpesvirus structural protein. Cell, 1997. 88(2): p. 223-33.

(56) References Cited

OTHER PUBLICATIONS

Dempsey, C.E., The actions of melittin on membranes. Biochim Biophys Acta, 1990. 1031(2): p. 143-61.
Konno, K., et al., Structure and biological activities of eumenine mastoparan-AF (EMP-AF), a new mast cell degranulating peptide in the venom of the solitary wasp (Anterhynchium flavomarginatum micado). Toxicon, 2000. 38(11): p. 1505-15.
Esteve, E., et al., Transduction of the scorpion toxin maurocalcine into cells. Evidence that the toxin crosses the plasma membrane. J Biol Chem, 2005. 280(13): p. 12833-9.
Nascimento, F.D., et al., Crotamine mediates gene delivery into cells through the binding to heparan sulfate proteoglycans. J Biol Chem, 2007. 282(29): p. 21349-60.
Kobayashi, S., et al., Membrane translocation mechanism of the antimicrobial peptide buforin 2. Biochemistry, 2004. 43(49): p. 15610-6.
Futaki, S., et al., Arginine-rich peptides. An abundant source of membrane-permeable peptides having potential as carriers for intracellular protein delivery. J Biol Chem, 2001. 276(8): p. 5836-40.
Pooga, M., et al., Cell penetration by transportan. FASEB J, 1998. 12(1): p. 67-77.
Nair et al. (2003, Nucleic Acids Res. 31(1): 397-399.
Kapoor et al. (2012, PLoS One 7(4): e35187.
Lim, Y.T., Vaccine adjuvant materials for cancer immunotherapy and control of infectious disease. Clin Exp Vaccine Res, 2015. 4(1): p. 54-8.
Baxevanis, C.N., I.F. Voutsas, and O.E. Tsitsilonis, Toll-like receptor agonists: current status and future perspective on their utility as adjuvants in improving anticancer vaccination strategies. Immunotherapy, 2013. 5(5): p. 497-511.
Duthie MS, Windish HP, Fox CB, Reed SG. Use of defined TLR ligands as adjuvants within human vaccines. Immunol Rev. 2011; 239:178-196.
Manicassamy S, Pulendran B. Modulation of adaptive immunity with Toll-like receptors. Semin Immunol. 2009; 21:185-193.
Zom GG, Khan S, Filippov DV, Ossendorp F. TLR ligand-peptide conjugate vaccines: toward clinical application. Adv Immunol. 2012;114:177-201.
Fujita, Y. and H. Taguchi, Overview and outlook of Toll-like receptor ligand-antigen conjugate vaccines. Ther Deliv, 2012. 3(6): p. 749-60.
Monie, T. P., Bryant, C. E., et al. 2009: Activating immunity: Lessons from the TLRs and NLRs. Trends Biochem. Sci. 34(11), 553-561.
Gay, N. J., and Gangloff, M. (2007): Structure and function of Toll receptors and their ligands. Annu. Rev. Biochem. 76, 141-165.
Spohn, R., Buwitt-Beckmann, U., et al. (2004): Synthetic lipopeptide adjuvants and Toll-like receptor 2-Structure-activity relationships. Vaccine 22(19), 2494-2499.
Bryant, C. E., Spring, D. R., et al. (2010). The molecular basis of the host response to lipopolysaccharide. Nat. Rev. Microbiol. 8(1), 8-14.
Barbalat R, Lau L, Locksley RM, Barton GM. Toll-like receptor 2 on inflammatory monocytes induces type I interferon in response to viral but not bacterial ligands. Nat Immunol. 2009: 10(11):1200-7.
Akira S, Uematsu S, Takeuchi O. Pathogen recognition and innate immunity. Cell. Feb. 24; 2006: 124(4):783-801.
Kumar H, Kawai T, Akira S. Toll-like receptors and innate immunity. Biochem Biophys Res Commun. Oct. 30, 2009 388(4):621-5.
Lasarte, J.J., et al., The extra domain A from fibronectin targets antigens to TLR4-expressing cells and induces cytotoxic T cell responses in vivo. J Immunol, 2007. 178(2): p. 748-56.
Applequist, S.E., R.P. Wallin, and H.G. Ljunggren, Variable expression of Toll-like receptor in murine innate and adaptive immune cell lines. Int Immunol, 2002. 14(9): p. 1065-74.
Okamura, Y., et al., The extra domain A of fibronectin activates Toll-like receptor 4. J Biol Chem, 2001. 276(13): p. 10229-33.
Jameson et al., Nature, 368,744-746 (1994).
Brady et al., Nature, 368,692-693 (1994).
Seifter et al. (1990) Analysis for protein modifications and nonprotein cofactors, Meth. Enzymol. 182: 626-646.
Rattan et al., (1992) Protein Synthesis: Post-translational Modifications and Aging, Ann NY Acad Sci, 663: 48-62.
Karlin et al. (1993), PNAS USA, 90:5873-5877.
Altschul et al., 1990, J. Mol. Biol. 215, 403-410.
Altschul et al. (1997), Nucleic Acids Res, 25:3389-3402.
Pearson (1990), Methods Enzymol. 183, 63-98.
Pearson and Lipman (1988), Proc. Natl. Acad. Sci. U. S. A 85, 2444-2448.
Devereux et al., 1984, Nucleic Acids Res., 387-395.
Smith and Waterman (1981), J. Mol. Biol. 147, 195-197.
Apostolopoulos et al., 1996 Immunol. Cell. Biol. 74: 457-464.
Pandey et al., 1995, Cancer Res. 55: 4000-4003.
Kierkegaard et al., 1995, Gynecol. Oncol. 59: 251-254.
Kievit et al., 1997, Int. J. Cancer 71: 237-245.
Lozza et al., 1997 Anticancer Res. 17: 525-529.
Mota et al., 1997, Am. J Pathol. 150: 1223-1229.
Fishman et al., 1997 Cancer 79: 1461-1464.
Notelet et al., 1997 Surg. Neurol. 47: 364-370.
Tacken, P.J., et al., "No Advantage of Cell-Penetrating Peptides over Receptor-Specific Antibodies in Targeting Antigen to Human Dendritic Cells for Cross-Presentation," The Journal of Immunology 180: 7687-7696 (2008).
Yadav, M., et al., "Predicting immunogenic tumor mutations by combining mass spectrometry and exome sequencing," Nature 515: 572-576 (2014).
Gnjatic, S., et al., "Toll-Like Receptor Agonists; Are They Good Adjuvants?," The Cancer Journal 16(4): 382-391 (2010).
Restriction Requirement from U.S. Appl. No. 15/557,647 dated Aug. 22, 2019.
Schmitz, M., et al., "Generation of Survivin-specific CD8+ T Effector Cells by Dendritic Cells Pulsed with Protein or Selected Peptides1," Cancer Research, 60: 4845-4849 (2000).
Hidekazu, K., et al., "Immunogenic enhancement and clinical effect by Type-I interferon of anti-apoptotic protein, survivin-derived peptide vaccine, in advanced colorectal cancer in patients," Cancer Science, 102(6): 1181-1187 (2011).
Friedrichs, B., et al., "Survivin-derived peptide epitopes and thier role for induction of antitumor immunity in hematological malignancies," Leukemia & Lymphoma, 47(6): 978-985 (2006).
Non-final Office Action from U.S. Appl. No. 15/557,649 dated Feb. 3, 2020.
Office Action from U.S. Appl. No. 15/557,653 dated Apr. 13, 2020.
Oh, T., et al., "Immunocompetent murine models for the study of glioblastoma immunotherapy," Journal of Translational Medicine, 12(107): 1-10 (2014).
Office Action issued in U.S. Appl. No. 15/557,651 dated Apr. 22, 2020.
Office Action from U.S. Appl. No. 15/557,647 dated Jun. 22, 2020.
Office Action from U.S. Appl. No. 15/557,649 dated Jul. 7, 2020.
Houot, R., and Levy, R., "T-cell modulation combined with intratumoral CpG cures lymphoma in a mouse model without the need for chemotherapy," Blood, 113(15): 3546-3552 (2009).
Office Action issued in corresponding RU Application No. 2018135097 dated Jul. 30, 2020.
Muller, S., et al., "Nucleic Acids From A to Z," Moscow: BINOM. Knowledge laboratory, p. 216 (2013).
Office Action from corresponding U.S. Appl. No. 15/557,653 dated Dec. 14, 2020.
Office Action from corresponding U.S. Appl. No. 16/084,170 dated Nov. 10, 2020.
Zamarin, D., and Postow, M.A., "Immune checkpoint modulation: Rational design of combination strategies," Pharmacology & Therapeutics, 150: 23-32 (2015).
Stewart, B. and C. Wild, World Cancer Report 2014, B. Stewart and C. Wild, Editors. 2014, International Agency for Research on Cancer: Geneva.
Burt, R.W., J.A. DiSario, and L. Cannon-Albright, Genetics of colon cancer: impact of inheritance on colon cancer risk. Annu Rev Med, 1995. 46: p. 371-9.

(56) References Cited

OTHER PUBLICATIONS

Sieber, O.M., et al., Multiple colorectal adenomas, classic adenomatous polyposis, and germ-line mutations in MYH. N Engl J Med, 2003. 348(9): p. 791-9.
Lynch, H.T., et al., Genetics, natural history, tumor spectrum, and pathology of hereditary nonpolyposis colorectal cancer: an updated review. Gastroenterology, 1993. 104(5): p. 1535-49.
Ekbom, A., et al., Ulcerative colitis and colorectal cancer. A population-based study. N Engl J Med, 1990. 323(18): p. 1228-33.
Jemal, A., et al., Global cancer statistics. CA Cancer J Clin, 2011. 61(2): p. 69-90.
Moertel, C.G., Chemotherapy for colorectal cancer. N Engl J Med, 1994. 330(16): p. 1136-42.
Meyerhardt, J.A. and R.J. Mayer, Systemic therapy for colorectal cancer. N Engl J Med, 2005. 352(5): p. 476-87.
Gallagher, D.J. and N. Kemeny, Metastatic colorectal cancer: from improved survival to potential cure. Oncology, 2010. 78(3-4): p. 237-48.
Smith, C.L., et al., Immunotherapy of colorectal cancer. Br Med Bull, 2002. 64: p. 181-200.
Koido, S., et al., Immunotherapy for colorectal cancer. World J Gastroenterol, 2013. 19(46): p. 8531-42.
Xiang, B., et al., Colorectal cancer immunotherapy. Discov Med, 2013. 15(84): p. 301-8.
Clarke, J.M. and H.I. Hurwitz, Ziv-aflibercept: binding to more than VEGF-A—does more matter? Nat Rev Clin Oncol, 2013. 10(1): p. 10-1.
Siegel, R., C. Desantis, and A. Jemal, Colorectal cancer statistics, 2014. CA Cancer J Clin, 2014. 64(2): p. 104-17.
Slingluff CL, Jr. The present and future of peptide vaccines for cancer: single or multiple, long or short, alone or in combination? Cancer journal 2011;17(5):343-50.
Melief CJ, van der Burg SH. Immunotherapy of established (pre-)malignant disease by synthetic long peptide vaccines. Nature reviews Cancer 2008;8(5):351-60.
Kruit WH, Suciu S, Dreno B, Mortier L, Robert C, Chiarion-Sileni V, et al. Selection of immunostimulant AS15 for active Immunization with MAGE-A3 protein: results of a randomized phase II study of the European Organisation for Research and Treatment of Cancer Melanoma Group in Metastatic Melanoma. Journal of clinical oncology : official Journal of the American Society of Clinical Oncology 2013;31(19):2413-20.
Vansteenkiste J, Zielinski M, Linder A, Dahabreh J, Gonzalez EE, Malinowski W, et al. Adjuvant MAGE-A3 immunotherapy in resected non-small-cell lung cancer: phase II randomized study results. Journal of clinical oncology :official journal of the American Society of Clinical Oncology 2013;31(19):2396-403.
Toes RE, Offringa R, Blom RJ, Melief CJ, Kast WM. Peptide vaccination can lead to enhanced tumor growth through specific T-cell tolerance induction. Proceedings of the National Academy of Sciences of the United States of America 1996;93(15):7855-60.
Rosalia RA, Quakkelaar ED, Redeker A, Khan S, Camps M, Drijfhout JW, et al. Dendritic cells process synthetic long peptides better than whole protein, improving antigen presentation and T-cell activation. European journal of Immunology 2013;43(10):2554-65.
Apetoh L, Locher C, Ghiringhelli F, Kroemer G, Zitvogel L. Harnessing dendritic cells in cancer. Semin Immunol. 2011; 23:42-49.
Banchereau J, Steinman RM. Dendritic cells and the control of immunity. Nature. 1998; 392:245-252.
Wang RF, Wang HY. Enhancement of antitumor immunity by prolonging antigen presentation on dendritic cells. Nat Biotechnol. 2002; 20:149-156.
Copolovici DM, Langel K, Eriste E, Langel U. Cell-penetrating peptides: design, synthesis, and applications. ACS nano 2014;8(3):1972-94.
Milletti, F., Cell-penetrating peptides: classes, origin, and current landscape. Drug Discov Today 17 (15-16): 850-60, 2012.
Berry CC. Intracellular delivery of nanoparticles via the HIV-1 tat peptide. Nanomedicine. 2008, 3:357-365.
Deshayes S, Morris MC, Divita G, Heitz F. Cell-penetrating peptides: Tools for intracellular delivery of therapeutics. Cell Mol Life Sci. 2005; 62:1839-1849.
Edenhofer F. Protein transduction revisited: Novel insights into the mechanism underlying intracellular delivery of proteins. Curr Pharm Des. 2008; 14:3628-3636.
Gupta B, Levchenko TS, Torchilin VP. Intracellular delivery of large molecules and small particles by cell-penetrating proteins and peptides. Adv Drug Deliv Rev. 2005; 57:637-651.
Torchilin VP. Recent approaches to intracellular delivery of drugs and DNA and organelle targeting. Annu Rev Biomed Eng. 2006; 8:343-375.
Wang HY, Fu T, Wang G, Gang Z, Donna MPL, Yang JC, Restifo NP, Hwu P, Wang RF. Induction of CD4+ T cell- dependent antitumor immunity by TAT-mediated tumor antigen delivery into dendritic cells. J Clin Invest. 2002a; 109:1463-1470.
Derouazi M. et al., (2015) "Novel cell-penetrating peptide-based vaccine induces robust CD4+ and CD8+ T cell-mediated antitumor immunity" Cancer Research, 75:15 3020-3031.
Minsig C. et al., (2014) "Identyfying Appropriate Colorectal Cancer-Associated Antigens for the Clinical Trials" Corrent Colorectal Cancer Reports, 11:1 29-36.
Novellino L. et al., (2005) "A listing of human tumor antigens recognizes by T-cells: Mar. 2004 update" Cancer Immunology, 54:3 187-207.
Pardoll, D. (2012), "The blockade of immune checkpoints in cancer immunotherapy", Nature Reviews Cancer, 12(4):252-264.
Vigneron N. et al., (2013) "Database of T cell-defined human tumor antigens: the 2013 update" Cancer Immunity. 13:15.
International Search Report issued in International Patent Application No. PCT/EP2016/000473 mailed Jun. 17, 2016.
Written Opinion issued in International Patent Application No. PCT/EP2016/000471, mailed Mar. 16, 2016.
International Search Report issued in International Patent Application No. PCT/EP2016/000471 mailed Mar. 16, 2017.
Reardon D. et al., (2013)"An update on vaccine therapy and other immunotherapeutic approaches for glioblastoma" Expert Review of Vaccines 12:6 597-615.
International Search Report issued in International Patent Application No. PCT/EP2016/000470, mailed Jun. 17, 2016.
Written Opinion issued in International Patent Application No. PCT/EP2016/000470, mailed Jun. 17, 2016.
International Search Report issued in PCT/EP2015/002598, mailed Mar. 16, 2016.
Written Opinion issued in PCT/EP2015/002598, mailed Mar. 16, 2016.
Written Opinion issued in International Patent Application No. PCT/EP2016/00473, mailed Jun. 17, 2016.
Office Action dated Oct. 5, 2018 as issued in U.S. Appl. No. 15/557,651.
Buhl, T., et al. (2013), Internalization routes of cell-penetrating melanoma antigen peptides into human dendritic cells, Experimental Dermatology, 23: 20-26.
Zhang, T., et al. (2012), "LAH4 enhances CD8+ T cell immunity of protein/peptide-based vaccines", Vaccine, 30: 784-793.
Walker, P, et al. (2016), "Cell-penetrating peptides—the Swiss Army knife of cancer vaccines", Oncoimmunology, 5(3): p. e1095435 (3 pages).
Aranda, F., et al. (2013), "Trial Watch: peptide vaccines in cancer therapy", OncoImmunology, 2(12): e26621.
International Search Report issued in PCT/EP2017/056034 dated May 24, 2017.
Written Opinion issued in PCT/EP2017/056034 dated May 24, 2017.
International Search Report and Written Opinion dated Jan. 8, 2014 issued in PCT Patent Application No. PCT/IB2013/058497.
Antón, L., et al. (1997), "MHC Class-I-Associated Peptides Produced from Endogenous Gene Products qwith Vastly Different Efficiencies", The Journal of Immunology, 158: 2535-2542.
Brooks, N. et al. (2010), "Cell-penetrating peptides: Applicantion in vaccine delivery", Biochimica et Biophysica Acta, 1805: 25-34.
Derouazi, M., et al. (2010), "Towards an Efficient DC Vaccine by Antigenic Protein Loading Using a Novel Protein Transduction

(56) References Cited

OTHER PUBLICATIONS

Domain", Poster at 11th International Sumposium on Dendritic Cells in Fundamental and Clinical Immunology—DC 2010, Palazzo dei Congressi, Lungano.
Durántez, M., et al. (2008), "Induction of Multiepitopic and Long-Lasting Immune Responses Against Tumour Antigens by Immunization with Peptides, DNA and Recombinant Adenoviruses Expressing Minigenes", Scandinavian Journal of Ummunology, 69: 80-89.
Ishioka G., et al. (1999), "Utilization of MHC Class I Transgenic Mic for Development of MINIgene DNA Vaccines Encoding Multiple HLAK-Rrestricted CTL Epitopes", The Journal of Immunology, 162: 3915-3925.
Mateo, L., et al. (1999), "An HLA-A2 Polyepitope Vaccine for Melanoma Immunoptherapy", The American Association of Immunologist, 163: 4058-4063.
McPherson, S., et al. (2003), Resting CD8 T cells recognize ß-galactosidase expressed in the immune-privileged retina and mediate autoimmune disease when activated, Immunology, 110: 386-396.
NCBI Reference YP01673.1-BZLF1 [Human herpesvirus 4]—Protein—www.ncbi.nlm.nih.gov/protein/YP_401673—3 pages, 2012.
Rosenzweig, M., et al. (2001), "Induction of cytotoxic T lymphocyte and antibody responses to enhanced green fluorescent protein following translplantation of transduced CD 34+ hematopoietic cells", Blood, 97(7): 1951-1959.
Rothe, R., et al. (2008), "Expression and Purification of ZEBRA Fusion Proteins and Applications for the Delivery of Macromolecules into Mammalian Cells", Current Protocols in Protein Science, Supplemental 54(18): 11.1-11.29.
Rothe, R., et al. (2010), "Characterization of the Cell-penetrating Properties of the Epstein-Barr Virus ZEBRA trans-Activator", The Journal of Biological Chemisry, 285(26): 20224-20233.
Rothe, R., et al. (2010), "PHD Thesis—Caractérisation de la propriété de la Protéine ZEBRA du virus Epstein-Barr á pénétrer dans les cellules", Universite De Grenoble, 156 pages.
Scardino, A., et al. (2007), "A Polyepitope DNA Vaccine Targeted to Her-2/ErbB-2 Elicits a Broad Range of Human and Murine CTL Effectors to Protect against Tumor Challenge", Cancer Research, 64(14): 7028-7036.
Stubbs, A., et al. (2001), "Whole recombinant yeast vaccine activates dendritic cells and elicits protective cell-mediated immunity", Nature Medicine, 7(5): 625-629.
Thomson, S., et al. (1995), "Minimal epitopes expressed in a recombinant polyepitope protein are processed and presented to CD8+ cytotoxi T cells: Implications for vaccine design", Proc. Natl. Acad. Sci. USA., 92: 5845-5849.
Thomson, S., et al. (1996), "Recombinant Polyepitope Vaccines for the Delivery of Multiple CD8 Cytotoxic T Cell Epitopes", The Journal of Immunology, 157: 822-826.
Tine, J., et al. (2005), "Enhanced multiepitope-based vaccines elicit CD8+ cytotoxic T cells against both immunodominant and cryptic epitopes", Vaccine, 23: 1085-1091.
Tünnemann, G., et al. (2006), "Cargo-dependent mode of uptake and bioavailability of TAT-Containing proteins and peptides in living cells", The FASEB Journal, 1775-1784.
van Montfoort, N., et al. (2009), "Antigen storage compartments in mature dendritic cells facilitate prolonged cytotoxic T lumphocytge cross-priming capacity", PNAS, 106(16): 6730-6735.
Waeckerle-Men Y., et al. (2005), "Dendritic cell-based multi-epitope immunotherapy of hormon-refractory prostate carcinoma", Cancer Immunol Immunother, 55: 1524-1533.
International Search Report and Written Opinion for PCT Application No. PCT/EP2017/073954 dated Dec. 22, 2017.
International Search Report issued in International Patent Application No. PCT/EP2016/000471, mailed Jun. 17, 2016.
Written Opinion issued in International Patent Application No. PCT/EP2016/000473, mailed Jun. 17, 2016.
Written Opinion issued in International Patent Application No. PCT/EP2016/000471. mailed Jun. 17, 2016.
Office Action dated Jul. 11, 2019 from U.S. Appl. No. 15/557,653.
Restriction Requirement from U.S. Appl. No. 15/557,649 dated Sep. 26, 2019.
Final Office Action from U.S. Appl. No. 15/557,651 dated Oct. 25, 2019.
Lucas et al., 1996 Anticancer Res. 16: 2493-2496.
Maes et al. 1996, J. Cancer Res. Clin. Oncol. 122: 296-300.
Tolliver and O'Brien, 1997, South Med. J. 90: 89-90.
Tsuruta at al., 1997 Urol. Int. 58: 20-24.
Huang et al., Exper Rev. Vaccines (2002)1:49-63.
Zantek et al., Cell Growth Differ. (1999) 10:629-38.
Carles-Kinch et al., Cancer Res. (2002) 62:2840-7.
Cheng at al., 2002, Cytokine Growth Factor Rev. 13:75-85.
Dahlenborg et al., 1997, Int. J Cancer 70: 63-71.
Zajac et al., 1997, Int. J Cancer 71: 491-496.
Deshpande and Danishefsky, 1997, Nature 387: 164-166.
Kawakami and Rosenberg, 1997, Int. Rev. Immunol. 14: 173-192.
Molldrem et al., Blood (1996) 88:2450-7.
Molldrem et al., Blood (1997) 90:2529-34.
De wit Amer 2010, Neuro Oncol, 12(3):304-16.
Maccalli, C., et al., Identification of a colorectal tumor-associated antigen (COA-1) recognized by CD4(+) T lymphocytes. Cancer Res, 2003. 63(20): p. 6735-43.
Derouazi M, Wang Y, Marlu R, et al. Optimal epitope composition after antigen screening using a live bacterial delivery vector: Application to TRP-2. Bioengineered Bugs. 2010;1(1):51-60. doi:10. 4161/bbug.1.1.9482.
Lu et al., Multiepitope trojan antigen peptide vaccines for the induction of antitumor CTL and Th immune responses J. Immunol., 172 (2004), pp. 4575-4582.
Rose et al. (1994), JACS 116, 30.
Means and Feeney, Chemical Modification of Proteins, Holden-Day, 1974, pp. 39-43.
Chen X. et al., 2013: Fusion Protein Linkers: Property, Design and Functionality. Adv Drug Deliv Rev. 65(10): 1357-1369.
Response Evaluation Criteria in Solid Tumors (RECIST) and World Health Organization (WHO) criteria; J. Natl. Cancer Inst. 2010, 102(18): 1388-1397.
Jewell, C.M., S.C. Lopez, and D.J. Irvine, In situ engineering of the lymph node microenvironment via intranodal injection of adjuvant-releasing polymer particles. Proc Natl Acad Sci US A, 2011. 108(38): p. 15745-50.
Newcomb, E. and D. Zagzag, The murine GL261 glioma experimental model to assess novel brain tumor treatments, in CNS Cancer Models, Markers, Prognostic, Factors, Targets, and Therapeutic Approaches, E.G. Van Meir, Editor. 2009, Humana Press: Atlanta. p. 227-241.
Jacobs, V.L., et al., Current review of in vivo GBM rodent models: emphasis on the CNS-1 tumour model. ASN Neuro, 2011. 3(3): p. e00063.
Zhu, X., et al., Poly-/CLC promotes the infiltration of effector T cells into intracranial gliomas via induction of CXCL10 in IFN-alpha and IFN-gamma dependent manners. Cancer Immunol Immunother, 2010. 59(9): p. 1401-9.
Zhu, X., et al., Toll like receptor-3 ligand poly-/CLC promotes the efficacy of peripheral vaccinations with tumor antigen-derived peptide epitopes in murine CNS tumor models. J Transl Med, 2007. 5: p. 10.
Ohlfest, J.R., et al., Vaccine injection site matters: qualitative and quantitative defects in CDB T cells primed as a function of proximity to the tumor in a murine glioma model. J Immunol, 2013. 190(2): p. 613-20.
Käll L, Canterbury JD, Weston J, Noble WS, MacCoss MJ (2007) Semi-supervised learning for peptide identification from shotgun proteomics datasets. Nat Methods 4(11):923-925.
Susumu Suzuki et al., 2016: Current status of immunotherapy. Japanese Journal of Clinical Oncology, 2016: doi: 10.1093/jjco/hyv201 [Epub ahead of print].
Hamid et al., 2013; N. Engl. J. Med. 369: 134-144.
Brignone et al., 2009, Clin. Cancer Res. 15: 6225-6231.
Keir, M.E., et al., PD-1 and its ligands in tolerance and immunity. Annu Rev Immunol, 2008. 26: p. 677-704.

(56) References Cited

OTHER PUBLICATIONS

Semakova, A.P., et al., "Adjuvant Technologies in the Construction of Advanced Vaccines", Problems of Particularly Dangerous Infections, 2: p. 28-35 (2016).
Cancer Statistic 2015. Americain Cancer Society.
Stupp, R., et al., Radiotherapy plus concomitant and adjuvant temozolomide for glioblastoma. N Engl J Med, 2005. 352(10): p. 987-96.
Hegi, M.E., et al., MGMT gene silencing and benefit from temozolomide in glioblastoma. N Engl J Med, 2005. 352(10): p. 997-1003.
Bechmann, I., I. Galea, and V.H. Perry, What is the blood-brain barrier (not)? Trends Immunol, 2007. 28(1): p. 5-11.
Walker, P.R., et al., T-cell immune responses in the brain and their relevance for cerebral malignancies. Brain Res Brain Res Rev, 2003. 42(2): p. 97-122.
Hickey, W.F., B.L. Hsu, and H. Kimura, T-lymphocyte entry into the central nervous system. J Neurosci Res, 1991. 28(2): p. 254-60).
Abou-Ghazal, M., et al., The incidence, correlation with tumor-infiltrating inflammation, and prognosis of phosphorylated STAT3 expression in human gliomas. Clin Cancer Res, 2008. 14(24): p. 8228-35.
Buckanovich, R.J., et al., Endothelin B receptor mediates the endothelial barrier to T cell homing to tumors and disables immune therapy. Nat Med, 2008. 14(1): p. 28-36.
Mittelbronn, M., et al., Elevated HLA-E levels in human glioblastomas but not in grade I to III astrocytomas correlate with infiltrating CD8+ cells. J Neuroimmunol, 2007. 189(1-2): p. 50-8.
Perrin, G., et al., Astrocytoma infiltrating lymphocytes include major T cell clonal expansions confined to the CD8 subset. Int Immunol, 1999. 11(8): p. 1337-50.
Bucciero, A., et al., Prognostic significance of lymphoid infiltration in cerebral malignant gliomas. J Neurosurg Sci, 1990. 34(2): p. 145-8.
Tang, J., et al., Glioblastoma patients exhibit circulating tumor-specific CD8+ T cells. Clin Cancer Res, 2005. 11(14): p. 5292-9.
Maus, M.V., et al., Antibody-modified T cells: CARs take the front seat for hematologic malignancies. Blood, 2014. 123(17): p. 2625-35.
Non-Final Office Action issued in U.S. Appl. No. 17/558,906 dated Dec. 28, 2023.
Schutze-Redelmeier et al. (2003). Antennapedia transduction sequence promotes anti tumor immunity to epicutaneously administered CTL epitopes. Vaccine, 22:1985-1991.
Witkowski et al. (1999). Conversion of B-Ketoacyl Synthase to a Malonyl Decarboxylase by Replacement of the Active-Site Cysteine with Glutamine. Biochemistry, 38:11643-11650.
Seffernick et al. (2001). Melamine Deaminase and Atrazine Chlorohydrolase: 98 Percent Identical but Functionally Different. Bacterial. 183(8): 2405-2410.
Non-Final Office Action from U.S. Appl. No. 17/501,155 dated Mar. 1, 2024.
Sahdev et al. (2014). Biomaterials for nanoparticle vaccine delivery systems, 31(10): 2563-82.
Non-Final Office Action from U.S. Appl. No. 17/718,975 dated Apr. 10, 2024.
Wikipedia Webpage (2015). Toll-like receptor. Retrieved from https://en.wikipedia.org/w/index.php?title=Toll-like_receptor&oldid=649029932.

```
                         SEQUENCE LISTING

<160> NUMBER OF SEQ ID NOS: 70

<210> SEQ ID NO 1
<211> LENGTH: 16
<212> TYPE: PRT
<213> ORGANISM: Artificial Sequence
<220> FEATURE:
<223> OTHER INFORMATION: CPP: Penetratin

<400> SEQUENCE: 1

Arg Gln Ile Lys Ile Tyr Phe Gln Asn Arg Arg Met Lys Trp Lys Lys
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: CPP: TAT minimal domain

<400> SEQUENCE: 2

Tyr Gly Arg Lys Lys Arg Arg Gln Arg Arg
1               5                   10

<210> SEQ ID NO 3
<211> LENGTH: 245
<212> TYPE: PRT
<213> ORGANISM: Artificial Sequence
<220> FEATURE:
<223> OTHER INFORMATION: ZEBRA amino acid sequence (natural sequence
      from Epstein - Barr virus (EBV)) (YP_401673)

<400> SEQUENCE: 3

Met Met Asp Pro Asn Ser Thr Ser Glu Asp Val Lys Phe Thr Pro Asp
1               5                   10                  15

Pro Tyr Gln Val Pro Phe Val Gln Ala Phe Asp Gln Ala Thr Arg Val
                20                  25                  30

Tyr Gln Asp Leu Gly Gly Pro Ser Gln Ala Pro Leu Pro Cys Val Leu
            35                  40                  45

Trp Pro Val Leu Pro Glu Pro Leu Pro Gln Gly Gln Leu Thr Ala Tyr
        50                  55                  60

His Val Ser Thr Ala Pro Thr Gly Ser Trp Phe Ser Ala Pro Gln Pro
65                  70                  75                  80

Ala Pro Glu Asn Ala Tyr Gln Ala Tyr Ala Ala Pro Gln Leu Phe Pro
                85                  90                  95

Val Ser Asp Ile Thr Gln Asn Gln Gln Thr Asn Gln Ala Gly Gly Glu
            100                 105                 110

Ala Pro Gln Pro Gly Asp Asn Ser Thr Val Gln Thr Ala Ala Ala Val
```

```
                    115                 120                 125
Val Phe Ala Cys Pro Gly Ala Asn Gln Gly Gln Gln Leu Ala Asp Ile
    130                 135                 140

Gly Val Pro Gln Pro Ala Pro Val Ala Ala Pro Ala Arg Arg Thr Arg
145                 150                 155                 160

Lys Pro Gln Gln Pro Glu Ser Leu Glu Glu Cys Asp Ser Glu Leu Glu
                165                 170                 175

Ile Lys Arg Tyr Lys Asn Arg Val Ala Ser Arg Lys Cys Arg Ala Lys
            180                 185                 190

Phe Lys Gln Leu Leu Gln His Tyr Arg Glu Val Ala Ala Ala Lys Ser
        195                 200                 205

Ser Glu Asn Asp Arg Leu Arg Leu Leu Lys Gln Met Cys Pro Ser
    210                 215                 220

Leu Asp Val Asp Ser Ile Ile Pro Arg Thr Pro Asp Val Leu His Glu
225                 230                 235                 240

Asp Leu Leu Asn Phe
                245

<210> SEQ ID NO 4
<211> LENGTH: 45
<212> TYPE: PRT
<213> ORGANISM: Artificial Sequence
<220> FEATURE:
<223> OTHER INFORMATION: CPP1 (Z11)

<400> SEQUENCE: 4

Lys Arg Tyr Lys Asn Arg Val Ala Ser Arg Lys Cys Arg Ala Lys Phe
1               5                   10                  15

Lys Gln Leu Leu Gln His Tyr Arg Glu Val Ala Ala Ala Lys Ser Ser
            20                  25                  30

Glu Asn Asp Arg Leu Arg Leu Leu Lys Gln Met Cys
        35                  40                  45

<210> SEQ ID NO 5
<211> LENGTH: 42
<212> TYPE: PRT
<213> ORGANISM: Artificial Sequence
<220> FEATURE:
<223> OTHER INFORMATION: CPP2 (Z12)

<400> SEQUENCE: 5

Lys Arg Tyr Lys Asn Arg Val Ala Ser Arg Lys Cys Arg Ala Lys Phe
1               5                   10                  15

Lys Gln Leu Leu Gln His Tyr Arg Glu Val Ala Ala Ala Lys Ser Ser
            20                  25                  30

Glu Asn Asp Arg Leu Arg Leu Leu Leu Lys
        35                  40

<210> SEQ ID NO 6
<211> LENGTH: 42
<212> TYPE: PRT
<213> ORGANISM: Artificial Sequence
<220> FEATURE:
<223> OTHER INFORMATION: CPP3 (Z13)

<400> SEQUENCE: 6

Lys Arg Tyr Lys Asn Arg Val Ala Ser Arg Lys Ser Arg Ala Lys Phe
1               5                   10                  15

Lys Gln Leu Leu Gln His Tyr Arg Glu Val Ala Ala Ala Lys Ser Ser
            20                  25                  30
```

```
Glu Asn Asp Arg Leu Arg Leu Leu Leu Lys
        35                  40

<210> SEQ ID NO 7
<211> LENGTH: 30
<212> TYPE: PRT
<213> ORGANISM: Artificial Sequence
<220> FEATURE:
<223> OTHER INFORMATION: CPP4 (Z14)

<400> SEQUENCE: 7

Lys Arg Tyr Lys Asn Arg Val Ala Ser Arg Lys Ser Arg Ala Lys Phe
1               5                   10                  15

Lys Gln Leu Leu Gln His Tyr Arg Glu Val Ala Ala Ala Lys
            20                  25                  30

<210> SEQ ID NO 8
<211> LENGTH: 17
<212> TYPE: PRT
<213> ORGANISM: Artificial Sequence
<220> FEATURE:
<223> OTHER INFORMATION: CPP5 (Z15)

<400> SEQUENCE: 8

Lys Arg Tyr Lys Asn Arg Val Ala Ser Arg Lys Ser Arg Ala Lys Phe
1               5                   10                  15

Lys

<210> SEQ ID NO 9
<211> LENGTH: 15
<212> TYPE: PRT
<213> ORGANISM: Artificial Sequence
<220> FEATURE:
<223> OTHER INFORMATION: CPP6 (Z16)

<400> SEQUENCE: 9

Gln His Tyr Arg Glu Val Ala Ala Ala Lys Ser Ser Glu Asn Asp
1               5                   10                  15

<210> SEQ ID NO 10
<211> LENGTH: 13
<212> TYPE: PRT
<213> ORGANISM: Artificial Sequence
<220> FEATURE:
<223> OTHER INFORMATION: CPP7 (Z17)

<400> SEQUENCE: 10

Gln Leu Leu Gln His Tyr Arg Glu Val Ala Ala Ala Lys
1               5                   10

<210> SEQ ID NO 11
<211> LENGTH: 19
<212> TYPE: PRT
<213> ORGANISM: Artificial Sequence
<220> FEATURE:
<223> OTHER INFORMATION: CPP8 (Z18)

<400> SEQUENCE: 11

Arg Glu Val Ala Ala Ala Lys Ser Ser Glu Asn Asp Arg Leu Arg Leu
1               5                   10                  15

Leu Leu Lys

<210> SEQ ID NO 12
<211> LENGTH: 8
```

```
<212> TYPE: PRT
<213> ORGANISM: Artificial Sequence
<220> FEATURE:
<223> OTHER INFORMATION: CPP9 (Z19)

<400> SEQUENCE: 12

Lys Arg Tyr Lys Asn Arg Val Ala
1               5

<210> SEQ ID NO 13
<211> LENGTH: 11
<212> TYPE: PRT
<213> ORGANISM: Artificial Sequence
<220> FEATURE:
<223> OTHER INFORMATION: CPP10 (Z20)

<400> SEQUENCE: 13

Val Ala Ser Arg Lys Ser Arg Ala Lys Phe Lys
1               5                   10

<210> SEQ ID NO 14
<211> LENGTH: 85
<212> TYPE: PRT
<213> ORGANISM: Artificial Sequence
<220> FEATURE:
<223> OTHER INFORMATION: MAD5 cargo

<400> SEQUENCE: 14

Glu Ser Leu Lys Ile Ser Gln Ala Val His Ala Ala His Ala Glu Ile
1               5                   10                  15

Asn Glu Ala Gly Arg Glu Val Val Gly Val Gly Ala Leu Lys Val Pro
            20                  25                  30

Arg Asn Gln Asp Trp Leu Gly Val Pro Arg Phe Ala Lys Phe Ala Ser
        35                  40                  45

Phe Glu Ala Gln Gly Ala Leu Ala Asn Ile Ala Val Asp Lys Ala Asn
    50                  55                  60

Leu Asp Val Glu Gln Leu Glu Ser Ile Ile Asn Phe Glu Lys Leu Thr
65                  70                  75                  80

Glu Trp Thr Gly Ser
                85

<210> SEQ ID NO 15
<211> LENGTH: 35
<212> TYPE: PRT
<213> ORGANISM: Artificial Sequence
<220> FEATURE:
<223> OTHER INFORMATION: TLR2 peptide agonist Anaxa

<400> SEQUENCE: 15

Ser Thr Val His Glu Ile Leu Cys Lys Leu Ser Leu Glu Gly Asp His
1               5                   10                  15

Ser Thr Pro Pro Ser Ala Tyr Gly Ser Val Lys Pro Tyr Thr Asn Phe
            20                  25                  30

Asp Ala Glu
        35

<210> SEQ ID NO 16
<211> LENGTH: 4
<212> TYPE: PRT
<213> ORGANISM: Artificial Sequence
<220> FEATURE:
<223> OTHER INFORMATION: enterokinase target site

<400> SEQUENCE: 16
```

```
Asp Asp Asp Lys
1

<210> SEQ ID NO 17
<211> LENGTH: 5
<212> TYPE: PRT
<213> ORGANISM: Artificial Sequence
<220> FEATURE:
<223> OTHER INFORMATION: factor Xa target site

<400> SEQUENCE: 17

Ile Glu Asp Gly Arg
1               5

<210> SEQ ID NO 18
<211> LENGTH: 6
<212> TYPE: PRT
<213> ORGANISM: Artificial Sequence
<220> FEATURE:
<223> OTHER INFORMATION: thrombin target site

<400> SEQUENCE: 18

Leu Val Pro Arg Gly Ser
1               5

<210> SEQ ID NO 19
<211> LENGTH: 7
<212> TYPE: PRT
<213> ORGANISM: Artificial Sequence
<220> FEATURE:
<223> OTHER INFORMATION: protease TEV target site

<400> SEQUENCE: 19

Glu Asn Leu Tyr Phe Gln Gly
1               5

<210> SEQ ID NO 20
<211> LENGTH: 8
<212> TYPE: PRT
<213> ORGANISM: Artificial Sequence
<220> FEATURE:
<223> OTHER INFORMATION: PreScission protease target site

<400> SEQUENCE: 20

Leu Glu Val Leu Phe Gln Gly Pro
1               5

<210> SEQ ID NO 21
<211> LENGTH: 4
<212> TYPE: PRT
<213> ORGANISM: Artificial Sequence
<220> FEATURE:
<223> OTHER INFORMATION: furin target site
<220> FEATURE:
<221> NAME/KEY: MISC_FEATURE
<222> LOCATION: (2)..(2)
<223> OTHER INFORMATION: X may be any amino acid
<220> FEATURE:
<221> NAME/KEY: MISC_FEATURE
<222> LOCATION: (3)..(3)
<223> OTHER INFORMATION: X is R or K

<400> SEQUENCE: 21

Arg Xaa Xaa Arg
1

<210> SEQ ID NO 22
```

-continued

```
<211> LENGTH: 5
<212> TYPE: PRT
<213> ORGANISM: Artificial Sequence
<220> FEATURE:
<223> OTHER INFORMATION: peptidic linker

<400> SEQUENCE: 22

Gly Gly Gly Gly Gly
1               5

<210> SEQ ID NO 23
<211> LENGTH: 4
<212> TYPE: PRT
<213> ORGANISM: Artificial Sequence
<220> FEATURE:
<223> OTHER INFORMATION: peptidic linker

<400> SEQUENCE: 23

Gly Gly Gly Gly
1

<210> SEQ ID NO 24
<211> LENGTH: 4
<212> TYPE: PRT
<213> ORGANISM: Artificial Sequence
<220> FEATURE:
<223> OTHER INFORMATION: peptidic linker

<400> SEQUENCE: 24

Glu Gln Leu Glu
1

<210> SEQ ID NO 25
<211> LENGTH: 4
<212> TYPE: PRT
<213> ORGANISM: Artificial Sequence
<220> FEATURE:
<223> OTHER INFORMATION: peptidic linker

<400> SEQUENCE: 25

Thr Glu Trp Thr
1

<210> SEQ ID NO 26
<211> LENGTH: 224
<212> TYPE: PRT
<213> ORGANISM: Artificial Sequence
<220> FEATURE:
<223> OTHER INFORMATION: EDAZ13Mad5

<400> SEQUENCE: 26

Met His His His His His Asn Ile Asp Arg Pro Lys Gly Leu Ala
1               5                   10                  15

Phe Thr Asp Val Asp Val Asp Ser Ile Lys Ile Ala Trp Glu Ser Pro
                20                  25                  30

Gln Gly Gln Val Ser Arg Tyr Arg Val Thr Tyr Ser Ser Pro Glu Asp
            35                  40                  45

Gly Ile Arg Glu Leu Phe Pro Ala Pro Asp Gly Glu Asp Asp Thr Ala
        50                  55                  60

Glu Leu Gln Gly Leu Arg Pro Gly Ser Glu Tyr Thr Val Ser Val Val
65                  70                  75                  80

Ala Leu His Asp Asp Met Glu Ser Gln Pro Leu Ile Gly Ile Gln Ser
                85                  90                  95

Thr Lys Arg Tyr Lys Asn Arg Val Ala Ser Arg Lys Ser Arg Ala Lys
```

```
                100             105             110
Phe Lys Gln Leu Leu Gln His Tyr Arg Glu Val Ala Ala Lys Ser
            115             120             125

Ser Glu Asn Asp Arg Leu Arg Leu Leu Lys Glu Ser Leu Lys Ile
130             135             140

Ser Gln Ala Val His Ala Ala His Ala Glu Ile Asn Glu Ala Gly Arg
145             150             155             160

Glu Val Val Gly Val Gly Ala Leu Lys Val Pro Arg Asn Gln Asp Trp
                165             170             175

Leu Gly Val Pro Arg Phe Ala Lys Phe Ala Ser Phe Glu Ala Gln Gly
            180             185             190

Ala Leu Ala Asn Ile Ala Val Asp Lys Ala Asn Leu Asp Val Glu Gln
            195             200             205

Leu Glu Ser Ile Ile Asn Phe Glu Lys Leu Thr Glu Trp Thr Gly Ser
            210             215             220

<210> SEQ ID NO 27
<211> LENGTH: 169
<212> TYPE: PRT
<213> ORGANISM: Artificial Sequence
<220> FEATURE:
<223> OTHER INFORMATION: AnaxaZ13Mad5

<400> SEQUENCE: 27

Met His His His His His Ser Thr Val His Glu Ile Leu Cys Lys
1               5               10              15

Leu Ser Leu Glu Gly Asp His Ser Thr Pro Pro Ser Ala Tyr Gly Ser
            20              25              30

Val Lys Pro Tyr Thr Asn Phe Asp Ala Glu Lys Arg Tyr Lys Asn Arg
        35              40              45

Val Ala Ser Arg Lys Ser Arg Ala Lys Phe Lys Gln Leu Leu Gln His
    50              55              60

Tyr Arg Glu Val Ala Ala Ala Lys Ser Ser Glu Asn Asp Arg Leu Arg
65              70              75              80

Leu Leu Lys Glu Ser Leu Lys Ile Ser Gln Ala Val His Ala Ala
            85              90              95

His Ala Glu Ile Asn Glu Ala Gly Arg Glu Val Val Gly Val Gly Ala
            100             105             110

Leu Lys Val Pro Arg Asn Gln Asp Trp Leu Gly Val Pro Arg Phe Ala
        115             120             125

Lys Phe Ala Ser Phe Glu Ala Gln Gly Ala Leu Ala Asn Ile Ala Val
    130             135             140

Asp Lys Ala Asn Leu Asp Val Glu Gln Leu Glu Ser Ile Ile Asn Phe
145             150             155             160

Glu Lys Leu Thr Glu Trp Thr Gly Ser
                165

<210> SEQ ID NO 28
<211> LENGTH: 169
<212> TYPE: PRT
<213> ORGANISM: Artificial Sequence
<220> FEATURE:
<223> OTHER INFORMATION: Z13Mad5Anaxa

<400> SEQUENCE: 28

Met His His His His His Lys Arg Tyr Lys Asn Arg Val Ala Ser
1               5               10              15
```

```
Arg Lys Ser Arg Ala Lys Phe Lys Gln Leu Leu Gln His Tyr Arg Glu
            20                  25                  30

Val Ala Ala Ala Lys Ser Ser Glu Asn Asp Arg Leu Arg Leu Leu Leu
        35                  40                  45

Lys Glu Ser Leu Lys Ile Ser Gln Ala Val His Ala Ala His Ala Glu
 50                  55                  60

Ile Asn Glu Ala Gly Arg Glu Val Val Gly Val Gly Ala Leu Lys Val
 65                  70                  75                  80

Pro Arg Asn Gln Asp Trp Leu Gly Val Pro Arg Phe Ala Lys Phe Ala
                85                  90                  95

Ser Phe Glu Ala Gln Gly Ala Leu Ala Asn Ile Ala Val Asp Lys Ala
            100                 105                 110

Asn Leu Asp Val Glu Gln Leu Glu Ser Ile Ile Asn Phe Glu Lys Leu
            115                 120                 125

Thr Glu Trp Thr Gly Ser Ser Thr Val His Glu Ile Leu Cys Lys Leu
130                 135                 140

Ser Leu Glu Gly Asp His Ser Thr Pro Pro Ser Ala Tyr Gly Ser Val
145                 150                 155                 160

Lys Pro Tyr Thr Asn Phe Asp Ala Glu
                165
```

<210> SEQ ID NO 29
<211> LENGTH: 134
<212> TYPE: PRT
<213> ORGANISM: Artificial Sequence
<220> FEATURE:
<223> OTHER INFORMATION: Z13Mad5

<400> SEQUENCE: 29

```
Met His His His His His His Lys Arg Tyr Lys Asn Arg Val Ala Ser
 1               5                  10                  15

Arg Lys Ser Arg Ala Lys Phe Lys Gln Leu Leu Gln His Tyr Arg Glu
            20                  25                  30

Val Ala Ala Ala Lys Ser Ser Glu Asn Asp Arg Leu Arg Leu Leu Leu
        35                  40                  45

Lys Glu Ser Leu Lys Ile Ser Gln Ala Val His Ala Ala His Ala Glu
 50                  55                  60

Ile Asn Glu Ala Gly Arg Glu Val Val Gly Val Gly Ala Leu Lys Val
 65                  70                  75                  80

Pro Arg Asn Gln Asp Trp Leu Gly Val Pro Arg Phe Ala Lys Phe Ala
                85                  90                  95

Ser Phe Glu Ala Gln Gly Ala Leu Ala Asn Ile Ala Val Asp Lys Ala
            100                 105                 110

Asn Leu Asp Val Glu Gln Leu Glu Ser Ile Ile Asn Phe Glu Lys Leu
            115                 120                 125

Thr Glu Trp Thr Gly Ser
130
```

<210> SEQ ID NO 30
<211> LENGTH: 92
<212> TYPE: PRT
<213> ORGANISM: Artificial Sequence
<220> FEATURE:
<223> OTHER INFORMATION: Mad5

<400> SEQUENCE: 30

```
Met His His His His His His Glu Ser Leu Lys Ile Ser Gln Ala Val
 1               5                  10                  15
```

His Ala Ala His Ala Glu Ile Asn Glu Ala Gly Arg Glu Val Val Gly
            20                  25                  30

Val Gly Ala Leu Lys Val Pro Arg Asn Gln Asp Trp Leu Gly Val Pro
        35                  40                  45

Arg Phe Ala Lys Phe Ala Ser Phe Glu Ala Gln Gly Ala Leu Ala Asn
50                  55                  60

Ile Ala Val Asp Lys Ala Asn Leu Asp Val Glu Gln Leu Glu Ser Ile
65                  70                  75                  80

Ile Asn Phe Glu Lys Leu Thr Glu Trp Thr Gly Ser
                85                  90

<210> SEQ ID NO 31
<211> LENGTH: 182
<212> TYPE: PRT
<213> ORGANISM: Artificial Sequence
<220> FEATURE:
<223> OTHER INFORMATION: EdaMad5

<400> SEQUENCE: 31

Met His His His His His Asn Ile Asp Arg Pro Lys Gly Leu Ala
1               5                   10                  15

Phe Thr Asp Val Asp Val Asp Ser Ile Lys Ile Ala Trp Glu Ser Pro
            20                  25                  30

Gln Gly Gln Val Ser Arg Tyr Arg Val Thr Tyr Ser Ser Pro Glu Asp
        35                  40                  45

Gly Ile Arg Glu Leu Phe Pro Ala Pro Asp Gly Glu Asp Asp Thr Ala
50                  55                  60

Glu Leu Gln Gly Leu Arg Pro Gly Ser Glu Tyr Thr Val Ser Val Val
65                  70                  75                  80

Ala Leu His Asp Asp Met Glu Ser Gln Pro Leu Ile Gly Ile Gln Ser
                85                  90                  95

Thr Glu Ser Leu Lys Ile Ser Gln Ala Val His Ala Ala His Ala Glu
            100                 105                 110

Ile Asn Glu Ala Gly Arg Glu Val Val Gly Val Gly Ala Leu Lys Val
        115                 120                 125

Pro Arg Asn Gln Asp Trp Leu Gly Val Pro Arg Phe Ala Lys Phe Ala
130                 135                 140

Ser Phe Glu Ala Gln Gly Ala Leu Ala Asn Ile Ala Val Asp Lys Ala
145                 150                 155                 160

Asn Leu Asp Val Glu Gln Leu Glu Ser Ile Ile Asn Phe Glu Lys Leu
                165                 170                 175

Thr Glu Trp Thr Gly Ser
            180

<210> SEQ ID NO 32
<211> LENGTH: 127
<212> TYPE: PRT
<213> ORGANISM: Artificial Sequence
<220> FEATURE:
<223> OTHER INFORMATION: Mad5Anaxa

<400> SEQUENCE: 32

Met His His His His His Glu Ser Leu Lys Ile Ser Gln Ala Val
1               5                   10                  15

His Ala Ala His Ala Glu Ile Asn Glu Ala Gly Arg Glu Val Val Gly
            20                  25                  30

Val Gly Ala Leu Lys Val Pro Arg Asn Gln Asp Trp Leu Gly Val Pro

```
                35                  40                  45
Arg Phe Ala Lys Phe Ala Ser Phe Glu Ala Gln Gly Ala Leu Ala Asn
        50                  55                  60

Ile Ala Val Asp Lys Ala Asn Leu Asp Val Glu Gln Leu Glu Ser Ile
65                  70                  75                  80

Ile Asn Phe Glu Lys Leu Thr Glu Trp Thr Gly Ser Ser Thr Val His
                85                  90                  95

Glu Ile Leu Cys Lys Leu Ser Leu Glu Gly Asp His Ser Thr Pro Pro
            100                 105                 110

Ser Ala Tyr Gly Ser Val Lys Pro Tyr Thr Asn Phe Asp Ala Glu
            115                 120                 125

<210> SEQ ID NO 33
<211> LENGTH: 157
<212> TYPE: PRT
<213> ORGANISM: Artificial Sequence
<220> FEATURE:
<223> OTHER INFORMATION: Z14Mad5Anaxa

<400> SEQUENCE: 33

Met His His His His His His Lys Arg Tyr Lys Asn Arg Val Ala Ser
1               5                   10                  15

Arg Lys Ser Arg Ala Lys Phe Lys Gln Leu Leu Gln His Tyr Arg Glu
            20                  25                  30

Val Ala Ala Ala Lys Glu Ser Leu Lys Ile Ser Gln Ala Val His Ala
        35                  40                  45

Ala His Ala Glu Ile Asn Glu Ala Gly Arg Glu Val Val Gly Val Gly
    50                  55                  60

Ala Leu Lys Val Pro Arg Asn Gln Asp Trp Leu Gly Val Pro Arg Phe
65                  70                  75                  80

Ala Lys Phe Ala Ser Phe Glu Ala Gln Gly Ala Leu Ala Asn Ile Ala
                85                  90                  95

Val Asp Lys Ala Asn Leu Asp Val Glu Gln Leu Glu Ser Ile Ile Asn
            100                 105                 110

Phe Glu Lys Leu Thr Glu Trp Thr Gly Ser Ser Thr Val His Glu Ile
        115                 120                 125

Leu Cys Lys Leu Ser Leu Glu Gly Asp His Ser Thr Pro Pro Ser Ala
    130                 135                 140

Tyr Gly Ser Val Lys Pro Tyr Thr Asn Phe Asp Ala Glu
145                 150                 155

<210> SEQ ID NO 34
<211> LENGTH: 146
<212> TYPE: PRT
<213> ORGANISM: Artificial Sequence
<220> FEATURE:
<223> OTHER INFORMATION: Z18Mad5Anaxa

<400> SEQUENCE: 34

Met His His His His His His Arg Glu Val Ala Ala Ala Lys Ser Ser
1               5                   10                  15

Glu Asn Asp Arg Leu Arg Leu Leu Lys Glu Ser Leu Lys Ile Ser
            20                  25                  30

Gln Ala Val His Ala Ala His Ala Glu Ile Asn Glu Ala Gly Arg Glu
        35                  40                  45

Val Val Gly Val Gly Ala Leu Lys Val Pro Arg Asn Gln Asp Trp Leu
    50                  55                  60
```

```
Gly Val Pro Arg Phe Ala Lys Phe Ala Ser Phe Glu Ala Gln Gly Ala
 65                  70                  75                  80

Leu Ala Asn Ile Ala Val Asp Lys Ala Asn Leu Asp Val Glu Gln Leu
                 85                  90                  95

Glu Ser Ile Ile Asn Phe Glu Lys Leu Thr Glu Trp Thr Gly Ser Ser
            100                 105                 110

Thr Val His Glu Ile Leu Cys Lys Leu Ser Leu Glu Gly Asp His Ser
        115                 120                 125

Thr Pro Pro Ser Ala Tyr Gly Ser Val Lys Pro Tyr Thr Asn Phe Asp
    130                 135                 140

Ala Glu
145

<210> SEQ ID NO 35
<211> LENGTH: 8
<212> TYPE: PRT
<213> ORGANISM: Artificial Sequence
<220> FEATURE:
<223> OTHER INFORMATION: SIINFEKL OVACD8

<400> SEQUENCE: 35

Ser Ile Ile Asn Phe Glu Lys Leu
1               5

<210> SEQ ID NO 36
<211> LENGTH: 17
<212> TYPE: PRT
<213> ORGANISM: Artificial Sequence
<220> FEATURE:
<223> OTHER INFORMATION: OVACD4 peptide

<400> SEQUENCE: 36

Ile Ser Gln Ala Val His Ala Ala His Ala Glu Ile Asn Glu Ala Gly
1               5                   10                  15

Arg

<210> SEQ ID NO 37
<211> LENGTH: 212
<212> TYPE: PRT
<213> ORGANISM: Artificial Sequence
<220> FEATURE:
<223> OTHER INFORMATION: EDAZ14Mad5

<400> SEQUENCE: 37

Met His His His His His Asn Ile Asp Arg Pro Lys Gly Leu Ala
1               5                   10                  15

Phe Thr Asp Val Asp Val Asp Ser Ile Lys Ile Ala Trp Glu Ser Pro
                20                  25                  30

Gln Gly Gln Val Ser Arg Tyr Arg Val Thr Tyr Ser Ser Pro Glu Asp
            35                  40                  45

Gly Ile Arg Glu Leu Phe Pro Ala Pro Asp Gly Glu Asp Asp Thr Ala
        50                  55                  60

Glu Leu Gln Gly Leu Arg Pro Gly Ser Glu Tyr Thr Val Ser Val Val
 65                  70                  75                  80

Ala Leu His Asp Asp Met Glu Ser Gln Pro Leu Ile Gly Ile Gln Ser
                 85                  90                  95

Thr Lys Arg Tyr Lys Asn Arg Val Ala Ser Arg Lys Ser Arg Ala Lys
            100                 105                 110

Phe Lys Gln Leu Leu Gln His Tyr Arg Glu Val Ala Ala Ala Lys Glu
        115                 120                 125
```

```
Ser Leu Lys Ile Ser Gln Ala Val His Ala Ala His Ala Glu Ile Asn
        130                 135                 140

Glu Ala Gly Arg Glu Val Gly Val Gly Ala Leu Lys Val Pro Arg
145                 150                 155                 160

Asn Gln Asp Trp Leu Gly Val Pro Arg Phe Ala Lys Phe Ala Ser Phe
                165                 170                 175

Glu Ala Gln Gly Ala Leu Ala Asn Ile Ala Val Asp Lys Ala Asn Leu
            180                 185                 190

Asp Val Glu Gln Leu Glu Ser Ile Ile Asn Phe Glu Lys Leu Thr Glu
        195                 200                 205

Trp Thr Gly Ser
        210

<210> SEQ ID NO 38
<211> LENGTH: 201
<212> TYPE: PRT
<213> ORGANISM: Artificial Sequence
<220> FEATURE:
<223> OTHER INFORMATION: EDAZ18Mad5

<400> SEQUENCE: 38

Met His His His His His Asn Ile Asp Arg Pro Lys Gly Leu Ala
1               5                   10                  15

Phe Thr Asp Val Asp Val Asp Ser Ile Lys Ile Ala Trp Glu Ser Pro
                20                  25                  30

Gln Gly Gln Val Ser Arg Tyr Arg Val Thr Tyr Ser Ser Pro Glu Asp
            35                  40                  45

Gly Ile Arg Glu Leu Phe Pro Ala Pro Asp Gly Glu Asp Asp Thr Ala
50                  55                  60

Glu Leu Gln Gly Leu Arg Pro Gly Ser Glu Tyr Thr Val Ser Val Val
65                  70                  75                  80

Ala Leu His Asp Asp Met Glu Ser Gln Pro Leu Ile Gly Ile Gln Ser
                85                  90                  95

Thr Arg Glu Val Ala Ala Ala Lys Ser Ser Glu Asn Asp Arg Leu Arg
                100                 105                 110

Leu Leu Leu Lys Glu Ser Leu Lys Ile Ser Gln Ala Val His Ala Ala
            115                 120                 125

His Ala Glu Ile Asn Glu Ala Gly Arg Glu Val Gly Val Gly Ala
        130                 135                 140

Leu Lys Val Pro Arg Asn Gln Asp Trp Leu Gly Val Pro Arg Phe Ala
145                 150                 155                 160

Lys Phe Ala Ser Phe Glu Ala Gln Gly Ala Leu Ala Asn Ile Ala Val
                165                 170                 175

Asp Lys Ala Asn Leu Asp Val Glu Gln Leu Glu Ser Ile Ile Asn Phe
            180                 185                 190

Glu Lys Leu Thr Glu Trp Thr Gly Ser
        195                 200

<210> SEQ ID NO 39
<211> LENGTH: 116
<212> TYPE: PRT
<213> ORGANISM: Artificial Sequence
<220> FEATURE:
<223> OTHER INFORMATION: Z13Mad8Anaxa

<400> SEQUENCE: 39

Lys Arg Tyr Lys Asn Arg Val Ala Ser Arg Lys Ser Arg Ala Lys Phe
```

```
              1               5                  10                 15
Lys Gln Leu Leu Gln His Tyr Arg Glu Val Ala Ala Ala Lys Ser Ser
                20                  25                  30

Glu Asn Asp Arg Leu Arg Leu Leu Lys Val Thr Tyr His Ser Pro
                35                  40                  45

Ser Tyr Ala Tyr His Gln Phe Glu Arg Arg Ala Ile Leu Asn Arg Leu
            50                  55                  60

Val Gln Phe Ile Lys Asp Arg Ile Ser Val Gln Ala Leu Val Leu
65                  70                  75                  80

Thr Ser Thr Val His Glu Ile Leu Cys Lys Leu Ser Leu Glu Gly Asp
                85                  90                  95

His Ser Thr Pro Pro Ser Ala Tyr Gly Ser Val Lys Pro Tyr Thr Asn
                100                 105                 110

Phe Asp Ala Glu
        115

<210> SEQ ID NO 40
<211> LENGTH: 110
<212> TYPE: PRT
<213> ORGANISM: Artificial Sequence
<220> FEATURE:
<223> OTHER INFORMATION: Z13Mad11Anaxa

<400> SEQUENCE: 40

Lys Arg Tyr Lys Asn Arg Val Ala Ser Arg Lys Ser Arg Ala Lys Phe
1               5                   10                  15

Lys Gln Leu Leu Gln His Tyr Arg Glu Val Ala Ala Ala Lys Ser Ser
                20                  25                  30

Glu Asn Asp Arg Leu Arg Leu Leu Lys Asn Tyr Arg Ile Ala Thr
                35                  40                  45

Phe Lys Asn Trp Pro Phe Leu Glu Asp Cys Ala Met Glu Glu Leu Thr
            50                  55                  60

Val Ser Glu Phe Leu Lys Leu Asp Arg Gln Arg Ser Thr Val His Glu
65                  70                  75                  80

Ile Leu Cys Lys Leu Ser Leu Glu Gly Asp His Ser Thr Pro Pro Ser
                85                  90                  95

Ala Tyr Gly Ser Val Lys Pro Tyr Thr Asn Phe Asp Ala Glu
                100                 105                 110

<210> SEQ ID NO 41
<211> LENGTH: 94
<212> TYPE: PRT
<213> ORGANISM: Artificial Sequence
<220> FEATURE:
<223> OTHER INFORMATION: Z13Mad9Anaxa

<400> SEQUENCE: 41

Lys Arg Tyr Lys Asn Arg Val Ala Ser Arg Lys Ser Arg Ala Lys Phe
1               5                   10                  15

Lys Gln Leu Leu Gln His Tyr Arg Glu Val Ala Ala Ala Lys Ser Ser
                20                  25                  30

Glu Asn Asp Arg Leu Arg Leu Leu Lys His Leu Glu Leu Ala Ser
                35                  40                  45

Met Thr Asn Met Glu Leu Met Ser Ser Ile Val Ser Thr Val His Glu
            50                  55                  60

Ile Leu Cys Lys Leu Ser Leu Glu Gly Asp His Ser Thr Pro Pro Ser
65                  70                  75                  80
```

Ala Tyr Gly Ser Val Lys Pro Tyr Thr Asn Phe Asp Ala Glu
            85                  90

<210> SEQ ID NO 42
<211> LENGTH: 17
<212> TYPE: PRT
<213> ORGANISM: Artificial Sequence
<220> FEATURE:
<223> OTHER INFORMATION: Mad9

<400> SEQUENCE: 42

His Leu Glu Leu Ala Ser Met Thr Asn Met Glu Leu Met Ser Ser Ile
1               5                   10                  15

Val

<210> SEQ ID NO 43
<211> LENGTH: 20
<212> TYPE: PRT
<213> ORGANISM: Artificial Sequence
<220> FEATURE:
<223> OTHER INFORMATION: Mad8

<400> SEQUENCE: 43

Val Thr Tyr His Ser Pro Ser Tyr Ala Tyr His Gln Phe Glu Arg Arg
1               5                   10                  15

Ala Ile Leu Asn
            20

<210> SEQ ID NO 44
<211> LENGTH: 33
<212> TYPE: PRT
<213> ORGANISM: Artificial Sequence
<220> FEATURE:
<223> OTHER INFORMATION: Mad11

<400> SEQUENCE: 44

Asn Tyr Arg Ile Ala Thr Phe Lys Asn Trp Pro Phe Leu Glu Asp Cys
1               5                   10                  15

Ala Met Glu Glu Leu Thr Val Ser Glu Phe Leu Lys Leu Asp Arg Gln
            20                  25                  30

Arg

<210> SEQ ID NO 45
<211> LENGTH: 90
<212> TYPE: PRT
<213> ORGANISM: Artificial Sequence
<220> FEATURE:
<223> OTHER INFORMATION: EDA

<400> SEQUENCE: 45

Asn Ile Asp Arg Pro Lys Gly Leu Ala Phe Thr Asp Val Asp Val Asp
1               5                   10                  15

Ser Ile Lys Ile Ala Trp Glu Ser Pro Gln Gly Gln Val Ser Arg Tyr
            20                  25                  30

Arg Val Thr Tyr Ser Ser Pro Glu Asp Gly Ile Arg Glu Leu Phe Pro
        35                  40                  45

Ala Pro Asp Gly Glu Asp Asp Thr Ala Glu Leu Gln Gly Leu Arg Pro
    50                  55                  60

Gly Ser Glu Tyr Thr Val Ser Val Val Ala Leu His Asp Asp Met Glu
65                  70                  75                  80

Ser Gln Pro Leu Ile Gly Ile Gln Ser Thr
            85                  90

<210> SEQ ID NO 46
<211> LENGTH: 115
<212> TYPE: PRT
<213> ORGANISM: Artificial Sequence
<220> FEATURE:
<223> OTHER INFORMATION: TatFMad5Anaxa

<400> SEQUENCE: 46

Arg Lys Lys Arg Arg Gln Arg Arg Arg Val Lys Arg Ile Ser Gln
1               5                   10                  15

Ala Val His Ala Ala His Ala Glu Ile Asn Glu Ala Gly Arg Arg Val
                20                  25                  30

Lys Arg Lys Val Pro Arg Asn Gln Asp Trp Leu Arg Val Lys Arg Ala
            35                  40                  45

Ser Phe Glu Ala Gln Gly Ala Leu Ala Asn Ile Ala Val Asp Lys Ala
    50                  55                  60

Arg Val Lys Arg Ser Ile Ile Asn Phe Glu Lys Leu Arg Val Lys Arg
65                  70                  75                  80

Ser Thr Val His Glu Ile Leu Cys Lys Leu Ser Leu Glu Gly Asp His
                85                  90                  95

Ser Thr Pro Pro Ser Ala Tyr Gly Ser Val Lys Pro Tyr Thr Asn Phe
            100                 105                 110

Asp Ala Glu
        115

<210> SEQ ID NO 47
<211> LENGTH: 314
<212> TYPE: PRT
<213> ORGANISM: Artificial Sequence
<220> FEATURE:
<223> OTHER INFORMATION: EpCAM

<400> SEQUENCE: 47

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
                20                  25                  30

Lys Leu Ala Val Asn Cys Phe Val Asn Asn Asn Arg Gln Cys Gln Cys
            35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
    115                 120                 125

Lys Asp Thr Glu Ile Thr Cys Ser Glu Arg Val Arg Thr Tyr Trp Ile
    130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr

```
                    180             185             190
Ile Asp Leu Val Gln Asn Ser Ser Gln Lys Thr Gln Asn Asp Val Asp
            195                 200                 205

Ile Ala Asp Val Ala Tyr Tyr Phe Glu Lys Asp Val Lys Gly Glu Ser
            210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
            245                 250                 255

Pro Glu Phe Ser Met Gln Gly Leu Lys Ala Gly Val Ile Ala Val Ile
            260                 265                 270

Val Val Val Val Ile Ala Val Ala Gly Ile Val Val Leu Val Ile
            275                 280                 285

Ser Arg Lys Lys Arg Met Ala Lys Tyr Glu Lys Ala Glu Ile Lys Glu
            290                 295                 300

Met Gly Glu Met His Arg Glu Leu Asn Ala
305                 310

<210> SEQ ID NO 48
<211> LENGTH: 9
<212> TYPE: PRT
<213> ORGANISM: Artificial Sequence
<220> FEATURE:
<223> OTHER INFORMATION: EpCAM epitope

<400> SEQUENCE: 48

Gly Leu Lys Ala Gly Val Ile Ala Val
1               5

<210> SEQ ID NO 49
<211> LENGTH: 1255
<212> TYPE: PRT
<213> ORGANISM: Artificial Sequence
<220> FEATURE:
<223> OTHER INFORMATION: MUC-1

<400> SEQUENCE: 49

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
            85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
        130                 135                 140

Arg Pro Ala Pro Gly Ser Thr Ala Pro Pro Ala His Gly Val Thr Ser
145                 150                 155                 160
```

```
Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
    370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
        435                 440                 445

Gly Ser Thr Ala Pro Pro Ala His Gly Val Thr Ser Ala Pro Asp Thr
    450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
    530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
```

-continued

```
                580                 585                 590
Pro Pro Ala His Gly Val Thr Ser Ala Pro Asp Thr Arg Pro Ala Pro
            595                 600                 605
Gly Ser Thr Ala Pro Ala His Gly Val Thr Ser Ala Pro Asp Thr
        610                 615                 620
Arg Pro Ala Pro Gly Ser Thr Ala Pro Ala His Gly Val Thr Ser
625                 630                 635                 640
Ala Pro Asp Thr Arg Pro Ala Pro Gly Ser Thr Ala Pro Ala His
                645                 650                 655
Gly Val Thr Ser Ala Pro Asp Thr Arg Pro Ala Pro Gly Ser Thr Ala
            660                 665                 670
Pro Pro Ala His Gly Val Thr Ser Ala Pro Asp Thr Arg Pro Ala Pro
        675                 680                 685
Gly Ser Thr Ala Pro Ala His Gly Val Thr Ser Ala Pro Asp Thr
        690                 695                 700
Arg Pro Ala Pro Gly Ser Thr Ala Pro Ala His Gly Val Thr Ser
705                 710                 715                 720
Ala Pro Asp Thr Arg Pro Ala Pro Gly Ser Thr Ala Pro Ala His
                725                 730                 735
Gly Val Thr Ser Ala Pro Asp Thr Arg Pro Ala Pro Gly Ser Thr Ala
            740                 745                 750
Pro Pro Ala His Gly Val Thr Ser Ala Pro Asp Thr Arg Pro Ala Pro
        755                 760                 765
Gly Ser Thr Ala Pro Ala His Gly Val Thr Ser Ala Pro Asp Thr
        770                 775                 780
Arg Pro Ala Pro Gly Ser Thr Ala Pro Ala His Gly Val Thr Ser
785                 790                 795                 800
Ala Pro Asp Thr Arg Pro Ala Pro Gly Ser Thr Ala Pro Ala His
                805                 810                 815
Gly Val Thr Ser Ala Pro Asp Thr Arg Pro Ala Pro Gly Ser Thr Ala
            820                 825                 830
Pro Pro Ala His Gly Val Thr Ser Ala Pro Asp Thr Arg Pro Ala Pro
        835                 840                 845
Gly Ser Thr Ala Pro Ala His Gly Val Thr Ser Ala Pro Asp Thr
        850                 855                 860
Arg Pro Ala Pro Gly Ser Thr Ala Pro Ala His Gly Val Thr Ser
865                 870                 875                 880
Ala Pro Asp Thr Arg Pro Ala Pro Gly Ser Thr Ala Pro Ala His
                885                 890                 895
Gly Val Thr Ser Ala Pro Asp Thr Arg Pro Ala Pro Gly Ser Thr Ala
            900                 905                 910
Pro Pro Ala His Gly Val Thr Ser Ala Pro Asp Thr Arg Pro Ala Pro
        915                 920                 925
Gly Ser Thr Ala Pro Ala His Gly Val Thr Ser Ala Pro Asp Asn
        930                 935                 940
Arg Pro Ala Leu Gly Ser Thr Ala Pro Pro Val His Asn Val Thr Ser
945                 950                 955                 960
Ala Ser Gly Ser Ala Ser Gly Ser Ala Ser Thr Leu Val His Asn Gly
                965                 970                 975
Thr Ser Ala Arg Ala Thr Thr Thr Pro Ala Ser Lys Ser Thr Pro Phe
            980                 985                 990
Ser Ile Pro Ser His His Ser Asp Thr Pro Thr Thr Leu Ala Ser His
        995                 1000                1005
```

```
Ser Thr Lys Thr Asp Ala Ser Ser Thr His His Ser Ser Val Pro
    1010            1015                1020

Pro Leu Thr Ser Ser Asn His Ser Thr Ser Pro Gln Leu Ser Thr
    1025            1030                1035

Gly Val Ser Phe Phe Phe Leu Ser Phe His Ile Ser Asn Leu Gln
    1040            1045                1050

Phe Asn Ser Ser Leu Glu Asp Pro Ser Thr Asp Tyr Tyr Gln Glu
    1055            1060                1065

Leu Gln Arg Asp Ile Ser Glu Met Phe Leu Gln Ile Tyr Lys Gln
    1070            1075                1080

Gly Gly Phe Leu Gly Leu Ser Asn Ile Lys Phe Arg Pro Gly Ser
    1085            1090                1095

Val Val Val Gln Leu Thr Leu Ala Phe Arg Glu Gly Thr Ile Asn
    1100            1105                1110

Val His Asp Val Glu Thr Gln Phe Asn Gln Tyr Lys Thr Glu Ala
    1115            1120                1125

Ala Ser Arg Tyr Asn Leu Thr Ile Ser Asp Val Ser Val Ser Asp
    1130            1135                1140

Val Pro Phe Pro Phe Ser Ala Gln Ser Gly Ala Gly Val Pro Gly
    1145            1150                1155

Trp Gly Ile Ala Leu Leu Val Leu Val Cys Val Leu Val Ala Leu
    1160            1165                1170

Ala Ile Val Tyr Leu Ile Ala Leu Ala Val Cys Gln Cys Arg Arg
    1175            1180                1185

Lys Asn Tyr Gly Gln Leu Asp Ile Phe Pro Ala Arg Asp Thr Tyr
    1190            1195                1200

His Pro Met Ser Glu Tyr Pro Thr Tyr His Thr His Gly Arg Tyr
    1205            1210                1215

Val Pro Pro Ser Ser Thr Asp Arg Ser Pro Tyr Glu Lys Val Ser
    1220            1225                1230

Ala Gly Asn Gly Gly Ser Ser Leu Ser Tyr Thr Asn Pro Ala Val
    1235            1240                1245

Ala Ala Thr Ser Ala Asn Leu
    1250            1255

<210> SEQ ID NO 50
<211> LENGTH: 9
<212> TYPE: PRT
<213> ORGANISM: Artificial Sequence
<220> FEATURE:
<223> OTHER INFORMATION: MUC-1 epitope

<400> SEQUENCE: 50

Gly Ser Thr Ala Pro Pro Val His Asn
1               5

<210> SEQ ID NO 51
<211> LENGTH: 10
<212> TYPE: PRT
<213> ORGANISM: Artificial Sequence
<220> FEATURE:
<223> OTHER INFORMATION: MUC-1 epitope

<400> SEQUENCE: 51

Thr Ala Pro Pro Ala His Gly Val Thr Ser
1               5                   10
```

```
<210> SEQ ID NO 52
<211> LENGTH: 142
<212> TYPE: PRT
<213> ORGANISM: Artificial Sequence
<220> FEATURE:
<223> OTHER INFORMATION: survivin

<400> SEQUENCE: 52
```

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140

```
<210> SEQ ID NO 53
<211> LENGTH: 10
<212> TYPE: PRT
<213> ORGANISM: Artificial Sequence
<220> FEATURE:
<223> OTHER INFORMATION: survivin epitope

<400> SEQUENCE: 53
```

Arg Ile Ser Thr Phe Lys Asn Trp Pro Phe
1               5                   10

```
<210> SEQ ID NO 54
<211> LENGTH: 701
<212> TYPE: PRT
<213> ORGANISM: Artificial Sequence
<220> FEATURE:
<223> OTHER INFORMATION: CEA

<400> SEQUENCE: 54
```

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

```
Ile Gln Asn Asp Thr Gly Phe Tyr Thr Leu His Val Ile Lys Ser Asp
            115                 120                 125

Leu Val Asn Glu Glu Ala Thr Gly Gln Phe Arg Val Tyr Pro Glu Leu
        130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
                180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
        210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
                260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
        290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
                340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
        370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
                420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
        450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
                500                 505                 510

Val Glu Asp Lys Asp Ala Val Ala Phe Thr Cys Glu Pro Glu Ala Gln
        515                 520                 525
```

-continued

```
Asn Thr Thr Tyr Leu Trp Trp Val Asn Gly Gln Ser Leu Pro Val Ser
            530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Asp Ser Ser Tyr Leu Ser Gly
            595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu
    690                 695                 700

<210> SEQ ID NO 55
<211> LENGTH: 10
<212> TYPE: PRT
<213> ORGANISM: Artificial Sequence
<220> FEATURE:
<223> OTHER INFORMATION: CEA epitope

<400> SEQUENCE: 55

Tyr Leu Ser Gly Ala Asn Leu Asn Leu Ser
1               5                   10

<210> SEQ ID NO 56
<211> LENGTH: 10
<212> TYPE: PRT
<213> ORGANISM: Artificial Sequence
<220> FEATURE:
<223> OTHER INFORMATION: CEA epitope

<400> SEQUENCE: 56

Ser Trp Arg Ile Asn Gly Ile Pro Gln Gln
1               5                   10

<210> SEQ ID NO 57
<211> LENGTH: 189
<212> TYPE: PRT
<213> ORGANISM: Artificial Sequence
<220> FEATURE:
<223> OTHER INFORMATION: Kirsten Ras

<400> SEQUENCE: 57

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
```

```
                    50                  55                  60
Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 58
<211> LENGTH: 9
<212> TYPE: PRT
<213> ORGANISM: Artificial Sequence
<220> FEATURE:
<223> OTHER INFORMATION: Kirsten Ras epitope

<400> SEQUENCE: 58

```
Val Val Val Gly Ala Gly Gly Val Gly
 1               5
```

<210> SEQ ID NO 59
<211> LENGTH: 314
<212> TYPE: PRT
<213> ORGANISM: Artificial Sequence
<220> FEATURE:
<223> OTHER INFORMATION: MAGE-A3

<400> SEQUENCE: 59

```
Met Pro Leu Glu Gln Arg Ser Gln His Cys Lys Pro Glu Glu Gly Leu
 1               5                  10                  15

Glu Ala Arg Gly Glu Ala Leu Gly Leu Val Gly Ala Gln Ala Pro Ala
                20                  25                  30

Thr Glu Glu Gln Glu Ala Ala Ser Ser Ser Thr Leu Val Glu Val
            35                  40                  45

Thr Leu Gly Glu Val Pro Ala Ala Glu Ser Pro Asp Pro Pro Gln Ser
 50                  55                  60

Pro Gln Gly Ala Ser Ser Leu Pro Thr Thr Met Asn Tyr Pro Leu Trp
 65                  70                  75                  80

Ser Gln Ser Tyr Glu Asp Ser Ser Asn Gln Glu Glu Glu Gly Pro Ser
                 85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Gly Asn Trp Gln
130                 135                 140

Tyr Phe Phe Pro Val Ile Phe Ser Lys Ala Phe Ser Ser Leu Gln Leu
145                 150                 155                 160
```

```
Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310

<210> SEQ ID NO 60
<211> LENGTH: 9
<212> TYPE: PRT
<213> ORGANISM: Artificial Sequence
<220> FEATURE:
<223> OTHER INFORMATION: MAGE-A3 epitope

<400> SEQUENCE: 60

Lys Val Ala Glu Leu Val His Phe Leu
1               5

<210> SEQ ID NO 61
<211> LENGTH: 380
<212> TYPE: PRT
<213> ORGANISM: Artificial Sequence
<220> FEATURE:
<223> OTHER INFORMATION: IL13Ralpha2

<400> SEQUENCE: 61

Met Ala Phe Val Cys Leu Ala Ile Gly Cys Leu Tyr Thr Phe Leu Ile
1               5                   10                  15

Ser Thr Thr Phe Gly Cys Thr Ser Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140
```

```
Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
                180                 185                 190

Gln Asn Ile Gly Cys Arg Phe Pro Tyr Leu Glu Ala Ser Asp Tyr Lys
            195                 200                 205

Asp Phe Tyr Ile Cys Val Asn Gly Ser Ser Glu Asn Lys Pro Ile Arg
        210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
                260                 265                 270

Glu Ile Glu Ile Arg Glu Asp Asp Thr Thr Leu Val Thr Ala Thr Val
                275                 280                 285

Glu Asn Glu Thr Tyr Thr Leu Lys Thr Thr Asn Glu Thr Arg Gln Leu
            290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Gly Glu Asp Leu
                325                 330                 335

Ser Lys Lys Thr Leu Leu Arg Phe Trp Leu Pro Phe Gly Phe Ile Leu
                340                 345                 350

Ile Leu Val Ile Phe Val Thr Gly Leu Leu Leu Arg Lys Pro Asn Thr
                355                 360                 365

Tyr Pro Lys Met Ile Pro Glu Phe Phe Cys Asp Thr
370                 375                 380

<210> SEQ ID NO 62
<211> LENGTH: 7
<212> TYPE: PRT
<213> ORGANISM: Artificial Sequence
<220> FEATURE:
<223> OTHER INFORMATION: IL13Ralpha2 epitope

<400> SEQUENCE: 62

Leu Pro Phe Gly Phe Ile Leu
1               5

<210> SEQ ID NO 63
<211> LENGTH: 50
<212> TYPE: PRT
<213> ORGANISM: Artificial Sequence
<220> FEATURE:
<223> OTHER INFORMATION: Mad12

<400> SEQUENCE: 63

Leu Phe Arg Ala Ala Gln Leu Ala Asn Asp Val Val Leu Gln Ile Met
1               5                   10                  15

Glu His Leu Glu Leu Ala Ser Met Thr Asn Met Glu Leu Met Ser Ser
                20                  25                  30

Ile Val Val Ile Ser Ala Ser Ile Ile Val Phe Asn Leu Leu Glu Leu
                35                  40                  45

Glu Gly
```

-continued

```
<210> SEQ ID NO 64
<211> LENGTH: 14
<212> TYPE: PRT
<213> ORGANISM: Artificial Sequence
<220> FEATURE:
<223> OTHER INFORMATION: gp70CD4 peptide

<400> SEQUENCE: 64

Leu Val Gln Phe Ile Lys Asp Arg Ile Ser Val Val Gln Ala
1               5                   10

<210> SEQ ID NO 65
<211> LENGTH: 9
<212> TYPE: PRT
<213> ORGANISM: Artificial Sequence
<220> FEATURE:
<223> OTHER INFORMATION: gp70CD8 peptide

<400> SEQUENCE: 65

Ser Pro Ser Tyr Val Tyr His Gln Phe
1               5

<210> SEQ ID NO 66
<211> LENGTH: 9
<212> TYPE: PRT
<213> ORGANISM: Artificial Sequence
<220> FEATURE:
<223> OTHER INFORMATION: adpgk peptide

<400> SEQUENCE: 66

Ala Ser Met Thr Asn Met Glu Leu Met
1               5

<210> SEQ ID NO 67
<211> LENGTH: 8
<212> TYPE: PRT
<213> ORGANISM: Artificial Sequence
<220> FEATURE:
<223> OTHER INFORMATION: survivin20-28

<400> SEQUENCE: 67

Ala Thr Lys Asn Trp Pro Phe Leu
1               5

<210> SEQ ID NO 68
<211> LENGTH: 8
<212> TYPE: PRT
<213> ORGANISM: Artificial Sequence
<220> FEATURE:
<223> OTHER INFORMATION: survivin97-104

<400> SEQUENCE: 68

Thr Val Ser Glu Phe Leu Lys Leu
1               5

<210> SEQ ID NO 69
<211> LENGTH: 127
<212> TYPE: PRT
<213> ORGANISM: Artificial Sequence
<220> FEATURE:
<223> OTHER INFORMATION: Z13Mad12Anaxa

<400> SEQUENCE: 69

Lys Arg Tyr Lys Asn Arg Val Ala Ser Arg Lys Ser Arg Ala Lys Phe
1               5                   10                  15
```

```
Lys Gln Leu Leu Gln His Tyr Arg Glu Val Ala Ala Lys Ser Ser
            20                  25                  30

Glu Asn Asp Arg Leu Arg Leu Leu Lys Leu Phe Arg Ala Ala Gln
        35                  40                  45

Leu Ala Asn Asp Val Val Leu Gln Ile Met Glu His Leu Glu Leu Ala
50                  55                  60

Ser Met Thr Asn Met Glu Leu Met Ser Ser Ile Val Val Ile Ser Ala
65                  70                  75                  80

Ser Ile Ile Val Phe Asn Leu Leu Glu Leu Glu Gly Ser Thr Val His
                85                  90                  95

Glu Ile Leu Cys Lys Leu Ser Leu Glu Gly Asp His Ser Thr Pro Pro
                100                 105                 110

Ser Ala Tyr Gly Ser Val Lys Pro Tyr Thr Asn Phe Asp Ala Glu
            115                 120                 125

<210> SEQ ID NO 70
<211> LENGTH: 1255
<212> TYPE: PRT
<213> ORGANISM: Artificial Sequence
<220> FEATURE:
<223> OTHER INFORMATION: Her2/neu

<400> SEQUENCE: 70

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
            130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
            210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255
```

```
His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
            645                 650                 655

Ala Val Val Gly Ile Leu Leu Val Val Leu Gly Val Val Phe Gly
            660                 665                 670
```

```
Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
```

-continued

```
            1085                1090                1095
Gln Ser Leu Pro Thr His Asp Pro Ser Pro Leu Gln Arg Tyr Ser
        1100            1105            1110

Glu Asp Pro Thr Val Pro Leu Pro Ser Glu Thr Asp Gly Tyr Val
        1115            1120            1125

Ala Pro Leu Thr Cys Ser Pro Gln Pro Glu Tyr Val Asn Gln Pro
        1130            1135            1140

Asp Val Arg Pro Gln Pro Pro Ser Pro Arg Glu Gly Pro Leu Pro
        1145            1150            1155

Ala Ala Arg Pro Ala Gly Ala Thr Leu Glu Arg Pro Lys Thr Leu
        1160            1165            1170

Ser Pro Gly Lys Asn Gly Val Val Lys Asp Val Phe Ala Phe Gly
        1175            1180            1185

Gly Ala Val Glu Asn Pro Glu Tyr Leu Thr Pro Gln Gly Gly Ala
        1190            1195            1200

Ala Pro Gln Pro His Pro Pro Pro Ala Phe Ser Pro Ala Phe Asp
        1205            1210            1215

Asn Leu Tyr Tyr Trp Asp Gln Asp Pro Pro Glu Arg Gly Ala Pro
        1220            1225            1230

Pro Ser Thr Phe Lys Gly Thr Pro Thr Ala Glu Asn Pro Glu Tyr
        1235            1240            1245

Leu Gly Leu Asp Val Pro Val
        1250            1255
```

COMPLEX COMPRISING A CELL PENETRATING PEPTIDE, A CARGO AND A TLR PEPTIDE AGONIST FOR TREATMENT OF COLORECTAL CANCER

CROSS-REFERENCE TO RELATED PATENT APPLICATIONS

This patent application is a continuation of U.S. patent application Ser. No. 15/557,649 filed 10 Jan. 2018, now abandoned, which is a national stage application of International Application No. PCT/EP2016/000473 filed 16 Mar. 2016, which claims priority to International Application No. PCT/EP2015/002244 filed 9 Nov. 2015 and International Application No. PCT/EP2015/000580 filed 16 Mar. 2015.

REFERENCE TO AN ELECTRONIC SEQUENCE LISTING

This application contains references to amino acid sequences and/or nucleic acid sequences which have been submitted concurrently herewith as the sequence listing .txt file entitled "Sequence_Listing.txt", file size 74,000 Bytes (B), created on 8 Aug. 2017. The aforementioned sequence listing is hereby incorporated by reference in its entirety.

FIELD

The present invention relates to the field of vaccination, in particular to vaccines for the prevention and/or treatment of colorectal cancer (CRC).

BACKGROUND

Colorectal cancer (CRC) Globally, CRC is a common and lethal disease and the third most commonly diagnosed cancer, third in males and second in females, with more than 1.36 million new cases and about 694,000 deaths occurring in 2012. The risk of developing CRC is influenced by human, environmental and genetic factors (Cancer, I.A.f.R.o. GLOBACAN 2012. 2012 [cited 2015 Jul. 5]; Available from: globocan.iarc.fr/Pages/burden_sel.aspx). Although the CRC incidence is more predominant in man than in woman, it is more significantly impacted by the age and life style. Indeed over 90% of patients diagnosed with CRC are 50 years old or more (Prevention, C.f.D.C.a. What Are the Risk Factors for Colorectal Cancer?2015 [cited 2015 Jul. 5]) while ⅔ of the cases occurred in developed countries. There is evidence that consumption of meat in general and more specifically red meat or consumption of alcoholic beverages that are leading to general obesity, are significantly increasing the risks of CRC (Stewart, B. and C. Wild, *World Cancer Report* 2014, B. Stewart and C. Wild, Editors. 2014, International Agency for Research on Cancer: Geneva). Two other factors are significantly impacting the risks of developing colorectal cancer: hereditary and inflammatory bowel disease. Familial adenomatous polyposis (FAP) is for example significantly increasing the risks of CRC for less than 50 years old people (Burt, R. W., J. A. DiSario, and L. Cannon-Albright, Genetics of colon cancer: impact of inheritance on colon cancer risk. Annu Rev Med, 1995. 46: p. 371-9). FAP, like MAP (MUTYH-associated polyposis) (Sieber, O. M., et al., Multiple colorectal adenomas, classic adenomatous polyposis, and germ-line mutations in MTH. N Engl J Med, 2003. 348(9): p. 791-9) or Lynch syndrome (Lynch, H. T., et al., Genetics, natural history, tumor spectrum, and pathology of hereditary non-polyposis colorectal cancer: an updated review. Gastroenterology, 1993. 104(5): p. 1535-49), is associated with gene mutations that predispose patients to inheritance of multiple colonic adenomas (Dennis J Ahnen, D. M., FA. *Colorectal cancer: Epidemiology, risk factors, and protective factors.* 2015 [cited 2015 Jul. 9]; Available from: www.uptodate.com/contents/colorectal-cancer-epidemiology-risk-factors-and-protective-factors). The influence of diseases such as ulcerative colitis or Crohn's disease in developing a CRC is well documented. Ulcerative colitis impact is for example linked to a 3 to 15-fold increase in risk (Ekbom, A., et al., Ulcerative colitis and colorectal cancer. A population-based study. N Engl J Med, 1990. 323(18): p. 1228-33). Although there are less data for Crohn's disease, similar relative risks are associated with this disease. For patients having family history in terms of CRC, adenomatous polyposis or inflammatory bowel disease, early screening is strongly recommended (Jemal, A., et al., Global cancer statistics. CA Cancer J Clin, 2011. 61(2): p. 69-90).

Like in many cancers, the CRC patient's survival time depends on disease development stage. Patients with early stages (Stage 0, I and II) have good prognosis (more than 75%). Stages III have a more heterogeneous survival rate (from 90% down to 50%) depending on the tumor invasion on peripheral tissues. Finally, only stage IV is showing a fast and significant effect on the patient survival time: Only about 10% of patients are surviving more than 60 months after diagnosis.

Existing treatments are generally based on a surgery followed or not by well-established chemotherapy, radiotherapy and/or targeted therapy (Moertel, C. G., Chemotherapy for colorectal cancer. N Engl J Med, 1994. 330(16): p. 1136-42; Meyerhardt, J. A. and R. J. Mayer, Systemic therapy for colorectal cancer. N Engl J Med, 2005. 352(5): p. 476-87). Depending on the disease progression stage, existing treatments allow a 30% to 95% survival rate two years after diagnosis. All early stage CRC treatment strategies are initiated with surgery, combined or not with additional regimen. The decision on the follow-up therapy regimen depends on the disease progression stage identified during the preliminary screening results. For advanced CRC, the use of chemotherapy or targeted therapy as first line treatment is generally recommended. The most commonly used regimens are FOLFOX, CapeOX or FOLFIRI. These treatments may be used in combination with one of the following recommended biological drugs targeting VEGF (Genentech bevacizumab/Avastin® or Regeneron-Sanofi aflibercept/Zaltrape) or EGFR (Merck-Serono cetuximab/Erbituxv). Other targeted therapies could be proposed as stand-alone first line treatment. Amgen's EGFR monoclonal antibody (panitumumab/Vectibix®) and, more recently, Bayer's small molecule kinase inhibitor Regorafenib (Stivarga©) have demonstrated their capacity to increase overall CRC patients' survival time. If the disease already importantly spread to other organs, the VEGF monoclonal antibody Ramucirumab (Cyramza®) from Eli Lilly may be used. For stage IV, radiation may be used to relieve symptoms such as pain.

Although CRC chemotherapy is well established (Moertel, C. G., Chemotherapy for colorectal cancer. N Engl J Med, 1994. 330(16): p. 1136-42) the momentum towards more effective and less subject to secondary effects strategies importantly evolved in the past decades, namely for stage IV CRC (Gallagher, D. J. and N. Kemeny, Metastatic colorectal cancer: from improved survival to potential cure. Oncology, 2010. 78(3-4): p. 237-48). The first trials were directed towards complementary adjuvant therapy. However after many years, the value of postoperative 5-FU based therapy remains controversial, in particular for patients with stage II CRC (Meyerhardt, J. A. and R. J. Mayer, Systemic therapy for colorectal cancer. N EnglJ Med, 2005. 352(5): p. 476-87).

In that context, immunotherapies have been carefully evaluated. The immune system can recognize and to some extent eliminate tumor cells, however, this anti-tumor response is often of low amplitude and inefficient. Boosting this weak anti-tumor response with therapeutic vaccination has been a long sought goal for cancer therapy. Modulating the immune system to enhance immune responses has thus become a promising therapeutic approach in oncology as it can be combined with standard of care treatments.

Promising preclinical data and advances in clinical trials, including the recent FDA approval of the Sipuleucel-T vaccine and of the anti-CTLA-4 antibody, show that active immunization is a safe and feasible treatment modality for certain cancer types. Induction of tumor-specific cytotoxic T lymphocytes (CTLs) mediated immune responses has been reported using different approaches including modified tumor cell vaccines, peptide vaccines, recombinant viral vectors, DNA, protein, or dendritic cell vaccines. However, the anti-tumoral immunity mediated by CTLs only occasionally correlates with tumor regression and only a few projects have reached the phase III clinical stage.

Overall, cancer vaccines showed very limited clinical efficacy so far. Indeed, at the end of 2011, amongst the 300 hundred ongoing cancer vaccine clinical trials, only 19 phase III trials were reported (globaldata, 2012). Amongst them, there are NeuVax, a peptide vaccine for breast cancer, Stimuvax, a liposome based vaccine for Non-Small Cell Lung Carcinoma (NSCLC) and breast cancer, TG4010, a vaccinia-based vaccine for NSCLC and GSK1572932A, an adjuvanted liposome for NSCLC. These four cancer vaccines are based on different technologies and have in common that they are targeting one single antigen.

Therapeutic cancer vaccines can be divided into two principal categories: personalized (autologous) and standardized vaccines, and further classified depending on the technology platform. Current personalized vaccines include tumor lysate vaccines as well as dendritic cells based vaccine (hereinafter cell based). For the latter, antigen loading can occur either with a pulse using tumor lysates, or transfection with RNA extracted from the tumors. In this case, the antigens are tumor specific or associated, but are not clearly defined. Dendritic cells can also be loaded with defined antigens either with peptide pulse or using a protein such as the Prostatic Acid Phosphatase (PAP) used to engineer the Provenge® vaccine. However, the manufacturing process of these cell-based therapies is time-consuming and labor-intensive while quality standards are difficult to reach and maintain. Immunomonitoring creates further complications. Moreover, the majority of the autologous cancer vaccines do not allow the identities or quantities of antigens used to be controlled, unlike defined and standardized vaccines.

In contrast to cell-based therapy (APCs, T cells, CARs, lysates), subunits vaccines (protein or peptides) allow the development of a standardized vaccine with an easier production and significantly better batch to batch reproducibility that can be administered to a broad range of patients. Furthermore, the antigens are fully defined allowing for better immune-monitoring and reducing the risk of unwanted effects of vaccine component.

The different approaches which were evaluated in preclinical and clinical development include short peptide vaccines (Slingluff C L, Jr. The present and future of peptide vaccines for cancer: single or multiple, long or short, alone or in combination?Cancer journal 2011; 17(5):343-50), long-peptide vaccines (Melief C J, van der Burg S H. Immunotherapy of established (pre)malignant disease by synthetic long peptide vaccines. Nature reviews Cancer 2008; 8(5):351-60) and proteins. In contrast to long peptide and protein vaccines, short peptide vaccines have a very short half-life and can have negative consequences on the immune response.

For the protein-based vaccines, the results of targeting MAGE-A3 with a recombinant fusion protein-based vaccine have been enthusiastically awaited after promising phase II data in metastatic melanoma (Kruit W H, Suciu S, Dreno B, Mortier L, Robert C, Chiarion-Sileni V, et al. Selection of immunostimulant AS15 for active immunization with MAGE-A3 protein: results of a randomized phase II study of the European Organisation for Research and Treatment of Cancer Melanoma Group in Metastatic Melanoma. Journal of clinical oncology: official journal of the American Society of Clinical Oncology 2013; 31(19):2413-20) and non-small cell lung cancer (NSLC)(Vansteenkiste J, Zielinski M, Linder A, Dahabreh J, Gonzalez E E, Malinowski W, et al. Adjuvant MAGE-A3 immunotherapy in resected non-small-cell lung cancer: phase II randomized study results. Journal of clinical oncology: official journal of the American Society of Clinical Oncology 2013; 31(19):2396-403). However, in 2013 the phase III DERMA trial in melanoma (NCT00796445) did not meet its first co-primary endpoint, followed in 2014 with a stop of the phase III MAGRIT study in NSCL (NCT00480025). Despite these very disappointing clinical results, protein based vaccines undeniably present many advantages.

Also in the context of colorectal cancer scientific progresses in tumor immunology led to a better understanding of anti-tumor immune response through cellular and humoral pathways (Smith, C. L., et al., Immunotherapy of colorectal cancer. Br Med Bull, 2002. 64: p. 181-200; Koido, S., et al., Immunotherapy for colorectal cancer. World J Gastroenterol, 2013. 19(46): p. 8531-42) and helped better identifying tumor antigens. This progresses opened new perspective for immunotherapies in CRC. Passive immunotherapies such as antibodies were proved as the first targeted therapies for CRC treatment. Thanks to their capacity in being able to interact with tumor growth pathway through the epidermal growth factor receptor (EGFR) or to inhibit the vascular endothelial growth factor (VEGF), antibodies such as cetuximab, panitumumab and bevacizumab received FDA approval for CRC treatment respectively in 2004, 2006 and 2009.

Adoptive cell transfer (ACT) therapy clinical trials for CRC have unfortunately returned poor results so far. Indeed the limited patient population for both non-engineered and engineered T-cells treatments seems being a major hurdle. Similarly, secondary effect observed on patients treated with T-cells fused with chimeric antigen receptors (CARs), failed to demonstrate ACT as a safe and efficient treatment (Koido, S., et al., Immunotherapy for colorectal cancer. World J Gastroenterol, 2013. 19(46): p. 8531-42; Xiang, B., et al., Colorectal cancer immunotherapy. Discov Med, 2013. 15(84): p. 301-8). Thus added to usual ACT drawbacks in terms of feasibility and cost and immune response memory seems blocking ACT option for the time being.

More recently, the positive clinical trial phase III results on patient survival for aflibercept, allowed this anti-VEGF fusion protein to be approved by the FDA for metastatic colorectal cancer (mCRC) (Clarke, J. M. and H. I. Hurwitz, Ziv-aflibercept: binding to more than VEGF-A—does more matter?Nat Rev Clin Oncol, 2013. 10(1): p. 10-1). This targeted therapy approval paves the way for non-antibody immunotherapies. So far, no active immunotherapies and no immuno-modulators have been approved for CRC. Structurally, the vast majority of the molecules tested for CRC are either small molecules, in general kinase inhibitors, or antibodies (respectively 52% and 28%).

In general, a therapeutic cancer vaccine is administrated to cancer patients to strengthen the capability of their immune system to recognize and kill the tumor cells. The main goal of a therapeutic cancer vaccine is to generate killer T cells (also called cytotoxic T lymphocytes) specific for the tumor cells. To this end and to achieve a potent immune response, the vaccine must contain molecules called antigens that are also present in the tumor and that need to be delivered to Antigen Presenting Cells (APCs), especially dendritic cells (DCs), to allow cancer immunity to be initiated. The DCs process these tumor antigens into small peptides that are presented on cell surface expressed MHC class I or MHC class II molecules to T cells. Peptides that are then recognized by T cells and thereby induce their stimulation are called epitopes. Presentation by MHC class I and MHC class II molecules allows activation of two classes of T cells, $CD8^+$ cytotoxic T lymphocytes (CTLs) and $CD4^+$ helper T ($T_h$) cells, respectively. In addition, to become fully activated, beside antigen recognition T cells require a second signal, the co-stimulatory signal, which is antigen non-specific and is provided by the interaction between co-stimulatory molecules expressed on the surface of APCs and the T cell. Therefore two major requirements for an efficient therapeutic cancer vaccine are the specificity of the tumor antigens and the ability to deliver them efficiently to DCs.

Taken together, induction of a tumor specific immune response thus requires three main steps: (i) an antigen must be delivered to dendritic cells, which will process it into epitopes, (ii) dendritic cells should receive a suitable activation signal, and (iii) activated tumor antigen-loaded dendritic cells must generate T-cell mediated immune responses in the lymphoid organs.

Since tumor cells can escape the immune system by down-regulating expression of individual antigens (passive immune escape), multi-epitopic antigen delivery provides an advantage. Indeed, protein based vaccines allow multi-epitopic antigen delivery to antigen presenting cells (APCs) such as dendritic cells (DCs) without the limitation of restriction to a single MHC allele. Another strength is long-lasting epitope presentation recently described in dendritic cells loaded with proteins (van Montfoort N, Camps M G, Khan S, Filippov D V, Weterings J J, Griffith J M, et al. Antigen storage compartments in mature dendritic cells facilitate prolonged cytotoxic T lymphocyte cross-priming capacity. Proceedings of the National Academy ofSciences of the United States of America 2009; 106(16):6730-5). Furthermore, proteins require uptake and processing by DCs to achieve MHC restricted presentation of their constituent epitopes. This reduces the risk of inducing peripheral tolerance as has been shown after vaccination with short peptides that do not have such stringent processing requirements (Toes R E, Offringa R, Blom R J, Melief C J, Kast W M. Peptide vaccination can lead to enhanced tumor growth through specific T-cell tolerance induction. Proceedings of the National Academy of Sciences of the United States of America 1996; 93(15):7855-60).

However, most soluble proteins are generally degraded in endolysosomes and are poorly cross-presented on MHC class I molecules and are therefore poorly immunogenic for $CD8^+$T cell responses (Rosalia R A, Quakkelaar E D, Redeker A, Khan S, Camps M, Drijfhout J W, et al. Dendritic cells process synthetic long peptides better than whole protein, improving antigen presentation and T-cell activation. European journal of immunology 2013; 43(10):2554-65). Moreover, although mature DCs are more potent than immature DCs in priming and eliciting T-cell responses (Apetoh L, Locher C, Ghiringhelli F, Kroemer G, Zitvogel L. Harnessing dendritic cells in cancer. Semin Immunol. 2011; 23:42-49), they lose the ability to efficiently take up exogenous antigens, particularly for MHC class II restricted antigens (Banchereau J, Steinman R M. Dendritic cells and the control of immunity. Nature. 1998; 392:245-252). As a result, peptide-pulsed DCs as vaccines have several limitations. For example, peptide degradation, rapid MHC class I turnover, and the disassociation of peptide from MHC class I molecules during the preparation and injection of DC/peptides may result in short half-lives of MHC class I/peptide complexes on the DC surface, leading to weak T-cell responses.

To improve the efficacy of protein-based vaccine delivery, the use of cell penetrating peptides for intracellular delivery of cancer peptides into DCs has been proposed (Wang R F, Wang H Y. Enhancement of antitumor immunity by prolonging antigen presentation on dendritic cells. Nat Biotechnol. 2002; 20:149-156). Cell penetrating peptides (CPPs) are peptides of 8 to 40 residues that have the ability to cross the cell membrane and enter into most cell types (Copolovici D M, Langel K, Eriste E, Langel U. Cell-penetrating peptides: design, synthesis, and applications. ACS nano 2014; 8(3): 1972-94, Milletti F. Cell-penetrating peptides: classes, origin, and current landscape. Drug Discov Today 2012). Alternatively, they are also called protein transduction domain (PTDs) reflecting their origin as occurring in natural proteins. Several potent CPPs have been identified from proteins, including the Tat protein of human immunodeficiency virus, the VP22 protein of herpes simplex virus, and fibroblast growth factor (Berry C C. Intracellular delivery of nanoparticles via the HIV-1 tat peptide. Nanomedicine. 2008; 3:357-365; Deshayes S, Morris M C, Divita G, Heitz F. Cell-penetrating peptides: Tools for intracellular delivery of therapeutics. Cell Mol Life Sci. 2005; 62:1839-1849; Edenhofer F. Protein transduction revisited: Novel insights into the mechanism underlying intracellular delivery of proteins. Curr Pharm Des. 2008; 14:3628-3636; Gupta B, Levchenko T S, Torchilin V P. Intracellular delivery of large molecules and small particles by cell-penetrating proteins and peptides. Adv Drug Deliv Rev. 2005; 57:637-651; Torchilin V P. Recent approaches to intracellular delivery of drugs and DNA and organelle targeting. Annu Rev Biomed Eng. 2006; 8:343-375). It was found that T-cell activity elicited by DC/TAT-TRP2 was 3- to 10-fold higher than that induced by DC/TRP2 (Wang H Y, Fu T, Wang G, Gang Z, Donna M P L, Yang J C, Restifo N P, Hwu P, Wang R F. Induction of CD4+ T cell-dependent antitumor immunity by TAT-mediated tumor antigen delivery into dendritic cells. J Clin Invest. 2002a; 109:1463-1470).

Moreover, subunits vaccines (peptides or proteins) are poorly immunogenic. Therefore in the context of therapeutic cancer vaccine, a potent adjuvant is mandatory to be added to the vaccine in order to increase the level of co-stimulatory molecules on DCs and therefore augment the immune system's response to the target antigens. Adjuvants accomplish this task by mimicking conserved microbial components that are naturally recognized by the immune system. They include, lipopolysaccharide (LPS), components of bacterial cell walls, and nucleic acids such as double-stranded RNA (dsRNA), single-stranded DNA (ssDNA), and unmethylated CpG dinucleotide-containing DNA. Their presence together with the vaccine can greatly increase the innate immune response to the antigen. Furthermore, this adjuvant should promote an adaptive immune response with CTLs and type polarized Th1 rather than a humoral immune response resulting in antibody production. Different adjuvants have been evaluated, with a limited number having gained regulatory approval for human use. These include Alum, MPL (monophosphoryl lipid A) and ASO+(Alum and MPL) in the US, and MF59 (oil-in-water emulsion), ASO+, liposomes in Europe (Lim, Y. T., Vaccine adjuvant materials for cancer immunotherapy and control of infectious disease. Clin Exp Vaccine Res, 2015. 4(1): p. 54-8).

Recently, Toll Like Receptor (TLR) ligands are emerging as promising class of adjuvants (Baxevanis, C. N., I. F. Voutsas, and O. E. Tsitsilonis, Toll-like receptor agonists: current status and future perspective on their utility as adjuvants in improving anticancer vaccination strategies. Immunotherapy, 2013. 5(5): p. 497-511). A significant development of cancer vaccine studies was thus to include various TLR agonists to vaccine formulations, including TLR-3 (poly I:C), TLR-4 (monophosphoryl lipid A; MPL), TLR-5 (flagellin), TLR-7 (imiquimod), and TLR-9 (CpG) (Duthie M S, Windish H P, Fox C B, Reed S G. Use of defined TLR ligands as adjuvants within human vaccines. Immunol Rev. 2011; 239:178-196). The types of signaling and cytokines produced by immune cells after TLR stimulation control $CD4^+$T-cell differentiation into Th 1, Th2, Th 17, and Treg cells. Stimulation of immune cells such as DCs and T cells by most TLR-based adjuvants produces proinflammatory cytokines and promotes Th1 and $CD8^+T$ responses (Manicassamy S, Pulendran B. Modulation of adaptive immunity with Toll-like receptors. Semin Immunol. 2009; 21:185-193).

Conjugating the vaccine to a TLR ligand is an attractive approach that offers several advantages over non-conjugated vaccines including (i) preferential uptake by the immune cells expressing the TLR, (ii) higher immune response and (iii) reduced risk of inducing peripheral tolerance. Indeed, all the antigen presenting cells loaded with the antigen will be simultaneously activated. Different groups explored this approach with various TLR ligands being mainly linked chemically to the peptide or protein vaccine (Zom G G, Khan S, Filippov D V, Ossendorp F. TLR ligand-peptide conjugate vaccines: toward clinical application. Adv Immunol. 2012; 114:177-201). As the chemical linkage to peptide is easily performed, the most highly investigated TLR ligands for conjugate vaccine are the TLR2 agonist Pam2Cys and PamsCys (Fujita, Y. and H. Taguchi, Overview and outlook of Toll-like receptor ligand-antigen conjugate vaccines. Ther Deliv, 2012. 3(6): p. 749-60).

However, to date the majority of cancer vaccines trials have shown limited efficacy. One explanation is the lack of a therapy that can simultaneously (i) stimulate multi-epitopic cytotoxic T cell-mediated immunity, (ii) induce $T_h$ cells and (iii) promote immunological memory. These three parameters are essential to generate potent, long lasting anti-tumor immunity. Indeed, CTLs specific for different epitopes will allow destruction of more cancer cells within a heterogeneous tumor mass and avoid the outgrowth of antigen-loss variants (tumor immune escape). $T_h$ cells are involved in the maintenance of long-lasting cellular immunity and tumor infiltration by Th cells is also an essential step for the recruitment and function of CD8+ CTLs. Immunological memory is essential to protect against tumor relapse.

SUMMARY

In view of the above, it is the object of the present invention to overcome the drawbacks of current cancer vaccines outlined above and to provide a novel complex for colorectal cancer immunotherapy applications representing a more potent vaccine, having improved anti-tumor activity for use in the prevention and/or treatment of colorectal cancer.

This object is achieved by means of the subject-matter set out below and in the appended claims.

BRIEF DESCRIPTION OF THE FIGURES

In the following a brief description of the appended figures will be given. The figures are intended to illustrate the present invention in more detail. However, they are not intended to limit the subject matter of the invention in any way.

Figure 25A:
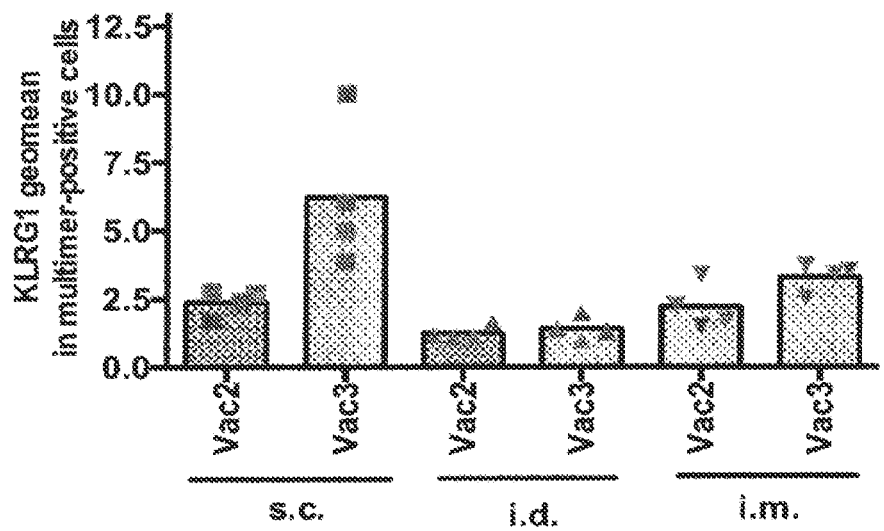
Figure 25B:
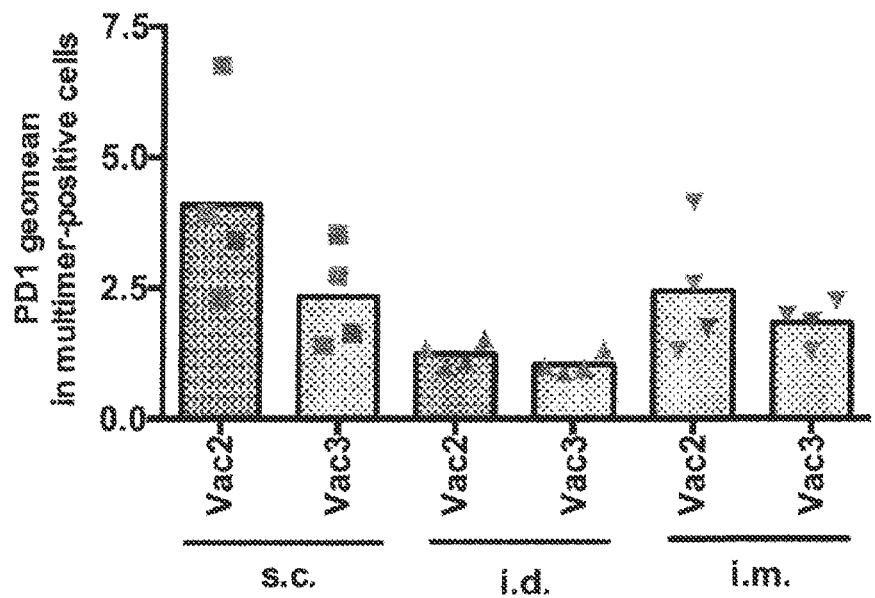

FIG. 25A-B shows for Example is KLRG1 expression (A) and PD-1 expression (B), which were analyzed on multimer-positive CD8 T cells (one experiment with 4 mice per group). Briefly, C57BL/6 mice were vaccinated three times (once at Wk0, once at Wk2 and once at Wk4) s.c., i.d. or i.m. with 2 nmol of Z13Mad5Anaxa. Blood was obtained from mice 7 days after the 2nd and the 3rd vaccination and FACS staining was performed.

Figure 26:
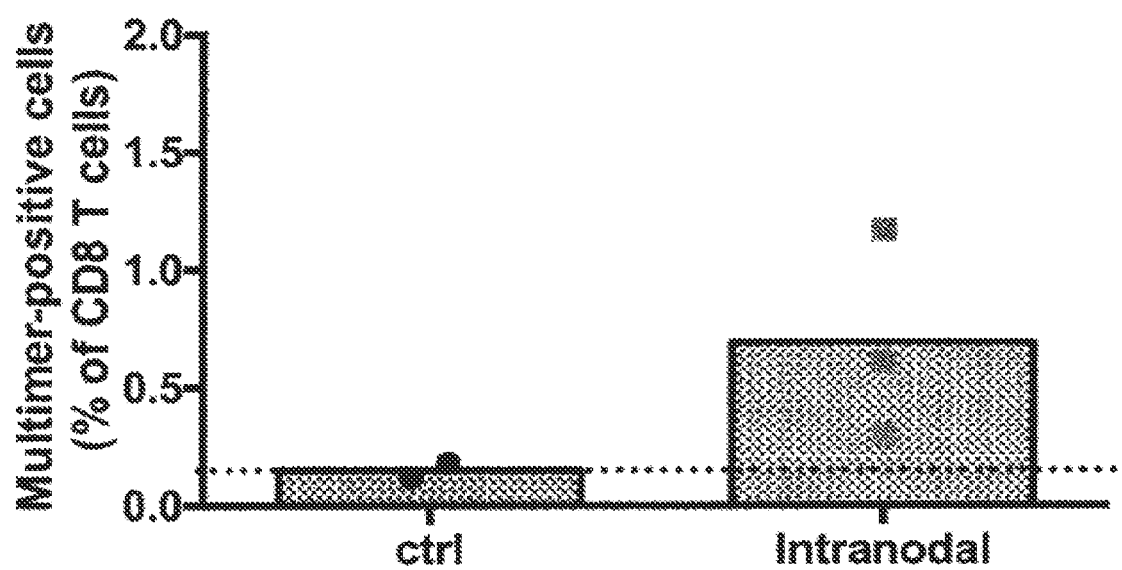

FIG. 26 shows for Example 14 SIINFEKL-specific CD8 T cell responses in C57BL/6 mice vaccinated two times (once at Wk0 and once at Wk2) intranodally with 0.5 nmol of Z13Mad5Anaxa. Blood was obtained from mice 7 days after the 2nd vaccination and multimer staining was performed (3 mice per group).

FIG. 27A-D shows for Example 15 the percentage of pentamer-positive cells among CD8 T cells (A and B; *, p<0.05) and KLRG1 geomean of pentamer-positive CD8 T cells (C and D). Briefly, C57BL/6 mice were vaccinated 3 times (A and C: Wk0, Wk2 and Wk4; B and D: Wk0, Wk2 and Wk8) s.c. with 2 nmol of Z13Mad5Anaxa. Mice were bled 7 days after last vaccination and pentamer staining was performed (one experiment with 4 mice per group).

FIG. 28A-F shows for Example 15 the percentage of multimer-positive cells among CD8 T cells (A and D); KLRG1 geomean of multimer-positive CD8 T cells (B and E) and PD1 geomean of multimer-positive CD8 T cells (C and F). A-C, C57BL/6 mice were vaccinated 3 times at Day0, Days and Day7 and bled at Day7 and Day14. D-F, C57BL/6 mice were vaccinated 3 times at Day0, Day7 and Day14 and bled at Day14 and Day21. Vaccination was performed s.c. with 0.5 nmol of Z13Mad5Anaxa. Multimer staining was performed on blood samples (one experiment with 4 mice per group).

Figure 29:
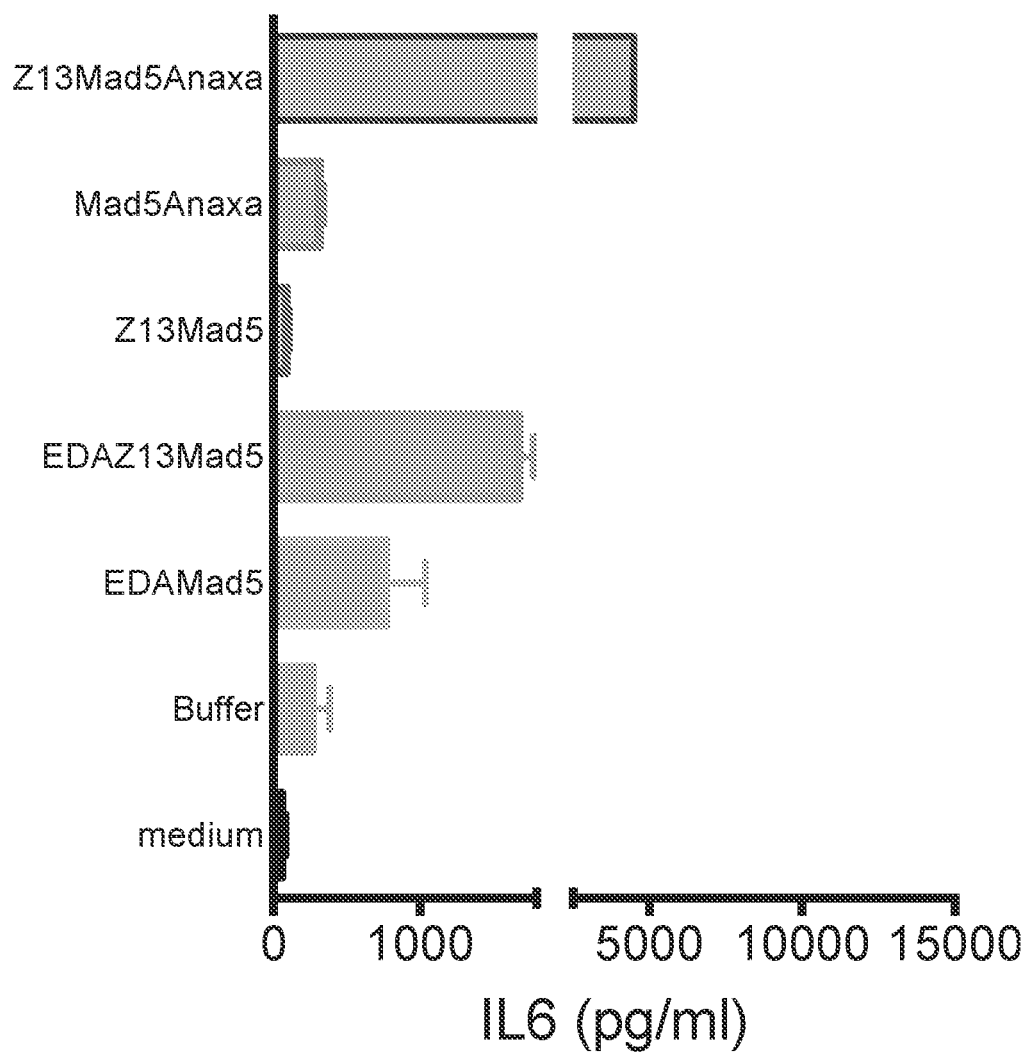

FIG. 29 shows for Example 16 the IL-6 secretion indicating the APC activation after incubation of BMDCs with various constructs as indicated in the Figure. Briefly, BMDCs were seeded in flat 96-well plate in culture medium, stimulated with 1 µM of Z13Mad5Anaxa, Mad5Anaxa, Z13Mad5, EDAZ13Mad5 or EDAMad5 and incubated for 24 h at 37° C. IL-6 secretion was quantified by ELISA in the supernatant. Mean±SEM of 2 to 3 individual experiments.

Figure 30:
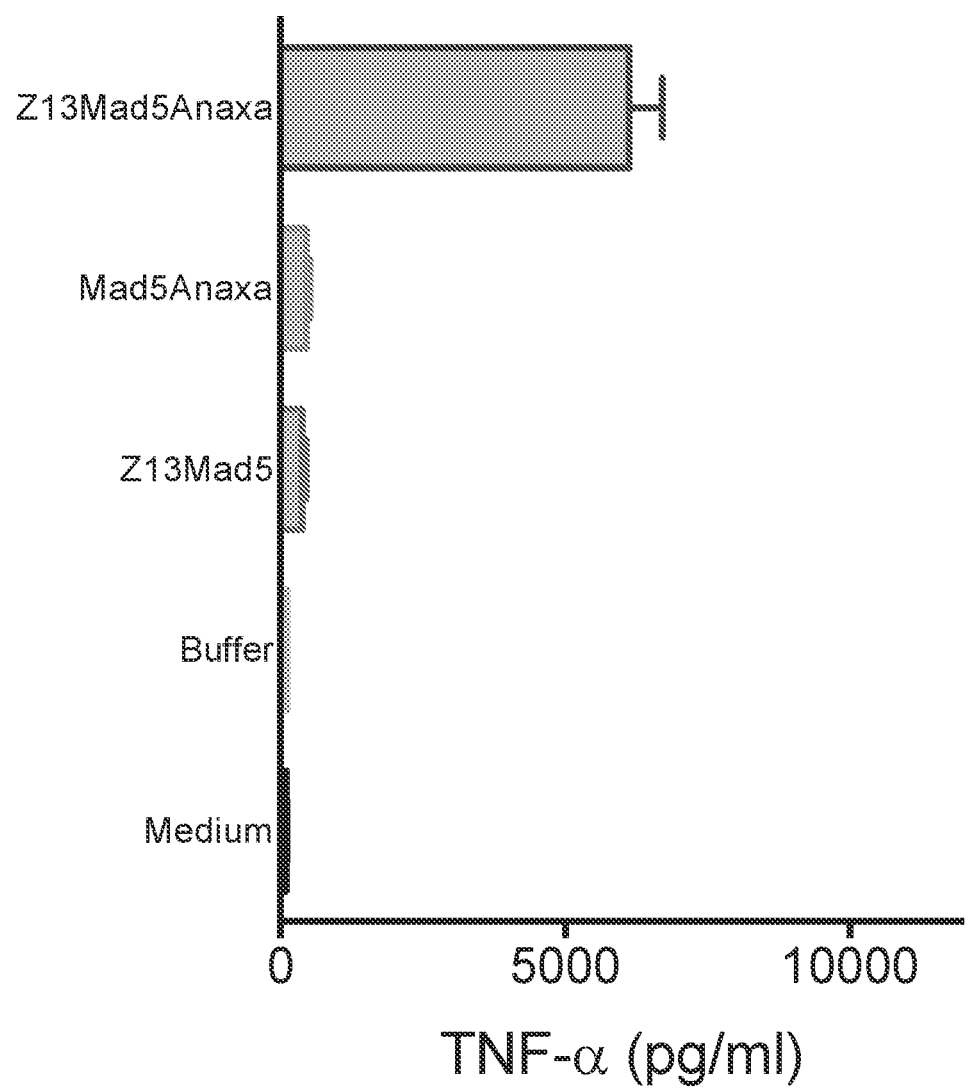

FIG. 30 shows for Example 16 the TNF-α secretion indicating the APC activation after incubation of Raw 264.7 cells with various constructs as indicated in the Figure. Briefly, Raw 264.7 cells were seeded in flat 96-well plate in culture medium, stimulated with 1 µM of Z13Mad5Anaxa, Mad5Anaxa or Z13Mad5 and incubated for 24 h at 37° C. TNF-α secretion was quantified by ELISA in the supernatant. Mean±SEM of 2 to 3 individual experiments.

Figure 31:
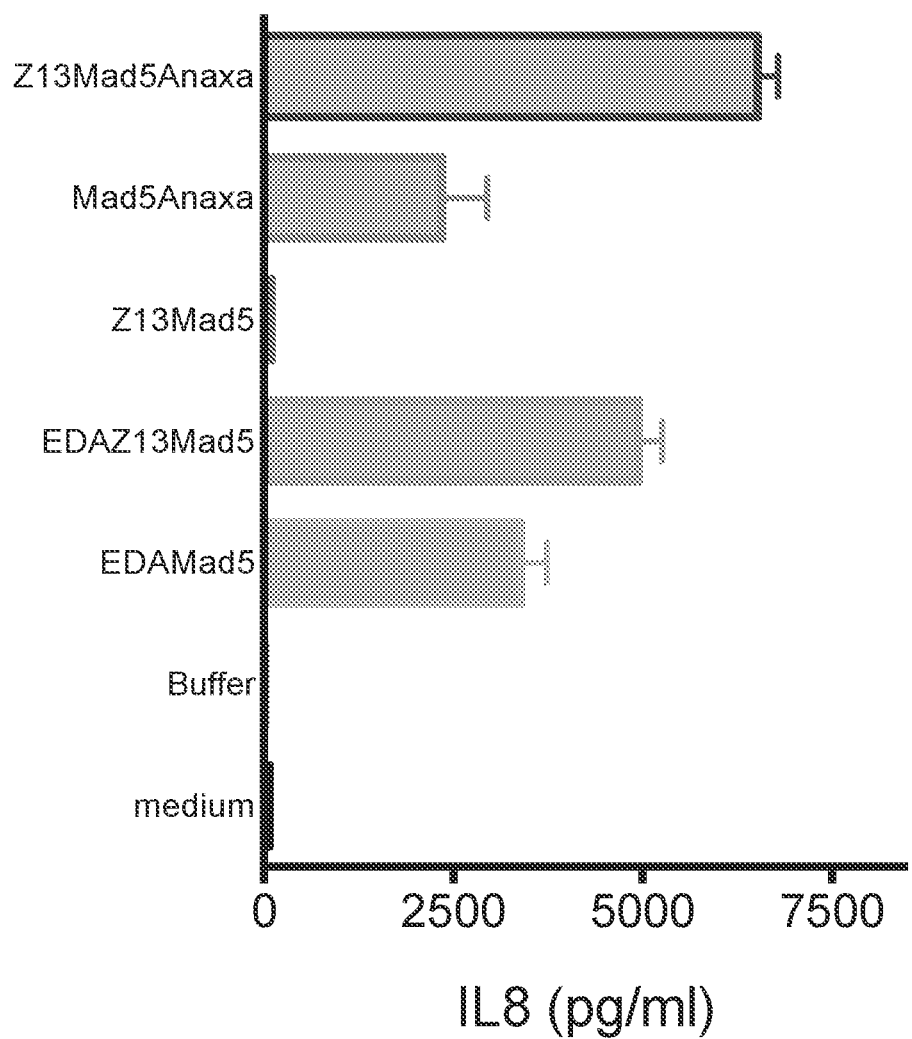

FIG. 31 shows for Example 17 the IL-8 secretion indicating TLR4 binding after incubation of HEK-hTLR4 cells with various constructs as indicated in the Figure. Briefly, HEK-hTLR4 were seeded in flat 96-well plate in culture medium, stimulated with 1 M of Z13Mad5Anaxa, Mad5Anaxa, Z13Mad5, EDAZ13Mad5 or EDAMad5 and incubated 24 h at 37° C. IL-8 secretion was quantified by ELISA in the supernatant. Mean±SEM of 2 individual experiments.

Figure 32:
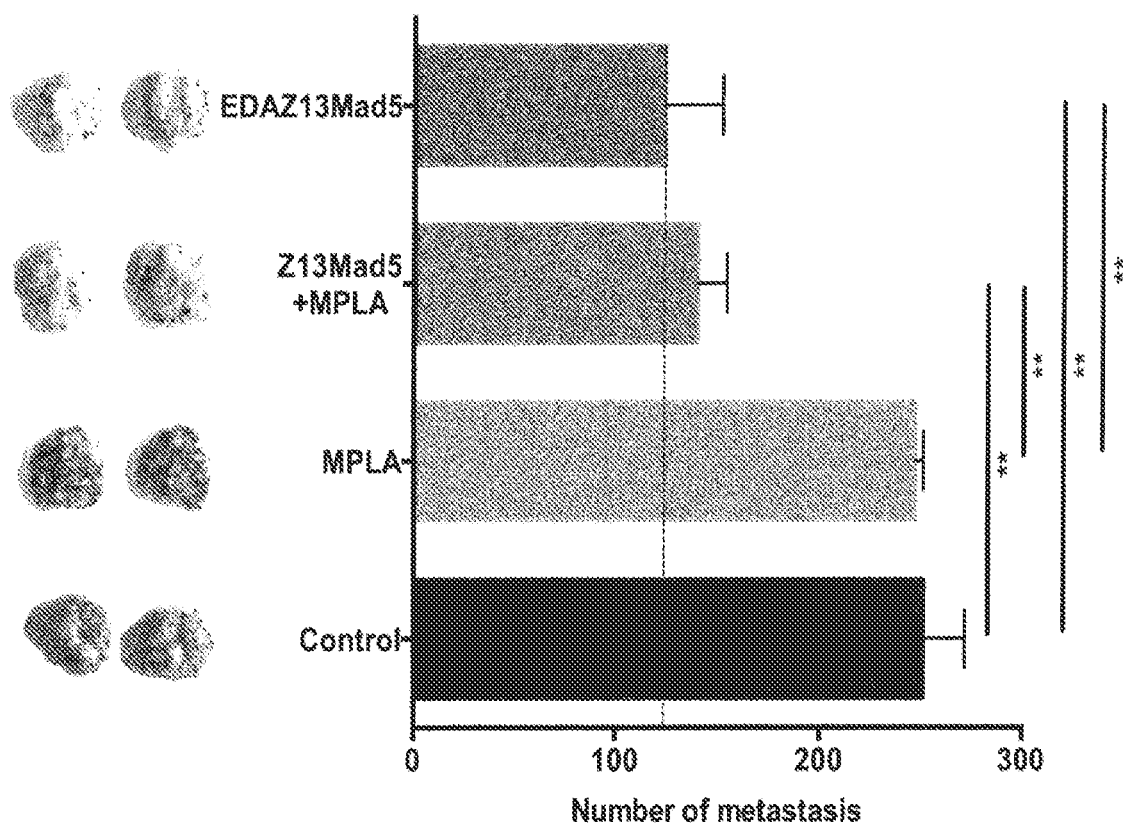

FIG. 32 shows for Example 18 the number of metastasis in a lung metastasis model with semitherapeutic settings. Briefly, C57BL/6 mice were implanted i.v. with $1 \times 10^5$ B 16-OVA melanoma tumor cells and vaccinated twice (do and d9) by subcutaneous injection of 2 nmol of EDAZ13Mad5, Z13Mad5+MPLA (equimolar to EDA) or MPLA alone s.c. in the right flank. Mice were euthanized at day 13 and lung recovered. Number of metastasis foci was counted for each lung. **, p<0.01 (One-way Anova with Tukey's multiple comparisons test).

Figure 33:
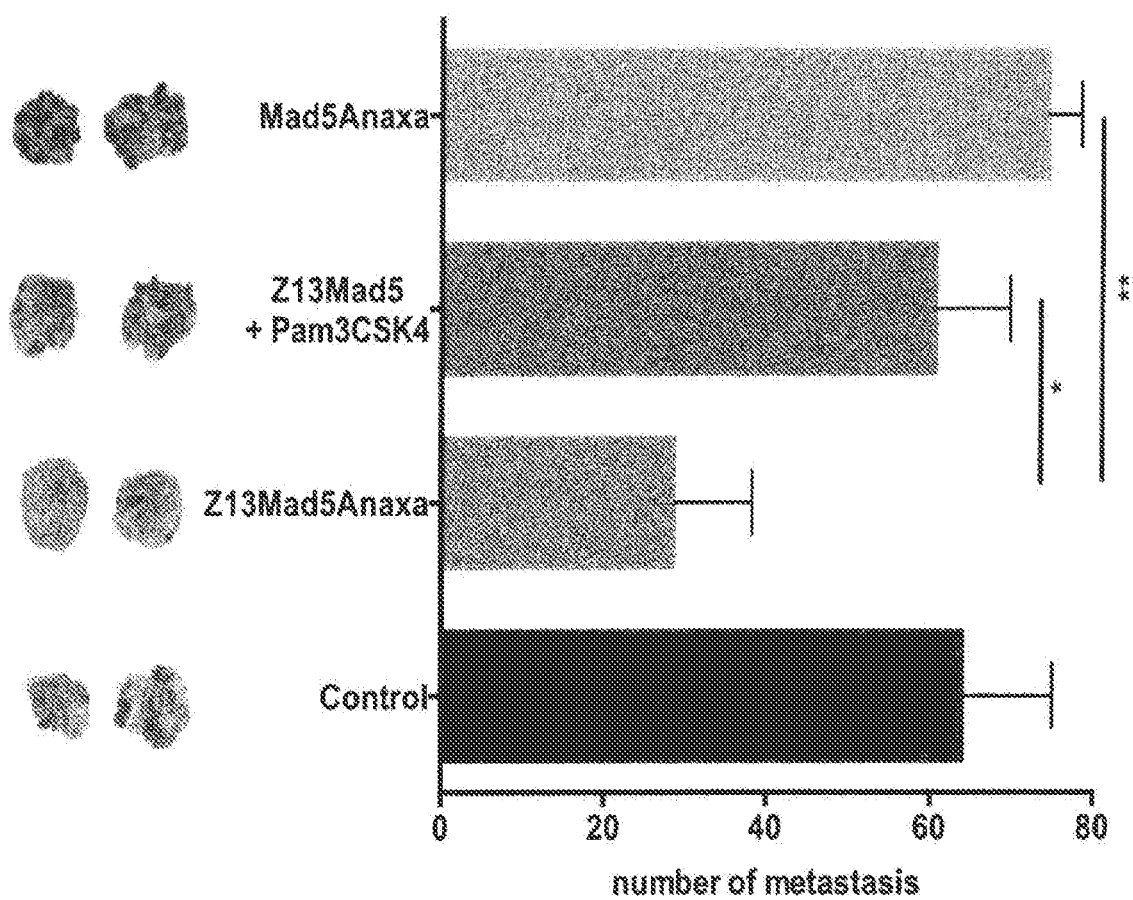

FIG. 33 shows for Example 19 the number of metastasis in a lung metastasis model with semitherapeutic settings. Briefly, C57BL/6 mice were implanted i.v. with $1 \times 10^5$ B16-OVA melanoma tumor cells and vaccinated twice (do and d9) by subcutaneous injection of 0.5 nmol of Z13Mad5Anaxa, Mad5Anaxa or Z13Mad5+Pam3CSK4 (equimolar to Anaxa) s.c. in the right flank. Mice were euthanized at day 21 and lung recovered. Number of metastasis foci was counted for each lung. *, p<0.05; **, p<0.01 (Unpaired t-test).

Figure 34:
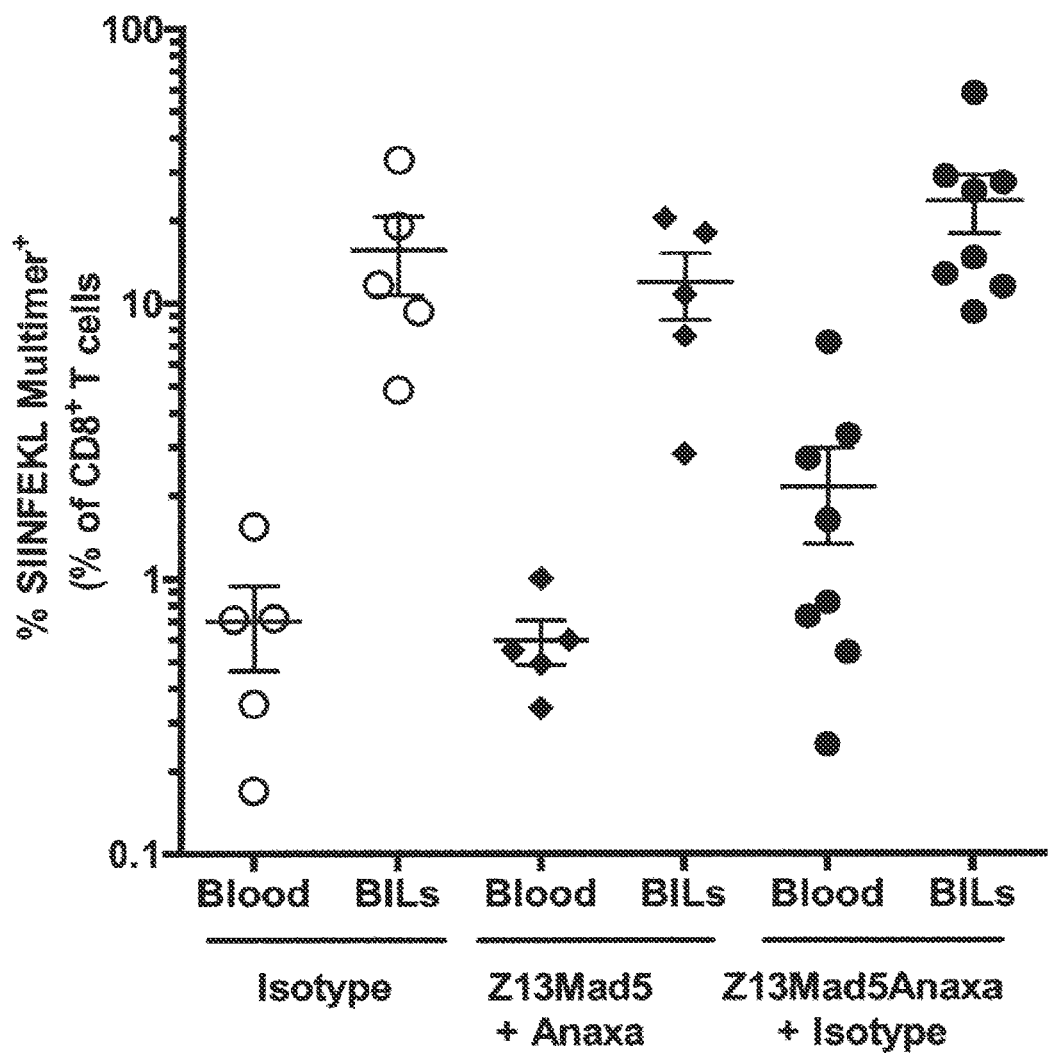

FIG. 34 shows for Example 20 the quantification of SIINFEKL-specific CD8 T cells in a Quad-Gl261 glioblastoma model. Briefly, C57BL/6 mice were implanted i.e. with $5 \times 10^5$ Gl261-Quad tumor cells and vaccinated twice (d7 and 21) by s.c. injection of 2 nmol of Z13Mad5Anaxa or 2 nmol of Z13Mad5 and 2 nmol of Anaxa. SIINFEKL-specific CDS T cells were quantified in blood and in BILs at d28 by multimer staining (5-8 mice per group).

Figure 35:
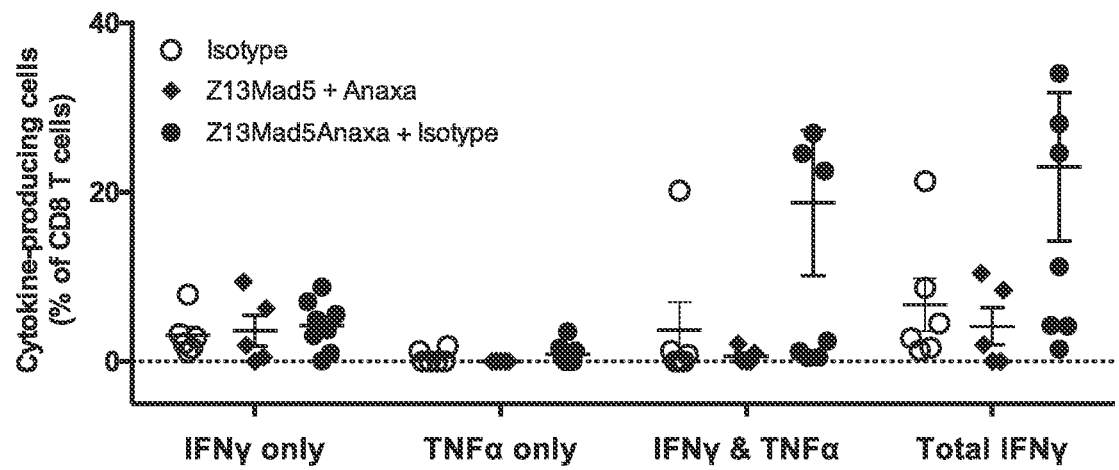

FIG. 35 shows for Example 20 the cytokine secretion. Briefly, C57BL/6 mice were implanted i.e. with $5 \times 10^5$ Gl261-Quad tumor cells and vaccinated twice (d7 and 21) by s.c. injection of 2 nmol of Z13Mad5Anaxa or 2 nmol of Z13Mad5 and 2 nmol of Anaxa. BILs were isolated and cultured during 6 h with matured BMDCs loaded or not with SlINFEKL peptide in presence of BrefeldinA before intracellular staining for cytokines. % of CD8 T cells secreting cytokine (5-8 mice per group).

Figure 36:
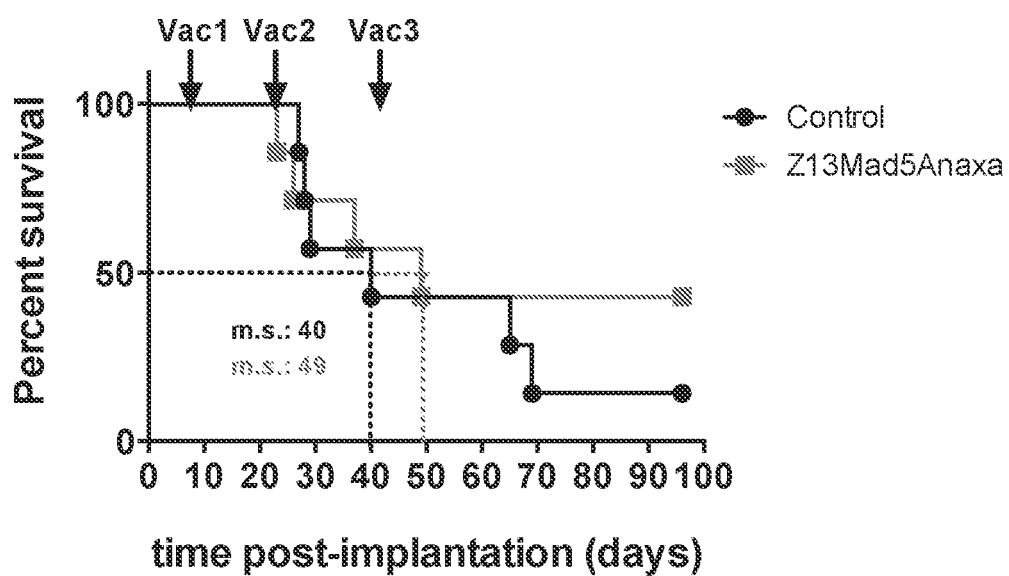

FIG. 36 shows for Example 21 the effect of Z13Mad5Anaxa on survival in the Quad-Gl261 glioblastoma model. Briefly, C57BL/6 mice were implanted i.e. with $5 \times 10^5$ Gl261-Quad tumor cells and vaccinated three times (d7, d21 and d35) by s.c. injection of 2 nmol of Z13Mad5Anaxa. Mice were weight daily and euthanized when weight loss reached more than 15%.

Figure 37A:
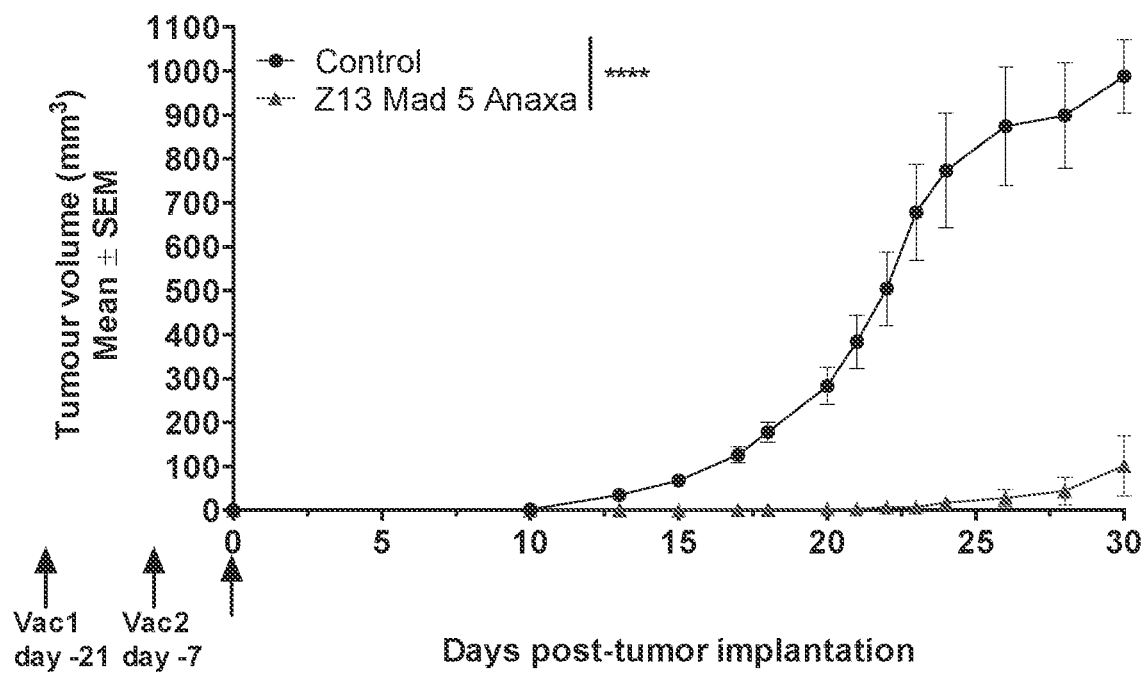
Figure 37B:
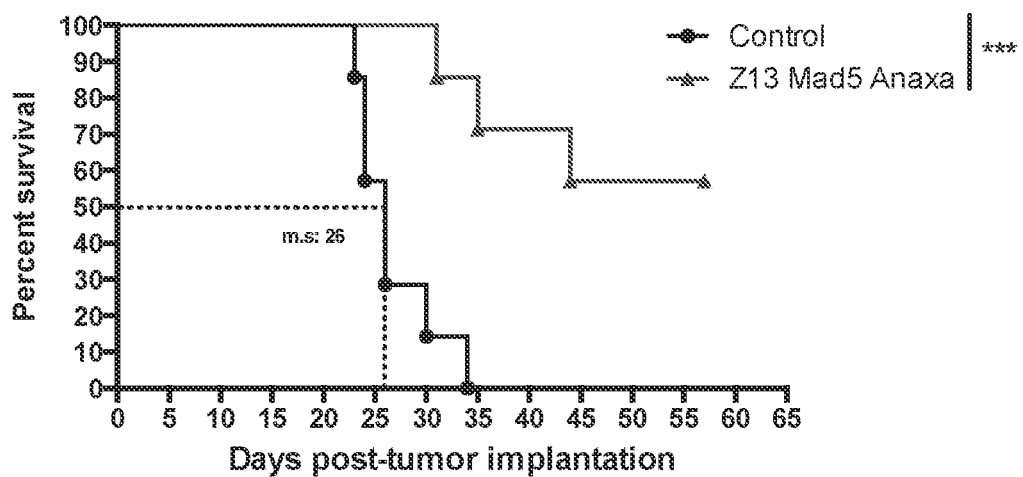

FIG. 37A-B shows for Example 22 the effect of Z13Mad5Anaxa on tumor growth and survival in subcutaneous EG7-OVA tumor model in a prophylactic setting. Briefly, C57BL/6 mice were vaccinated twice (d-21 and d-7) by s.c. injection of 0.5 nmol of Z13Mad5Anaxa in the right flank and then implanted at day0 s.c. with $3 \times 10^5$ EG7-OVA tumor cells in the left flank. Tumor size was measured with a caliper. (A) Tumor growth of 7 mice per group (mean±SEM); **, p<0.0001 (2-way Anova test at day 30). (B) Survival curve of 7 mice per group. Median survival is indicated on the graph (m.s.). *, p<0.001 (Log-rank test).

Figure 38A:
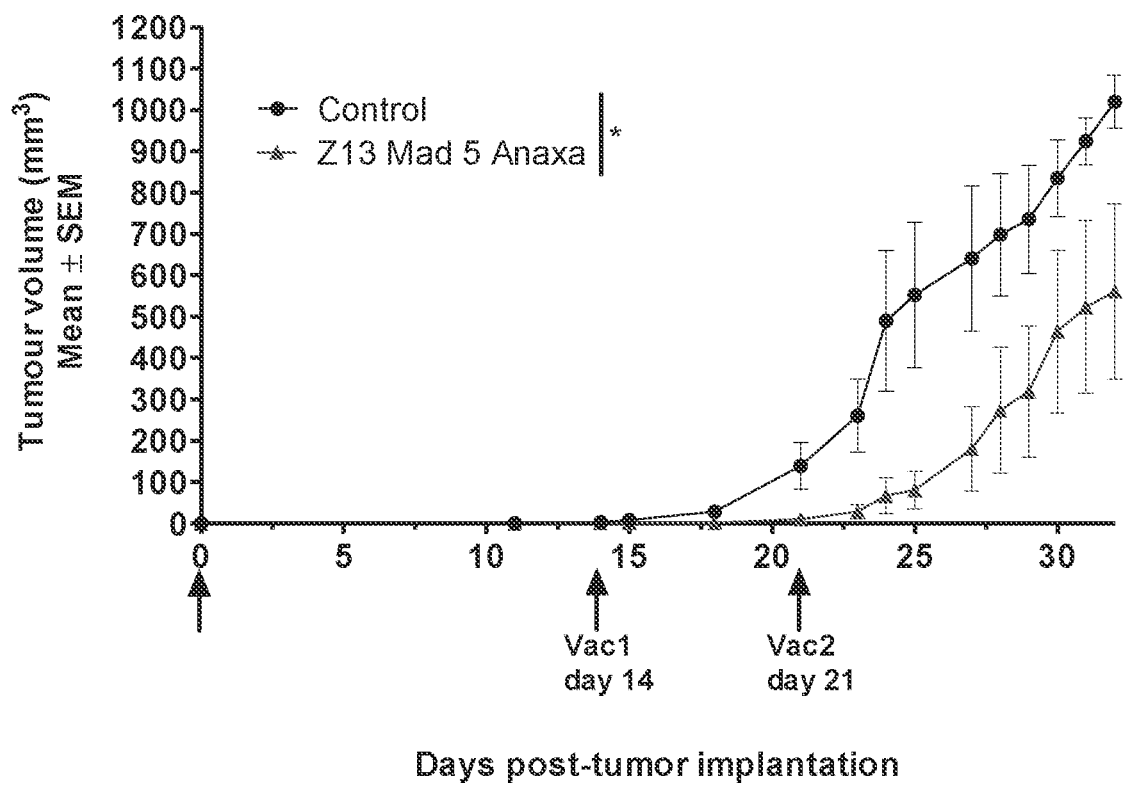
Figure 38B:
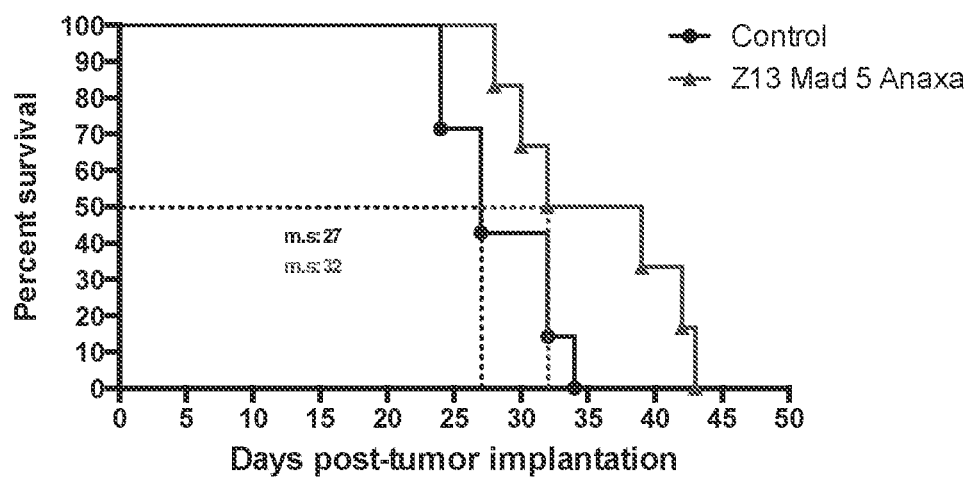

FIG. 38A-B shows for Example 23 the effect of Z13Mad5Anaxa on tumor growth and survival in subcutaneous B16-OVA tumor model in a therapeutic setting on an established tumor. Briefly, C57BL/6 mice were implanted s.c. with $1 \times 10^5$ B16-OVA tumor cells in the left flank and vaccinated twice (d14 and d21) by s.c. injection of 0.5 nmol of Z13Mad5Anaxa in the right flank. (A) Tumor growth of 7 mice per group (mean±SEM); *, p<0.05 (2-way Anova test at day 32). (B) Survival curve of 7 mice per group. Median survival is indicated on the graph (m.s.).

Figure 39A:
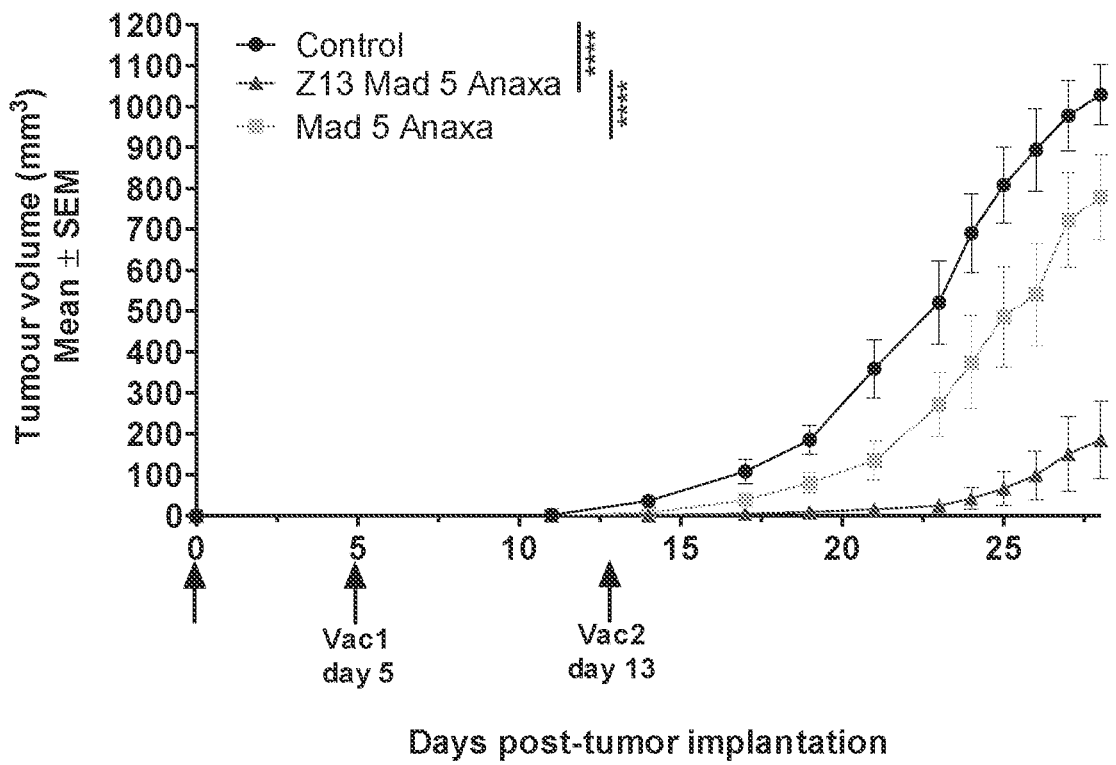
Figure 39B:
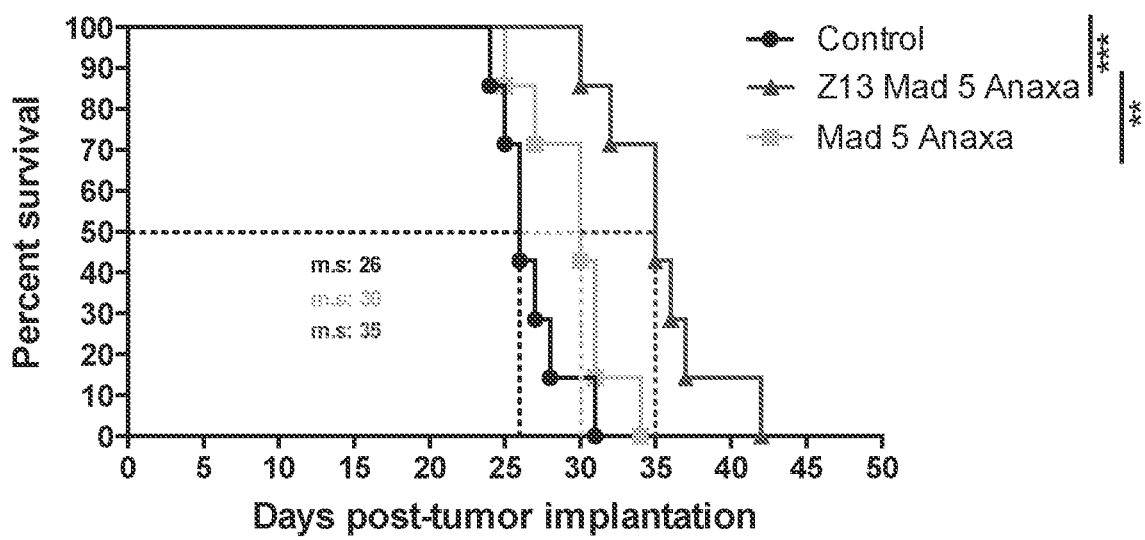

FIG. 39A-B shows for Example 24 the effect of the CPP in Z13Mad5Anaxa on tumor growth and survival in subcutaneous EG7-OVA tumor model. Briefly, C57BL/6 mice were implanted at day0 s.c. with 3×105 EG7-OVA tumor cells in the left flank and then vaccinated twice (d5 and d13) by s.c. injection of 0.5 nmol of Z13Mad5Anaxa or Mad5Anaxa in the right flank. Tumor size was measured with a caliper. (A) Tumor growth of 7 mice per group (mean±SEM); \*\*\*\*, p<0.0001. (B) Survival curve of 7 mice per group. Median survival is indicated on the graph (m.s.). \*, p<0.01; \*\*, p<0.001.

Figure 40A:
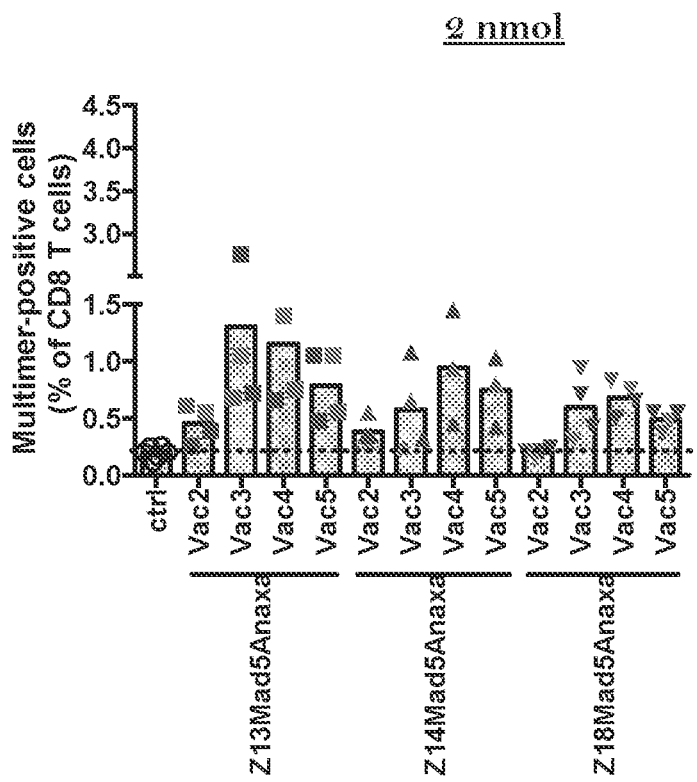
Figure 40B:
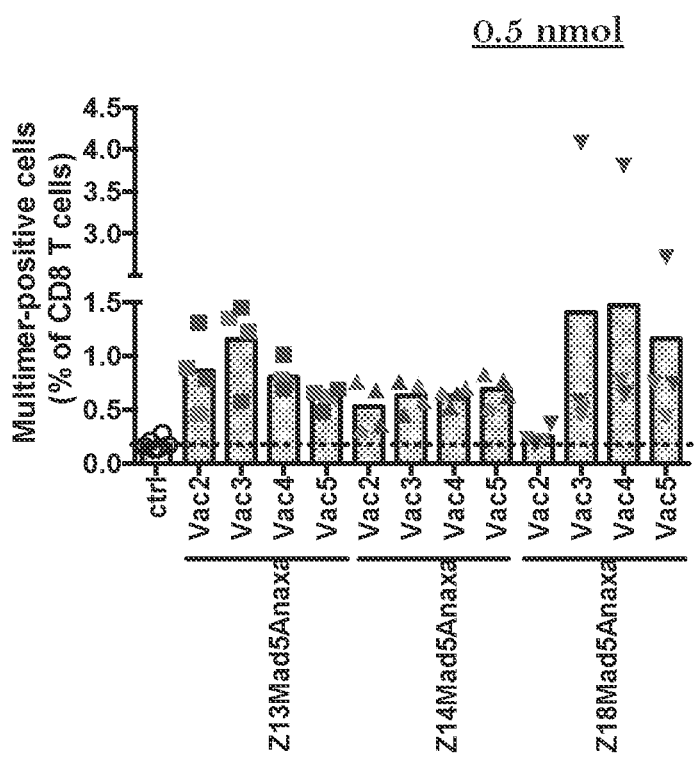

FIG. 40A-B shows for Example 25 the effect of complexes having different CPPs on the immune response. C57BL/6 mice were vaccinated five times (Wk0, Wk2, Wk4, Wk6 and Wk8) s.c. with either 2 nmol (A) or 0.5 nmol (B) of Z13Mad5Anaxa, Z14Mad5Anaxa or Z18Mad5Anaxa. Mice were bled 7 days after the $2^{nd}$, $3^{rd}$, $4^{th}$ and $5^{th}$ vaccination and multimer staining was performed (one experiment with 4 mice per group). \*, p<0.05 between vaccinated versus naïve mice at each time point except after Vac2 for Z18Mad5Anaxa-vaccinated mice.

Figure 41A:
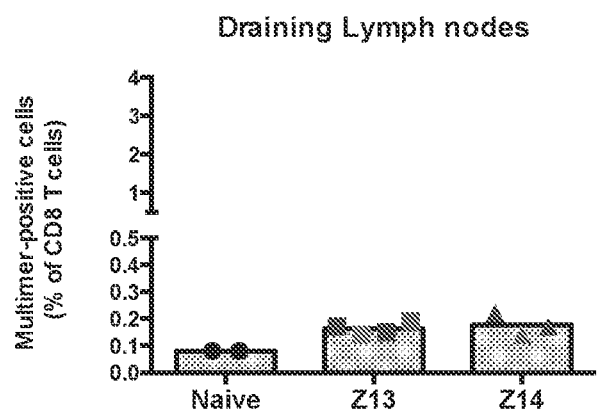
Figure 41B:
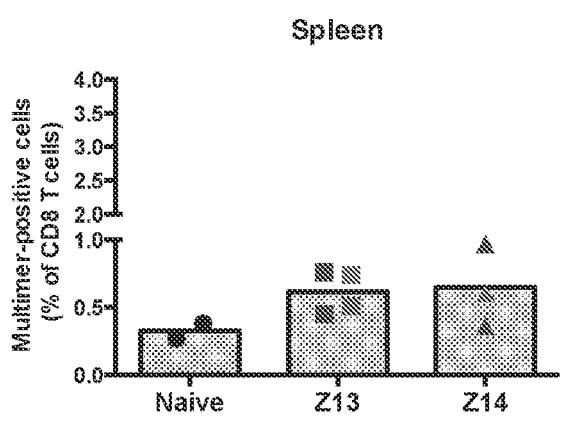
Figure 41C:
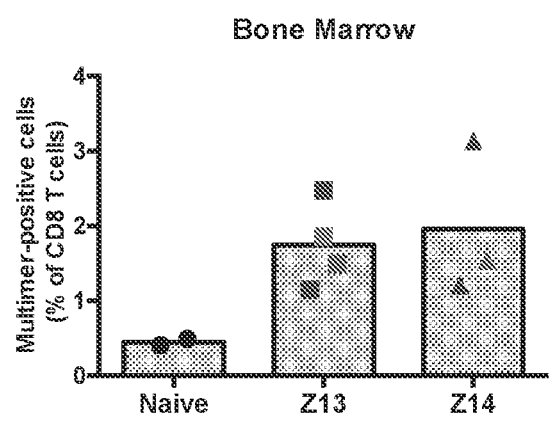

FIG. 41A-C shows for Example 26 the effect of complexes having different CPPs on CD8 T cells in spleen (A), draining lymph nodes (B) and bone marrow (C). C57BL/6 mice were vaccinated five times (Wk0, Wk2, Wk4, Wk6 and Wk8) s.c. with 2 nmol of Z13Mad5Anaxa or Z14Mad5Anaxa. Nine days after the $5^{th}$ vaccination, mice were euthanized, organs recovered and multimer staining was performed.

Figure 42A:
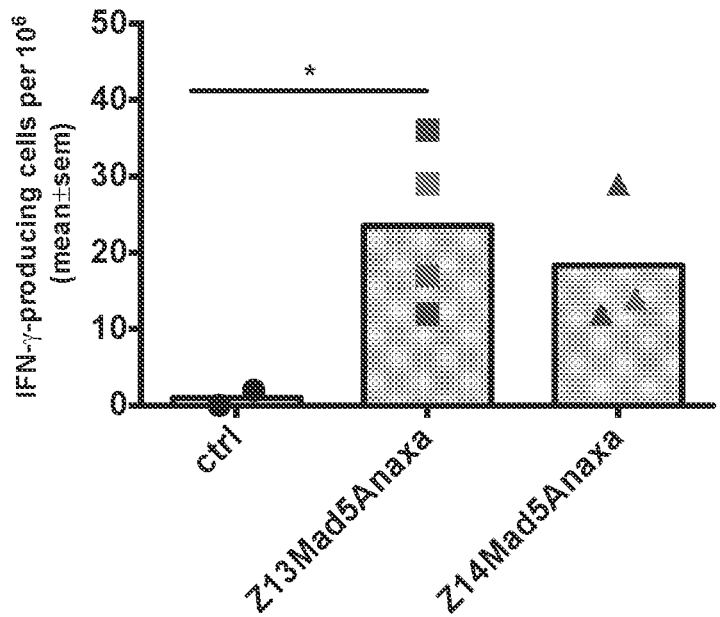
Figure 42B:
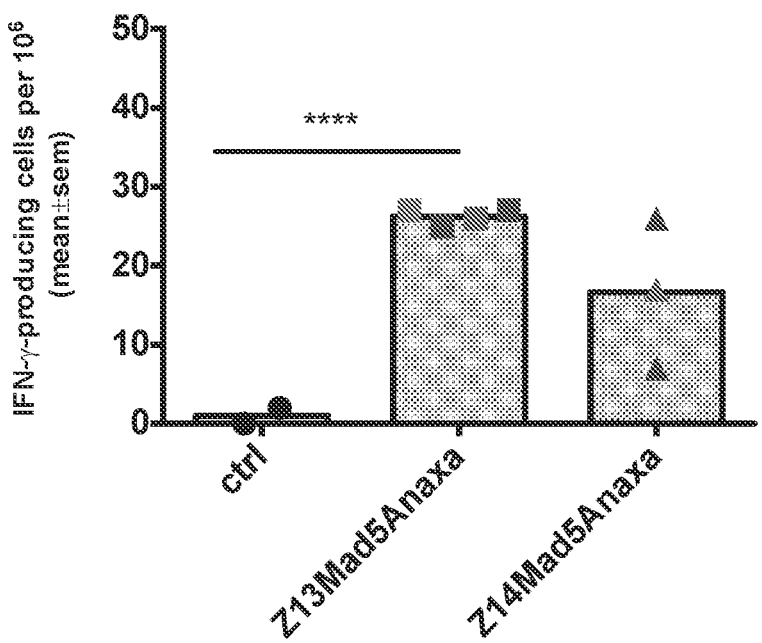

FIG. 42A-B shows for Example 26 the effect of complexes having different CPPs on T cells in spleen (CD8 T cell response (A) and CD4 T cell response (B)). C57BL/6 mice were vaccinated five times (Wk0, Wk2, Wk4, Wk6 and Wk8) s.c. with 2 nmol of Z13Mad5Anaxa or Z14Mad5Anaxa. (A) nine days after the $5^{th}$ vaccination, Elispot assay was performed on spleen cells stimulated with SIINFEKL OVACD8 peptide. (B) nine days after the $5^{th}$ vaccination, Elispot assay was performed on spleen cells stimulated with OVACD4 peptide.

Figure 43:
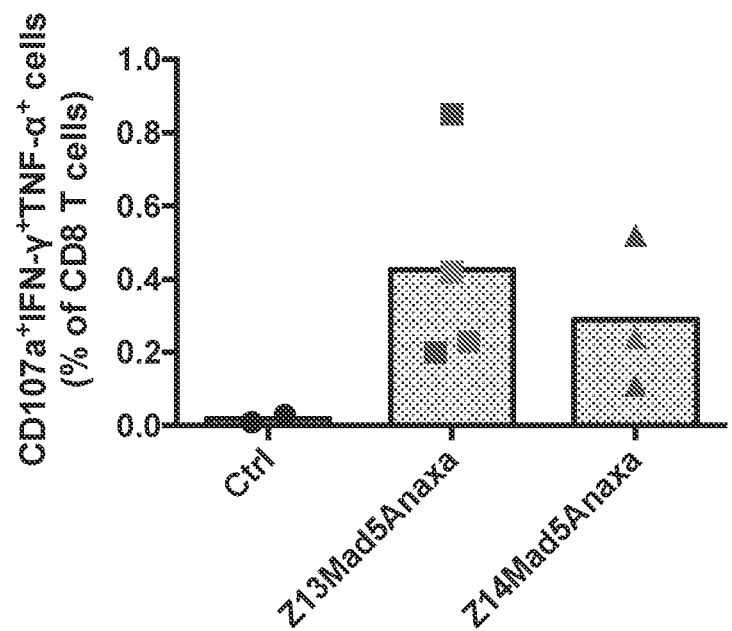

FIG. 43 shows for Example 26 the effect of complexes having different CPPs on CD8 T cell effector function. C57BL/6 mice were vaccinated five times (Wk0, Wk2, Wk4, Wk6 and Wk8) s.c. with 2 nmol of Z13Mad5Anaxa or Z14Mad5Anaxa. Nine days after the $5^{th}$ vaccination, intracellular staining was performed on spleen cells stimulated with SIINFEKL OVACD8 peptide.

Figure 44A:
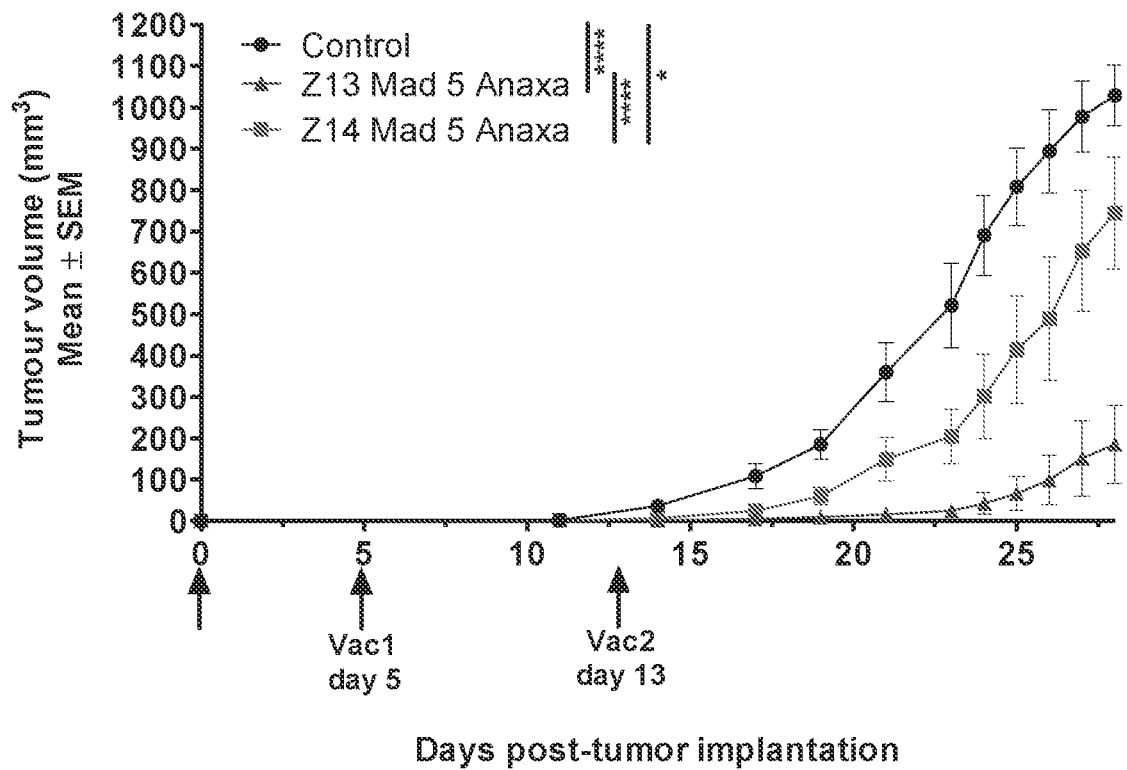
Figure 44B:
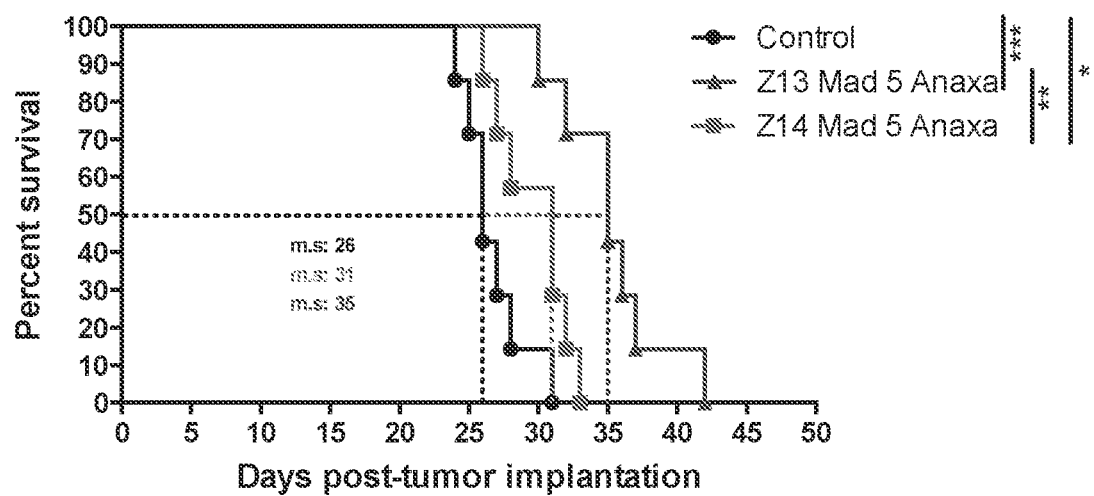

FIG. 44A-B shows for Example 27 the effect of complexes having different CPPs on tumor growth (A) and survival rates (B). C57BL/6 mice were implanted s.c. with $3 \times 10^5$ EG7-OVA tumor cells in the left flank and vaccinated twice (d5 and d13) by s.c. injection of 0.5 nmol of Z13Mad5Anaxa or Z14Mad5Anaxa in the right flank. (A) Tumor growth of 7 mice per group (mean±SEM); \*, p<0.05; \*\*\*\*, p<0.000 (2-way Anova test at day 28). (B) Survival curve of 7 mice per group. Median survival is indicated on the graph (m.s.). \*, p<0.05; \*\*, p<0.01; \*\*\*, p<0.001 (Log-rank test).

Figure 45A:
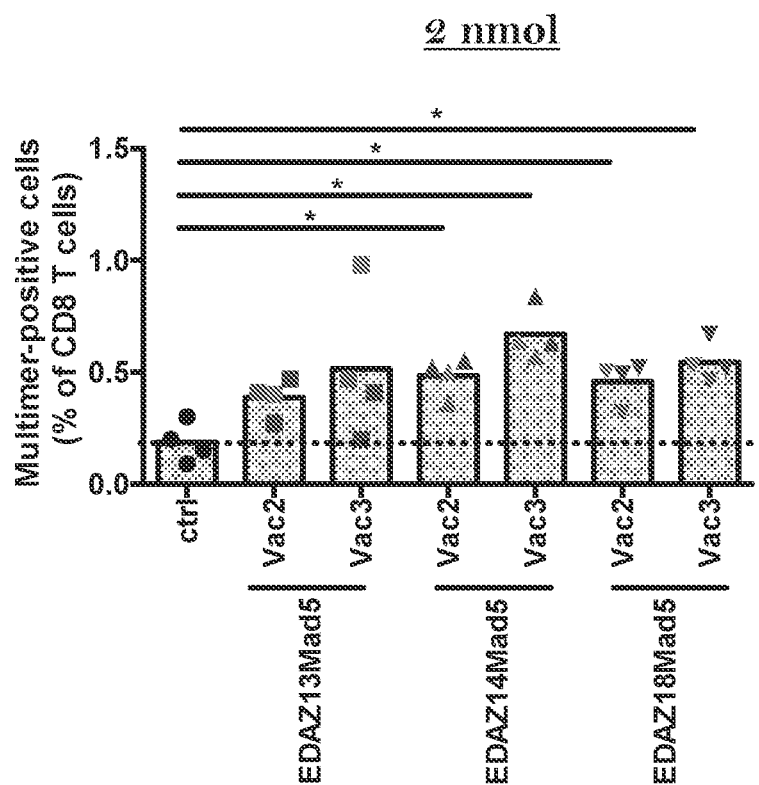
Figure 45B:
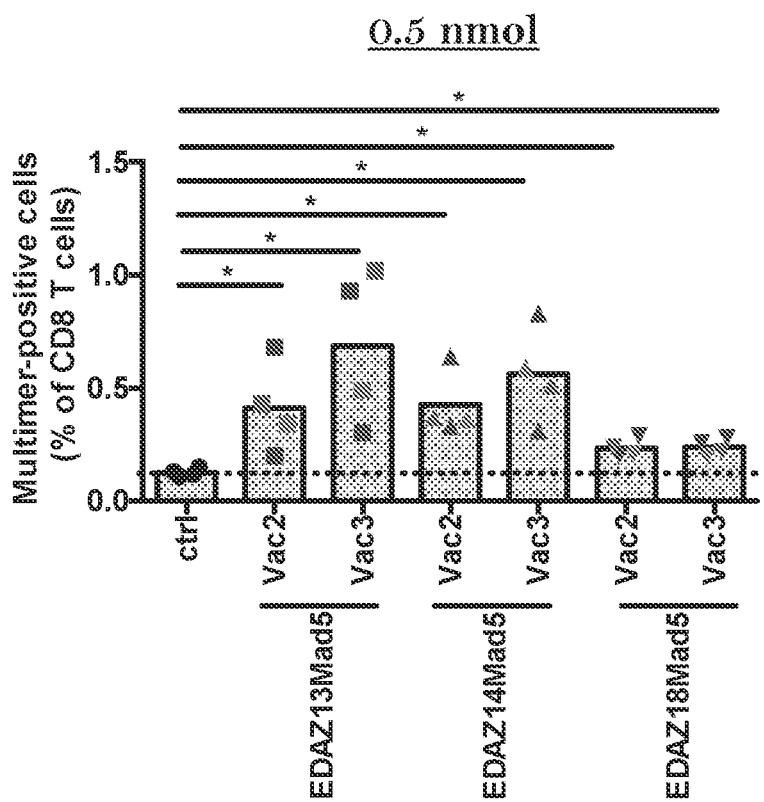
Figure 46A:
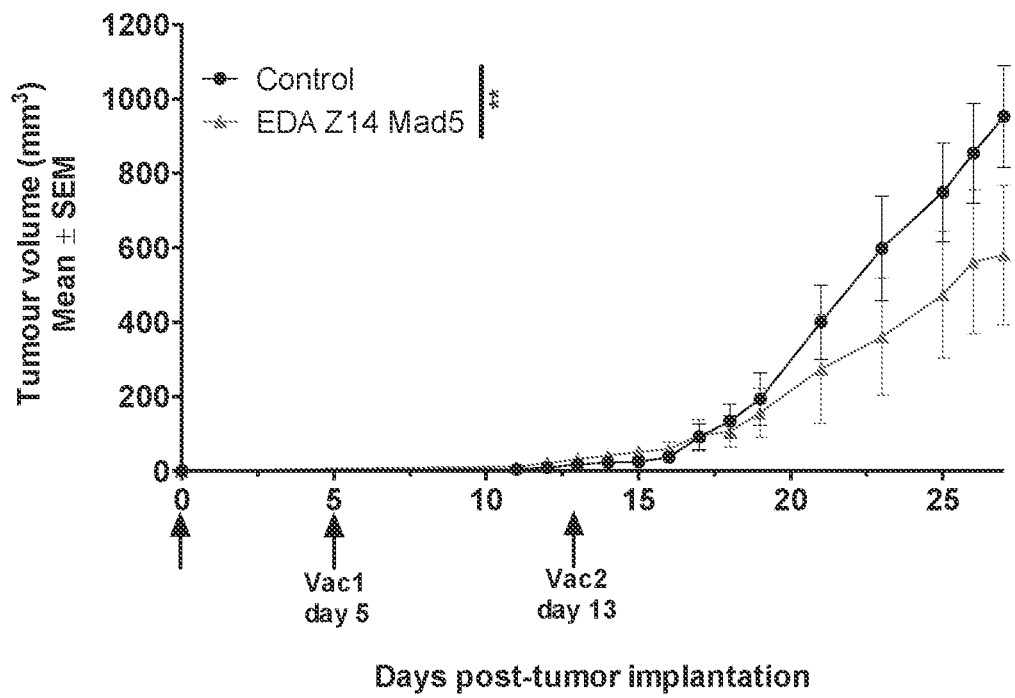
Figure 46B:
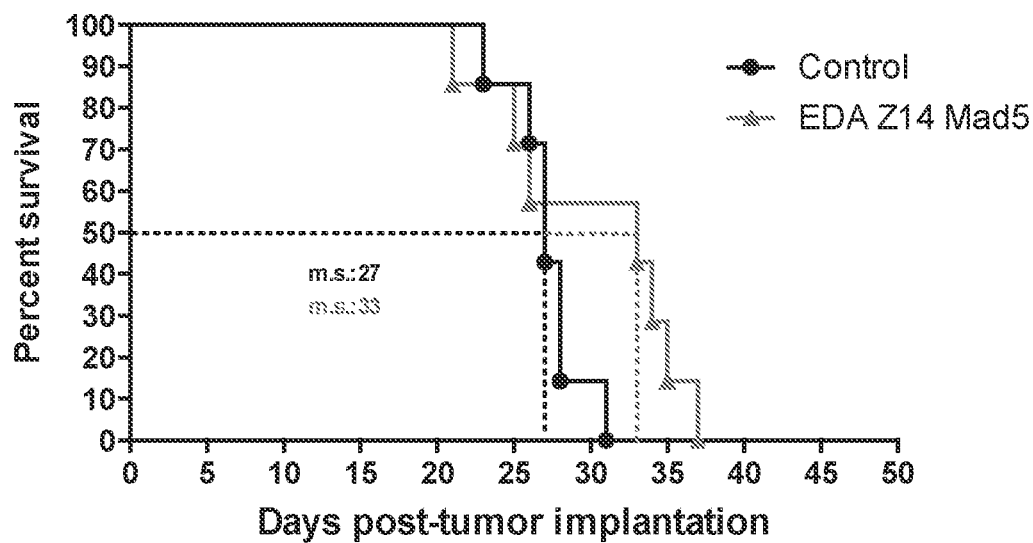

FIG. 45A-B shows for Example 28 the effect of complexes having different CPPs on the immune response. C57BL/6 mice were vaccinated three times (Wk0, Wk2 and Wk4) s.c. with 2 nmol (A) or 0.5 nmol (B) of EDAZ13Mad5, EDAZ14Mad5 or EDAZ18Mad5. Mice were bled 7 days after the $3^{rd}$ vaccination and multimer staining was performed (one experiment with 4 mice per group). \*, p<0.05 FIG. 46A-B shows for Example 29 the effect of EDAZ14Mad5 on tumor growth (A) and survival rates (B). C57BL/6 mice were implanted s.c. with $3 \times 10^5$ EG7-OVA tumor cells in the left flank and vaccinated twice (d5 and d13) by s.c. injection of 2 nmoles of EDAZ14Mad5 in the right flank. Left panel: Tumor growth of 7 mice per group (mean±SEM); \*\*, p<0.01 (2-way Anova test at day 27). Right panel: Survival curve of 7 mice per group. Median survival is indicated on the graph (m.s.).

Figure 47A:
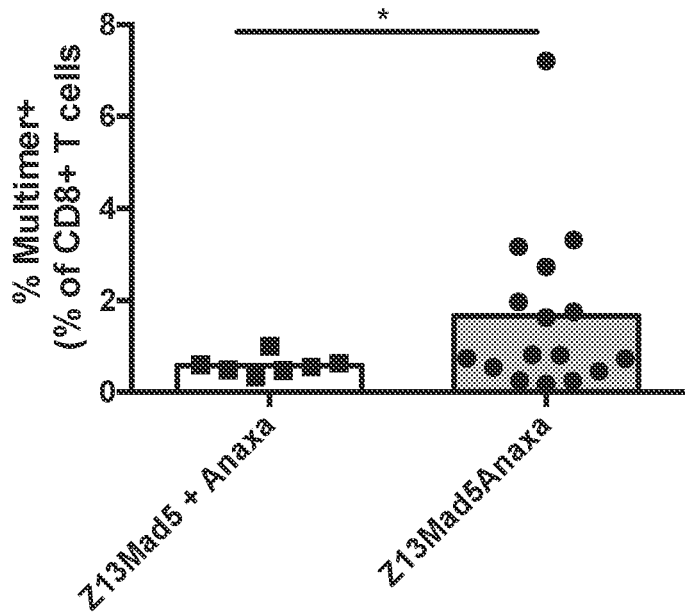
Figure 47B:
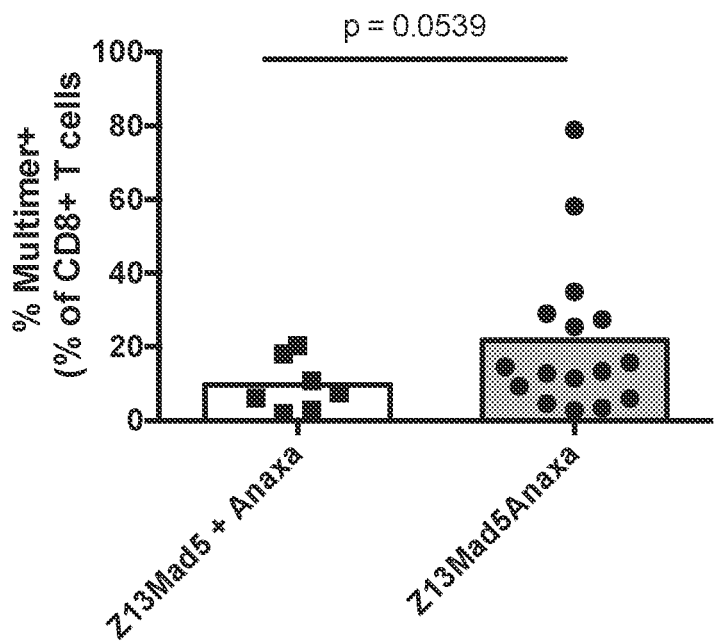

FIG. 47A-B shows for Example 30 the quantification of SIINFEKL-specific CD8 T cells in a Quad-Gl261 glioblastoma model. Briefly, C57BL/6 mice were implanted i.e. with $5 \times 10^5$ Gl261-Quad tumor cells and vaccinated twice (d7 and 21) by s.c. injection of 2 nmol of Z13Mad5Anaxa or 2 nmol of Z13Mad5 and 2 nmol of Anaxa. SIINFEKL-specific CD8 T cells were quantified in blood (A) and in BILs (B) at d28 by multimer staining (7-16 mice per group).

Figure 48:
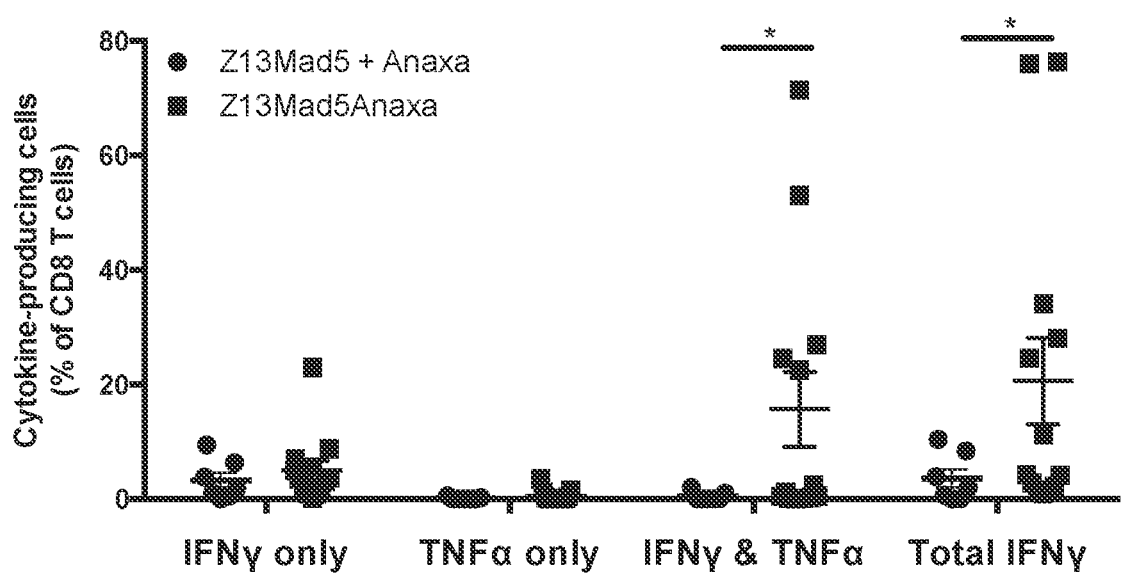

FIG. 48 shows for Example so the cytokine secretion. Briefly, C57BL/6 mice were implanted i.e. with $5 \times 10^5$ Gl261-Quad tumor cells and vaccinated twice (d7 and 21) by s.c. injection of 2 nmol of Z13Mad5Anaxa or 2 nmol of Z13Mad5 and 2 nmol of Anaxa. BILs were isolated and cultured during 6 h with matured BMDCs loaded or not with SIINFEKL peptide in presence of BrefeldinA before intracellular staining for cytokines. % of CD8 T cells secreting cytokine (7-16 mice per group).

Figure 49A:
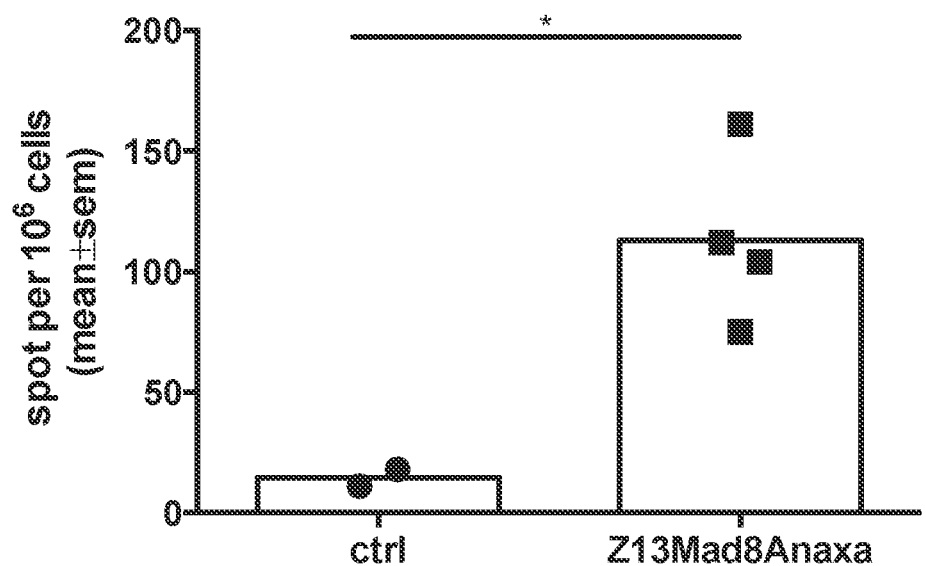
Figure 49B:
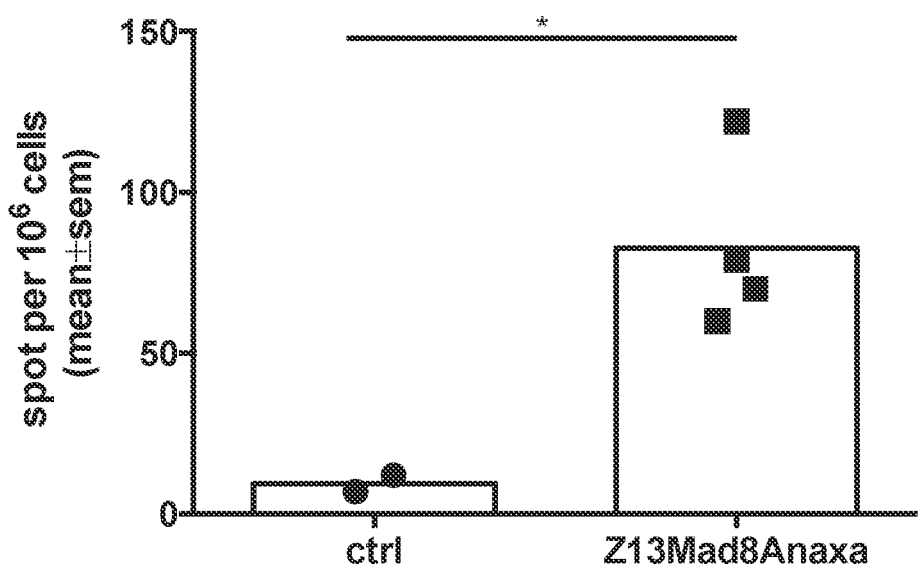

FIG. 49A-B shows for Example si the effect of Z13Mad8Anaxa on T cells in spleen (CD8 T cell response (A) and CD4 T cell response (B)). C57BL/6 mice were vaccinated four times (Wk0, Wk2, Wk4 and Wk6) s.c. with 2 nmol of Z13Mad8Anaxa. (A) one week after the $4^{th}$ vaccination, Elispot assay was performed on spleen cells stimulated gp70CD8 peptide. (B) one week after the $4^{th}$ vaccination, Elispot assay was performed on spleen cells stimulated with gp70CD4 peptide.

Figure 50A:
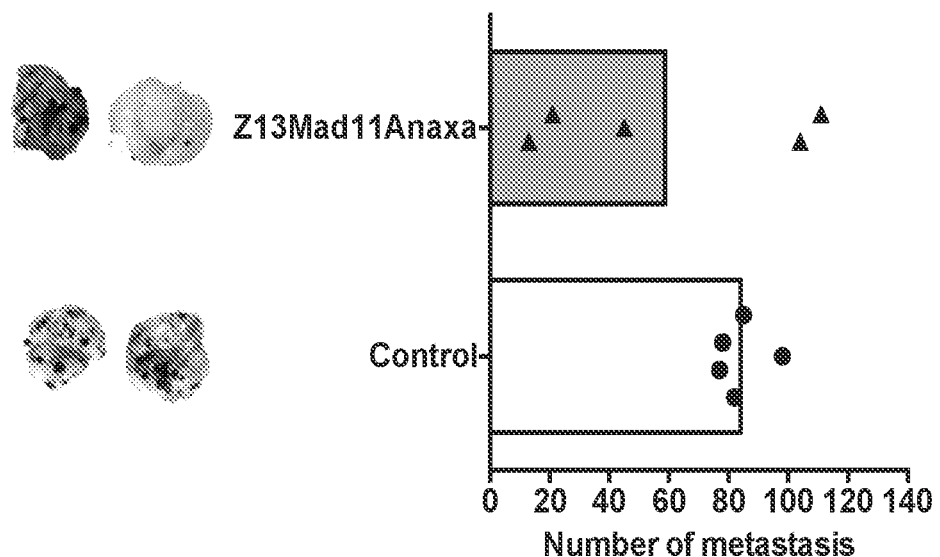
Figure 50B:
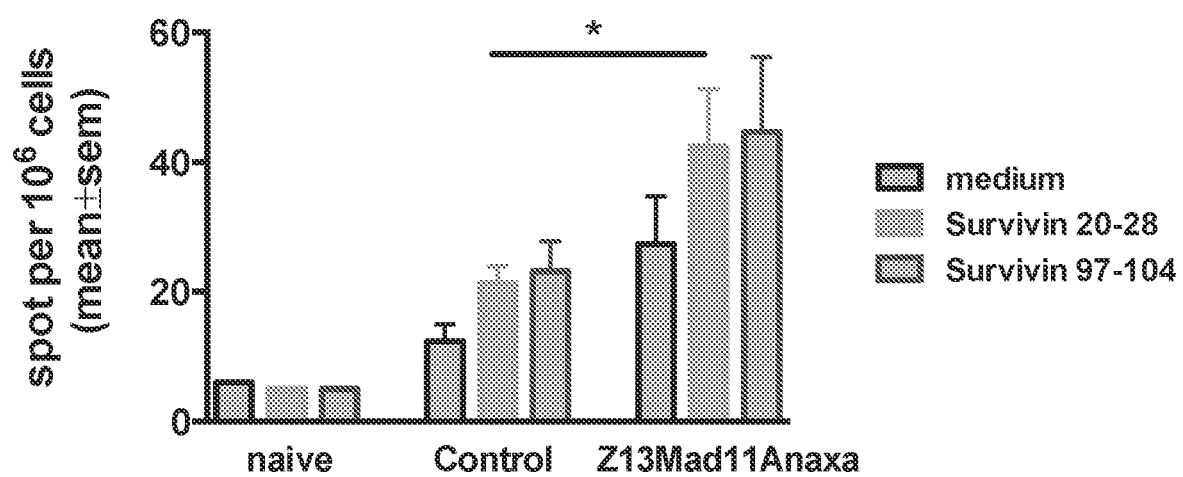

FIG. 50A-B shows for Example 32 the effect of Z13Mad11Anaxa on the number of metastasis in the B16 lung metastasis model (A) and on the T cell response in spleen (B). C57BL/6 mice were vaccinated two times (day0, day10) s.c. with 1 nmol of Z13Mad11Anaxa.

Figure 51:
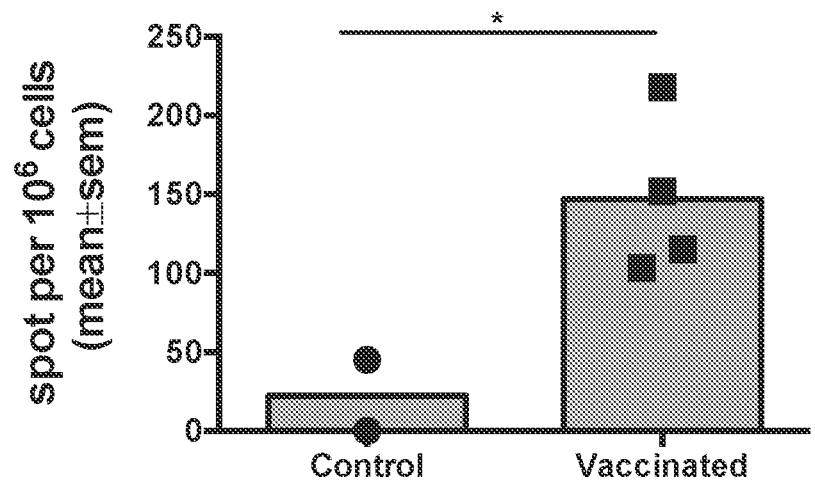

FIG. 51 shows for Example 33 the effect of Z13Mad9Anaxa on T cells in spleen (CD8 T cell response. C57BL/6 mice were vaccinated four times (Wk0, Wk2, Wk4 and Wk6) s.c. with 2 nmol of Z13Mad9Anaxa. One week after the $4^{th}$ vaccination, Elispot assay was performed on spleen cells stimulated with adpgk peptide.

Figure 52:
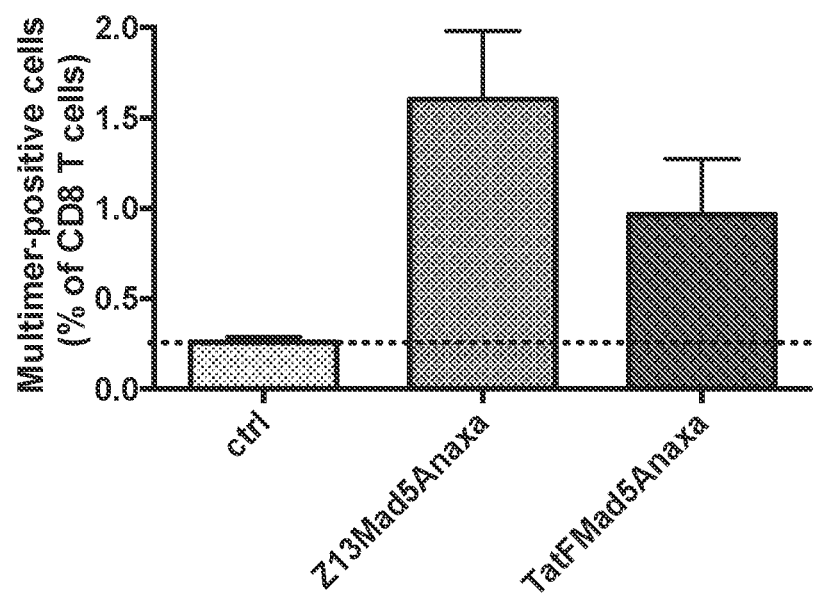

FIG. 52 shows for Example 34 the effect of complexes having different CPPs on the immune response. C57BL/6 mice were vaccinated two times (Wk0 and Wk2) s.c. with 2 nmol of either Z13Mad5Anaxa or TatFMad5Anaxa. Mice were bled 7 days after the $2^{nd}$ vaccination and multimer staining was performed (one experiment with 8 mice per group).

Figure 53:
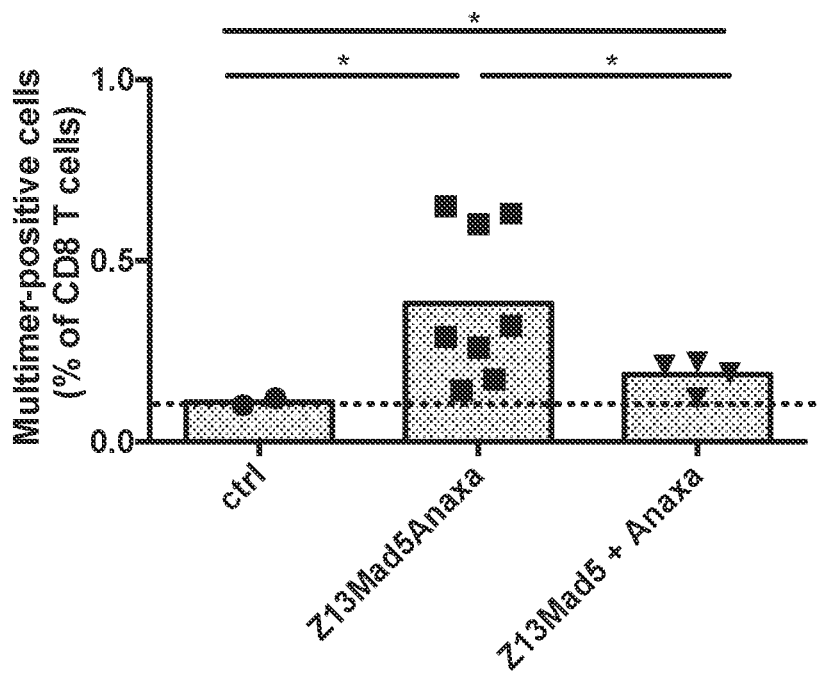

FIG. 53 shows for Example 35 the quantification of SIINFEKL-specific CD8 T cells in naïve mice. Briefly, C57BL/6 mice were vaccinated once (day0) by s.c. injection of 2 nmol of Z13Mad5Anaxa (group "Z13Mad5Anaxa") or 2 nmol of Z13Mad5 and 2 nmol of Anaxa (group "Z13Mad5+Anaxa"). SIINFEKL-specific CD8 T cells were quantified in blood at d7 by multimer staining (4-8 mice per group).

Figure 54:
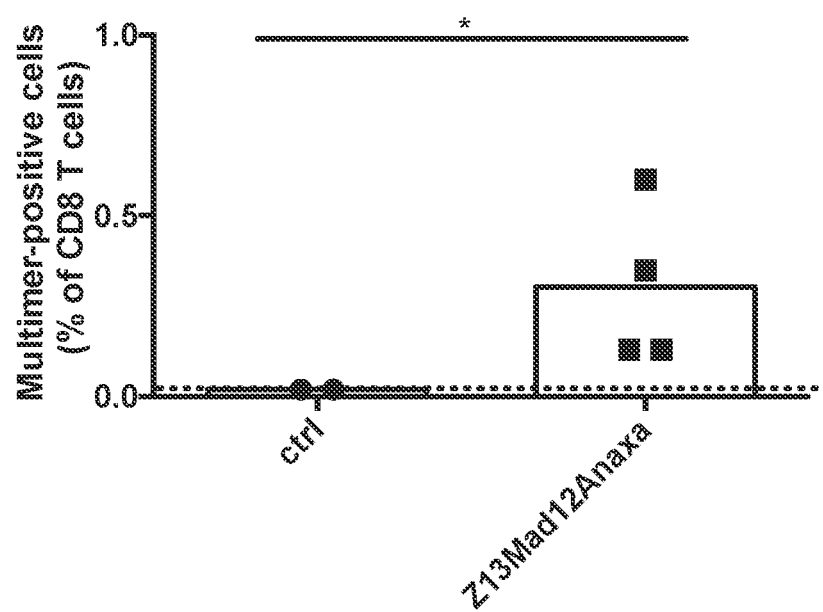

FIG. 54 shows for Example 36 the effect of Z13Mad12Anaxa on T cells in blood (CD8 T cell response). C57BL/6 mice were vaccinated twice (Wk0 and Wk2) s.c. with 2 nmol of Z13Mad12Anaxa. One week after the 2nd vaccination, multimer staining for the neoantigen reps1 was performed on blood cells.

Figure 55:
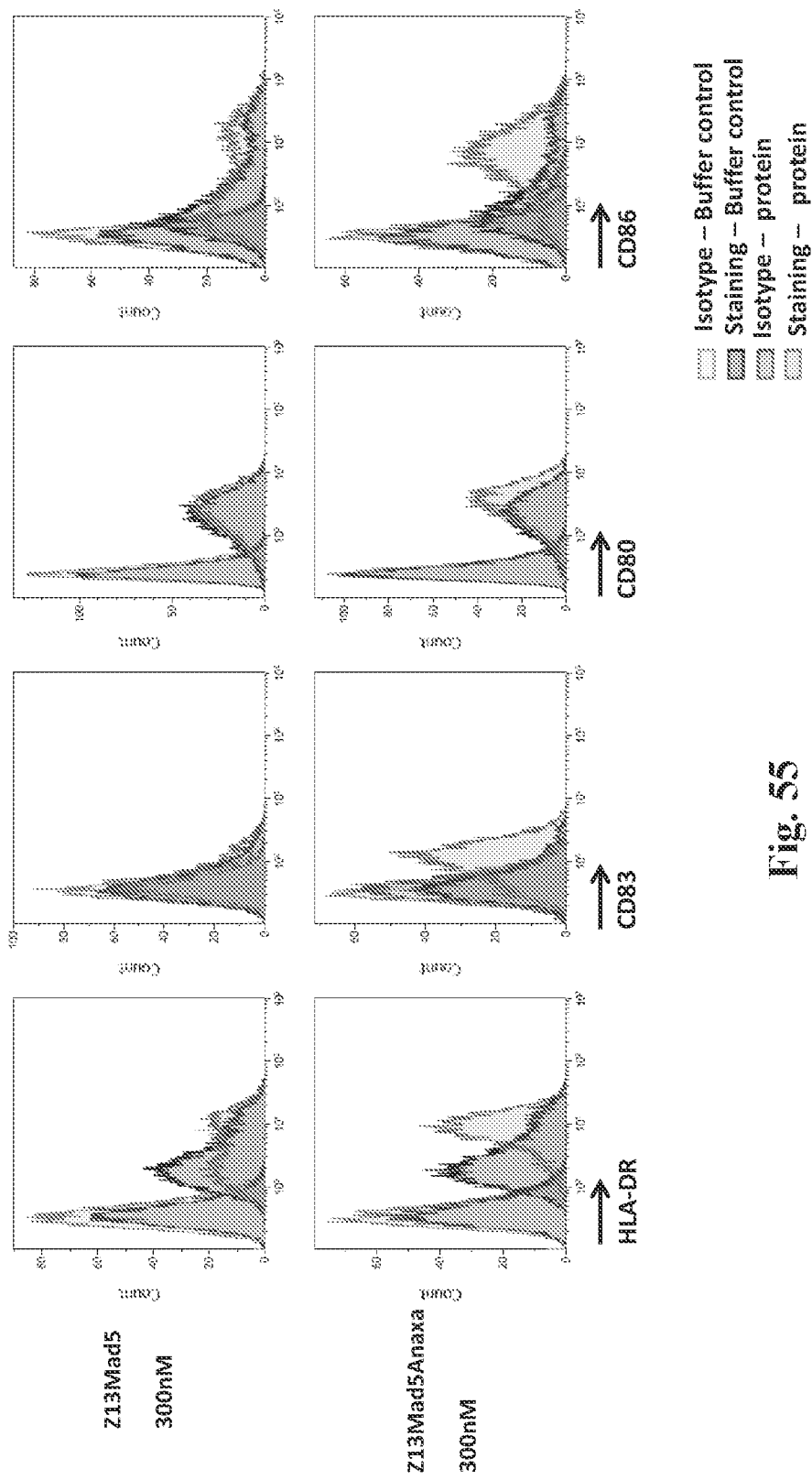

FIG. 55 shows for Example 37 expression of activation marker HLA-DR, CD83, CD80 and CD86 (from left to right) by human blood monocyte-derived dendritic cells (DCs) from one single buffy. The DCs were stimulated with 300 nM of Z13Mad5Anaxa (lower panels) or Z13Mad5 (upper panels) during 48 h. Isotype staining for each condition was also performed as shown.

DETAILED DESCRIPTION

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of" The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x ±10%.

Complexes for Use According to the Present Invention

In a first aspect the present invention provides a complex comprising:
  a) a cell penetrating peptide;
  b) at least one antigen or antigenic epitope; and
  c) at least one TLR peptide agonist,
wherein the components a)-c), i.e. the cell penetrating peptide, the at least one antigen or antigenic epitope and the at least one TLR peptide agonist, are covalently linked, for use in the prevention and/or treatment of colorectal cancer.

Such a complex for use according to the present invention provides simultaneous (i) stimulation of multi-epitopic cytotoxic T cell-mediated immunity, (ii) induction of $T_h$ cells and (iii) promotion of immunological memory. Thereby, a complex for use according to the present invention provides a potent vaccine, in particular having improved anti-tumor activity.

Preferably, the complex for use according to the present invention is a polypeptide or a protein, in particular a recombinant polypeptide or a recombinant protein, preferably a recombinant fusion protein or a recombinant fusion polypeptide. The term "recombinant" as used herein means that it (here: the polypeptide or the protein) does not occur naturally. Accordingly, the complex for use according to the present invention, which is a recombinant polypeptide or a recombinant protein, typically comprises components a) to c), wherein components a) to c) are of different origins, i.e. do not naturally occur in this combination.

In the context of the present invention, i.e. throughout the present application, the terms "peptide", "polypeptide", "protein" and variations of these terms refer to peptide, oligopeptide, oligomer or protein including fusion protein, respectively, comprising at least two amino acids joined to each other preferably by a normal peptide bond, or, alternatively, by a modified peptide bond, such as for example in the cases of isosteric peptides. A peptide, polypeptide or protein can be composed of L-amino acids and/or D-amino acids. Preferably, a peptide, polypeptide or protein is either (entirely) composed of L-amino acids or (entirely) of D-amino acids, thereby forming "retro-inverso peptide sequences". The term "retro-inverso (peptide) sequences" refers to an isomer of a linear peptide sequence in which the direction of the sequence is reversed and the chirality of each amino acid residue is inverted (see e.g. Jameson et al., Nature, 368, 744-746 (1994); Brady et al., Nature, 368, 692-693 (1994)). In particular, the terms "peptide", "polypeptide", "protein also include "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. In particular, a peptide, polypeptide or protein can comprise amino acids other than the 20 amino acids defined by the genetic code in addition to these amino acids, or it can be composed of amino acids other than the 20 amino acids defined by the genetic code. In particular, a peptide, polypeptide or protein in the context of the present invention can equally be composed of amino acids modified by natural processes, such as post-translational maturation processes or by chemical processes, which are well known to a person skilled in the art.

Such modifications are fully detailed in the literature. These modifications can appear anywhere in the polypeptide: in the peptide skeleton, in the amino acid chain or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" preferably include for example lipopeptides, lipoproteins, glycopeptides, glycoproteins and the like.

However, in a particularly preferred embodiment, the complex for use according to the present invention is a "classical" peptide, polypeptide or protein, whereby a "classical" peptide, polypeptide or protein is typically composed of amino acids selected from the 20 amino acids defined by the genetic code, linked to each other by a normal peptide bond.

If the complex for use according to the present invention is a polypeptide or a protein, it is preferred that it comprises at least 50, at least 60, at least 70, preferably at least 80, at least 90, more preferably at least 100, at least 110, even more preferably at least 120, at least 130, particularly preferably at least 140, or most preferably at least 150 amino acid residues.

Component a)—Cell-Penetrating-Peptide

The CPP allows for efficient delivery, i.e. transport and loading, in particular of at least one antigen or antigenic epitope, into the antigen presenting cells (APCs), in particular into the dendritic cells (DCs) and thus to the dendritic cells' antigen processing machinery.

The term "cell penetrating peptides" ("CPPs") is generally used to designate short peptides that are able to transport different types of cargo molecules across plasma membrane, and, thus, facilitate cellular uptake of various molecular cargoes (from nanosize particles to small chemical molecules and large fragments of DNA). "Cellular internalization" of the cargo molecule linked to the cell penetrating peptide generally means transport of the cargo molecule across the plasma membrane and thus entry of the cargo molecule into the cell. Depending on the particular case, the cargo molecule can, then, be released in the cytoplasm, directed to an intracellular organelle, or further presented at the cell surface. Cell penetrating ability, or internalization, of the cell penetrating peptide or complex comprising said cell penetrating peptide, according to the invention can be checked by standard methods known to one skilled in the art, including flow cytometry or fluorescence microscopy of live and fixed cells, immunocytochemistry of cells transduced with said peptide or complex, and Western blot.

Cell penetrating peptides typically have an amino acid composition that either contains a high relative abundance of positively charged amino acids such as lysine or arginine or have a sequence that contains an alternating pattern of polar/charged amino acids and non-polar, hydrophobic amino acids. These two types of structures are referred to as polycationic or amphipathic, respectively. Cell-Penetrating peptides are of different sizes, amino acid sequences, and charges but all CPPs have a common characteristic that is the ability to translocate the plasma membrane and facilitate the delivery of various molecular cargoes to the cytoplasm or to an organelle of a cell. At present, the theories of CPP translocation distinguish three main entry mechanisms: direct penetration in the membrane, endocytosis-mediated entry, and translocation through the formation of a transitory structure. CPP transduction is an area of ongoing research. Cell-penetrating peptides have found numerous applications in medicine as drug delivery agents in the treatment of different diseases including cancer and virus inhibitors, as well as contrast agents for cell labeling and imaging.

Typically, cell penetrating peptides (CPPs) are peptides of 8 to 50 residues that have the ability to cross the cell membrane and enter into most cell types. Alternatively, they are also called protein transduction domain (PTDs) reflecting their origin as occurring in natural proteins. Frankel and Pabo simultaneously to Green and Lowenstein described the ability of the trans-activating transcriptional activator from the human immunodeficiency virus 1 (HIV-TAT) to penetrate into cells (Frankel, A. D. and C. O. Pabo, Cellular uptake of the tat protein from human immunodeficiency virus. Cell, 1988. 0.55(6): p. 1189-93). In 1991, transduction into neural cells of the Antennapedia homeodomain (DNA-binding domain) from Drosophila melanogaster was described (Joliot, A., et al., Antennapedia homeobox peptide regulates neural morphogenesis. Proc Natl Acad Sci USA, 1991. 88(5): p. 1864-8). In 1994, the first 16-mer peptide CPP called Penetratin, having the amino acid sequence RQIKIYFQNRRMKWKK (SEQ ID NO: 1) was characterized from the third helix of the homeodomain of Antennapedia (Derossi, D., et al., The third helix of the Antennapedia homeodomain translocates through biological membranes. J Biol Chem, 1994. 269(14): p. 10444-50), followed in 1998 by the identification of the minimal domain of TAT, having the amino acid sequence YGRKKRRQRRR (SEQ ID NO: 2) required for protein transduction (Vives, E., P. Brodin, and B. Lebleu, A truncated HIV-1 Tat protein basic domain rapidly translocates through the plasma membrane and accumulates in the cell nucleus. J Biol Chem, 1997. 272(25): p. 16010-7). Over the past two decades, dozens of peptides were described from different origins including viral proteins, e.g. VP22 (Elliott, G. and P. O'Hare, Intercellular trafficking and protein delivery by a herpesvirus structural protein. Cell, 1997. 88(2): p. 223-33) and ZEBRA (Rothe, R., et al., Characterization of the cell-penetrating properties of the Epstein-Barr virus ZEBRA trans-activator. J Biol Chem, 2010. 285(26): p. 20224-33), or from venoms, e.g. melittin (Dempsey, C. E., The actions of melittin on membranes. Biochim Biophys Acta, 1990. 1031(2): p. 143-61), mastoporan (Konno, K., et al., Structure and biological activities of eumenine mastoparan-AF (EMP-AF), a new mast cell degranulating peptide in the venom of the solitary wasp (Anterhynchium flavomarginatum micado). Toxicon, 2000. 38(11): p. 1505-15), maurocalcin (Esteve, E., et al., Transduction of the scorpion toxin maurocalcine into cells. Evidence that the toxin crosses the plasma membrane. J Biol Chem, 2005. 280(13): p. 12833-9), crotamine (Nascimento, F. D., et al., Crotamine mediates gene delivery into cells through the binding to heparan sulfate proteoglycans. J Biol Chem, 2007. 282(29): p. 21349-60) or buforin (Kobayashi, S., et al., Membrane translocation mechanism of the antimicrobial peptide buforin 2. Biochemistry, 2004. 43(49): p. 15610-6). Synthetic CPPs were also designed including the poly-arginine (R8, R9, R10 and R12) (Futaki, S., et al., Arginine-rich peptides. An abundant source of membrane-permeable peptides having potential as carriers for intracellular protein delivery. J Biol Chem, 2001. 276(8): p. 5836-40) or transportan (Pooga, M., et al., Cell penetration by transportan. FASEB J, 1998. 12(1): p. 67-77). Any of the above described CPPs may be used as cell penetrating peptide, i.e. as component a), in the complex for use according to the present invention. In particular, the component a), i.e. the CPP, in the complex for use according to the present invention may comprise the minimal domain of TAT, having the amino acid sequence YGRKKRRQRRR (SEQ ID NO: 2). In particular, the component a), i.e. the CPP, in the complex for use according to the present invention may comprise Penetratin having the amino acid sequence RQIKIYFQNRRMKWKK (SEQ ID NO: 1).

Various CPPs, which can be used as cell penetrating peptide, i.e. as component a), in the complex for use according to the present invention, are also disclosed in the review: Milletti, F., Cell-penetrating peptides: classes, origin, and current landscape. Drug Discov Today 17 (15-16): 850-60, 2012. In other words, the CPPs disclosed in Milletti, F., 2012, Cell-penetrating peptides: classes, origin, and current landscape. Drug Discov Today 17 (15-16): 850-60 can be used as cell penetrating peptide, i.e. as component a), in the complex for use according to the present invention. This includes in particular cationic CPPs, amphipatic CPPs, and hydrophobic CPPs as well as CPPs derived from heparan-, RNA- and DNA-binding proteins (cf. Table 1 of Milletti, F., Cell-penetrating peptides: classes, origin, and current landscape. Drug Discov Today 17 (15-16): 850-60, 2012), CPPs derived from signal peptides (cf. Table 2 of Milletti, F., Cell-penetrating peptides: classes, origin, and current landscape. Drug Discov Today 17 (15-16): 850-60, 2012), CPPs derived from antimicrobial peptides (cf. Table 3 of Milletti, F., Cell-penetrating peptides: classes, origin, and current landscape. Drug Discov Today 17 (15-16): 850-60, 2012), CPPs derived from viral proteins (cf. Table 4 of Milletti, F., Cell-penetrating peptides: classes, origin, and current landscape. Drug Discov Today 17 (15-16): 850-60, 2012), CPPs derived from various natural proteins (cf.

Table 5 of Milletti, F., Cell-penetrating peptides: classes, origin, and current landscape. Drug Discov Today 17 (15-16): 850-60, 2012), and Designed CPPs and CPPs derived from peptide libraries (cf. Table 6 of Milletti, F., Cell-penetrating peptides: classes, origin, and current landscape. Drug Discov Today 17 (15-16): 850-60, 2012).

Preferably, the cell penetrating peptide, which is comprised by the complex for use according to the present invention,
i) has a length of the amino acid sequence of said peptide of 5 to 50 amino acids in total, preferably of 10 to 45 amino acids in total, more preferably of 15 to 45 amino acids in total; and/or
ii) has an amino acid sequence comprising a fragment of the minimal domain of ZEBRA, said minimal domain extending from residue 170 to residue 220 of the ZEBRA amino acid sequence according to SEQ ID NO: 3, wherein, optionally, 1, 2, 3, 4, or 5 amino acids have been substituted, deleted, and/or added without abrogating said peptide's cell penetrating ability, or a sequence variant of such a fragment.

Thereby, it is preferred that the cell penetrating peptide, which is comprised by the complex for use according to the present invention,
i) has a length of the amino acid sequence of said peptide of 5 to 50 amino acids in total, preferably of 10 to 45 amino acids in total, more preferably of 15 to 45 amino acids in total; and
ii) has an amino acid sequence comprising a fragment of the minimal domain of ZEBRA, said minimal domain extending from residue 170 to residue 220 of the ZEBRA amino acid sequence according to SEQ ID NO: 3, wherein, optionally, 1, 2, 3, 4, or 5 amino acids have been substituted, deleted, and/or added without abrogating said peptide's cell penetrating ability, or a sequence variant of such a fragment.

Such preferred CPPs are disclosed in WO 2014/041505.

The term "ZEBRA" (also known as Zta, Z, EB1, or BZLF1) generally means the basic-leucine zipper (bZIP) transcriptional activator of the Epstein-Barr virus (EBV). The minimal domain of ZEBRA, which exhibits cell penetrating properties, has been identified as spanning from residue 170 to residue 220 of ZEBRA. The amino acid sequence of ZEBRA is disclosed under NCBI accession number YP_401673 and comprises 245 amino acids represented in SEQ ID NO: 3:

```
MMDPNSTSEDVKFTPDPYQVPFVQAFDQATRVYQDLGGPSQAPLPCVLW

PVLPEPLPQGQLTAYHVSTAPTGSWFSAPQPAPENAYQAYAAPQLFPVS

DITQNQQTNQAGGEAPQPGDNSTVQTAAAVVFACPGANQGQQLADIGVP

QPAPVAAPARRTRKPQQPESLEECDSELEIKRYKNRVASRKCRAKFKQL

LQHYREVAAAKSSENDRLRLLLKQMCPSLDVDSIIPRTPDVLHEDLLNF
(SEQ ID NO: 3-ZEBRA amino acid sequence (natural
sequence from Epstein-Barr virus (EBV))
(YP_401673))
```

Recently, a CPP derived from the viral protein ZEBRA was described to transduce protein cargoes across biological membranes by both (i) direct translocation and (ii) lipid raft-mediated endocytosis (Rothe R, Liguori L, Villegas-Mendez A, Marques B, Grunwald D, Drouet E, et al. Characterization of the cell-penetrating properties of the Epstein-Barr virus ZEBRA trans-activator. The Journal of biological chemistry 2010; 285(26):20224-33). The present inventors assume that these two mechanisms of entry should promote both MHC class I and II restricted presentation of cargo antigens to CD8+ and CD4$^+$T cells, respectively. Accordingly, such a CPP can deliver multi-epitopic peptides to dendritic cells (DCs), and subsequently to promote CTL and Th cell activation and anti-tumor function. Such a CPP can thus efficiently deliver the complex for use according to the present invention to antigen presenting cells (APCs) and lead to multi-epitopic MHC class I and II restricted presentation.

In the context of the present invention, the term "MHC class I" designates one of the two primary classes of the Major Histocompatibility Complex molecules. The MHC class I (also noted "MHC I") molecules are found on every nucleated cell of the body. The function of MHC class I is to display an epitope to cytotoxic cells (CTLs). In humans, MHC class I molecules consist of two polypeptide chains, α- and β2-microglobulin (b2m). Only the a chain is polymorphic and encoded by a HLA gene, while the b2m subunit is not polymorphic and encoded by the Beta-2 microglobulin gene. In the context of the present invention, the term "MHC class II" designates the other primary class of the Major Histocompatibility Complex molecules. The MHC class II (also noted "MHC II") molecules are found only on a few specialized cell types, including macrophages, dendritic cells and B cells, all of which are dedicated antigen-presenting cells (APCs).

Preferably, the sequence variant of a fragment of the minimal domain of ZEBRA as described above shares, in particular over the whole length, at least 70%, at least 75%, preferably at least 80%, more preferably at least 85%, even more preferably at least 90%, particularly preferably at least 95%, most preferably at least 99% amino acid sequence identity with the fragment of the minimal domain of ZEBRA as described above without abrogating the cell penetrating ability of the cell penetrating peptide. In particular, a "fragment" of the minimal domain of ZEBRA as defined above is preferably to be understood as a truncated sequence thereof, i.e. an amino acid sequence, which is N-terminally, C-terminally and/or intrasequentially truncated compared to the amino acid sequence of the native sequence. Moreover, such a "fragment" of the minimal domain of ZEBRA has preferably a length of 5 to 50 amino acids in total, preferably of 10 to 45 amino acids in total, more preferably of 15 to 45 amino acids in total.

Accordingly, the term "sequence variant" as used in the context of the present invention, i.e. throughout the present application, refers to any alteration in a reference sequence. The term "sequence variant" includes nucleotide sequence variants and amino acid sequence variants.

Preferably, a reference sequence is any of the sequences listed in the "Table of Sequences and SEQ ID Numbers" (Sequence listing), i.e. SEQ ID NO: 1 to SEQ ID NO: 70. Preferably, a sequence variant shares, in particular over the whole length of the sequence, at least 70%, at least 75%, preferably at least 80%, more preferably at least 85%, even more preferably at least 90%, particularly preferably at least 95%, most preferably at least 99% sequence identity with a reference sequence, whereby sequence identity is calculated as described below. In particular, a sequence variant preserves the specific function of the reference sequence. Sequence identity is calculated as described below. In particular, an amino acid sequence variant has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 70%, at least 75%, preferably at least 80%, more preferably at least 85%, even more preferably at least 90%, particularly preferably at least 95%, most preferably at least 99% identical to the reference sequence. For example, variant sequences which are at least 90% identical have no more than 10 alterations, i.e. any combination of deletions, insertions or substitutions, per 100 amino acids of the reference sequence.

In the context of the present invention, an amino acid sequence "sharing a sequence identity" of at least, for example, 95% to a query amino acid sequence of the present invention, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted, preferably within the above definitions of variants or fragments. The same, of course, also applies similarly to nucleic acid sequences.

For (amino acid or nucleic acid) sequences without exact correspondence, a "% identity" of a first sequence may be determined with respect to a second sequence. In general, these two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length.

Methods for comparing the identity and homology of two or more sequences are well known in the art. The percentage to which two sequences are identical can e.g. be determined using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S.A 85, 2444-2448.). Sequences which are identical to other sequences to a certain extent can be identified by these programmes. Furthermore, programs available in the Wisconsin Sequence Analysis Package, version 9.1 (Devereux et al., 1984, Nucleic Acids Res., 387-395), for example the programs BESTFIT and GAP, may be used to determine the % identity between two polynucleotides and the % identity and the % homology or identity between two polypeptide sequences. BESTFIT uses the "local homology" algorithm of(Smith and Waterman (1981), J. Mol. Biol. 147, 195-197.) and finds the best single region of similarity between two sequences.

More preferably, the fragments of the cell penetrating peptide according to the invention or the variants thereof as described above further retain said peptide's ability to present a cargo molecule such as antigens or antigenic epitopes at the surface of a cell, such as an antigen-presenting cell, in the context of MHC class I and/or MHC class II molecules. The ability of a cell penetrating peptide or complex comprising said cell penetrating peptide to present a cargo molecule such as antigens or antigenic epitopes at the surface of a cell in the context of MHC class I and/or MHC class II molecules can be checked by standard methods known to one skilled in the art, including capacity to stimulate proliferation and/or function of MHC-restricted CD4+ or $CD8^+$T cells with specificity for these epitopes.

The preferred cell penetrating peptide, which i) has a length of the amino acid sequence of said peptide of 5 to 50 amino acids in total, preferably of 10 to 45 amino acids in total, more preferably of 15 to 45 amino acids in total; and/or ii) has an amino acid sequence comprising a fragment of the minimal domain of ZEBRA, said minimal domain extending from residue 170 to residue 220 of the ZEBRA amino acid sequence according to SEQ ID NO: 3, wherein, optionally, 1, 2, 3, 4, or 5 amino acids have been substituted, deleted, and/or added without abrogating said peptide's cell penetrating ability, or a variant of such a fragment preferably comprises an amino acid sequence having at least one conservatively substituted amino acid compared to the referenced sequence, meaning that a given amino acid residue is replaced by a residue having similar physiochemical characteristics.

Generally, substitutions for one or more amino acids present in the referenced amino acid sequence should be made conservatively. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity properties, are well known (Kyte and Doolittle, 1982, *J. Mol. Biol.* 157(1):105-132). Substitutions of one or more L-amino acids with one or more D-amino acids are to be considered as conservative substitutions in the context of the present invention. Exemplary amino acid substitutions are presented in Table 1 below:

TABLE 1

| Original residues | Examples of substitutions |
|---|---|
| Ala (A) | Val, Leu, Ile, Gly |
| Arg (R) | His, Lys |
| Asn (N) | Gln |
| Asp (D) | Glu |
| Cys (C) | Ser |
| Gln (Q) | Asn |
| Glu (E) | Asp |
| Gly (G) | Pro, Ala |
| His (H) | Lys, Arg |
| Ile (I) | Leu, Val, Met, Ala, Phe |
| Leu (L) | Ile, Val, Met, Ala, Phe |
| Lys (K) | Arg, His |
| Met (M) | Leu, Ile, Phe |
| Phe (F) | Leu, Val, Ile, Tyr, Trp, Met |
| Pro (P) | Ala, Gly |
| Ser (S) | Thr |
| Thr (T) | Ser |
| Trp (W) | Tyr, Phe |
| Tyr (Y) | Trp, Phe |
| Val (V) | Ile, Met, Leu, Phe, Ala |

Particularly preferably, the preferred cell penetrating peptide, which
  i) has a length of the amino acid sequence of said peptide of 5 to 50 amino acids in total, preferably of 10 to 45 amino acids in total, more preferably of 15 to 45 amino acids in total; and/or
  ii) has an amino acid sequence comprising a fragment of the minimal domain of ZEBRA, said minimal domain extending from residue 170 to residue 220 of the ZEBRA amino acid sequence according to SEQ ID NO: 3, wherein, optionally, 1, 2, 3, 4, or 5 amino acids have been substituted, deleted, and/or added without abrogating said peptide's cell penetrating ability, or a variant of such a fragment
comprises a Cys (C) substituted into a Ser (S), at the equivalent of position 189 relative to ZEBRA amino acid sequence of SEQ ID NO: 3.

Thereby, it is preferred that such a preferred cell penetrating peptide has an amino acid sequence comprising a sequence according to the following general formula (I):

$$X_1X_2X_3X_4X_5X_6X_7X_8X_9X_{10}X_{11}X_{12}X_{13}X_{14}X_{15}X_{16}X_{17}$$

with 0, 1, 2, 3, 4, or 5 amino acids which are substituted, deleted, and/or added without abrogating said peptide's cell penetrating ability, wherein $X_1$ is K, R, or H, preferably $X_1$ is K or R;
$X_2$ is R, K, or H, preferably $X_2$ is R or K;
$X_3$ is Y, W, or F, preferably $X_3$ is Y, W, or F;
$X_4$ is K, R, or H, preferably $X_4$ is K or R;
$X_5$ is N or Q;
$X_6$ is R, K, or H, preferably $X_6$ is R or K;
$X_7$ is V, I, M, L, F, or A, preferably $X_7$ is V, I, M or L;
$X_8$ is A, V, L, I, or G, preferably $X_8$ is A or G;
$X_9$ is S or T;
$X_{10}$ is R, K, or H, preferably $X_{10}$ is R or K;
$X_{11}$ is K, R, or H, preferably $X_{11}$ is K or R;
$X_{13}$ is R, K, or H, preferably $X_{13}$ is R or K;
$X_{14}$ is A, V, L, I, or G, preferably $X_{14}$ is A or G;
$X_{15}$ is K, R, or H, preferably $X_{15}$ is K or R;
$X_{16}$ is F, L, V, I, Y, W, or M, preferably $X_{16}$ is F, Y or W; and
$X_{17}$ is K, R, or H, preferably $X_{17}$ is K or R.

Preferably, such a peptide, polypeptide or protein is either (entirely) composed of L-amino acids or (entirely) of D-amino acids, thereby forming "retro-inverso peptide sequences". The term "retro-inverso (peptide) sequences" refers to an isomer of a linear peptide sequence in which the direction of the sequence is reversed and the chirality of each amino acid residue is inverted (see e.g. Jameson et al., Nature, 368, 744-746 (1994); Brady et al., Nature, 368, 692-693 (1994)).

In a particular embodiment, the cell penetrating peptide according to the invention is as generically defined above by general formula (I), wherein $X_1$ is K.

In a particular embodiment, the cell penetrating peptide according to the invention is as generically defined above by general formula (I), wherein $X_2$ is R.

In a particular embodiment, the cell penetrating peptide according to the invention is as generically defined above by general formula (I), wherein $X_3$ is Y.

In a particular embodiment, the cell penetrating peptide according to the invention is as generically defined above by general formula (I), wherein $X_4$ is K.

In a particular embodiment, the cell penetrating peptide according to the invention is as generically defined above by general formula (I), wherein $X_5$ is N.

In a particular embodiment, the cell penetrating peptide according to the invention is as generically defined above by general formula (I), wherein $X_6$ is R.

In a particular embodiment, the cell penetrating peptide according to the invention is as generically defined above by general formula (I), wherein $X_7$ is V.

In a particular embodiment, the cell penetrating peptide according to the invention is as generically defined above by general formula (I), wherein $X_8$ is A.

In a particular embodiment, the cell penetrating peptide according to the invention is as generically defined above by general formula (I), wherein $X_9$ is S.

In a particular embodiment, the cell penetrating peptide according to the invention is as generically defined above by general formula (I), wherein $X_{10}$ is R.

In a particular embodiment, the cell penetrating peptide according to the invention is as generically defined above by general formula (I), wherein $X_{11}$ is K.

In a particular embodiment, the cell penetrating peptide according to the invention is as generically defined above by general formula (I), wherein $X_{13}$ is R.

In a particular embodiment, the cell penetrating peptide according to the invention is as generically defined above by general formula (I), wherein $X_{14}$ is A.

In a particular embodiment, the cell penetrating peptide according to the invention is as generically defined above by general formula (I), wherein $X_{15}$ is K.

In a particular embodiment, the cell penetrating peptide according to the invention is as generically defined above by general formula (I), wherein $X_{16}$ is F.

In a particular embodiment, the cell penetrating peptide according to the invention is as generically defined above by general formula (I), wherein $X_{17}$ is K.

In a particular embodiment, the cell penetrating peptide according to the invention is as generically defined above by general formula (I), wherein the amino acid at position equivalent to position 12 relative to general formula (I) is a Ser (S).

It is also particularly preferred, that the preferred cell penetrating peptide, which i) has a length of the amino acid sequence of said peptide of 5 to 50 amino acids in total, preferably of 10 to 45 amino acids in total, more preferably of 15 to 45 amino acids in total; and/or
ii) has an amino acid sequence comprising a fragment of the minimal domain of ZEBRA, said minimal domain extending from residue 170 to residue 220 of the ZEBRA amino acid sequence according to SEQ ID NO: 3, wherein, optionally, 1, 2, 3, 4, or 5 amino acids have been substituted, deleted, and/or added without abrogating said peptide's cell penetrating ability, or a variant of such a fragment comprises or consists of an amino acid sequence selected from the group consisting of amino acid sequences according to SEQ ID NO: 4-13, or sequence variants thereof without abrogating said peptide's cell penetrating ability, preferably sequence variants having 0, 1, 2, 3, 4, or 5 amino acids substituted, deleted and/or added without abrogating said peptide's cell penetrating ability.

```
CPP1 (Z11):
                                      (SEQ ID NO: 4)
KRYKNRVASRKCRAKFKQLLQHYREVAAAKSSENDRLRLLLKQMC

CPP2 (Z12):
                                      (SEQ ID NO: 5)
KRYKNRVASRKCRAKFKQLLQHYREVAAAKSSENDRLRLLLK

CPP3 (Z13):
                                      (SEQ ID NO: 6)
KRYKNRVASRKSRAKFKQLLQHYREVAAAKSSENDRLRLLLK

CPP4 (Z14):
                                      (SEQ ID NO: 7)
KRYKNRVASRKSRAKFKQLLQHYREVAAAK

CPP5 (Z15):
                                      (SEQ ID NO: 8)
KRYKNRVASRKSRAKFK

CPP6 (Z16):
                                      (SEQ ID NO: 9)
QHYREVAAAKSSEND

CPP7 (Z17):
                                      (SEQ ID NO: 10)
QLLQHYREVAAAK

CPP8 (Z18):
                                      (SEQ ID NO: 11)
REVAAAKSSENDRLRLLLK

CPP9 (Z19):
                                      (SEQ ID NO: 12)
KRYKNRVA

CPP10 (Z20):
                                      (SEQ ID NO: 13)
VASRKSRAKFK
```

Thereby, a cell penetrating peptide is particularly preferred, which has an amino acid sequence comprising or consisting of an amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18), or sequence variants thereof without abrogating said peptide's cell penetrating ability, preferably sequence variants having 0, 1, 2, 3, 4, or 5 amino acids substituted, deleted and/or added without abrogating said peptide's cell penetrating ability. Moreover, a cell penetrating peptide is more preferred, which has an amino acid sequence comprising or consisting of an amino acid sequence according to SEQ ID NO: 6 (CPP3/Z13) or SEQ ID NO: 7 (CPP4/Z14) or sequence variants thereof without abrogating said peptide's cell penetrating ability, preferably sequence variants having 0, 1, 2, 3, 4, or 5 amino acids substituted, deleted and/or added without abrogating said peptide's cell penetrating ability. Moreover, a cell penetrating peptide is most preferred, which has an amino acid sequence comprising or consisting of an amino acid sequence according to SEQ ID NO: 6 (CPP3/Z13) or sequence variants thereof without abrogating said peptide's cell penetrating ability, preferably sequence variants having 0, 1, 2, 3, 4, or 5 amino acids substituted, deleted and/or added without abrogating said peptide's cell penetrating ability.

In one preferred embodiment, the cell penetrating peptide according to the invention has an amino acid sequence comprising or consisting of SEQ ID NO: 6 (CPP3/Z13).

In another preferred embodiment, the cell penetrating peptide according to the invention has an amino acid sequence comprising or consisting of SEQ ID NO: 7 (CPP4/Z14).

In another preferred embodiment, the cell penetrating peptide according to the invention has an amino acid sequence comprising or consisting of SEQ ID NO: 8 (CPP5/Z15).

In another preferred embodiment, the cell penetrating peptide according to the invention has an amino acid sequence comprising or consisting of SEQ ID NO: 11 (CPP8/Z18).

It will be understood by one skilled in the art that the primary amino acid sequence of the cell penetrating peptide of the invention may further be post-translationally modified, such as by glycosylation or phosphorylation, without departing from the invention.

In a further embodiment, the cell penetrating peptide according to the invention optionally further comprises, in addition to its amino acid sequence as described above, any one of, or any combination of:
(i) a nuclear localization signal (NLS). Such signals are well known to the skilled person and are described in Nair et al. (2003, *Nucleic Acids Res.* 31(1): 397-399)
(ii) a targeting peptide, including tumor homing peptides such as those described in Kapoor et al. (2012, *PLoS ONE* 7(4): e35187) and listed in crdd.osdd.net/raghava/tumorhope/general.php?

Preferably, the cell penetrating peptide according to the invention is linked to an antigen or antigenic epitope and facilitates the cellular internalization of said antigen or antigenic epitope.

The complex for use according to the present invention may comprise one single cell penetrating peptide or more than one cell penetrating peptides. Preferably, the complex for use according to the present invention comprises no more than five cell penetrating peptides, more preferably the complex for use according to the present invention comprises no more than four cell penetrating peptides, even more preferably the complex for use according to the present invention comprises no more than three cell penetrating peptides, particularly preferably the complex for use according to the present invention comprises no more than two cell penetrating peptides and most preferably the complex for use according to the present invention comprises one single cell penetrating peptide.

Component b)—Antigen/Antigenic Epitope

The complex for use according to the present invention comprises as component b) at least one antigen or antigenic epitope.

As used herein, an "antigen" is any structural substance which serves as a target for the receptors of an adaptive immune response, in particular as a target for antibodies, T cell receptors, and/or B cell receptors. An "epitope", also known as "antigenic determinant", is the part (or fragment) of an antigen that is recognized by the immune system, in particular by antibodies, T cell receptors, and/or B cell receptors. Thus, one antigen has at least one epitope, i.e. a single antigen has one or more epitopes. In the context of the present invention, the term "epitope" is mainly used to designate T cell epitopes, which are presented on the surface of an antigen-presenting cell, where they are bound to Major Histocompatibility Complex (MHC). T cell epitopes presented by MHC class I molecules are typically, but not exclusively, peptides between 8 and 11 amino acids in length, whereas MHC class II molecules present longer peptides, generally, but not exclusively, between 12 and 25 amino acids in length.

Preferably, in the complex for use according to the present invention, the at least one antigen or antigenic epitope is selected from the group consisting of: (i) a peptide, a polypeptide, or a protein, (ii) a polysaccharide, (iii) a lipid, (iv) a lipoprotein or a lipopeptide, (v) a glycolipid, (vi) a nucleic acid, and (vii) a small molecule drug or a toxin. Thus, the at least one antigen or antigenic epitope may be a peptide, a protein, a polysaccharide, a lipid, a combination thereof including lipoproteins and glycolipids, a nucleic acid (e.g. DNA, siRNA, shRNA, antisense oligonucleotides, decoy DNA, plasmid), or a small molecule drug (e.g. cyclosporine A, paclitaxel, doxorubicin, methotrexate, 5-aminolevulinic acid), or any combination thereof in particular if more than one antigen or antigenic epitope is comprised by the inventive complex.

It is understood that the at least one antigen or antigenic epitope can comprise for example at least one, i.e. one or more, peptides, polypeptides or proteins linked together and/or at least one, i.e. one or more, nucleic acids, e.g. where each one encodes one peptide or polypeptide. Also the at least one antigen or antigenic epitope can be a combination of a protein, a lipid, and/or a polysaccharide including lipoproteins and glycolipids. Thus, in particular if the complex for use according to the present invention comprises more than one antigen or antigenic epitope, it can comprise more than one peptide, polypeptide, or protein, more than one polysaccharide, more than one lipid, more than one lipoprotein, more than one glycolipid, more than one nucleic acid, more than one small molecule drug or toxin, or a combination thereof.

Preferably, the complex for use according to the invention comprises at least one antigen or antigenic epitope comprising one or more epitope(s) from a cancer/tumor-associated antigen, a cancer/tumor-specific antigen, and/or an antigenic protein from a pathogen, including viral, bacterial, fungal, protozoal and multicellular parasitic antigenic protein.

More preferably, the at least one antigen or antigenic epitope comprises or consists of (i) at least one pathogen epitope and/or (ii) at least one cancer/tumor epitope, in particular at least one tumor epitope. Most preferably, the at least one antigen or antigenic epitope comprises or consists of at least one cancer/tumor epitope, in particular at least one tumor epitope.

It is particularly preferred that the complex for use according to the present invention comprises only such antigen(s) or antigenic epitope(s), which are cancer/tumor-associated antigen(s), cancer/tumor-specific antigen(s) and/or cancer/tumor epitope(s); in particular, which are tumor-associated antigen(s), tumor-specific antigen(s), and/or tumor epitope(s).

As used herein, "cancer epitope" means an epitope from a cancer-associated antigen or from a cancer-specific antigen. Accordingly, "tumor epitope" means an epitope from a tumor-associated antigen or from a tumor-specific antigen. Such epitopes are typically specific (or associated) for a certain kind of cancer/tumor. In particular, cancer/tumor-associated (also cancer/tumor-related) antigens are antigens, which are expressed by both, cancer/tumor cells and normal cells. Accordingly, those antigens are normally present since birth (or even before). Accordingly, there is a chance that the immune system developed self-tolerance to those antigens. Cancer/tumor-specific antigens, in contrast, are antigens, which are expressed specifically by cancer/tumor cells, but not by normal cells. Cancer/tumor-specific antigens include in particular neoantigens. In general neoantigens are antigens, which were not present before and are, thus, "new" to the immune system. Neoantigens are typically due to somatic mutations. In the context of cancer/tumors, cancer/tumor-specific neoantigens were typically not present before the cancer/tumor developed and cancer/tumor-specific neoantigens are usually encoded by somatic gene mutations in the cancerous cells/tumor cells. Since neoantigens are new to the immune system, the risk of self-tolerance of those antigens is considerably lower as compared to cancer/tumor-associated antigens. However, every cancer's set of tumor-specific mutations appears to be unique. Accordingly, in the context of the present invention it is preferred that such cancer/tumor-specific antigens, in particular neoantigens, are identified in a subject diagnosed with colorectal cancer by methods known to the skilled person, e.g., cancer genome sequencing. After identification, the respective cancer/tumor-specific neoantigens and/or cancer/tumor-specific neoantigenic epitopes are used in a complex for use according to the present invention.

Preferably, a complex for use according to the present invention comprises one or more cancer/tumor-associated epitopes and/or one or more cancer/tumor-associated antigens (but preferably no cancer/tumor-specific epitopes). It is also preferred that a complex for use according to the present invention comprises one or more cancer/tumor-specific epitopes and/or one or more cancer/tumor-specific antigens (but preferably no cancer/tumor-associated epitopes). A complex for use according to the present invention may also preferably comprise both, (i) one or more cancer/tumor-associated epitopes and/or one or more cancer/tumor-associated antigens and (ii) one or more cancer/tumor-specific epitopes and/or one or more cancer/tumor-specific antigens.

In particular, the cancer/tumor with which the antigens or antigenic epitopes are associated or for which the antigens or antigenic epitopes are specific is colorectal cancer as described herein. Thus, the antigens are preferably CRC-associated or CRC-specific antigens and the epitopes are preferably CRC-associated or CRC-specific epitopes.

Suitable cancer/tumor epitopes can be retrieved for example from cancer/tumor epitope databases, e.g. from van der Bruggen P, Stroobant V, Vigneron N, Van den Eynde B. Peptide database: T cell-defined tumor antigens. *Cancer Immun* 2013; URL: www.cancerimmunity.org/peptide/, wherein human tumor antigens recognized by CD4+ or CD8$^+$T cells are classified into four major groups on the basis of their expression pattern, or from the database "Tantigen" (TANTIGEN version 1.0, Dec. 1, 2009; developed by Bioinformatics Core at Cancer Vaccine Center, Dana-Farber Cancer Institute; URL: cvc.dfci.harvard.edu/ tadb/). Examples of cancer/tumor epitopes include e.g. TRP2-derived epitopes, glycoprotein 100 (gp100) melanoma antigen-derived epitopes, glycoprotein 70 (gp70) antigen-derived epitopes, survivin epitopes, IEa epitopes, IL13rα2, Epha2 (ephrin type-A receptor 2), immunogenic fragments thereof, and fusions of such antigens and/or fragments. Furthermore, examples of cancer/tumor epitopes include epitopes of neoantigens, such as, for example, a neoantigen from MC-38 tumor cell line as described by Yadav et al. Nature. 2014 Nov. 27; 515(7528):572-6. As described above, neoantigens are antigens, which are entirely absent from the normal human genome. As compared with nonmutated self-antigens, neoantigens are of relevance to tumor control, as the quality of the T cell pool that is available for these antigens is not affected by central T cell tolerance. In particular, neoantigens may be based on individual tumor genomes. Potential neoantigens may be predicted by methods known to the skilled person, such as cancer genome sequencing or deep-sequencing technologies identifying mutations within the protein-coding part of the (cancer) genome.

Specific examples of cancer/tumor-associated, in particular tumor-related, or tissue-specific antigens useful in a complex for use according to the present invention include, but are not limited to, the following antigens: Her-2/neu, SPAS-1, TRP-2, tyrosinase, Melan A/Mart-1, gp100, BAGE, GAGE, GM2 ganglioside, kinesin 2, TATA element modulatory factor 1, tumor protein D52, MAGE D, ING2, HIP-55, TGF-1 anti-apoptotic factor, HOM-Mel-40/SSX2, epithelial antigen (LEA 135), DF31MUC1 antigen (Apostolopoulos et al., 1996 Immunol. Cell. Biol. 74:457-464; Pandey et al., 1995, Cancer Res. 55: 4000-4003), MAGE-1, HOM-Mel-40/SSX2, NY-ESO-1, EGFR, CEA, Epha2, Epha4, PCDGF, HAAH, Mesothelin; EPCAM; NY-ESO-1, glycoprotein MUC1 and NIUC10 mucins p5 (especially mutated versions), EGFR, cancer-associated serum antigen (CASA) and cancer antigen 125 (CA 125) (Kierkegaard et al., 1995, Gynecol. Oncol. 59: 251-254), the epithelial glycoprotein 40 (EGP40) (Kievit et al., 1997, Int. J. Cancer 71: 237-245), squamous cell carcinoma antigen (SCC) (Lozza et al., 1997 Anticancer Res. 17: 525-529), cathepsin E (Mota et al., 1997, Am. J Pathol. 150: 1223-1229), tyrosinase in melanoma (Fishman et al., 1997 Cancer 79: 1461-1464), cell nuclear antigen (PCNA) of cerebral cavernomas (Notelet et al., 1997 Surg. Neurol. 47: 364-370), a 35 kD tumor-associated autoantigen in papillary thyroid carcinoma (Lucas et al., 1996 Anticancer Res. 16: 2493-2496), CDC27 (including the mutated form of the protein), antigens triosephosphate isomerase, 707-AP, A60 mycobacterial antigen (Macs et al., 1996, J. Cancer Res. Clin. Oncol. 122: 296-300), Annexin II, AFP, ART-4, BAGE, p3-catenin/m, BCL-2, bcr-abl, bcr-abl p190, bcr-abl p210, BRCA-1, BRCA-2, CA 19-9 (Tolliver and O'Brien, 1997, South Med. J. 90: 89-90; Tsuruta at al., 1997 Urol. Int. 58: 20-24), CAMEL, CAP-1, CASP-8, CDC27/m, CDK-4/m, CEA (Huang et al., Exper Rev. Vaccines (2002)1:49-63), CT9, CT10, Cyp-B, Dek-cain, DAM-6 (MAGE-B2), DAM-10 (MAGE-B1), EphA2 (Zantek et al., Cell Growth Differ. (1999) 10:629-38; Carles-Kinch et al., Cancer Res. (2002) 62:2840-7), EphA4 (Cheng at al., 2002, Cytokine Growth Factor Rev. 13:75-85), tumor associated Thomsen-Friedenreich antigen (Dahlenborg et al., 1997, Int. J Cancer 70: 63-71), ELF2M, ETV6-AML1, G250, GAGE-1, GAGE-2, GAGE-3, GAGE-4, GAGE-5, GAGE-6, GAGE-7B, GAGE-8, GnT-V, gp100 (Zajac et al., 1997, Int. J Cancer 71: 491-496), HAGE, HER2/neu, HLA-A*0201-R170I, HPV-E7, HSP70-2M, HST-2, hTERT, hTRT, iCE, inhibitors ofapoptosis (e.g., survivin), KH-1 adenocarcinoma antigen (Deshpande and Danishefsky, 1997, Nature 387: 164-166), KIAA0205, K-ras, LAGE, LAGE-1, LDLR/FUT, MAGE-1, MAGE-2, MAGE-3, MAGE-6, MAGE-A1, MAGE-A2, MAGE-A3, MAGE-A4, MAGE-A6, MAGE-A10, MAGE-A12, MAGE-B5, MAGE-B6, MAGE-C2, MAGE-C3, MAGE D, MART-1, MART-1/Melan-A (Kawakami and Rosenberg, 1997, Int. Rev. Immunol. 14: 173-192), MC1R, MDM-2, Myosin/m, MUC1, MUC2, MUM-1, MUM-2, MUM-3, neo-polyA polymerase, NA88-A, NY-ESO-1, NY-ESO-1a (CAG-3), PAGE-4, PAP, Proteinase 3 (Molldrem et al., Blood (1996) 88:2450-7; Molldrem et al., Blood (1997) 90:2529-34), P15, p190, Pm1/RARα, PRAME, PSA, PSM, PSMA, RAGE, RAS, RCAS1, RU 1, RU2, SAGE, SART-1, SART-2, SART-3, SP17, SPAS-1, TEL/AML1, TPI/m, Tyrosinase, TARP, TRP-1 (gp75), TRP-2, TRP-2/INT2, WT-1, and alternatively translated NY-ESO—ORF2 and CAMEL proteins, derived from the NY-ESO-1 and LAGE-1 genes. Numerous other cancer antigens are well known in the art.

Preferably, the cancer/tumor antigen or the cancer/tumor epitope is a recombinant cancer/tumor antigen or a recombinant cancer/tumor epitope. Such a recombinant cancer/tumor antigen or a recombinant cancer/tumor epitope may be designed by introducing mutations that change (add, delete or substitute) particular amino acids in the overall amino acid sequence of the native cancer/tumor antigen or the native cancer/tumor epitope. The introduction of mutations does not alter the cancer/tumor antigen or the cancer/tumor epitope so much that it cannot be universally applied across a mammalian subject, and preferably a human or dog subject, but changes it enough that the resulting amino acid sequence breaks tolerance or is considered a foreign antigen in order to generate an immune response. Another manner may be creating a consensus recombinant cancer/tumor antigen or cancer/tumor epitope that has at least 85% and up to 99% amino acid sequence identity to its' corresponding native cancer/tumor antigen or native cancer/tumor epitope; preferably at least 90% and up to 98% sequence identity; more preferably at least 93% and up to 98% sequence identity; or even more preferably at least 95% and up to 98% sequence identity. In some instances the recombinant cancer/tumor antigen or the recombinant cancer/tumor epitope has 95%, 96%, 97%, 98%, or 99% amino acid sequence identity to its' corresponding native cancer/tumor antigen or cancer/tumor epitope. The native cancer/tumor antigen is the antigen normally associated with the particular cancer or cancer tumor. Depending upon the cancer/tumor antigen, the consensus sequence of the cancer/tumor antigen can be across mammalian species or within subtypes of a species or across viral strains or serotypes. Some cancer/tumor antigen do not vary greatly from the wild type amino acid sequence of the cancer/tumor antigen. The aforementioned approaches can be combined so that the final recombinant cancer/tumor antigen or cancer/tumor epitope has a percent similarity to native cancer antigen amino acid sequence as discussed above. Preferably, however, the amino acid sequence of an epitope of a cancer/tumor antigen as described herein is not mutated and, thus, identical to the reference epitope sequence.

As used herein "pathogen epitope" means an epitope from an antigenic protein, an antigenic polysaccharide, an antigenic lipid, an antigenic lipoprotein or an antigenic glycolipid from a pathogen including viruses, bacteria, fungi, protozoa and multicellular parasites. Antigenic proteins, polysaccharides, lipids, lipoproteins or glycolipids from pathogens include, herewith, proteins, polysaccharides, lipids, lipoproteins and glycolipids, respectively, from pathogens responsible of diseases which can be a target for vaccination including, for instance, Amoebiasis, Anthrax, Buruli Ulcer (Mycobacterium ulcerans), Caliciviruses associated diarrhoea, Campylobacter diarrhoea, Cervical Cancer (Human papillomavirus), Chlamydia trachomatis associated genital diseases, Cholera, Crimean-Congo haemorrhagic fever, Dengue Fever, Diptheria, Ebola haemorrhagic fever, Enterotoxigenic Escherichia coli (ETEC) diarrhoea, Gastric Cancer (Helicobacter pylori), Gonorrhea, Group A Streptococcus associated diseases, Group B Streptococcus associated diseases, Haemophilus influenzae B pneumonia and invasive disease, Hepatitis A, Hepatitis B, Hepatitis C, Hepatitis E diarrhoea, Herpes simplex type 2 genital ulcers, HIV/AIDS, Hookworm Disease, Influenza, Japanese encephalitis, Lassa Fever, Leishmaniasis, Leptospirosi, Liver cancer (Hepatitis B), Liver Cancer (Hepatitis C), Lyme Disease, Malaria, Marburg haemorrhagic fever, Measles, Mumps, Nasopharyngeal cancer (Epstein-Barr virus), Neisseria meningitidis Meningitis, Parainfluenza associated pneumonia, Pertussis, Plague, Poliomyelitis, Rabies, Respiratory syncytial virus (RSV) pneumonia, Rift Valley fever, Rotavirus diarrhoea, Rubella, Schistosomiasis, Severe Acute Respiratory Syndrome (SARS), Shigellosis, Smallpox, Staphylococcus aureus associated diseases, Stomach Cancer (Helicobacter pylori), Streptococcus pneumoniae and invasive disease, Tetanus, Tick-borne encephalitis, Trachoma, Tuberculosis, Tularaemia, Typhoid fever, West-Nile virus associated disease, Yellow fever.

Preferably, the at least one antigen or antigenic epitope will be presented at the cell surface in an MHC class I and/or MHC class II context and/or in a CD1 context, whereby presentation at the cell surface in an MHC class I and/or MHC class II context is preferred. The phrase "epitope presentation in the MHC class I context" refers in particular to a $CD8^+$ epitope lying in the groove of a MHC class I molecule at the surface of a cell. The phrase "epitope presentation in the MHC class II context" refers in particular to a $CD4^+$ epitope lying in the groove of a MHC class II molecule at the surface of a cell. The phrase "epitope presentation in the CD1 context" refers in particular to a lipidic epitope lying in the groove of a cluster of differentiation 1 molecule at the surface of a cell.

Advantageously, the complex for use according to the invention comprises a cell penetrating peptide and at least one antigen or antigenic epitope, and allows the transport and presentation of said epitopes at the cell surface of antigen presenting cells in an MHC class I and MHC class II context, and is, thus, useful in vaccination and immunotherapy.

Preferably, the complex for use according to the present invention comprises at least one antigen or antigenic epitope, which is at least one $CD4^+$ epitope and/or at least one $CD8^+$ epitope.

The terms "$CD4^+$ epitope" or "CD4+-restricted epitope", as used herein, designate an epitope recognized by a $CD4^+$T cell, said epitope in particular consisting of an antigen fragment lying in the groove of a MHC class II molecule. A single $CD4^+$ epitope comprised in the complex for use according to the present invention preferably consists of about 12-25 amino acids. It can also consist of, for example, about 8-25 amino acids or about 6-100 amino acids.

The terms "$CD8^+$ epitope" or "CD8+-restricted epitope", as used herein, designate an epitope recognized by a $CD8^+$T cell, said epitope in particular consisting of an antigen fragment lying in the groove of a MHC class I molecule. A single $CD8^+$ epitope comprised in the complex for use according to the present invention preferably consists of about 8-11 amino acids. It can also consist of, for example, about 8-15 amino acids or about 6-100 amino acids.

Preferably, the at least one antigen can comprise or the at least one antigenic epitope can consist of a $CD4^+$ epitope and/or a $CD8^+$ epitope corresponding to antigenic determinant(s) of a cancer/tumor-associated antigen, a cancer/tumor-specific antigen, or an antigenic protein from a pathogen. More preferably, the at least one antigen can comprise or the at least one antigenic epitope can consist of a $CD4^+$ epitope and/or a $CD8^+$ epitope corresponding to antigenic determinant(s) of a cancer/tumor-associated antigen or a cancer/tumor-specific antigen. Most preferably, the at least one antigen can comprise or the at least one antigenic epitope can consist of a $CD4^+$ epitope and/or a $CD8^+$ epitope corresponding to antigenic determinant(s) of a tumor-associated antigen or a tumor-specific antigen.

It is also preferred that the complex for use according to the present invention comprises at least two antigens or antigenic epitopes, wherein at least one antigen or antigenic epitope comprises or consists a $CD4^+$ epitope and at least one antigen or antigenic epitope comprises or consists a CD8+ epitope. It is now established that $T_h$ cells (CD4+) play a central role in the anti-tumor immune response both in DC licensing and in the recruitment and maintenance of CTLs (CD8+) at the tumor site. Therefore, a complex for use according to the present invention comprising at least two antigens or antigenic epitopes, wherein at least one antigen or antigenic epitope comprises or consists of a $CD4^+$ epitope and at least one antigen or antigenic epitope comprises or consists a $CD8^+$ epitope, provides an integrated immune response allowing simultaneous priming of CTLs and $T_h$ cells and is thus preferable to immunity against only one $CD8^+$ epitope or only one $CD4^+$ epitope. For example, the complex for use according to the present invention may preferably comprise an Ealpha-$CD4^+$ epitope and a gp100-$CD8^+$ epitope.

Preferably, the complex for use according to the present invention comprises at least two antigens or antigenic epitopes, wherein the at least two antigens or antigenic epitopes comprise or consist of at least two, e.g. 2, 3, 4, 5, 6, 7, 8, 9, or more, $CD4^+$ epitopes and/or at least two, e.g. 2, 3, 4, 5, 6, 7, 8, 9, or more, $CD8^+$ epitopes. Thereby, the at least two antigens or antigenic epitopes are preferably different antigens or antigenic epitopes, more preferably the at least two antigens or antigenic epitopes are different from each other but relating to the same kind of tumor. A multi-antigenic vaccine will (i) avoid outgrowth of antigen-loss variants, (ii) target different tumor cells within a heterogeneous tumor mass and (iii) circumvent patient-to-patient tumor variability. Thus, the complex for use according to the present invention particularly preferably comprises at least four antigens or antigenic epitopes, in particular with at least two $CD8^+$ epitopes and at least two $CD4^+$ epitopes. Such a complex for use according to the present invention induces multi-epitopic CD8 CTLs and CD4 $T_h$ cells to function synergistically to counter tumor cells and promote efficient anti-tumor immunity. $T_h$ cells are also involved in the maintenance of long-lasting cellular immunity that was monitored after vaccination. Such a complex for use according to the present invention induces polyclonal, multi-epitopic immune responses and poly-functional $CD8^+$ and $CD4^+$ T cells, and thus efficacious anti-tumor activity.

Preferably, the complex for use according to the present invention comprises at least two antigens or antigenic epitopes, more preferably the complex for use according to the present invention comprises at least three antigens or antigenic epitopes, even more preferably the complex for use according to the present invention comprises at least four antigens or antigenic epitopes, particularly preferably the complex for use according to the present invention comprises at least five antigens or antigenic epitopes and most preferably the complex for use according to the present invention comprises at least six antigens or antigenic epitopes. The antigens or antigenic epitopes comprised by the complex for use according to the present invention may be the same or different, preferably the antigens or antigenic epitopes comprised by the complex for use according to the present invention are different from each other. Preferably, the complex for use according to the present invention comprises at least one CD4+ epitope and at least one CD8+ epitope.

Preferably, the complex for use according to the present invention comprises more than one CD4+ epitope, e.g. two or more CD4+ epitopes from the same antigen or from different antigens, and preferably no CD8+ epitope. It is also preferred that the complex for use according to the present invention comprises more than one CD8+ epitope, e.g. two or more CD8+ epitopes from the same antigen or from different antigens, and preferably no CD4+ epitope. Most preferably, however, the complex for use according to the present invention comprises (i) at least one CD4+ epitope, e.g. two or more CD4+ epitopes from the same antigen or from different antigens, and (ii) at least one CD8+ epitope, e.g. two or more CD8+ epitopes from the same antigen or from different antigens.

For example, the complex for use according to the present invention may preferably comprise a gp100-CD8+ epitope, an Ealpha-CD4+ epitope, and a further CD4+ epitope and a further CD8+ epitope. Even more preferably, the complex for use according to the present invention may comprise a polypeptide or protein comprising a gp100-CD8+ epitope and an Ealpha-CD4+ epitope. For example, such a polypeptide or protein comprised by the complex for use according to the present invention comprises or consists of an amino acid sequence according to SEQ ID NO: 14 or sequence variants thereof as defined above:

```
(MAD5-cargo comprising OVA-CD4+, gp100-CD8+,
Ealpha-CD4+, and OVA-CD8+ epitopes)
                                        SEQ ID NO: 14
ESLKIS QAVHAAHAEI NEAGREVVGV GALKVPRNQD WLGVPRFAKF

ASFEAQGALA NIAVDKANLD VEQLESIINF EKLTEWTGS
```

For example, the complex for use according to the present invention may also comprise a gp70-CD8+ epitope and/or a gp70-CD4+ epitope. In particular, the complex for use according to the present invention may comprise a polypeptide or protein comprising a gp70-CD8+ epitope and/or a gp70-CD4+ epitope. For example, such a polypeptide or protein comprised by the complex for use according to the present invention comprises or consists of an amino acid sequence according to SEQ ID NO: 43 or sequence variants thereof as defined above:

```
       (Mad8-cargo comprising a gp70-CD8+ and a
    gp70-CD4+ epitope)
                                        SEQ ID NO: 43
    VTYHSPSYAYHQFERRAILNRLVQFIKDRI
```

For example, the complex for use according to the present invention may preferably comprise at least one survivin epitope, such as a survivin CD8+ epitope and/or a survivin CD4+ epitope. More preferably, the complex for use according to the present invention may comprise a polypeptide or protein comprising a survivin CD8+ epitope and/or a survivin CD4+ epitope. More preferably, the complex for use according to the present invention may comprise a polypeptide or protein comprising more than one survivin CD8+ epitope and/or more than one survivin CD4+ epitope, such as two different survivin CD8+ epitopes. For example, such a polypeptide or protein comprised by the complex for use according to the present invention comprises or consists of an amino acid sequence according to SEQ ID NO: 44 or sequence variants thereof as defined above:

```
(Mad11-cargo comprising survivin CD8+ epitope 1
and survivin CD8+ epitope 2)
                                        SEQ ID NO: 44
NYRIATFKNWPFLEDCAMEELTVSEFLKLDRQR
```

For example, the complex for use according to the present invention may preferably comprise an epitope from a neoantigen. Even more preferably, the complex for use according to the present invention may comprise a polypeptide or protein comprising an epitope from a neoantigen, such as the neoantigen from MC-38 tumor cell line identified by Yadav et al. Nature. 2014 Nov. 27; 515(7528):572-6. For example, such a polypeptide or protein comprised by the complex for use according to the present invention comprises or consists of an amino acid sequence according to SEQ ID NO: 42 or sequence variants thereof as defined above:

```
(Mad9-cargo comprising the epitope from a
neoantigen as described by Yadav et al. Nature.
2014 November 27;515(7528):572-6).
                                        SEQ ID NO: 42
HLELASMTNMELMSSIV
```

For example, the complex for use according to the present invention may preferably comprise more than one, e.g. two or three, epitopes from neoantigens. Even more preferably, the complex for use according to the present invention may comprise a polypeptide or protein comprising more than one, e.g. two or three, epitopes from neoantigens, such as the neoantigens from MC-38 tumor cell line identified by Yadav et al. Nature. 2014 Nov. 27; 515(7528):572-6. For example, such a polypeptide or protein comprised by the complex for use according to the present invention comprises or consists of an amino acid sequence according to SEQ ID NO: 63 or sequence variants thereof as defined above:

```
(Mad12-cargo comprising the epitope from a
neoantigen as described by Yadav et al. Nature.
2014 November 27;515(7528):572-6).
                                        SEQ ID NO: 63
LFRAAQLANDVVLQIMEHLELASMTNMELMSSIVVISASIIVFNLLELEG
```

Preferably, the at least one antigen or antigenic epitope comprised by the complex for use according to the present invention is a peptide, polypeptide, or a protein. Examples of antigen or antigenic epitope of peptidic, polypeptidic, or proteic nature useful in the invention, include cancer/tumor antigens or antigenic epitopes thereof, allergy antigens or antigenic epitopes thereof, auto-immune self-antigens or antigenic epitopes thereof, pathogenic antigens or antigenic epitopes thereof, and antigens or antigenic epitopes thereof from viruses, preferably from cytomegalovirus (CMV), orthopox variola virus, orthopox alastrim virus, parapox ovis virus, molluscum contagiosum virus, herpes simplex virus 1, herpes simplex virus 2, herpes B virus, varicella zoster virus, pseudorabies virus, human cytomegaly virus, human herpes virus 6, human herpes virus 7, Epstein-Barr virus, human herpes virus 8, hepatitis B virus, chikungunya virus, O'nyong'nyong virus, rubivirus, hepatitis C virus, GB virus C, West Nile virus, dengue virus, yellow fever virus, louping ill virus, St. Louis encephalitis virus, Japan B encephalitis virus, Powassan virus, FSME virus, SARS, SARS-associated corona virus, human corona virus 229E, human corona virus Oc43, Torovirus, human T cell lymphotropic virus type 1, human T cell lymphotropic virus type II, HIV (AIDS), i.e. human immunodeficiency virus type 1 or human immunodeficiency virus type 2, influenza virus, Lassa virus, lymphocytic choriomeningitis virus, Tacaribe virus, Junin virus, Machupo virus, Borna disease virus, Bunyamwera virus, California encephalitis virus, Rift Valley fever virus, sand fly fever virus, Toscana virus, Crimean-Congo haemorrhagic fever virus, Hazara virus, Khasan virus, Hantaan virus, Seoul virus, Prospect Hill virus, Puumala virus, Dobrava Belgrade virus, Tula virus, sin nombre virus, Lake Victoria Marburg virus, Zaire Ebola virus, Sudan Ebola virus, Ivory Coast Ebola virus, influenza virus A, influenza virus B, influenza viruses C, parainfluenza virus, malaria parasite (Plasmodium falciparum, Plasmodium vivax, Plasmodium ovale, Plasmodium malariae, Plasmodium knowlesi), Marburg virus, measles virus, mumps virus, respiratory syncytial virus, human metapneumovirus, vesicular stomatitis Indiana virus, rabies virus, Mokola virus, Duvenhage virus, European bat lyssavirus 1+2, Australian bat lyssavirus, adenoviruses A-F, human papilloma viruses, condyloma virus 6, condyloma virus 11, polyoma viruses, adeno-associated virus 2, rotaviruses, orbiviruses, varicella including varizella zoster, etc., or antigens or antigenic epitopes from leishmania, typanosomes, amibes, bacteria, etc., or may be selected from epitopes or from variants of the above antigens or antigenic epitopes. Preferably, epitopes as well as variants of antigens as defined above exhibit a sequence homology or identity of about 10%, in particular at least 10%, about 20%, in particular at least 20%, about 30%, in particular at least so %, about 40%, in particular at least 40%, about 50%, in particular at least so %, about 60%, in particular at least 60%, about 70%, in particular at least 70%, about 80%, in particular at least 80%, about 90% in particular at least 90%, at least 95% or at least 98% with one of the antigens or antigen sequences as shown or described above. In this context, the definition of epitopes and variants similarly applies as defined.

Examples of antigens or antigenic epitopes in the category of peptide, polypeptide or protein include a combination of multiple glioma epitopes such as those described in Novellino et al. (2005, *Cancer Immunol Immunother,* 54(3):187-207), Vigneron et al. (2013, *Cancer Immun.* 13:15). However, a single complex for use according to the present invention may also comprise only a subset, i.e. one or more of all of said glioma epitopes. In such a case preferably different complexes according to the present invention comprise different subsets of all of said glioma epitopes, so that for example a vaccine according to the present invention comprising such different complexes according to the present invention comprises all of said glioma epitopes but distributed in the different complexes.

Moreover, a complex for use according to the invention may also comprise at least one antigen or antigenic epitope, wherein said antigen or antigenic epitope is a polysaccharide, a lipid, a lipoprotein, and/or a glycolipid, in particular a polysaccharidic, lipidic, lipoproteic, and/or glycolipidic epitope, which can be, for example, pathogen epitopes as defined herewith.

In particular, the complex for use according to the invention may comprise at least one antigen or antigenic epitope, wherein said antigen or antigenic epitope is polysaccharidic, lipidic, lipoproteic, and/or glycolipidic, including viral, bacterial, fungal, protozoal and multicellular parasitic antigens or antigenic epitopes.

Preferably, said epitopes will be presented at the cell surface in an MHC class I and/or MHC class II context.

Preferably, said lipidic epitopes will be presented at the cell surface in a CD1 (cluster of differentiation 1) context.

The complex for use according to the present invention may also comprise at least one antigen or antigenic epitope, wherein said antigen or antigenic epitope is a small molecule drug or toxin.

Examples of cargo molecules within the category of small molecule drugs or toxins useful in the invention include cyclosporine A, paclitaxel, doxorubicin, methotrexate, 5-aminolevulinic acid, diphtheria toxin, sunitinib and those molecules reviewed in De wit Amer (2010, *Neuro Oncol,* 12(3):304-16).

The complex for use according to the present invention comprises at least one antigen or antigenic epitope, preferably the complex for use according to the present invention comprises more than one antigen or antigenic epitope, in particular 2, 3, 4, 5, 6, 7, 8, 9, 10 or more antigens or antigenic epitopes, more preferably the complex for use according to the present invention comprises (at least) two or three antigens or antigenic epitopes, even more preferably the complex for use according to the present invention comprises (at least) four or five antigens or antigenic epitopes.

If more than one antigen or antigenic epitope is comprised by the complex for use according to the present invention it is understood that said antigen or antigenic epitope is in particular also covalently linked in the complex for use according to the present invention, e.g. to another antigen or antigenic epitope and/or to a component a), i.e. a cell penetrating peptide, and/or to a component c), i.e. a TLR peptide agonist.

The various antigens or antigenic epitopes comprised by the complex for use according to the present invention may be the same or different. Preferably, the various antigens or antigenic epitopes comprised by the complex for use according to the present invention are different from each other, thus providing a multi-antigenic and/or multi-epitopic complex.

Moreover, it is preferred that the more than one antigen or antigenic epitope, in particular 2, 3, 4, 5, 6, 7, 8, 9, 10 or more antigens or antigenic epitopes, are positioned consecutively in the complex for use according to the present invention. This means in particular that all antigens and/or antigenic epitopes comprised by the complex are positioned in a stretch, which is neither interrupted by component a), i.e. a cell penetrating peptide, nor by component c), i.e. a TLR peptide agonist. Rather, component a) and component c) are positioned in the complex for example before or after such a stretch of all antigens and/or antigenic epitopes. However, the antigens and/or antigenic epitopes positioned consecutively in such a way may be linked to each other for example by a spacer or linker as described below, which is neither component a), i.e. a cell penetrating peptide, nor component c), i.e. a TLR peptide agonist.

Alternatively, however, the various antigens and/or antigenic epitopes may also be positioned in any other way in the complex for use according to the present invention, for example with component a) and/or component c) positioned in between two or more antigens and/or antigenic epitopes, i.e. with one or more antigens and/or antigenic epitopes positioned between component a) and component c) (or vice versa) and, optionally, one or more antigens and/or antigenic epitopes positioned at the respective other end of component a) and/or component c).

It is understood that a number of different antigens or antigenic epitopes relating to colorectal cancer may be advantageously comprised by a single complex for use according to the present invention. Alternatively, a number of different antigens or antigenic epitopes relating to colorectal cancer may be distributed to subsets of different antigens or antigenic epitopes, in particular subsets complementing each other in the context of colorectal cancer which are comprised by different complexes according to the present invention, whereby such different complexes comprising different subsets may advantageously be administered simultaneously, e.g. in a single vaccine, to a subject in need thereof.

Preferably, the complex for use according to the present invention comprises at least one tumor epitope, which is an epitope of an antigen selected from the group consisting of EpCAM, HER-2, MUC-1, TOMM34, RNF 43, KOC1, VEGFR, @hCG, survivin, CEA, TGF@R2, p53, KRas, OGT, CASP5, COA-1, MAGE, SART and IL13Ralpha2. Those antigens are particularly useful in the context of colorectal cancer. It is also preferred that the complex for use according to the present invention comprises at least one tumor antigen selected from the group consisting of EpCAM, HER-2, MUC-1, TOMM34, RNF 43, KOC1, VEGFR, βhCG, survivin, CEA, TGF@R2, p53, KRas, OGT, CASP5, COA-1, MAGE, SART and IL13Ralpha2, or a fragment thereof, or a sequence variant of a tumor antigen or a sequence variant of a fragment thereof. As used herein, a "fragment" of an antigen comprises at least 10 consecutive amino acids of the antigen, preferably at least 15 consecutive amino acids of the antigen, more preferably at least 20 consecutive amino acids of the antigen, even more preferably at least 25 consecutive amino acids of the antigen and most preferably at least 30 consecutive amino acids of the antigen. A "sequence variant" is as defined above, namely a sequence variant has an (amino acid) sequence which is at least 70%, at least 75%, preferably at least 80%, more preferably at least 85%, even more preferably at least 90%, particularly preferably at least 95%, most preferably at least 99% identical to the reference sequence. A "functional" sequence variant means in the context of an antigen/antigen fragment/epitope, that the function of the epitope(s), e.g. comprised by the antigen (fragment), is not impaired or abolished. Preferably, however, the amino acid sequence of the epitope(s), e.g. comprised by the cancer/tumor antigen (fragment) as described herein, is not mutated and, thus, identical to the reference epitope sequence.

As described above, suitable cancer/tumor epitopes of those antigens are known from the literature or can be identified by using cancer/tumor epitope databases, e.g. from van der Bruggen P, Stroobant V, Vigneron N, Van den Eynde B. Peptide database: T cell-defined tumor antigens. *Cancer Immun* 2013; URL: www.cancerimmunity.org/peptide/, wherein human tumor antigens recognized by CD4[+] or CDS+ T cells are classified into four major groups on the basis of their expression pattern, or from the database "Tantigen" (TANTIGEN version 1.0, Dec. 1, 2009; developed by Bioinformatics Core at Cancer Vaccine Center, Dana-Farber Cancer Institute; URL: cvc.dfci.harvard.edu/tadb/).

EpCAM

Ep-Cam is a glycoprotein mediating cellular adhesion. The amino acid sequence of EpCAM is shown in the following:

```
                                            [SEQ ID NO: 47]
MAPPQVLAFGLLLAAATATFAAAQEECVCENYKLAVNCFVNNNRQCQCT

SVGAQNTVICSKLAAKCLVMKAEMNGSKLGRRAKPEGALQNNDGLYDPD

CDESGLFKAKQCNGTSMCWCVNTAGVRRTDKDTEITCSERVRTYWIIIE

LKHKAREKPYDSKSLRTALQKEITTRYQLDPKFITSILYENNVITIDLV

QNSSQKTQNDVDIADVAYYFEKDVKGESLFHSKKMDLTVNGEQLDLDPG

QTLIYYVDEKAPEFSMQGLKAGVIAVIVVVVIAVVAGIVVLVISRKKRM

AKYEKAEIKEMGEMHRELNA
```

Accordingly, a preferred complex for use according to the present invention comprises an amino acid sequence according to SEQ ID NO: 47 or a fragment or a variant thereof as described herein.

Several epitopes of EpCAM are known to the skilled person. A preferred EpCAM epitope, which is preferably comprised by the complex for use according to the present invention, includes the following epitope (the epitope sequence shown in the following is a fragment of the above EpCAM sequence and is, thus, shown in the above EpCAM sequence underlined; the following epitope sequence may refer to one epitope or more than one (overlapping) epitopes):

```
                             [SEQ ID NO: 48]
     GLKAGVIAV
```

Accordingly, a preferred complex for use according to the present invention comprises an amino acid sequence according to SEQ ID NO: 48 or a fragment or a variant thereof as described herein.

HER-2/neu

Her-2 belongs to the EGFR (epidermal growth factor receptor) family. Many HLA-A epitopes are known to the skilled person. The amino acid sequence of HER2 is shown in the following:

```
                                            [SEQ ID NO: 70]
    MELAALCRWGLLLALLPPGAASTQVCTGTDMKLRLPASPETHLD

MLRHLYQGCQVVQGNLELTYLPTNASLSFLQDIQEVQGYVLIAH

NQVRQVPLQRLRIVRGTQLFEDNYALAVLDNGDPLNNTTPVTGA

SPGGLRELQLRSLTEILKGGVLIQRNPQLCYQDTILWKDIFHKN

NQLALTLIDTNRSRACHPCSPMCKGSRCWGESSEDCQSLTRTVC

AGGCARCKGPLPTDCCHEQCAAGCTGPKHSDCLACLHFNHSGIC

ELHCPALVTYNTDTFESMPNPEGRYTFGASCVTACPYNYLSTDV

GSCTLVCPLHNQEVTAEDGTQRCEKCSKPCARVCYGLGMEHLRE

VRAVTSANIQEFAGCKKIFGSLAFLPESFDGDPASNTAPLQPEQ

LQVFETLEEITGYLYISAWPDSLPDLSVFQNLQVIRGRILHNGA
```

-continued
```
YSLTLQGLGISWLGLRSLRELGSGLALIHHNTHLCFVHTVPWDQ

LFRNPHQALLHTANRPEDECVGEGLACHQLCARGHCWGPGPTQC

VNCSQFLRGQECVEECRVLQGLPREYVNARHCLPCHPECQPQNG

SVTCFGPEADQCVACAHYKDPPFCVARCPSGVKPDLSYMPIWKF

PDEEGACQPCPINCTHSCVDLDDKGCPAEQRASPLTSIISAVVG

ILLVVVLGVVFGILIKRRQQKIRKYTMRRLLQETELVEPLTPSG

AMPNQAQMRILKETELRKVKVLGSGAFGTVYKGIWIPDGENVKI

PVAIKVLRENTSPKANKEILDEAYVMAGVGSPYVSRLLGICLTS

TVQLVTQLMPYGCLLDHVRENRGRLGSQDLLNWCMQIAKGMSYL

EDVRLVHRDLAARNVLVKSPNHVKITDFGLARLLDIDETEYHAD

GGKVPIKWMALESILRRRFTHQSDVWSYGVTVWELMTFGAKPYD

GIPAREIPDLLEKGERLPQPPICTIDVYMIMVKCWMIDSECRPR

FRELVSEFSRMARDPQRFVVIQNEDLGPASPLDSTFYRSLLEDD

DMGDLVDAEEYLVPQQGFFCPDPAPGAGGMVHHRHRSSSTRSGG

GDLTLGLEPSEEEAPRSPLAPSEGAGSDVFDGDLGMGAAKGLQS

LPTHDPSPLQRYSEDPTVPLPSETDGYVAPLTCSPQPEYVNQPD

VRPQPPSPREGPLPAARPAGATLERPKTLSPGKNGVVKDVFAFG

GAVENPEYLTPQGGAAPQPHPPPAFSPAFDNLYYWDQDPPERGA

PPSTFKGTPTAENPEYLGLDVPV
```

Accordingly, a preferred complex for use according to the present invention comprises an amino acid sequence according to SEQ ID NO: 70 or a fragment or a variant thereof as described herein. As described above, suitable cancer/tumor epitopes of Her-2 are known from the literature or can be identified by using cancer/tumor epitope databases, e.g. from van der Bruggen P, Stroobant V, Vigneron N, Van den Eynde B. Peptide database: T cell-defined tumor antigens. *Cancer Immun* 2013; URL: www.cancerimmunity.org/peptide/, wherein human tumor antigens recognized by CD4+ or CD8+ T cells are classified into four major groups on the basis of their expression pattern, or from the database "Tantigen" (TANTIGEN version 1.0, Dec. 1, 2009; developed by Bioinformatics Core at Cancer Vaccine Center, Dana-Farber Cancer Institute; URL: cvc.dfci.harvard.edu/tadb/).

Mucin-1 (MUC-1)

MUC-1 is a human epithelial mucin, acting on cell adhesion. The amino acid sequence of MUC-I is shown in the following:

```
                                        [SEQ ID NO: 49]
MTPGTQSPFFLLLLLTVLTVVTGSGHASSTPGGEKETSATQRSS

VPSSTEKNAVSMTSSVLSSHSPGSGSSTTQGQDVTLAPATEPAS

GSAATWGQDVTSVPVTRPALGSTTPPAHDVTSAPDNKPAPGSTA

PPAHGVTSAPDTRPAPGSTAPPAHGVTSAPDTRPAPGSTAPPAH

GVTSAPDTRPAPGSTAPPAHGVTSAPDTRPAPGSTAPPAHGVTS

APDTRPAPGSTAPPAHGVTSAPDTRPAPGSTAPPAHGVTSAPDT

RPAPGSTAPPAHGVTSAPDTRPAPGSTAPPAHGVTSAPDTRPAP

GSTAPPAHGVTSAPDTRPAPGSTAPPAHGVTSAPDTRPAPGSTA

PPAHGVTSAPDTRPAPGSTAPPAHGVTSAPDTRPAPGSTAPPAH

GVTSAPDTRPAPGSTAPPAHGVTSAPDTRPAPGSTAPPAHGVTS

APDTRPAPGSTAPPAHGVTSAPDTRPAPGSTAPPAHGVTSAPDT

RPAPGSTAPPAHGVTSAPDTRPAPGSTAPPAHGVTSAPDTRPAP

GSTAPPAHGVTSAPDTRPAPGSTAPPAHGVTSAPDTRPAPGSTA

PPAHGVTSAPDTRPAPGSTAPPAHGVTSAPDTRPAPGSTAPPAH

GVTSAPDTRPAPGSTAPPAHGVTSAPDTRPAPGSTAPPAHGVTS

APDTRPAPGSTAPPAHGVTSAPDTRPAPGSTAPPAHGVTSAPDT

RPAPGSTAPPAHGVTSAPDNRPALGSTAPPVHNVTSASGSASGS

ASTLVHNGTSARATTTPASKSTPFSIPSHHSDTPTTLASHSTKT

DASSTHHSSVPPLTSSNHSTSPQLSTGVSFFFLSFHISNLQFNS

SLEDPSTDYYQELQRDISEMFLQIYKQGGFLGLSNIKFRPGSVV

VQLTLAFREGTINVHDVETQFNQYKTEAASRYNLTISDVSVSDV

PFPFSAQSGAGVPGWGIALLVLVCVLVALAIVYLIALAVCQCRR

KNYGQLDIFPARDTYHPMSEYPTYHTHGRYVPPSSTDRSPYEKV

SAGNGGSSLSYTNPAVAATSANL
```

Accordingly, a preferred complex for use according to the present invention comprises an amino acid sequence according to SEQ ID NO: 49 or a fragment or a variant thereof as described herein.

Several epitopes of MUC-1 are known to the skilled person. Preferred MUC-1 epitopes, which are preferably comprised by the complex for use according to the present invention, include the following epitopes (the epitope sequences shown in the following are fragments of the above MUC-1 sequence and are, thus, shown in the above MUC-1 sequence underlined; each of the following epitope sequences may refer to one epitope or more than one (overlapping) epitopes):

```
                        [SEQ ID NO: 50]
GSTAPPVHN

[SEQ ID NO: 51]
TAPPAHGVTS
```

Accordingly, a preferred complex for use according to the present invention comprises an amino acid sequence according to SEQ ID NO: 50 and/or an amino acid sequence according to SEQ ID NO: 61.

TOMM34

TOMM34 is involved in the import of precursor proteins into mitochondria. Many epitopes thereof are known to the skilled person.

RNF 43

RNF43 is a RING-type E3 ubiquitin ligase and is predicted to contain a transmembrane domain, a protease-associated domain, an ectodomain, and a cytoplasmic RING domain. RNF43 is thought to negatively regulate Wnt signaling, and expression of RNF43 results in an increase in ubiquitination of frizzled receptors, an alteration in their subcellular distribution, resulting in reduced surface levels of these receptors. Many epitopes thereof are known to the skilled person.

KOC1

KOC1, also known as insulin-like growth factor 2 mRNA-binding protein 3 (IGF2BP3) is an mRNA binding protein. No expression data are however available.

Vascular Endothelial Growth Factor (VEGF)/Vascular Endothelial Growth Factor Receptor (VEGFR)

Vascular endothelial growth factor (VEGF), originally known as vascular permeability factor (VPF), is a signal protein produced by cells that stimulates vasculogenesis and angiogenesis. It is part of the system that restores the oxygen supply to tissues when blood circulation is inadequate. VEGF's normal function is to create new blood vessels during embryonic development, new blood vessels after injury, muscle following exercise, and new vessels (collateral circulation) to bypass blocked vessels. There are three main subtypes of the receptors for VEGF (VEGFR), namely VEGFR1, VEGFR2 and VEGFR3.

Beta Subunit of Human Chorionic Gonadotropin (βhCG)

Human chorionic gonadotropin (hCG) is a hormone produced by the embryo following implantation. Some cancerous tumors produce this hormone; therefore, elevated levels measured when the patient is not pregnant can lead to a cancer diagnosis. hCG is heterodimeric with an a (alpha) subunit identical to that of luteinizing hormone (LH), follicle-stimulating hormone (FSH), thyroid-stimulating hormone (TSH), and @(beta) subunit that is unique to hCG. The @-subunit of hCG gonadotropin (beta-hCG) contains 145 amino acids and is encoded by six highly homologous genes.

Survivin

Survivin, also called baculoviral inhibitor of apoptosis repeat-containing 5 or BIRC5, is a member of the inhibitor of apoptosis (IAP) family. The survivin protein functions to inhibit caspase activation, thereby leading to negative regulation of apoptosis or programmed cell death. The amino acid sequence of survivin is shown in the following:

[SEQ ID NO: 52]
MGAPTLPPAWQPFLKDHRISTFKNWPFLEGCACTPERMAEAGFI

HCPTENEPDLAQCFFCFKELEGWEPDDDPIEEHKKHSSGCAFLS

VKKQFEELTLGEFLKLDRERAKNKIAKETNNKKKEFEETAKKVR

RAIEQLAAMD

Accordingly, a preferred complex for use according to the present invention comprises an amino acid sequence according to SEQ ID NO: 52 or a fragment or a variant thereof as described herein.

Several epitopes of survivin are known to the skilled person. A preferred survivin epitope, which is preferably comprised by the complex for use according to the present invention, includes the following epitope (the epitope sequence shown in the following is a fragment of the above survivin sequence and is, thus, shown in the above survivin sequence underlined; the following epitope sequence may refer to one epitope or more than one (overlapping) epitopes):

[SEQ ID NO: 53]
RISTFKNWPF

Accordingly, a preferred complex for use according to the present invention comprises an amino acid sequence according to SEQ ID NO: 53.

Carcino-Embryonic Antigen (CEA)

CEA is an intracellular adhesion glycoprotein. CEA is normally produced in gastrointestinal tissue during fetal development, but the production stops before birth. Therefore, CEA is usually present only at very low levels in the blood of healthy adults. The amino acid sequence of CEA is shown in the following:

[SEQ ID NO: 54]
MESPSAPPHRWCIPWQRLLLTASLLTFWNPPTTAKLTIESTPFN

VAEGKEVLLLVHNLPQHLFGYSWYKGERVDGNRQIIGYVIGTQQ

ATPGPAYSGREIIYPNASLLIQNIIQNDTGFYTLHVIKSDLVNE

EATGQFRVYPELPKPSISSNNSKPVEDKDAVAFTCEPETQDATY

LWWVNNQSLPVSPRLQLSNGNRTLTLFNVTRNDTASYKCETQNP

VSARRSDSVILNVLYGPDAPTISPLNTSYRSGENLNLSCHAASN

PPAQYSWFVNGTFQQSTQELFIPNITVNNSGSYTCQAHNSDTGL

NRTTVTTITVYAEPPKPFITSNNSNPVEDEDAVALTCEPEIQNT

TYLWWVNNQSLPVSPRLQLSNDNRTLTLLSVTRNDVGPYECGIQ

NKLSVDHSDPVILNVLYGPDDPTISPSYTYYRPGVNLSLSCHAA

SNPPAQYSWLIDGNIQQHTQELFISNITEKNSGLYTCQANNSAS

GHSRTTVKTITVSAELPKPSISSNNSKPVEDKDAVAFTCEPEAQ

NTTYLWWVNGQSLPVSPRLQLSNGNRTLTLFNVTRNDARAYVCG

IQNSVSANRSDPVTLDVLYGPDTPIISPPDSSYLSGANLNLSCH

SASNPSPQYSWRINGIPQQHTQVLFIAKITPNNNGTYACFVSNL

ATGRNNSIVKSITVSASGTSPGLSAGATVGIMIGVLVGVAL

Accordingly, a preferred complex for use according to the present invention comprises an amino acid sequence according to SEQ ID NO: 54 or a fragment or a variant thereof as described herein.

Several epitopes of CEA are known to the skilled person. Preferred CEA epitopes, which are preferably comprised by the complex for use according to the present invention, include the following epitopes (the epitope sequences shown in the following are fragments of the above CEA sequence and are, thus, shown in the above CEA sequence underlined; each of the following epitope sequences may refer to one epitope or more than one (overlapping) epitopes):

[SEQ ID NO: 55]
YLSGANLNLS

[SEQ ID NO: 56]
SWRINGIPQQ

Accordingly, a preferred complex for use according to the present invention comprises an amino acid sequence according to SEQ ID NO: 55 and/or an amino acid sequence according to SEQ ID NO: 56.

Transforming growth factor beta receptor 2 (TGFβR2)

TGFβ receptors are single pass serine/threonine kinase receptors. They exist in several different isoforms. TGFβR2 is a transmembrane protein that has a protein kinase domain, forms a heterodimeric complex with another receptor protein, and binds TGF-beta. This receptor/ligand complex phosphorylates proteins, which then enter the nucleus and regulate the transcription of a subset of genes related to cell proliferation.

P53

P53 is a tumor suppressor protein having a role in preventing genome mutation. P53 has many mechanisms of anticancer function and plays a role in apoptosis, genomic stability, and inhibition of angiogenesis. In its anti-cancer role, p53 works through several mechanisms: it an activate DNA repair proteins when DNA has sustained damage; it can arrest growth by holding the cell cycle at the G1/S regulation point on DNA damage recognition; and it can initiate apoptosis.

Kirsten Ras (KRas)

GTPase KRas also known as V-Ki-ras2 Kirsten rat sarcoma viral oncogene homolog and KRAS, performs an essential function in normal tissue signaling, and the mutation of a KRAS gene is an essential step in the development of many cancers. Like other members of the ras subfamily, the KRAS protein is a GTPase and is an early player in many signal transduction pathways. KRAS is usually tethered to cell membranes because of the presence of an isoprene group on its C-terminus. The amino acid sequence of KRas is shown in the following:

```
                                            [SEQ ID NO: 57]
MTEYKLVVVGAGGVGKSALTIQLIQNHFVDEYDPTIEDSYRKQV

VIDGETCLLDILDTAGQEEYSAMRDQYMRTGEGFLCVFAINNTK

SFEDIHHYREQIKRVKDSEDVPMVLVGNKCDLPSRTVDTKQAQD

LARSYGIPFIETSAKTRQRVEDAFYTLVREIRQYRLKKISKEEK

TPGCVKIKKCIIM
```

Accordingly, a preferred complex for use according to the present invention comprises an amino acid sequence according to SEQ ID NO: 57 or a fragment or a variant thereof as described herein.

Several epitopes of Kirsten Ras are known to the skilled person. A preferred Kirsten Ras epitope, which is preferably comprised by the complex for use according to the present invention, includes the following epitope (the epitope sequence shown in the following is a fragment of the above Kirsten Ras sequence and is, thus, shown in the above Kirsten Ras sequence underlined; the following epitope sequence may refer to one epitope or more than one (overlapping) epitopes):

```
                       [SEQ ID NO: 58]
VVVGAGGVG
```

Accordingly, a preferred complex for use according to the present invention comprises an amino acid sequence according to SEQ ID NO: 58.

O-Linked N-Acetylglucosamine (GlcNAc) Transferase (OGT)

OGT (O-Linked N-Acetylglucosamine (GlcNAc) Transferase, O-GlcNAc transferase, OGTase, 0-linked N-acetyl-glucosaminyltransferase, uridine diphospho-N-acetylglucosamine:polypeptide beta-N-acetylglucosaminyltransferase, protein O-linked beta-N-acetylglucosamine transferase) is an enzyme with system name UDP-N-acetyl-D-glucosamine:protein-O-beta-N-acetyl-D-glucosaminyl transferase) is an enzyme with system name "UDP-N-acetyl-D-glucosamine:protein-O-beta-N-acetyl-D-glucosaminyl transferase". OGT catalyzes the addition of a single N-acetylglucosamine in O-glycosidic linkage to serine or threonine residues of intracellular proteins. OGT is a part of a host of biological functions within the human body. OGT is involved in the resistance of insulin in muscle cells and adipocytes by inhibiting the Threonine 308 phosphorylation of AKT1, increasing the rate of IRS1 phosphorylation (at Serine 307 and Serine 632/635), reducing insulin signaling, and glycosylating components of insulin signals. Additionally, OGT catalyzes intracellular glycosylation of serine and threonine residues with the addition of N-acetylglucosamine. Studies show that OGT alleles are vital for embryogenesis, and that OGT is necessary for intracellular glycosylation and embryonic stem cell vitality. OGT also catalyzes the posttranslational modification that modifies transcription factors and RNA polymerase II, however the specific function of this modification is mostly unknown.

Caspase 5 (CASP5)

Caspase 5 is an enzyme that proteolytically cleaves other proteins at an aspartic acid residue, and belongs to a family of cysteine proteases called caspases. It is an inflammatory caspase, along with caspase 1, caspase 4 and the murine caspase 4 homolog caspase 11, and has a role in the immune system.

Colorectal Tumor-Associated Antigen-1 (COA-1)

COA-1 was identified in 2003 by Maccalli et al. (Maccalli, C., et al., Identification of a colorectal tumor-associated antigen (COA-1) recognized by CD4(+) T lymphocytes. Cancer Res, 2003. 63(20): p. 6735-43) as strongly expressed by colorectal and melanoma cells (no data available). Its mutation may interfere with the differential recognition of tumor and normal cells.

Melanoma-Associated Antigen (MAGE)

The mammalian members of the MAGE (melanoma-associated antigen) gene family were originally described as completely silent in normal adult tissues, with the exception of male germ cells and, for some of them, placenta. By contrast, these genes were expressed in various kinds of tumors. Therefore, the complex for use according to the present invention preferably comprises an antigen of the MAGE-family (a "MAGE" antigen) or an epitope thereof. Of the MAGE family, in particular MAGE-A3 and MAGE-D4 are preferred, and MAGE-A3 is particularly preferred. The normal function of MAGE-A3 in healthy cells is unknown. MAGE-A3 is a tumor-specific protein, and has been identified on many tumors. The amino acid sequence of MAGE-A3 is shown in the following:

```
                                            [SEQ ID NO: 59]
MPLEQRSQHCKPEEGLEARGEALGLVGAQAPATEEQEAASSSST

LVEVTLGEVPAAESPDPPQSPQGASSLPTTMNYPLWSQSYEDSS

NQEEEGPSTFPDLESEFQAALSRKVAELVHFLLLKYRAREPVTK

AEMLGSVVGNWQYFFPVIFSKAFSSLQLVFGIELMEVDPIGHLY

IFATCLGLSYDGLLGDNQIMPKAGLLIIVLAIIAREGDCAPEEK
```

```
-continued
IWEELSVLEVFEGREDSILGDPKKLLTQHFVQENYLEYRQVPGS

DPACYEFLWGPRALVETSYVKVLHHMVKISGGPHIS YPPLHEW

VLREGEE
```

Accordingly, a preferred complex for use according to the present invention comprises an amino acid sequence according to SEQ ID NO: 59.

Several epitopes of MAGE-As are known to the skilled person. A preferred MAGE-A3 epitope, which is preferably comprised by the complex for use according to the present invention, includes the following epitope (the epitope sequence shown in the following is a fragment of the above MAGE-A3 sequence and is, thus, shown in the above MAGE-A3 sequence underlined; the following epitope sequence may refer to one epitope or more than one (overlapping) epitopes):

```
                                    [SEQ ID NO: 60]
            KVAELVHFL
```

Accordingly, a preferred complex for use according to the present invention comprises an amino acid sequence according to SEQ ID NO: 60.

Squamous Cell Carcinoma Antigen Recognized by T-Cells (SART)

Within the SART family, SART-3 is most preferred. Thus, the complex for use according to the present invention preferably comprises an antigen of the SART-family (a "SART" antigen) or an epitope thereof; the complex for use according to the present invention more preferably comprises SART-3 or an epitope thereof. Squamous cell carcinoma antigen recognized by T-cells 3 possesses tumor epitopes capable of inducing HLA-A24-restricted and tumor-specific cytotoxic T lymphocytes in cancer patients. SART-3 is thought to be involved in the regulation of mRNA splicing.

IL 13Ralpha2

IL13Ralpha2 binds interleukin 13 (IL-13) with very high affinity (and can therefore sequester it) but does not allow IL-4 binding. It acts as a negative regulator of both IL-13 and IL-4, however the mechanism of this is still undetermined. The amino acid sequence of IL13Ralpha2 is shown in the following:

```
                                    [SEQ ID NO: 61]
    MAFVCLAIGCLYTFLISTTFGCTSSSDTEIKVNPPQDFEIVDPG

YLGYLYLQWQPPLSLDHFKECTVEYELKYRNIGSETWKTIITKN

LHYKDGFDLNKGIEAKIHTLLPWQCTNGSEVQSSWAETTYWISP

QGIPETKVQDMDCVYYNWQYLLCSWKPGIGVLLDTNYNLFYWYE

GLDHALQCVDYIKADGQNIGCRFPYLEASDYKDFYICVNGSSEN

KPIRSSYFTFQLQNIVKPLPPVYLTFTRESSCEIKLKWSIPLGP

IPARCFDYEIEIREDDTTLVTATVENETYTLKTTNETRQLCFVV

RSKVNIYCSDDGIWSEWSDKQCWEGEDLSKKTLLRFWLPFGFIL

ILVIFVTG LLLRKPNTYPKMIPEFFCDT
```

Accordingly, a preferred complex for use according to the present invention comprises an amino acid sequence according to SEQ ID NO: 61 or a fragment or a variant thereof as described herein.

Several epitopes of IL13Ralpha2 are known to the skilled person. A preferred ILisRalpha2 epitope, which is preferably comprised by the complex for use according to the present invention, includes the following epitope (the epitope sequence shown in the following is a fragment of the above IL13Ralpha2 sequence and is, thus, shown in the above IL13Ralpha2 sequence underlined; the following epitope sequence may refer to one epitope or more than one (overlapping) epitopes):

```
                                    [SEQ ID NO: 62]
            LPFGFIL
```

Accordingly, a preferred complex for use according to the present invention comprises an amino acid sequence according to SEQ ID NO: 62.

Preferably, the complex for use according to the present invention comprises at least one tumor epitope, which is an epitope of an antigen selected from the group consisting of EpCAM, MUC-1, survivin, CEA, KRas, MAGE-A3 and IL13Ralpha2, such as an epitope according to any of SEQ ID NOs 48, 50, 51, 53, 55, 56, 58, 60 and 62; more preferably the at least one tumor epitope is an epitope of an antigen selected from the group consisting of EpCAM, MUC-1, survivin, CEA, KRas and MAGE-AS, such as an epitope according to any of SEQ ID NOs 48, 50, 51, 53, 55, 56, 58 and 60; and even more preferably the at least one tumor epitope is an epitope of an antigen selected from the group consisting of EpCAM, MUC-1, survivin and CEA, such as an epitope according to any of SEQ ID NOs 48, 50, 51, 53, 55 and 56.

It is also preferred that the complex for use according to the present invention comprises one or more epitopes of EpCAM (such as the epitope according to SEQ ID NO: 48) or functional sequence variants thereof;

one or more epitopes of MUC-I (such as the epitope according to SEQ ID NO: 50 and/or the epitope according to SEQ ID NO: 51) or functional sequence variants thereof;

one or more epitopes of survivin (such as the epitope according to SEQ ID NO: 53) or functional sequence variants thereof;

one or more epitopes of CEA (such as the epitope according to SEQ ID NO: 55 and/or the epitope according to SEQ ID NO: 56) or functional sequence variants thereof;

one or more epitopes of KRas (such as the epitope according to SEQ ID NO: 58) or functional sequence variants thereof; and/or one or more epitopes of MAGE-A3 (such as the epitope according to SEQ ID NO: 60) or functional sequence variants thereof.

As described above, further epitopes of those antigens (in addition to the exemplified epitopes) can easily be retrieved from cancer/tumor epitope databases, e.g. from van der Bruggen P, Stroobant V, Vigneron N, Van den Eynde B. Peptide database: T cell-defined tumor antigens. *Cancer Immun* 2013; URL: www.cancerimmunity.org/peptide/, or from the database "Tantigen" (TANTIGEN version 1.0, Dec. 1, 2009; developed by Bioinformatics Core at Cancer Vaccine Center, Dana-Farber Cancer Institute; URL: cvc.dfci-.harvard.edu/tadb/).

A "sequence variant" is as defined above, namely a sequence variant has an (amino acid) sequence which is at least 70%, at least 75%, preferably at least 80%, more preferably at least 85%, even more preferably at least 90%, particularly preferably at least 95%, most preferably at least 99% identical to the reference sequence. A "functional" sequence variant means in the context of an epitope, that the function as an epitope is not impaired or abolished. Preferably, however, the amino acid sequence of an epitope of a cancer/tumor antigen as described herein is not mutated and, thus, identical to the reference epitope sequence.

It is also preferred that the complex for use according to the present invention comprises
- a fragment of EpCAM comprising one or more epitopes or a functional sequence variant thereof;
- a fragment of MUC-1 comprising one or more epitopes or a functional sequence variant thereof;
- a fragment of survivin comprising one or more epitopes or a functional sequence variant thereof;
- a fragment of CEA comprising one or more epitopes or a functional sequence variant thereof;
- a fragment of KRas comprising one or more epitopes or a functional sequence variant thereof; and/or
- a fragment of MAGE-AS comprising one or more epitopes or a functional sequence variant thereof.

As used herein, a "fragment" of an antigen comprises at least 10 consecutive amino acids of the antigen, preferably at least 15 consecutive amino acids of the antigen, more preferably at least 20 consecutive amino acids of the antigen, even more preferably at least 25 consecutive amino acids of the antigen and most preferably at least 30 consecutive amino acids of the antigen. Accordingly, a fragment of EpCAM comprises at least 10 consecutive amino acids of EpCAM (SEQ ID NO: 47), preferably at least 15 consecutive amino acids of EpCAM (SEQ ID NO: 47), more preferably at least 20 consecutive amino acids of EpCAM (SEQ ID NO: 47), even more preferably at least 25 consecutive amino acids of EpCAM (SEQ ID NO: 47) and most preferably at least 30 consecutive amino acids of EpCAM (SEQ ID NO: 47); a fragment of MUC-1 comprises at least 10 consecutive amino acids of MUC-1 (SEQ ID NO: 49), preferably at least 15 consecutive amino acids of MUC-1 (SEQ ID NO: 49), more preferably at least 20 consecutive amino acids of MUC-1 (SEQ ID NO: 49), even more preferably at least 25 consecutive amino acids of MUC-1 (SEQ ID NO: 49) and most preferably at least 30 consecutive amino acids of MUC-1 (SEQ ID NO: 49); a fragment of survivin comprises at least 10 consecutive amino acids of survivin (SEQ ID NO: 52), preferably at least 15 consecutive amino acids of survivin (SEQ ID NO: 52), more preferably at least 20 consecutive amino acids of survivin (SEQ ID NO: 52), even more preferably at least 25 consecutive amino acids of survivin (SEQ ID NO: 52) and most preferably at least 30 consecutive amino acids of survivin (SEQ ID NO: 52); a fragment of CEA comprises at least 10 consecutive amino acids of CEA (SEQ ID NO: 54), preferably at least 15 consecutive amino acids of CEA (SEQ ID NO: 54), more preferably at least 20 consecutive amino acids of CEA (SEQ ID NO: 54), even more preferably at least 25 consecutive amino acids of CEA (SEQ ID NO: 54) and most preferably at least 30 consecutive amino acids of CEA (SEQ ID NO: 54); a fragment of KRas comprises at least 10 consecutive amino acids of KRas (SEQ ID NO: 57), preferably at least 15 consecutive amino acids of KRas (SEQ ID NO: 57), more preferably at least 20 consecutive amino acids of KRas (SEQ ID NO: 57), even more preferably at least 25 consecutive amino acids of KRas (SEQ ID NO: 57) and most preferably at least 30 consecutive amino acids of KRas (SEQ ID NO: 57); and a fragment of MAGE-As comprises at least 10 consecutive amino acids of MAGE-As (SEQ ID NO: 59), preferably at least 15 consecutive amino acids of MAGE-As (SEQ ID NO: 59), more preferably at least 20 consecutive amino acids of MAGE-As (SEQ ID NO: 59), even more preferably at least 25 consecutive amino acids of MAGE-As (SEQ ID NO: 59) and most preferably at least 30 consecutive amino acids of MAGE-As (SEQ ID NO: 59).

A functional sequence variant of such a fragment has an (amino acid) sequence, which is at least 70%, at least 75%, preferably at least 80%, more preferably at least 85%, even more preferably at least 90%, particularly preferably at least 95%, most preferably at least 99% identical to the reference sequence, and the epitope function of at least one, preferably all, epitope(s) comprised by the fragment is maintained.

Preferably, such a complex comprises
- one or more epitopes of EpCAM (such as the epitope according to SEQ ID NO: 48) or functional sequence variants thereof;
- one or more epitopes of CEA (such as the epitope according to SEQ ID NO: 55 and/or the epitope according to SEQ ID NO: 56) or functional sequence variants thereof; and
- one or more epitopes of MAGE-As (such as the epitope according to SEQ ID NO: 60) or functional sequence variants thereof.

Such a complex does preferably not comprise any epitope of HER-2, MUC-1, TOMMS4, RNF 43, KOC1, VEGFR, βhCG, survivin, TGFβR2, p53, KRas, OGT, CASP5, COA-1, SART or IL1sRalpha2.

It is also preferred that such a complex comprises
- one or more epitopes of EpCAM (such as the epitope according to SEQ ID NO: 48) or functional sequence variants thereof;
- one or more epitopes of MUC-1 (such as the epitope according to SEQ ID NO: 50 and/or the epitope according to SEQ ID NO: 51) or functional sequence variants thereof;
- one or more epitopes of CEA (such as the epitope according to SEQ ID NO: 55 and/or the epitope according to SEQ ID NO: 56) or functional sequence variants thereof; and
- one or more epitopes of MAGE-As (such as the epitope according to SEQ ID NO: 60) or functional sequence variants thereof.

Such a complex does preferably not comprise any epitope of HER-2, TOMM34, RNF 43, KOC1, VEGFR, RhCG, survivin, TGFβR2, p53, KRas, OGT, CASP5, COA-1, SART or IL13Ralpha2.

It is also preferred that such a complex comprises
- one or more epitopes of EpCAM (such as the epitope according to SEQ ID NO: 48) or functional sequence variants thereof;
- one or more epitopes of MUC-1 (such as the epitope according to SEQ ID NO: 50 and/or the epitope according to SEQ ID NO: 51) or functional sequence variants thereof;
- one or more epitopes of CEA (such as the epitope according to SEQ ID NO: 55 and/or the epitope according to SEQ ID NO: 56) or functional sequence variants thereof; and
- one or more epitopes of KRas (such as the epitope according to SEQ ID NO: 58) or functional sequence variants thereof.

Such a complex does preferably not comprise any epitope of HER-2, TOMM34, RNF 43, KOC1, VEGFR, @hCG, survivin, TGFβR2, p53, OGT, CASP5, COA-1, MAGE, SART or IL13Ralpha2.

It is also preferred that such a complex comprises
one or more epitopes of EpCAM (such as the epitope according to SEQ ID NO: 48) or functional sequence variants thereof,
one or more epitopes of survivin (such as the epitope according to SEQ ID NO: 53) or functional sequence variants thereof;
one or more epitopes of CEA (such as the epitope according to SEQ ID NO: 55 and/or the epitope according to SEQ ID NO: 56) or functional sequence variants thereof; and
one or more epitopes of MAGE-As (such as the epitope according to SEQ ID NO: 60) or functional sequence variants thereof.

Such a complex does preferably not comprise any epitope of HER-2, MUC-1, TOMM34, RNF 43, KOC1, VEGFR, phCG, TGFβR2, p53, KRas, OGT, CASP5, COA-1, SART or IL13Ralpha2.

It is also preferred that such a complex comprises
one or more epitopes of MUC-1 (such as the epitope according to SEQ ID NO: 50 and/or the epitope according to SEQ ID NO: 51) or functional sequence variants thereof;
one or more epitopes of survivin (such as the epitope according to SEQ ID NO: 53) or functional sequence variants thereof; and
one or more epitopes of MAGE-A3 (such as the epitope according to SEQ ID NO: 60) or functional sequence variants thereof.

Such a complex does preferably not comprise any epitope of EpCAM, HER-2, TOMM34, RNF 43, KOC1, VEGFR, @hCG, CEA, TGFβR2, p53, KRas, OGT, CASP5, COA-1, SART or IL13Ralpha2.

More preferably, such a complex comprises
one or more epitopes of EpCAM (such as the epitope according to SEQ ID NO: 48) or functional sequence variants thereof;
one or more epitopes of MUC-I (such as the epitope according to SEQ ID NO: 50 and/or the epitope according to SEQ ID NO: 51) or functional sequence variants thereof;
one or more epitopes of survivin (such as the epitope according to SEQ ID NO: 53) or functional sequence variants thereof; and/or
one or more epitopes of CEA (such as the epitope according to SEQ ID NO: 55 and/or the epitope according to SEQ ID NO: 56) or functional sequence variants thereof.

Such a complex does preferably not comprise any epitope of HER-2, TOMM34, RNF 43, KOC1, VEGFR, βhCG, TGFβR2, p53, KRas, OGT, CASP5, COA-1, MAGE, SART or IL13Ralpha2.

Particularly preferably, such a complex comprises
one or more epitopes of EpCAM (such as the epitope according to SEQ ID NO: 48) or functional sequence variants thereof;
one or more epitopes of MUC-1 (such as the epitope according to SEQ ID NO: 50 and/or the epitope according to SEQ ID NO: 51) or functional sequence variants thereof;
one or more epitopes of survivin (such as the epitope according to SEQ ID NO: 53) or functional sequence variants thereof; and
one or more epitopes of CEA (such as the epitope according to SEQ ID NO: 55 and/or the epitope according to SEQ ID NO: 56) or functional sequence variants thereof.

Such a complex does preferably not comprise any epitope of HER-2, TOMM34, RNF 43, KOC1, VEGFR, βhCG, TGFβR2, p53, KRas, OGT, CASP5, COA-1, MAGE, SART or IL13Ralpha2.

It is also particularly preferred that such a complex comprises
one or more epitopes of EpCAM (such as the epitope according to SEQ ID NO: 48) or functional sequence variants thereof;
one or more epitopes of MUC-1 (such as the epitope according to SEQ ID NO: 50 and/or the epitope according to SEQ ID NO: 51) or functional sequence variants thereof; and
one or more epitopes of CEA (such as the epitope according to SEQ ID NO: 55 and/or the epitope according to SEQ ID NO: 56) or functional sequence variants thereof.

Such a complex does preferably not comprise any epitope of HER-2, TOMM34, RNF 43, KOC1, VEGFR, βhCG, survivin, TGFβR2, p53, KRas, OGT, CASP5, COA-1, MAGE, SART or ILISRalpha2.

It is also particularly preferred that such a complex comprises
one or more epitopes of EpCAM (such as the epitope according to SEQ ID NO: 48) or functional sequence variants thereof; and
one or more epitopes of CEA (such as the epitope according to SEQ ID NO: 55 and/or the epitope according to SEQ ID NO: 56) or functional sequence variants thereof.

Such a complex does preferably not comprise any epitope of HER-2, MUC-1, TOMM34, RNF 43, KOC1, VEGFR, (hCG, survivin, TGFβR2, p53, KRas, OGT, CASP5, COA-1, MAGE, SART or IL13Ralpha2.

It is also particularly preferred that such a complex comprises
one or more epitopes of EpCAM (such as the epitope according to SEQ ID NO: 48) or functional sequence variants thereof.

Such a complex does preferably not comprise any epitope of HER-2, MUC-1, TOMM34, RNF 43, KOC1, VEGFR, βhCG, survivin, CEA, TGFβR2, p53, KRas, OGT, CASP5, COA-1, MAGE, SART or IL13Ralpha2.

It is also particularly preferred that such a complex comprises
one or more epitopes of CEA (such as the epitope according to SEQ ID NO: 55 and/or the epitope according to SEQ ID NO: 56) or functional sequence variants thereof.

Such a complex does preferably not comprise any epitope of EpCAM, HER-2, MUC-1, TOMM34, RNF 43, KOC1, VEGFR, RhCG, survivin, TGF3R2, p53, KRas, OGT, CASP5, COA-1, MAGE, SART or IL13Ralpha2.

Component c)—TLR Peptide Agonist

In the complex for use according to the present invention, the TLR peptide agonist allows an increased targeting of the vaccine towards dendritic cells along with self-adjuvancity. Physical linkage of a TLR peptide agonist to the CPP and the at least one antigen or antigenic epitope according to the present invention in the complex for use according to the present invention provides an enhanced immune response by simultaneous stimulation of antigen presenting cells, in particular dendritic cells, that internalize, metabolize and display antigen(s).

As used in the context of the present invention, a "TLR peptide agonist" is an agonist of a Toll-like receptor (TLR), i.e. it binds to a TLR and activates the TLR, in particular to produce a biological response. Moreover, the TLR peptide agonist is a peptide, a polypeptide or a protein as defined above. Preferably, the TLR peptide agonist comprises from 10 to 150 amino acids, more preferably from 15 to 130 amino acids, even more preferably from 20 to 120 amino acids, particularly preferably from 25 to 110 amino acids, and most preferably from 30 to 100 amino acids.

Toll like receptors (TLRs) are transmembrane proteins that are characterized by extracellular, transmembrane, and cytosolic domains. The extracellular domains containing leucine-rich repeats (LRRs) with horseshoe-like shapes are involved in recognition of common molecular patterns derived from diverse microbes. Toll like receptors include TLRs1-10. Compounds capable of activating TLR receptors and modifications and derivatives thereof are well documented in the art. TLR1 may be activated by bacterial lipoproteins and acetylated forms thereof, TLR2 may in addition be activated by Gram positive bacterial glycolipids, LPS, LP A, LTA, fimbriae, outer membrane proteins, heat shock proteins from bacteria or from the host, and Mycobacterial lipoarabinomannans. TLR3 may be activated by dsRNA, in particular of viral origin, or by the chemical compound poly(LC). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B streptococcus heat labile soluble factor (GBS-F) or staphylococcus modulins. TLR7 may be activated by imidazoquinolines. TLR9 may be activated by unmethylated CpG DNA or chromatin—IgG complexes.

Preferably, the TLR peptide agonist comprised by the complex for use according to the present invention is an agonist of TLRI, 2, 4, 5, 6, and/or 10. TLRs are expressed either on the cell surface (TLR1, 2, 4, 5, 6, and 10) or on membranes of intracellular organelles, such as endosomes (TLR3, 4, 7, 8, and 9). The natural ligands for the endosomal receptors turned out to be nucleic acid-based molecules (except for TLR4). The cell surface-expressed TLR1, 2, 4, 5, 6, and 10 recognize molecular patterns of extracellular microbes (Monie, T. P., Bryant, C. E., et al. 2009: Activating immunity: Lessons from the TLRs and NLRs. Trends Biochem. Sci. 34(11), 553-561). TLRs are expressed on several cell types but virtually all TLRs are expressed on DCs allowing these specialized cells to sense all possible pathogens and danger signals.

However, TLR2, 4, and 5 are constitutively expressed at the surface of DCs. Accordingly, the TLR peptide agonist comprised by the complex for use according to the present invention is more preferably a peptide agonist of TLR2, TLR4 and/or TLR5. Even more preferably, the TLR peptide agonist is a TLR2 peptide agonist and/or a TLR4 peptide agonist. Particularly preferably, the TLR peptide agonist is a TLR4 peptide agonist. Most preferably, the TLR peptide agonist is one TLR peptide agonist, which is both, a TLR2 and a TLR4 agonist. TLR2 can detect a wide variety of ligands derived from bacteria, viruses, parasites, and fungi. The ligand specificity is often determined by the interaction of TLR2 with other TLRs, such as TLR1, 6, or 10, or non-TLR molecules, such as dectin-1, CD14, or CD36. The formation of a heterodimer with TLR1 enables TLR2 to identify triacyl lipoproteins or lipopeptides from (myco) bacterial origin, such as Pam3CSK4 and peptidoglycan (PGA; Gay, N. J., and Gangloff, M. (2007): Structure and function of Toll receptors and their ligands. Annu. Rev. Biochem. 76, 141-165; Spohn, R., Buwitt-Beckmann, U., et al. (2004): Synthetic lipopeptide adjuvants and Toll-like receptor 2-Structure-activity relationships. Vaccine 22(19), 2494-2499). Heterodimerization of TLR2 and 6 enables the detection of diacyl lipopeptides and zymosan. Lipopolysaccharide (LPS) and its derivatives are ligands for TLR4 and flagellin for TLR5 (Bryant, C. E., Spring, D. R., et al. (2010). The molecular basis of the host response to lipopolysaccharide. Nat. Rev. Microbiol. 8(1), 8-14).

TLR2 interacts with a broad and structurally diverse range of ligands, including molecules expressed by microbes and fungi. Multiple TLR2 agonists have been identified, including natural and synthetic lipopeptides (e.g. Mycoplasmafermentas macrophage-activating lipopeptide (MALP-2)), peptidoglycans (PG such as those from *S. aureus*), lipopolysaccharides from various bacterial strains (LPS), polysaccharides (e.g. zymosan), glycosylphosphatidyl-inositol-anchored structures from gram positive bacteria (e.g. lipoteichoic acid (LTA) and lipo-arabinomannan from mycobacteria and lipomannas from *M. tuberculosis*). Certain viral determinants may also trigger via TLR2 (Barbalat R, Lau L, Locksley R M, Barton G M. Toll-like receptor 2 on inflammatory monocytes induces type I interferon in response to viral but not bacterial ligands. Nat Immunol. 2009: 10(11):1200-7). Bacterial lipopeptides are structural components of cell walls. They consist of an acylated s-glycerylcysteine moiety to which a peptide can be conjugated via the cysteine residue. Examples of TLR2 agonists, which are bacterial lipopeptides, include MALP-2 and it's synthetic analogue di-palmitoyl-S-glyceryl cysteine ($Pam_2Cys$) or tri-palmitoyl-S-glyceryl cysteine (PamsCys).

A diversity of ligands interact with TLR4, including Monophosphoryl Lipid A from Salmonella minnesota R595 (MPLA), lipopolysaccharides (LPS), mannans (Candida albicans), glycoinositolphospholipids (Trypanosoma), viral envelope proteins (RSV and MMTV) and endogenous antigens including fibrinogen and heat-shock proteins. Such agonists of TLR4 are for example described in Akira S, Uematsu S, Takeuchi O. Pathogen recognition and innate immunity. Cell. February 24; 2006: 124(4):783-801 or in Kumar H, Kawai T, Akira S. Toll-like receptors and innate immunity. Biochem Biophys Res Commun. October 30; 2009 388(4):621-5. LPS, which is found in the outer membrane of gram negative bacteria, is the most widely studied of the TLR4 ligands. Suitable LPS-derived TLR4 agonist peptides are described for example in WO 2013/120073 (A1).

TLR5 is triggered by a region of the flagellin molecule expressed by nearly all motile bacteria. Thus, flagellin, or peptides or proteins derived from flagellin and/or variants or fragments of flagellin are also suitable as TLR peptide agonists comprised by the complex for use according to the present invention.

Examples of TLR peptide agonists thus include the TLR2 lipopeptide agonists MALP-2, Pam2Cys and $Pam_9Cys$ or modifications thereof, different forms of the TLR4 agonist LPS, e.g. N. meningitidis wild-type L3-LPS and mutant penta-acylated LpxL1-LPS, and the TLR5 agonist flagellin.

However, it is preferred that the TLR peptide agonist comprised by the complex for use according to the present invention is neither a lipopeptide nor a lipoprotein, neither a glycopeptide nor a glycoprotein, more preferably, the TLR peptide agonist comprised by the complex for use according to the present invention is a classical peptide, polypeptide or protein as defined herein.

A preferred TLR2 peptide agonist is annexin II or an immunomodulatory fragment thereof, which is described in detail in WO 2012/048190 A 1 and U.S. patent application Ser. No. 13/0331546, in particular a TLR2 peptide agonist comprising an amino acid sequence according to SEQ ID NO: 4 or SEQ ID NO: 7 of WO 2012/048190 A1 or fragments or variants thereof are preferred.

Thereby, a TLR2 peptide agonist comprising or consisting of an amino acid sequence according to SEQ ID NO: 15 or a sequence variant thereof as described above is particularly preferred as component c), i.e. as the at least one TLR peptide agonist, comprised by the complex for use according to the present invention.

(TLR2 peptide agonist Anaxa)
SEQ ID NO: 15
STVHEILCKLSLEGDHSTPPSAYGSVKPYTNFDAE

Regarding TLR4, TLR peptides agonists are particularly preferred, which correspond to motifs that bind to TLR4, in particular (i) peptides mimicking the natural LPS ligand (RS01: Gln-Glu-Ile-Asn-Ser-Ser-Tyr and RS09: Ala-Pro-Pro-His-Ala-Leu-Ser) and (ii) Fibronectin derived peptides. The cellular glycoprotein Fibronectin (FN) has multiple isoforms generated from a single gene by alternative splicing of three exons. One of these isoforms is the extra domain A (EDA), which interacts with TLR4.

Further suitable TLR peptide agonists comprise a fibronectin EDA domain or a fragment or variant thereof. Such suitable fibronectin EDA domains or a fragments or variants thereof are disclosed in EP 1 913 954 B1, EP 2 476 440 A 1, US 2009/0220532 A1, and WO 2011/101332 A1. Thereby, a TLR4 peptide agonist comprising or consisting of an amino acid sequence according to SEQ ID NO: 45 or a sequence variant thereof as described above is particularly preferred as component c), i.e. as the at least one TLR peptide agonist, comprised by the complex for use according to the present invention.

(TLR4 peptide agonist EDA)
SEQ ID NO: 45
NIDRPKGLAFTDVDVDSIKIAWESPQGQVSRYRVTYSSPEDGI

RELFPAPDGEDDTAELQGLRPGSEYTVSVVALHDDMESQPLIG

IQST

In addition, high-mobility group box 1 protein (HMGB1) and peptide fragments thereof are assumed to be TLR4 agonists. Such HMGB1-derived peptides are for example disclosed in US 2011/0236406 A1.

The complex for use according to the present invention comprises at least one TLR peptide agonist, preferably the complex for use according to the present invention comprises more than one TLR peptide agonist, in particular 2, 3, 4, 5, 6, 7, 8, 9, 10 or more TLR peptide agonists, more preferably the complex for use according to the present invention comprises (at least) two or three TLR peptide agonists, even more preferably the complex for use according to the present invention comprises (at least) four or five TLR peptide agonists. If more than one TLR peptide agonist is comprised by the complex for use according to the present invention it is understood that said TLR peptide agonist is in particular also covalently linked in the complex for use according to the present invention, e.g. to another TLR peptide agonist and/or to a component a), i.e. a cell penetrating peptide, and/or to a component b), i.e. an antigen or antigenic epitope.

In a particularly preferred embodiment, the complex for use according to the present invention comprises one single TLR peptide agonist. In particularly, in this particularly preferred embodiment, the complex for use according to the present invention comprises one single TLR peptide agonist and no further component having TLR agonist properties except the one single TLR peptide agonist as described.

The various TLR peptide agonists comprised by the complex for use according to the present invention may be the same or different. Preferably, the various TLR peptide agonists comprised by the complex for use according to the present invention are different from each other.

Moreover, it is preferred that the more than one antigen or antigenic epitope, in particular 2, 3, 4, 5, 6, 7, 8, 9, 10 antigens or antigenic epitopes, or more TLR peptide agonists, in particular 2, 3, 4, 5, 6, 7, 8, 9, 10 TLR agonists, are positioned consecutively in the complex for use according to the present invention. This means in particular that all TLR peptide agonists comprised by the complex are positioned in a stretch, which is neither interrupted by component a), i.e. a cell penetrating peptide, nor by component b), i.e. at least one antigen or antigenic epitope. Rather, component a) and component b) are positioned in the complex for example before or after such a stretch of all TLR peptide agonists. However, the TLR peptide agonists positioned consecutively in such a way may be linked to each other for example by a spacer or linker as described below, which is neither component a), i.e. a cell penetrating peptide, nor component b), i.e. at least one antigen or antigenic epitope.

Alternatively, however, the various TLR peptide agonists may also be positioned in any other way in the complex for use according to the present invention, for example with component a) and/or component b) positioned in between two or more TLR peptide agonists, i.e. with one or more TLR peptide agonist positioned between component a) and component b) (or vice versa) and, optionally, one or more TLR peptide agonists positioned at the respective other end of component a) and/or component b).

It is understood that a number of different TLR peptide agonists activating the same or different TLR receptors may be advantageously comprised by a single complex for use according to the present invention. Alternatively, a number of different TLR peptide agonists activating the same or different TLR receptors may be distributed to subsets of different TLR peptide agonists activating the same or different TLR receptors, which are comprised by different complexes according to the present invention, whereby such different complexes comprising different subsets may advantageously be administered simultaneously, e.g. in a single vaccine, to a subject in need thereof.

Linkage of Components a), b), and c) in the Complex for Use According to the Present Invention In the complex for use according to the present invention, components a), b) and c) are covalently linked, i.e. the linkage between two out of the three components a), b), and c) of the complex for use according to the present invention is a covalent linkage. Preferably, two out of the three components a), b), and c) of the complex for use according to the present invention are covalently linked to each other (i.e. the "first" and the "second" component), and the third component out of the three components a), b), and c) is covalently linked either to the first component out of the three components a), b), and c) or to the second component out of the three components a), b), and c). Thereby, preferably a linear molecule is formed. However, it is also conceivable that each of the three components a), b), and c)

is covalently linked to both of the other components out of the three components a), b), and c).

A "covalent linkage" (also covalent bond), as used in the context of the present invention, refers to a chemical bond that involves the sharing of electron pairs between atoms. A "covalent linkage" (also covalent bond) in particular involves a stable balance of attractive and repulsive forces between atoms when they share electrons. For many molecules, the sharing of electrons allows each atom to attain the equivalent of a full outer shell, corresponding to a stable electronic configuration. Covalent bonding includes many kinds of interactions, including for example σ-bonding, α-bonding, metal-to-metal bonding, agostic interactions, and three-center two-electron bonds. Accordingly, the complex for use according to the present invention may also be referred to as "compound", in particular it may be referred to as "molecule".

Preferably, in the complex for use according to the present invention, components a), b), and c) are covalently linked by chemical coupling in any suitable manner known in the art, such as cross-linking methods. However, attention is drawn to the fact that many known chemical cross-linking methods are non-specific, i.e., they do not direct the point of coupling to any particular site on the components a), b), and c). Thus, the use of non-specific cross-linking agents may attack functional sites or sterically block active sites, rendering the fused components of the complex for use according to the present invention biologically inactive. It is referred to the knowledge of the skilled artisan to block potentially reactive groups by using appropriate protecting groups. Alternatively, the use of the powerful and versatile oxime and hydrazone ligation techniques, which are chemo-selective entities that can be applied for the cross-linking of components a), b), and c) may be employed. This linking technology is described e.g. by Rose et al. (1994), JACS 116, 30.

Coupling specificity can be increased by direct chemical coupling to a functional group found only once or a few times in components a), b), and/or c), which functional group is to be cross-linked to the another of the components a), b), and c). As an example, the cystein thiol group may be used, if just one cystein residue is present in a certain component a), b), or c) of complex for use according to the present invention. Also, for example, if a certain component a), b), or c) contains no lysine residues, a cross-linking reagent specific for primary amines will be selective for the amino terminus of the respective component. Alternatively, cross-linking may also be carried out via the side chain of a glutamic acid residue placed at the N-terminus of the peptide such that a amide bond can be generated through its side-chain. Therefore, it may be advantageous to link a glutamic acid residue to the N-terminus of a certain component a), b), or c). However, if a cysteine residue is to be introduced into a certain component a), b), or c), introduction at or near its N- or C-terminus is preferred. Conventional methods are available for such amino acid sequence alterations based on modifications of certain component a), b), or c) by either adding one or more additional amino acids, e.g. inter alia an cystein residue, to the translocation sequence or by substituting at least one residue of the translocation sequence(s) being comprised in the respective component. In case a cystein side chain is used for coupling purposes, a certain component a), b), or c) has preferably one cystein residue. Any second cystein residue should preferably be avoided and can, optionally, be replaced when they occur in the respective component comprised by the complex for use according to the present invention. When a cysteine residue is replaced in the original sequence of a certain component a), b), or c), it is typically desirable to minimize resulting changes in the peptide folding of the respective component. Changes in folding are minimized when the replacement is chemically and sterically similar to cysteine. Therefore, serine is preferred as a replacement for cystein.

Coupling of two out of the three components a), b), and c) can be accomplished via a coupling or conjugating agent including standard peptide synthesis coupling reagents such as HOBt, HBTU, DICI, TBTU. There are several intermolecular cross-linking agents which can be utilized, see for example, Means and Feeney, Chemical Modification of Proteins, Holden-Day, 1974, pp. 39-43. Among these reagents are, for example, N-succinimidyl 3-(2-pyridyldithio)propionate (SPDP) or N,N'-(1,3-phenylene)bismaleimide; N,N'-ethylene-bis-(iodoacetamide) or other such reagent having 6 to 11 carbon methylene bridges; and 1,5-difluoro-2,4-dinitrobenzene. Other cross-linking agents useful for this purpose include: p,p'-difluoro-m,m'-dinitrodiphenylsulfone; dimethyl adipimidate; phenol-1,4-disulfonylchloride; hexamethylenediisocyanate or diisothiocyanate, or azophenyl-p-diisocyanate; glutaraldehyde and disdiazobenzidine. Cross-linking agents may be homobifunctional, i.e., having two functional groups that undergo the same reaction. A preferred homobifunctional cross-linking agent is bismaleimidohexane (BMH). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of proteins (or polypeptides) that contain cysteine residues. Cross-linking agents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are Succinimidyl-4-(N-maleimidomethyl)-cyclohexane-1-carboxylate (SMCC), m-maleimidobenzoyl-N-hydroxysuccinimide ester (MBS), and succinimide 4-(p-maleimidophenyl) butyrate (SMPB), an extended chain analog of MBS. The succinimidyl group of these cross-linkers reacts with a primary amine, and the thiol-reactive maleimide forms a covalent bond with the thiol of a cysteine residue. Because cross-linking agents often have low solubility in water, a hydrophilic moiety, such as a sulfonate group, may be added to the cross-linking agent to improve its water solubility. Sulfo-MBS and sulfo-SMCC are examples of cross-linking agents modified for water solubility. Many cross-linking agents yield a conjugate that is essentially non-cleavable under cellular conditions. Therefore, some cross-linking agents contain a covalent bond, such as a disulfide, that is cleavable under cellular conditions. For example, Traut's reagent, dithiobis (succinimidylpropionate) (DSP), and N-succinimidyl 3-(2-pyridyldithio)propionate (SPDP) are well-known cleavable cross-linkers. The use of a cleavable cross-linking agent permits the cell penetrating peptide, the at least one antigen or antigenic epitope and the at least one TLR peptide agonist comprised by the complex for use according to the present invention to separate from each other after delivery into the target cell. For this purpose, direct disulfide linkage may also be useful. Chemical cross-linking may also include the use of spacer arms. Spacer arms provide intramolecular flexibility or adjust intramolecular distances between conjugated moieties and thereby may help preserve biological activity. A spacer arm may be in the form of a protein (or polypeptide) moiety that includes spacer amino acids, e.g. proline. Alternatively, a spacer arm may be part of the cross-linking agent, such as in "long-chain SPDP" (Pierce Chem. Co., Rockford, Ill., cat. No. 21651 H). Numerous cross-linking agents, including the ones discussed above, are commercially available. Detailed instructions for their use are readily available from the commercial suppliers. More detailed information on protein cross-linking and conjugate preparation, which is useful in the context of linkage of components a), b), and c) comprised by the complex for use according to the present invention can be retrieved from: Wong, Chemistry of Protein Conjugation and Cross-Linking, CRC Press (1991).

Cross-linking agents for peptide or protein crosslinking include for example (i) amine-to-amine crosslinkers, e.g. homobifunctional amine-specific protein crosslinking reagents based on NHS-ester and imidoester reactive groups for selective conjugation of primary amines; available in short, long, cleavable, irreversible, membrane permeable, and cell surface varieties; (ii) sulfhydryl-to-carbohydrate crosslinkers, e.g. crosslinking reagents based on maleimide and hydrazide reactive groups for conjugation and formation of covalent crosslinks; (iii) sulfhydryl-to-sulfhydryl crosslinkers, e.g. homobifunctional sulfhydryl-specific crosslinking reagents based on maleimide or pyridyldithiol reactive groups for selective covalent conjugation of protein and peptide thiols (reduced cysteines) to form stable thioether bonds; (iv) photoreactive crosslinkers, e.g. aryl azide, diazirine, and other photo-reactive (light-activated) chemical heterobifunctional crosslinking reagents to conjugate proteins, nucleic acids and other molecular structures involved in receptor-ligand interaction complexes via two-step activation; (v) amine-to-sulfhydryl crosslinkers, e.g. heterobifunctional protein crosslinking reagents for conjugation between primary amine (lysine) and sulfhydryl (cysteine) groups of proteins and other molecules; available with different lengths and types of spacer arms; and (vi) amine-to-amine crosslinkers, e.g. carboxyl-to-amine crosslinkers, e.g. Carbodiimide crosslinking reagents, DCC and EDC (EDAC), for conjugating carboxyl groups (glutamate, aspartate, C-termini) to primary amines (lysine, N-termini) and also N-hydroxysuccinimide (NHS) for stable activation of carboxylates for amine-conjugation.

Examples of crosslinkers in general, which can be used in the complex for use according to the present invention, include N-(α-Maleimidoacetoxy)-succinimide ester, N-5-Azido-2-nitrobenzyloxy-succinimide, 1,4-Bis-Maleimidobutane, 1,4-Bis-Maleimmidyl-2,3-dihydroxy-butane, Bis-Maleimidohexane, Bis-Maleimidoethane, N-(β-Maleimidopropionic acid)hydrazide*TFA, N-(β-Maleimidopropyloxy)succinimide ester, 1,8-Bis-Maleimidodiethylene-glycol, 1,11-Bis-Maleimidotriethyleneglycol, Bis (sulfosuccinimidyl) suberate, Bis (sulfosuccinimidyl)glutarate-do, Bis (sulfosuccinimidyl)2,2,4,4-glutarate-d4, Bis (sulfosuccinimidyl)suberate-do, Bis (sulfosuccinimidyl)2,2,7,7-suberate-d4, Bis (NHS)PEG5, Bis (NHS)PEG9, Bis (2-[succinimidoxycarbonyloxy]ethyl)sulfone, N,N-Dicyclohexylcarbodiimide, 1-5-Difluoro-2,4-dinitrobenzene, Dimethyl adipimidate*2HCl, Dimethyl pimelimidate*2HCl, Dimethyl suberimidate*2HCl, Disuccinimidyl glutarate, Dithiobis(succimidylpropionate) (Lomant's Reagent), Disuccinimidyl suberate, Disuccinimidyl tartarate, Dimethyl 3,3'-dithiobispropionimidate*2HCl, Dithiobis-maleimidoethane, 3,3'-Dithiobis (sulfosuccinimidylpropionate), 1-Ethyl-s-(3-dimethylaminopropyl) carbodiimide hydrochloride, Ethylene glycol bis (succinimidylsuccinate), N-ε-Maleimidocaproic acid, N-(ε-Maleimidocaproic acid)hydrazide, N-(ε-Maleimidocaproyloxy)succinimide ester, N-(γ-Maleimidobutyryloxy)succinimide ester, N-(κ-Maleimidoundecanoic acid)hydrazide, NHS-LC-Diazirine, Succinimidyl 4-(N-maleimidomethyl) cyclohexane-1-carboxy-(6-amidocaproate, Succinimidyl 6-(3'-[2-pyridyldithio]propionamido)hexanoate, L-Photo-Leucine, L-Photo-Methionine, m-Maleimidobenzoyl-N-hydroxysuccinimide ester, 4-(4-N-Maleimidophenyl)-butyric acid hydrazide*HCl, 2-[N2-(4-Azido-2,3,5,6-tetrafluorobenzoyl)-N6-(6-biotinamidocaproyl)-L-lysinyl]ethylmethanethiosulfate, 2-{N2-[N6-(4-Azido-2,3,5,6-tetrafluorobenzoyl)-N6-(6-biotinamidocaproyl)-L-lysinyl] }ethylmethanethiosulfate, N-Hydroxysuccinimide, N-hydroxysuccinimide ester ethane azide, N-hydroxysuccinimide ester tetraoxapentadecane azide, N-hydroxysuccinimide ester dodecaoxanonatriacontane azide, NHS-Phosphine, 3-(2-IPyridyldithio)propionylhydrazide, 2-pyridyldithiol-tetraoxatetradecane-N-hydroxysuccinimide, 2-pyridyldithiol-tetraoxaoctatriacontane-N-hydroxysuccinimide, N-(p-Maleimidophenyl)isocyanate, Succinimdyl 3-(bromoacetamido)propionate, NHS-Diazirine, NHS—SS-Diazirine, N-succinimidyl iodoacetate, N-Succinimidyl(4-iodoacetyl)aminobenzoate, Succinimidyl 4-(N-maleimido-methyl)cyclohexane-1-carboxylate, NHS-PEG2-Maliemide, NHS-PEG4-Maliemide, NHS-PEG6-Maleimide, NHS-PEG8-Maliemide, NHS-PEG12-Maliemide, NHS-PEG24-Maleimide, Succinimidyl 4-(p-maleimido-phenyl)butyrate, Succinimidyl-6-(s-maleimidopropionamido)hexanoate, 4-Succinimidyloxycarbonyl-methyl-α-(2-pyridyldithio) toluene, Succinimidyl-(4-psoralen-8-yloxy)butyrate, N-Succinimidyl 3-(2-pyridyldithio)propionate, Ethylene glycol bis (sulfo-succinimidyl succinate), N-(ε-Maleimidocaproyloxy) sulfosuccinimide ester, N-(γ-Maleimidobutryloxy)sulfosuccinimide ester, N-(κ-Maleimidoundecanoyloxy)sulfosuccinimide ester, Sulfo-NHS-LC-Diazirine, Sulfosuccinimidyl 6-(3'-[2-pyridyldithio]propionamido)hexanoate, m-Maleimidobenzoyl-N-hydroxysulfosuccinimide ester, N-Hydroxysuccinimide, Sulfo-NHS-Phosphine, Sulfosuccinimidyl 6-(4'-azido-2'-nitrophenylamino)hexanoate, Sulfo-NHS-(2-6-[Biotinamido]-2-(p-azidobezamido), Sulfo-NHS-Diazirine, Sulfo-NHS—SS-Diazirine, Sulfosuccinimidyl(4-iodo-acetyl)aminobenzoate, Sulfosuccinimidyl 4-(N-maleimidomethyl)cyclohexane-1-carboxylate, Sulfosuccinimidyl 4-(p-maleimidophenyl)butyrate, Tris-(2-Maleimidoethyl)amine (Trifunctional), and Tris-(succimimidyl aminotricetate) (Trifunctional).

The linkage between two out of the three components a), b), and c) of the complex for use according to the present invention may be directly or indirectly, i.e. two components directly adjoin or they may be linked by an additional component of the complex, e.g. a spacer or a linker.

A direct linkage may be realized preferably by an amide bridge, if the components to be linked have reactive amino or carboxy groups. More specifically, if the components to be linked are peptides, polypeptides or proteins, a peptide bond is preferred. Such a peptide bond may be formed using a chemical synthesis involving both components (an N-terminal end of one component and the C-terminal end of the other component) to be linked, or may be formed directly via a protein synthesis of the entire peptide sequence of both components, wherein both (protein or peptide) components are preferably synthesized in one step. Such protein synthesis methods include e.g., without being limited thereto, liquid phase peptide synthesis methods or solid peptide synthesis methods, e.g. solid peptide synthesis methods according to Merrifield, t-Boc solid-phase peptide synthesis, Fmoc solid-phase peptide synthesis, BOP (Benzotriazole-1-yl-oxy-tris-(dimethylamino)-phosphonium hexafluorophosphate) based solid-phase peptide synthesis, etc. Alternatively, ester or ether linkages are preferred.

Moreover, in particular if the components to be linked are peptides, polypeptides or proteins, a linkage may occur via the side chains, e.g. by a disulfide bridge. Further components of other chemical nature, e.g. the at least one antigen or antigenic epitope if it is not of peptidic nature, may be likewise attached to the components of peptidic nature, e.g. the cell penetrating peptide, the at least one TLR peptide agonist, and the at least one antigen or antigenic epitope if it is of peptidic nature. The linkage via a side chain will preferably be based on side chain amino, thiol or hydroxyl groups, e.g. via an amide or ester or ether linkage. A linkage of a peptidic main chain with a peptidic side chain of another component may also be via an isopeptide bond. An isopeptide bond is an amide bond that is not present on the main chain of a protein. The bond forms between the carboxyl terminus of one peptide or protein and the amino group of a lysine residue on another (target) peptide or protein.

The complex for use according to the present invention may optionally comprise a spacer or linker, which are non-immunologic moieties, which are preferably cleavable, and which link component a) and b) and/or component a) and c), and/or component b) and c), and/or link consecutive antigens or antigenic epitopes, and/or link consecutive TLR peptide agonists, and/or link consecutive cell penetrating peptides, and/or which can be placed at the C-terminal part of components b) and/or c). A linker or spacer may preferably provide further functionalities in addition to linking of the components, and preferably being cleavable, more preferably naturally cleavable inside the target cell, e.g. by enzymatic cleavage. However, such further functionalities do in particular not include any immunological functionalities. Examples of further functionalities, in particular regarding linkers in fusion proteins, can be found in Chen X. et al., 2013: Fusion Protein Linkers: Property, Design and Functionality. Adv Drug Deliv Rev. 65(10): 1357-1369, wherein for example also in vivo cleavable linkers are disclosed. Moreover, Chen X. et al., 2013: Fusion Protein Linkers: Property, Design and Functionality. Adv Drug Deliv Rev. 65(10): 1357-1369 also discloses various linkers, e.g. flexible linkers and rigid linkers, and linker designing tools and databases, which can be useful in the complex for use according to the present invention or to design a linker to be used in the complex for use according to the present invention.

Said spacer may be peptidic or non-peptidic, preferably the spacer is peptidic. Preferably, a peptidic spacer consists of about 1, 2, 3, 4, 5, 6, 7, 8, 9, or 10 amino acids, more preferably of about 1, 2, 8, 4, or 5 amino acids. The amino acid sequence of the peptidic spacer may be identical to that of the N-terminal or C-terminal flanking region of any of the components a), b), or c). Alternatively a peptidic spacer can consist of non-natural amino acid sequences such as an amino acid sequence resulting from conservative amino acid substitutions of said natural flanking regions or sequences of known cleavage sites for proteases such as an enterokinase target site (amino acid sequence: DDDK, SEQ ID NO: 16), factor Xa target site (amino acid sequence: IEDGR, SEQ ID NO: 17), thrombin target site (amino acid sequence: LVPRGS, SEQ ID NO: 18), protease TEV target site (amino acid sequence: ENLYFQG, SEQ ID NO: 19), PreScission protease target site (amino acid sequence LEVLFQGP, SEQ ID NO: 20), polycationic amino acids, e.g. poly K, furin target site (amino acid sequence RX(R/K)R, SEQ ID NO: 21). In a particular embodiment, the peptide spacer does not contain any Cys (C) residues. In a preferred embodiment the linker sequence contains at least 20%, more preferably at least 40% and even more preferably at least 50% Gly or β-alanine residues, e.g. GlyGlyGlyGlyGly (SEQ ID NO: 22), GlyGlyGlyGly (SEQ ID NO: 23), GlyGlyGly, CysGlyGly or GlyGlyCys, etc. Appropriate linker sequences can be easily selected and prepared by a person skilled in the art. They may be composed of D and/or L amino acids. Further examples of a peptidic spacer include the amino acid sequences EQLE (SEQ ID NO: 24) or TEWT (SEQ ID NO: 25) or any conservative substitutions thereof.

A non-peptidic spacer can include or may be an ester, a thioester, and a di-sulfide.

In particular, the complex for use according to the invention may comprise a spacer or linker, in particular a peptidic spacer, placed between component a) and b) and/or between component a) and c), and/or between component b) and c). This peptidic spacer can be chosen by one skilled in the art so that it may be cut by the cell machinery once the complex comprising the cell penetrating peptide and the cargo molecule has been internalized.

When the complex comprises several antigens or antigenic epitopes or when the complex comprises several TLR peptide agonists, it will be clear for one skilled in the art that each of the antigens or antigenic epitopes and/or each of the TLR peptide agonists comprised in the complex of the invention can be either directly linked to each other or linked via spacers or linkers such as, e.g., a peptidic spacer consisting of a few amino acids. Alternatively, when the complex for use according to the present invention comprises several antigens or antigenic epitopes or when the complex comprises several TLR peptide agonists, it is also possible that some antigens or antigenic epitopes and/or some TLR peptide agonists comprised by the complex of the invention are directly linked to each other and some other antigens or antigenic epitopes and/or some other TLR peptide agonists are linked via spacers or linkers such as a peptidic spacer consisting of a few amino acids.

For example, two successive antigens or antigenic epitopes or two successive TLR peptide agonists comprised in the complex of the invention are linked to each other by spacers consisting of the natural flanking regions of said antigens or antigenic epitopes or of said TLR peptide agonists, respectively. For example, the spacer used to link a first antigen/antigenic epitope or a first TLR peptide agonist to a second antigen/antigenic epitope or to a second TLR peptide agonist, respectively, may consists of up to about 8 amino acids corresponding to up to about 4 amino acids of the N-terminal or C-terminal flanking region of the first antigen/antigenic epitope or the first TLR peptide agonist, followed by up to about 4 amino acids of the N-terminal or C-terminal flanking region of the second antigen/antigenic epitope or the second TLR peptide agonist. In an illustration of the present invention, the spacer used to link a first antigen/antigenic epitope or a first TLR peptide agonist ("antigen/epitope/TLR peptide agonist 1") to a second epitope ("antigen/epitope/TLR peptide agonist 2") consists of about 8 amino acids corresponding to any possible combination ranging from: 0 flanking amino acid of antigen/epitope/TLR peptide agonist 1 and 8 flanking amino acids of antigen/epitope/TLR peptide agonist 2, to 8 flanking amino acids of antigen/epitope/TLR peptide agonist 1 and 0 flanking amino acid of antigen/epitope/TLR peptide agonist 2, i.e. including 1 flanking amino acid of antigen/epitope/TLR peptide agonist 1 and 7 flanking amino acids of antigen/epitope/TLR peptide agonist 2, 2 flanking amino acid of antigen/epitope/TLR peptide agonist 1 and 6 flanking amino acids of antigen/epitope/TLR peptide agonist 2, 3 flanking amino acid of antigen/epitope/TLR peptide agonist 1 and 5 flanking amino acids of antigen/epitope/TLR peptide agonist 2, 4 flanking amino acid of antigen/epitope/TLR peptide agonist 1 and 4 flanking amino acids of antigen/epitope/TLR peptide agonist 2, 5 flanking amino acid of antigen/epitope/TLR peptide agonist 1 and 3 flanking amino acids of antigen/epitope/TLR peptide agonist 2, 6 flanking amino acid of antigen/epitope/TLR peptide agonist 1 and 2 flanking amino acids of antigen/epitope/TLR peptide agonist 2, 7 flanking amino acid of antigen/epitope/TLR peptide agonist 1 and 1 flanking amino acid of antigen/epitope/TLR peptide agonist 2, 8 flanking amino acid of antigen/epitope/TLR peptide agonist 1 and 0 flanking amino acids of antigen/epitope/TLR peptide agonist 2. It will be understood that the total of 8 amino acids constituting a spacer linking two consecutive antigen/epitope/TLR peptide agonist is not an absolute value and the spacer could also be composed of a total of, for instance, 3 amino acids, 4 amino acids, 5 amino acids, 6 amino acids, 7 amino acids, 9 amino acids or 10 amino acids. Similarly, equivalent combinations as mentioned above are also an illustration of the invention in the situation where a spacer has less or more than 8 amino acids.

In another particular illustration of the present invention, the spacer used to link a first antigen/antigenic epitope or a first TLR peptide agonist ("antigen/epitope/TLR peptide agonist 1") to a second antigen/antigenic epitope or to a second TLR peptide agonist, respectively, ("antigen/epitope/TLR peptide agonist 2") consists of e.g. 1, 2, 3, 4, or 5 amino acids. More particularly, said spacer's amino acid sequence can correspond to the 4 amino acids of the N-terminal or C-terminal flanking region of antigen/epitope/TLR peptide agonist 1 or antigen/epitope/TLR peptide agonist 2. A spacer as described above may also be placed at the C-terminal part of the last antigen/epitope/TLR peptide agonist comprised in the complex for use according to the present invention.

The technics for linking two of the three components a), b), and c) are well documented in the literature and can depend on the nature of the at least one antigen or antigenic epitope. For instance, linkages between two of the three components a), b), and c) can be achieved via cleavable disulphide linkages through total stepwise solid-phase synthesis or solution-phase or solid-phase fragment coupling, stable amide, thiazolidine, oxime and hydrazine linkage, disulphide linkage, stable thiomaleimide linkage, peptide bond (including peptide bonds between amino acids of a fusion protein), or electrostatic or hydrophobic interactions.

Preferably, the at least one antigen or antigenic epitope comprised by the complex for use according to the present invention as well as any optional spacer or linker comprised by the complex for use according to the present invention are of peptidic nature. More preferably, all components of the complex for use according to the present invention, e.g. the cell penetrating peptide, the at least one antigen or antigenic epitope, which is a peptide, polypeptide or protein, the at least one TLR peptide agonist and any optional peptidic linker or spacer are linked in the complex for use according to the present invention by a peptide bond. Most preferably, the complex for use according to the present invention is thus a peptide, polypeptide or protein, such as a fusion protein, e.g. a recombinant fusion protein.

In this context, a complex comprising or consisting of an amino acid sequence according to SEQ ID NO: 26, SEQ ID NO: 27, SEQ ID NO: 28, SEQ ID NO: 33, SEQ ID NO: 34, SEQ ID NO: 37, SEQ ID NO: 38, SEQ ID NO: 39, SEQ ID NO: 40, SEQ ID NO: 41, SEQ ID NO: 46 or SEQ ID NO: 69 or a complex comprising or consisting of an amino acid sequence sharing at least 50%, at least 60%, at least 70%, at least 75%, at least 80%, at least 85%, at least 90%, at least 95% or at least 98% sequence identity with any of SEQ ID NO: 26, SEQ ID NO: 27, SEQ ID NO: 28, SEQ ID NO: 33, SEQ ID NO: 34, SEQ ID NO: 37, SEQ ID NO: 38, SEQ ID NO: 39, SEQ ID NO: 40, SEQ ID NO: 41, SEQ ID NO: 46 or SEQ ID NO: 69 is preferred; a complex comprising or consisting of an amino acid sequence according to SEQ ID NO: 27, SEQ ID NO: 28, SEQ ID NO: 33, SEQ ID NO: 37, SEQ ID NO: 39, SEQ ID NO: 40, SEQ ID NO: 41 or SEQ ID NO: 69 or a complex comprising or consisting of an amino acid sequence sharing at least 50%, at least 60%, at least 70%, at least 75%, at least 80%, at least 85%, at least 90%, at least 95% or at least 98% sequence identity with any of SEQ ID NO: 27, SEQ ID NO: 28, SEQ ID NO: 33, SEQ ID NO: 37, SEQ ID NO: 39, SEQ ID NO: 40, SEQ ID NO: 41 or SEQ ID NO: 69 is more preferred; a complex comprising or consisting of an amino acid sequence according to SEQ ID NO: 28, SEQ ID NO: 37, SEQ ID NO: 39, SEQ ID NO: 40, SEQ ID NO: 41 or SEQ ID NO: 69 or a complex comprising or consisting of an amino acid sequence sharing at least 50%, at least 60%, at least 70%, at least 75%, at least 80%, at least 85%, at least 90%, at least 95% or at least 98% sequence identity with SEQ ID NO: 28, SEQ ID NO: 37, SEQ ID NO: 39, SEQ ID NO: 40, SEQ ID NO: 41 or SEQ ID NO: 69 is even more preferred; and a complex comprising or consisting of an amino acid sequence according to SEQ ID NO: 28, SEQ ID NO: 39, SEQ ID NO: 40, SEQ ID NO: 41 or SEQ ID NO: 69 or a complex comprising or consisting of an amino acid sequence sharing at least 50%, at least 60%, at least 70%, at least 75%, at least 80%, at least 85%, at least 90%, at least 95% or at least 98% sequence identity with SEQ ID NO: 28, SEQ ID NO: 39, SEQ ID NO: 40, SEQ ID NO: 41 or SEQ ID NO: 69 is particularly preferred.

```
SEQ ID NO: 26:
MHHHHHHNID RPKGLAFTDV DVDSIKIAWE SPQGQVSRYR

VTYSSPEDGI RELFPAPDGEDDTAELQGLR PGSEYTVSVV

ALHDDMESQP LIGIQSTKRY KNRVASRKSR AKFKQLLQHY

REVAAAKSSE NDRLRLLLKE SLKISQAVHA AHAEINEAGR

EVVGVGALKV PRNQDWLGVP RFAKFASFEA QGALANIAVD

KANLDVEQLE SIINFEKLTE WTGS

SEQ ID NO: 27:
MHHHHHHSTV HEILCKLSLE GDHSTPPSAY GSVKPYTNFD

AEKRYKNRVA SRKSRAKFKQ LLQHYREVAA AKSSENDRLR

LLLKESLKIS QAVHAAHAEI NEAGREVVGV GALKVPRNQD

WLGVPRFAKF ASFEAQGALA NIAVDKANLD VEQLESIINF

EKLTEWTGS

SEQ ID NO: 28:
MHHHHHHKRYKNRVA SRKSRAKFKQ LLQHYREVAA

AKSSENDRLR LLLKESLKIS QAVHAAHAEI NEAGREVVGV

GALKVPRNQD WLGVPRFAKF ASFEAQGALA NIAVDKANLD

VEQLESIINF EKLTEWTGSS TVHEILCKLS LEGDHSTPPS

AYGSVKPYTN FDAE
```

-continued

SEQ ID NO: 33:
MHHHHHHKRY KNRVASRKSR AKFKQLLQHY REVAAAKESL

KISQAVHAAH AEINEAGREV VGVGALKVPR NQDWLGVPRF

AKFASFEAQG ALANIAVDKA NLDVEQLESI INFEKLTEWT

GSSTVHEILC KLSLEGDHST PPSAYGSVKP YTNFDAE

SEQ ID NO: 34:
MHHHHHHREV AAAKSSENDR LRLLLKESLK ISQAVHAAHA

EINEAGREVV GVGALKVPRN QDWLGVPRFA KFASFEAQGA

LANIAVDKAN LDVEQLESII NFEKLTEWTG SSTVHEILCK

LSLEGDHSTP PSAYGSVKPY TNFDAE

SEQ ID NO: 37:
MHHHHHHNID RPKGLAFTDV DVDSIKIAWE SPQGQVSRYR

VTYSSPEDGI RELFPAPDGE DDTAELQGLR PGSEYTVSVV

ALHDDMESQP LIGIQSTKRY KNRVASRKSR AKFKQLLQHY

REVAAAKESL KISQAVHAAH AEINEAGREV VGVGALKVPR

NQDWLGVPRF AKFASFEAQG ALANIAVDKA NLDVEQLESI

INFEKLTEWT GS

SEQ ID NO: 38:
MHHHHHHNID RPKGLAFTDV DVDSIKIAWE SPQGQVSRYR

VTYSSPEDGI RELFPAPDGE DDTAELQGLR PGSEYTVSVV

ALHDDMESQP LIGIQSTREV AAAKSSENDR LRLLLKESLK

ISQAVHAAHA EINEAGREVV GVGALKVPRN QDWLGVPRFA

KFASFEAQGA LANIAVDKAN LDVEQLESII NFEKLTEWTG

S

SEQ ID NO: 39:
KRYKNRVASRKSRAKFKQLLQHYREVAAAKSSENDRLRLLLKV

TYHSPSYAYHQFERRAILNRLVQFIKDRISVVQALVLTSTVHE

ILCKLSLEGDHSTPPSAYGSVKPYTN FDAE

SEQ ID NO: 40:
KRYKNRVASRKSRAKFKQLLQHYREVAAAKSSENDRLRLLLKN

YRIATFKNWPFLEDCAMEELTVSEFLKLDRQRSTVHEILCKLS

LEGDHSTPPSAYGSVKPYTNFDAE

SEQ ID NO: 41:
KRYKNRVASRKSRAKFKQLLQHYREVAAAKSSENDRLRLLLKH

LELASMTNMELMSSIVSTVHEILCKLSLEGDHSTPPSAYGSVK

PYTNFDAE

SEQ ID NO: 46:
RKKRRQRRRVKRISQAVHAAHAEINEAGRRVKRKVPRNQDWL

RVKRASFEAQGALANIAVDKARVKRSIINFEKLRVKRSTVHEI

LCKLSLEGDHSTPPSAYGSVKPYTNFDAE

SEQ ID NO: 69:
KRYKNRVASRKSRAKFKQLLQHYREVAAAKSSENDRLRLLLKL

FRAAQLANDVVLQIMEHLELASMTNMELMSSIVVISASIIVFN

LLELEGSTVHEILCKLSLEGDHSTPPSAYGSVKPYTNFDAE

Arrangement of Components a), b-), and c) in the Complex for Use According to the Present Invention The components a), b), and c) may be arranged in the complex for use according to the present invention in any way.

In particular if more than one cell penetrating peptide and/or more than one antigen or antigenic epitope and/or more than one TLR peptide agonist are comprised by the complex for use according to the present invention, the more than one cell penetrating peptide may be positioned in a non-consecutive manner, i.e. at least one antigen or antigenic epitope (component b)) and/or at least one TLR peptide agonist (component c)) may interrupt a stretch of consecutively positioned cell penetrating peptides and/or the cell penetrating peptides may be positioned with component b) and/or with component c) in an alternating manner. Similarly, the more than one antigen or antigenic epitope may be positioned in a non-consecutive manner, i.e. at least one cell penetrating peptide (component a)) and/or at least one TLR peptide agonist (component c)) may interrupt a stretch of consecutively positioned antigens or antigenic epitopes and/or the antigens or antigenic epitopes may be positioned with component a) and/or with component c) in an alternating manner. Similarly, the more than one TLR peptide agonist may be positioned in a non-consecutive manner, i.e. at least one cell penetrating peptide (component a)) and/or at least one antigen or antigenic epitope (component b)) may interrupt a stretch of consecutively positioned TLR peptide agonists and/or the TLR peptide agonists may be positioned with component a) and/or with component b) in an alternating manner.

However, it is preferred that the more than one cell penetrating peptide is positioned in the complex for use according to the present invention in a consecutive manner and/or the more than one antigen or antigenic epitope is positioned in the complex for use according to the present invention in a consecutive manner and/or the more than one TLR peptide agonist is positioned in the complex for use according to the present invention in a consecutive manner. This means in particular that all single units of a certain component, i.e. all cell penetrating peptides, all antigens or antigenic epitopes or all TLR peptide agonists, which are comprised by the complex are positioned in a stretch, which is not interrupted by any of the other two components. Rather, the other two components are positioned in the complex for example before or after such a stretch of all single units of said certain component. However, the single units of said certain component positioned consecutively in such a way may be linked to each other for example by a spacer or linker as described herein, which is not of the other two components.

It is particularly preferred that each of the components a), b), and c) is positioned in a consecutive manner.

Structurally each component a), b), and c) typically comprises a single main chain and at least one side chain. The term "main chain" (also "backbone chain"), as used in the context of the present invention, refers to the main continuous chain of covalently bond atoms in a molecule. For example, in peptides, polypeptides and proteins, the main chain (backbone) typically comprises alpha-carbon atoms and nitrogen atoms of the constituent amino acids linked by the peptide bond. The backbone does not include the side chains. The term "side chain" (also "pendant chain"), as used in the context of the present invention, refers to a chemical group that is attached to a core part of the molecule called "main chain" or backbone. For example, in peptides, polypeptides and proteins, the side chains typically represent the (main) parts of the constituent amino acids, which are attached to the alpha-carbon atoms of the backbone.

In the complex for use according to the present invention, the components a), b), and c) may be covalently linked via a linker or spacer as described herein or they may be directly covalently linked. Independently of whether a spacer or linker is used for covalent linkage or not, there are in principle four options of how two of the three components are linked to each other in the complex for use according to the present invention, namely:
  (i) via main-chain/main-chain linkage,
  (ii) via main-chain/side-chain linkage,
  (iii) via side-chain/main-chain linkage or
  (iv) via side-chain/side chain linkage.

Preferably, all three components a), b), and c) are linked via main-chain/main-chain linkage, thus resulting in particular in a main chain of the complex for use according to the present invention, which comprises the main chain of one or more cell penetrating peptide(s), the main chain of one or more antigen(s) or antigenic epitope(s), and the main chain of one or more TLR peptide agonist(s). In other words, the main chain of one or more cell penetrating peptide(s), the main chain of one or more antigen(s) or antigenic epitope(s), and the main chain of one or more TLR peptide agonist(s) constitute the main chain of the complex for use according to the present invention, optionally together with further components, for example linker(s), spacer(s), etc. Accordingly, the following arrangements of the components a), b), and c) are preferred, in particular if the at least one antigen or antigenic epitope is a peptide, polypeptide or protein, whereby said preferred arrangements are shown below in N-terminus→C-terminus direction of the main chain of the complex and wherein all three components a), b), and c) are linked via main-chain/main-chain linkage and may be optionally linked by a linker, a spacer or another additional component:
  (α) component a) (cell penetrating peptide)—component b) (at least one antigen or antigenic epitope)—component c) (at least one TLR peptide agonist);
  (β) component c) (at least one TLR peptide agonist)—component a) (cell penetrating peptide)—component b) (at least one antigen or antigenic epitope);
  (γ) component a) (cell penetrating peptide)—component c) (at least one TLR peptide agonist)—component b) (at least one antigen or antigenic epitope);
  (δ) component c) (at least one TLR peptide agonist)—component b) (at least one antigen or antigenic epitope)—component a) (cell penetrating peptide);
  (ε) component b) (at least one antigen or antigenic epitope)—component a) (cell penetrating peptide)—component c) (at least one TLR peptide agonist); or
  (ζ) component b) (at least one antigen or antigenic epitope)—component c) (at least one TLR peptide agonist)—component a) (cell penetrating peptide).

In particular if all three components a), b), and c) are linked via main-chain/main-chain linkage, it is preferred that the at least one antigen or antigenic epitope is positioned C-terminally of the cell penetrating peptide, whereby the cell penetrating peptide and the at least one antigen or antigenic epitope are optionally linked by a further component, e.g. a linker, a spacer, or by the at least one TLR peptide agonist. Accordingly, this corresponds to the arrangements (α), (β), and (γ) from the arrangements shown above, i.e. from the above arrangements arrangements (α), (β), and (γ) are more preferred.

Even more preferably, the at least one antigen or antigenic epitope is positioned C-terminally of the cell penetrating peptide, whereby the cell penetrating peptide and the at least one antigen or antigenic epitope are optionally linked by a further component, e.g. a linker, a spacer, but not by the at least one TLR peptide agonist. Accordingly, this corresponds to the arrangements (α) and (β) from the arrangements shown above, i.e. from the above arrangements arrangements (α) and (β) are even more preferred. Particularly preferably, the complex for use according to the present invention is a recombinant polypeptide or a recombinant protein and the components a) to c) are positioned in N-terminus→C-terminus direction of the main chain of said complex in the order:
  (α) component a)—component b)—component c); or
  (β) component c)—component a)—component b),
wherein the components may be linked by a further component, in particular by a linker or a spacer.

Particularly preferred is arrangement (a), wherein the at least one TLR agonist comprises or consists of at least one TLR2 agonist, for example:
  (α1) component a) (cell penetrating peptide)—component b) (at least one antigen or antigenic epitope)—one or more TLR2 peptide agonist, e.g. 1, 2, 3, 4, or 5 TLR2 peptide agonist(s);
  (α2) component a) (cell penetrating peptide)—component b) (at least one antigen or antigenic epitope)—one or more TLR2 peptide agonist, e.g. 1, 2, 3, 4, or 5 TLR2 peptide agonist(s), one or more TLR4 peptide agonist, e.g. 1, 2, 3, 4, or 5 TLR4 peptide agonist(s) and one or more TLR5 peptide agonist, e.g. 1, 2, 3, 4, or 5 TLR5 peptide agonist(s);
  (α3) component a) (cell penetrating peptide)—component b) (at least one antigen or antigenic epitope)—one or more TLR2 peptide agonist, e.g. 1, 2, 3, 4, or 5 TLR2 peptide agonist(s) and one or more TLR4 peptide agonist, e.g. 1, 2, 3, 4, or 5 TLR4 peptide agonist(s); or
  (α4) component a) (cell penetrating peptide)—component b) (at least one antigen or antigenic epitope)—one or more TLR2 peptide agonist, e.g. 1, 2, 3, 4, or 5 TLR2 peptide agonist(s) and one or more TLR5 peptide agonist, e.g. 1, 2, 3, 4, or 5 TLR5 peptide agonist(s).

Alternatively, in such an arrangement comprising a TLR2 peptide agonist, additional TLR peptide agonists may also be arranged at other positions in the complex, for example:
  (α5) one or more TLR4 peptide agonist, e.g. 1, 2, 3, 4, or 5 TLR4 peptide agonist(s)—component a) (cell penetrating peptide)—component b) (at least one antigen or antigenic epitope)—one or more TLR2 peptide agonist, e.g. 1, 2, 3, 4, or 5 TLR2 peptide agonist(s);
  (α6) one or more TLR5 peptide agonist, e.g. 1, 2, 3, 4, or 5 TLR5 peptide agonist(s)—component a) (cell penetrating peptide)—component b) (at least one antigen or antigenic epitope)—one or more TLR2 peptide agonist, e.g. 1, 2, 3, 4, or 5 TLR2 peptide agonist(s); or
  (α7) one or more TLR4 peptide agonist, e.g. 1, 2, 3, 4, or 5 TLR4 peptide agonist(s) and one or more TLR5 peptide agonist, e.g. 1, 2, 3, 4, or 5 TLR5 peptide agonist(s)—component a) (cell penetrating peptide)—component b) (at least one antigen or antigenic epitope)—one or more TLR2 peptide agonist, e.g. 1, 2, 3, 4, or 5 TLR2 peptide agonist(s).

Particularly preferred is arrangement (0), wherein the at least one TLR agonist comprises or consists of at least one TLR4 agonist, for example:

(β1) one or more TLR4 peptide agonist, e.g. 1, 2, 3, 4, or 5 TLR4 peptide agonist(s)—component a) (cell penetrating peptide)—component b) (at least one antigen or antigenic epitope);

(β2) one or more TLR4 peptide agonist, e.g. 1, 2, 3, 4, or 5 TLR4 peptide agonist(s), one or more TLR2 peptide agonist, e.g. 1, 2, 3, 4, or 5 TLR2 peptide agonist(s) and one or more TLR5 peptide agonist, e.g. 1, 2, 3, 4, or 5 TLR5 peptide agonist(s)—component a) (cell penetrating peptide)—component b) (at least one antigen or antigenic epitope);

(β3) one or more TLR4 peptide agonist, e.g. 1, 2, 3, 4, or 5 TLR4 peptide agonist(s) and one or more TLR2 peptide agonist, e.g. 1, 2, 3, 4, or 5 TLR2 peptide agonist(s)—component a) (cell penetrating peptide)—component b) (at least one antigen or antigenic epitope); or (β4) one or more TLR4 peptide agonist, e.g. 1, 2, 3, 4, or 5 TLR4 peptide agonist(s) and one or more TLR5 peptide agonist, e.g. 1, 2, 3, 4, or 5 TLR5 peptide agonist(s)—component a) (cell penetrating peptide)—component b) (at least one antigen or antigenic epitope).

Alternatively, in such an arrangement comprising a TLR4 peptide agonist, additional TLR peptide agonists may also be arranged at other positions in the complex, for example:

(β5) one or more TLR4 peptide agonist, e.g. 1, 2, 3, 4, or 5 TLR4 peptide agonist(s)—component a) (cell penetrating peptide)—component b) (at least one antigen or antigenic epitope)—one or more TLR2 peptide agonist, e.g. 1, 2, 3, 4, or 5 TLR2 peptide agonist(s);

(β6) one or more TLR4 peptide agonist, e.g. 1, 2, 3, 4, or 5 TLR4 peptide agonist(s)—component a) (cell penetrating peptide)—component b) (at least one antigen or antigenic epitope)—one or more TLR5 peptide agonist, e.g. 1, 2, 3, 4, or 5 TLR5 peptide agonist(s); or (β7) one or more TLR4 peptide agonist, e.g. 1, 2, 3, 4, or 5 TLR4 peptide agonist(s)—component a) (cell penetrating peptide)—component b) (at least one antigen or antigenic epitope)—one or more TLR2 peptide agonist, e.g. 1, 2, 3, 4, or 5 TLR2 peptide agonist(s) and one or more TLR5 peptide agonist, e.g. 1, 2, 3, 4, or 5 TLR5 peptide agonist(s).

Alternatively, only two of the three components a), b), and c) are linked via main-chain/main-chain linkage in the complex for use according to the present invention.

For example components a) and b) are linked via main-chain/main-chain linkage, resulting thus in the following arrangements of the components a) and b) in the complex, shown in N-terminus→C-terminus direction of the main chain of the complex, whereby the components a) and b) may be optionally linked by a further component, e.g. a linker, a spacer etc.:

(1) cell penetrating peptide (a)—antigen/antigenic epitope (b); or (2) antigen/antigenic epitope (b)—cell penetrating peptide (a).

In such a case, component c), i.e. the at least one TLR peptide agonist, may then be arranged via main-chain/side-chain linkage, via side-chain/main-chain linkage or via side-chain/side chain linkage to either the cell penetrating peptide (a) or to the antigen/antigenic epitope (b) or, if present, to an additional component like a spacer or linker, which may be, for example, positioned between the cell penetrating peptide (a) and the antigen/antigenic epitope (b). This includes the following arrangements:

(i) component c) may be linked—optionally via a spacer or a linker—via main-chain/side-chain linkage to component a), i.e. the main chain of the at least one TLR peptide agonist is covalently linked—optionally via a spacer or a linker—to the side chain of the cell penetrating peptide;

(ii) component c) may be linked—optionally via a spacer or a linker—via side-chain/main-chain linkage to component a), i.e. the side chain of the at least one TLR peptide agonist is covalently linked—optionally via a spacer or a linker—to the main chain of the cell penetrating peptide;

(iii) component c) may be linked—optionally via a spacer or a linker—via side-chain/side-chain linkage to component a), i.e. the side chain of the at least one TLR peptide agonist is covalently linked—optionally via a spacer or a linker—to the side chain of the cell penetrating peptide;

(iv) component c) may be linked—optionally via a spacer or a linker—via main-chain/side-chain linkage to component b), i.e. the main chain of the at least one TLR peptide agonist is covalently linked—optionally via a spacer or a linker—to the side chain of the at least one antigen or antigenic epitope;

(v) component c) may be linked—optionally via a spacer or a linker—via side-chain/main-chain linkage to component b), i.e. the side chain of the at least one TLR peptide agonist is covalently linked—optionally via a spacer or a linker—to the main chain of the at least one antigen or antigenic epitope;

(vi) component c) may be linked—optionally via a spacer or a linker—via side-chain/side-chain linkage to component b), i.e. the side chain of the at least one TLR peptide agonist is covalently linked—optionally via a spacer or a linker—to the side chain of the at least one antigen or antigenic epitope;

(vii) component c) may be linked—optionally via a spacer or a linker—via main-chain/side-chain linkage to a linker or a spacer positioned between component a) and component b), i.e. the main chain of the at least one TLR peptide agonist is covalently linked—optionally via a spacer or a linker—to the side chain of a linker or a spacer positioned between component a) and component b);

(viii) component c) may be linked—optionally via a spacer or a linker—via side-chain/main-chain linkage to a linker or a spacer positioned between component a) and component b), i.e. the side chain of the at least one TLR peptide agonist is covalently linked—optionally via a spacer or a linker—to the main chain of a linker or a spacer positioned between component a) and component b); or (ix) component c) may be linked—optionally via a spacer or a linker—via side-chain/side-chain linkage to a linker or a spacer positioned between component a) and component b), i.e. the side chain of the at least one TLR peptide agonist is covalently linked—optionally via a spacer or a linker—to the side chain of a linker or a spacer positioned between component a) and component b).

For example components b) and c) are linked via main-chain/main-chain linkage, resulting thus in the following arrangements of the components b) and c) in the complex, shown in N-terminus→C-terminus direction of the main chain of the complex, whereby the components b) and c) may be optionally linked by a further component, e.g. a linker, a spacer etc.:

(3) antigen/antigenic epitope (b)—TLR peptide agonist (c); or (4) TLR peptide agonist (c)—antigen/antigenic epitope (b).

In such a case, component a), i.e. the cell penetrating peptide, may then be arranged via main-chain/side-chain linkage, via side-chain/main-chain linkage or via side-chain/side chain linkage to either the antigen/antigenic epitope (b) or to the TLR peptide agonist (c) or, if present, to an additional component like a spacer or linker, which may be, for example, positioned between the antigen/antigenic epitope (b) and the TLR peptide agonist (c). This includes the following arrangements:

(x) component a) may be linked—optionally via a spacer or a linker—via main-chain/side-chain linkage to component b), i.e. the main chain of the cell penetrating peptide is covalently linked—optionally via a spacer or a linker—to the side chain of the at least one antigen or antigenic epitope;

(xi) component a) may be linked—optionally via a spacer or a linker—via side-chain/main-chain linkage to component b), i.e. the side chain of the cell penetrating peptide is covalently linked—optionally via a spacer or a linker—to the main chain of the at least one antigen or antigenic epitope;

(xii) component a) may be linked—optionally via a spacer or a linker—via side-chain/side-chain linkage to component b), i.e. the side chain of the cell penetrating peptide is covalently linked—optionally via a spacer or a linker—to the side chain of the at least one antigen or antigenic epitope;

(xiii) component a) may be linked—optionally via a spacer or a linker—via main-chain/side-chain linkage to component c), i.e. the main chain of the cell penetrating peptide is covalently linked—optionally via a spacer or a linker—to the side chain of the at least one TLR peptide agonist;

(xiv) component a) may be linked—optionally via a spacer or a linker—via side-chain/main-chain linkage to component c), i.e. the side chain the cell penetrating peptide is covalently linked—optionally via a spacer or a linker—to the main chain of the at least one TLR peptide agonist;

(xv) component a) may be linked—optionally via a spacer or a linker—via side-chain/side-chain linkage to component c), i.e. the side chain of the cell penetrating peptide is covalently linked—optionally via a spacer or a linker—to the side chain of the at least one TLR peptide agonist;

(xvi) component a) may be linked—optionally via a spacer or a linker—via main-chain/side-chain linkage to a linker or a spacer positioned between component b) and component c), i.e. the main chain of the cell penetrating peptide is covalently linked—optionally via a spacer or a linker—to the side chain of a linker or a spacer positioned between component b) and component c);

(xvii) component a) may be linked—optionally via a spacer or a linker—via side-chain/main-chain linkage to a linker or a spacer positioned between component b) and component c), i.e. the side chain of the cell penetrating peptide is covalently linked—optionally via a spacer or a linker—to the main chain of a linker or a spacer positioned between component b) and component c); or (xviii) component a) may be linked—optionally via a spacer or a linker—via side-chain/side-chain linkage to a linker or a spacer positioned between component b) and component c), i.e. the side chain of the cell penetrating peptide is covalently linked—optionally via a spacer or a linker—to the side chain of a linker or a spacer positioned between component b) and component c).

For example components a) and c) are linked via main-chain/main-chain linkage, resulting thus in the following arrangements of the components a) and b) in the complex, shown in N-terminus→C-terminus direction of the main chain of the complex, whereby the components a) and c) may be optionally linked by a further component, e.g. a linker, a spacer etc.:

(5) cell penetrating peptide (a)—TLR peptide agonist (c); or (6) TLR peptide agonist (c)—cell penetrating peptide (a).

In such a case, component b), i.e. the at least one antigen or antigenic epitope, may then be arranged via main-chain/side-chain linkage, via side-chain/main-chain linkage or via side-chain/side chain linkage to either the cell penetrating peptide (a) or to the TLR peptide agonist (c) or, if present, to an additional component like a spacer or linker, which may be, for example, positioned between the cell penetrating peptide (a) and the TLR peptide agonist (c). This includes the following arrangements:

(xix) component b) may be linked—optionally via a spacer or a linker—via main-chain/side-chain linkage to component a), i.e. the main chain of the at least one antigen or antigenic epitope is covalently linked—optionally via a spacer or a linker—to the side chain of the cell penetrating peptide;

(xx) component b) may be linked—optionally via a spacer or a linker—via side-chain/main-chain linkage to component a), i.e. the side chain of the at least one antigen or antigenic epitope is covalently linked—optionally via a spacer or a linker—to the main chain of the cell penetrating peptide;

(xxi) component b) may be linked—optionally via a spacer or a linker—via side-chain/side-chain linkage to component a), i.e. the side chain of the at least one antigen or antigenic epitope is covalently linked—optionally via a spacer or a linker—to the side chain of the cell penetrating peptide;

(xxii) component b) may be linked—optionally via a spacer or a linker—via main-chain/side-chain linkage to component c), i.e. the main chain of the at least one antigen or antigenic epitope is covalently linked—optionally via a spacer or a linker—to the side chain of the at least one TLR peptide agonist;

(xxiii) component b) may be linked—optionally via a spacer or a linker—via side-chain/main-chain linkage to component c), i.e. the side chain of the at least one antigen or antigenic epitope is covalently linked—optionally via a spacer or a linker—to the main chain of the at least one TLR peptide agonist;

(xxiv) component b) may be linked—optionally via a spacer or a linker—via side-chain/side-chain linkage to component c), i.e. the side chain of the at least one antigen or antigenic epitope is covalently linked—optionally via a spacer or a linker—to the side chain of the at least one TLR peptide agonist;

(xxv) component b) may be linked—optionally via a spacer or a linker—via main-chain/side-chain linkage to a linker or a spacer positioned between component a) and component c), i.e. the main chain of the at least one antigen or antigenic epitope is covalently linked— optionally via a spacer or a linker—to the side chain of a linker or a spacer positioned between component a) and component c);

(xxvi) component b) may be linked—optionally via a spacer or a linker—via side-chain/main-chain linkage to a linker or a spacer positioned between component a) and component c), i.e. the side chain of the at least one antigen or antigenic epitope is covalently linked—optionally via a spacer or a linker—to the main chain of a linker or a spacer positioned between component a) and component c); or (xxvii) component b) may be linked—optionally via a spacer or a linker—via side-chain/side-chain linkage to a linker or a spacer positioned between component a) and component c), i.e. the side chain of the at least one antigen or antigenic epitope is covalently linked—optionally via a spacer or a linker—to the side chain of a linker or a spacer positioned between component a) and component c).

Alternatively, it is also conceivable that in the complex for use according to the present invention all three of the components a), b), and c) are arranged via main-chain/side-chain linkage, via side-chain/main-chain linkage or via side-chain/side chain linkage, optionally linked by an additional component, e.g. a spacer or a linker.

Colorectal Cancer

The present invention provides the complex as described above for use in the prevention and/or treatment of colorectal cancer.

Colorectal cancer (CRC, also known as "bowel cancer") is a cancer that comprises colon cancers and rectal cancers (CC). Both individual cancers have many features in common, but the cancer starting point. According to Siegel, R., C. Desantis, and A. Jemal, Colorectal cancer statistics, 2014. CA Cancer J Clin, 2014. 64(2): p. 104-17, in the United States between 2006 and 2010, the incidence by tumor site is slightly more important in the proximal colon (first and middle parts of the colon). With about 19 cases on 100,000 people, it represents 42% of the cases. It is followed by the rectal cancer, with 28% of the cases and the distal colon (bottom part of the colon) with an incidence of cases on 100,000 people.

Anatomically, the term "colorectal cancer" includes (i) cancers of colon, such as cancers of cecum (including cancers the ileocecal valve), appendix, ascending colon, hepatic flexure, transverse colon, splenic flexure, descending colon, sigmoid colon (including cancers of sigmoid (flexure)) as well as cancers of overlapping sites of colon; (ii) cancers of rectosigmoid junction, such as cancers of colon and rectum and cancers of rectosigmoid; and (iii) cancers of rectum, such as cancers of rectal ampulla.

Preferably, the colorectal cancer is a cancer of colon, such as a cancer of cecum (including cancer the ileocecal valve), cancer of appendix, cancer of ascending colon, cancer of hepatic flexure, cancer of transverse colon, cancer of splenic flexure, cancer of descending colon, cancer of sigmoid colon (including cancers of sigmoid (flexure)) or a combination thereof.

It is also preferred that the colorectal cancer is a cancer of rectosigmoid junction, such as (i) a cancer of colon and rectum or (ii) a cancer of rectosigmoid.

Furthermore, it is also preferred that the colorectal cancer is a cancer of rectum, such as a cancer of rectal ampulla.

Regarding the cell type, colorectal cancers include colorectal adenocarcinoma, colorectal stromal tumors, primary colorectal lymphoma, colorectal leiomyosarcoma, colorectal melanoma, colorectal squamous cell carcinoma and colorectal carcinoid tumors, such as, for example, carcinoid tumors of cecum, appendix, ascending colon, transverse colon, descending colon, sigmoid colon and/or rectum. Thus, preferred types of colorectal cancers include colorectal adenocarcinoma, colorectal stromal tumors, primary colorectal lymphoma, colorectal leiomyosarcoma, colorectal melanoma, colorectal squamous cell carcinoma and colorectal carcinoid tumors, such as, for example, carcinoid tumors of cecum, appendix, ascending colon, transverse colon, descending colon, sigmoid colon and/or rectum. More preferably, the colorectal cancer is a colorectal adenocarcinoma or a colorectal carcinoid carcinoma. Even more preferably, the colorectal cancer is a colorectal adenocarcinoma.

More than 95% of CRCs are adenocarcinomas. Colorectal adenocarcinomas typically start from glandular cells that make mucus to lubricate the colon or rectum. CRC typically starts in the innermost layer and can grow through some or all of the other layers. In rare cases, CRC could form in a polyp, which facilitates its growth into the wall of starting region. In advanced stage (stage III and IV), the cancer travels to nearby lymph nodes or to distant parts of the body through blood vessels.

For example, in colorectal cancer, the TNM staging system includes the following stages for primary tumors ("T" stages): TX—Primary tumour cannot be assessed, T0—No evidence of primary tumour, Ta—Non-invasive papillary carcinoma, Tis—Carcinoma in situ: intraepithelial or invasion of lamina propria, T1—Tumour invades submucosa, T2—Tumour invades muscularis propria, T3—Tumour invades through the muscularis propria into the pericolorectal tissues, T4a—Tumour penetrates to the surface of the visceral peritoneum and T4b—Tumour directly invades or is adherent to other organs or structures; following stages for lymph nodes ("N" stages): NX—Regional lymph nodes cannot be assessed, No—No regional lymph node metastasis, N1-Metastasis in 1-3 regional lymph nodes with NIa—Metastasis in 1 regional lymph node, N1b—Metastasis in 2-3 regional lymph nodes and N1c—Tumor deposit(s) in the subserosa, mesentery, or nonperitonealized pericolic or perirectal tissues without regional nodal metastasis, N2-Metastasis in 4 or more lymph nodes with N2a—Metastasis in 4-6 regional lymph nodes and N2b—Metastasis in 7 or more regional lymph nodes; and the following stages for distant metastasis ("M" stages): M0—No distant metastasis and M1—Distant metastasis with M1a—Metastasis confined to 1 organ or site (eg, liver, lung, ovary, nonregional node) and M1b—Metastases in more than 1 organ/site or the peritoneum.

This stages can be integrated into the following numerical staging of colorectal cancer: Stage 0: Tis, N0, M0; Stage I: T1, N0, M0 or T2, N0, M0; Stage IIA: T3, N0, M0; Stage IIB: T4a, N0, M0; Stage IIC: T4b, N0, M0; Stage IIIA: T1-T2, N1/N1c, M0 or T1, N2a, M0; Stage IIIB: T3-T4a, N1/N1c, M0 or T2-T3, N2a, M0 or T1-T2, N2b, M0; Stage IIIC: T4a, N2a, M0 or T3-T4a, N2b, M0 or T4b, N1-N2, M0; Stage IVA: any T, any N, M1a and Stage IVB: any T, any N, M1b. Briefly, in Stage 0, the cancer has not grown beyond the inner layer of the colon or rectum; in Stage I the cancer has spread from the mucosa to the muscle layer; in Stage II the cancer has spread through the muscle layer to the serosa nearby organs; in Stage III the cancer has spread to nearby lymph node(s) or cancer cells have spread to tissues near the lymph nodes; and in Stage IV the cancer has spread through the blood and lymph nodes to other parts of the body.

Despite the term "cancer", colorectal cancer includes all numerical stages as described above, and, thus, a preferred stage of colorectal cancer may be selected from the group consisting of Stage 0 (Tis, N0, M0), Stage I (T1, N0, M0 or T2, N0, M0), Stage IIA (T3, N0, M0), Stage IIB (T4a, N0, M0), Stage IIC (T4b, N0, M0), Stage IIIA (T1-T2, N1/N1c, M0 or T1, N2a, M0), Stage IIIB (T3-T4a, N1/N1c, M0 or T2-T3, N2a, M0 or T1-T2, N2b, M0), Stage IIIC (T4a, N2a, M0 or T3-T4a, N2b, M0 or T4b, N1-N2, M0), Stage IVA (any T, any N, M1a) and Stage IVB (any T, any N, M1b). More preferably, the colorectal cancer is selected from the group consisting of Stage I (T1, N0, M0 or T2, N0, M0), Stage IIA (T3, N0, M0), Stage IIB (T4a, N0, M0), Stage IIC (T4b, N0, M0), Stage IIIA (T1-T2, N1/N1c, M0 or T1, N2a, M0), Stage IIIB (T3-T4a, N1/N1c, M0 or T2-T3, N2a, M0 or T1-T2, N2b, M0), Stage IIIC (T4a, N2a, M0 or T3-T4a, N2b, M0 or T4b, N1-N2, M0), Stage IVA (any T, any N, M1a) and Stage IVB (any T, any N, M1b). Even more preferably, the colorectal cancer is selected from the group consisting of Stage IIA (T3, N0, M0), Stage IIB (T4a, N0, M0), Stage IIC (T4b, N0, M0), Stage IIIA (T1-T2, N1/N1c, M0 or T1, N2a, M0), Stage IIIB (T3-T4a, N1/N1c, M0 or T2-T3, N2a, M0 or T1-T2, N2b, M0), Stage IIIC (T4a, N2a, M0 or T3-T4a, N2b, M0 or T4b, N1-N2, M0), Stage IVA (any T, any N, M1a) and Stage IVB (any T, any N, M1b). Most preferably, the colorectal cancer is (i) Stage III colorectal cancer, such as Stage IIIA (T1-T2, N1/N1c, M0 or T1, N2a, M0), Stage IIIB (T3-T4a, N1/N1c, M0 or T2-TS, N2a, M0 or T1-T2, N2b, M0), or Stage IIIC (T4a, N2a, M0 or T3-T4a, N2b, M0 or T4b, N1-N2, M0), or (ii) Stage IV colorectal cancer, such as Stage IVA (any T, any N, M1a) and Stage IVB (any T, any N, M1b).

Nucleic Acid Encoding the Peptides and Protein Complexes

In another aspect the present invention provides a nucleic acid encoding the complex as described herein, wherein the complex is a polypeptide or a protein, for use in the prevention and/or treatment of colorectal cancer. In particular, the present invention provides polynucleotides for use in the prevention and/or treatment of colorectal cancer, said polynucleotides encoding the complex as defined above.

In this context, nucleic acids preferably comprise single stranded, double stranded or partially double stranded nucleic acids, preferably selected from genomic DNA, cDNA, RNA, siRNA, antisense DNA, antisense RNA, ribozyme, complimentary RNA/DNA sequences with or without expression elements, a mini-gene, gene fragments, regulatory elements, promoters, and combinations thereof.

Preferably, the invention relates to a nucleic acid for use according to the present invention, said nucleic acid encoding a complex, which is in particular a polypeptide or protein, said complex comprising a cell penetrating peptide, at least one antigen or antigenic epitope, which is a polypeptide or protein, and at least one TLR peptide agonist, wherein the cell penetrating peptide, the at least one antigen or antigenic epitope, and the at least one TLR peptide agonist are covalently linked, optionally with peptidic spacer(s) or linker(s) as described herein. If more than one antigen or antigenic epitope, which is a polypeptide or protein, is comprised by said complex, the more than one antigens or antigenic epitopes are also covalently linked, optionally with peptidic spacer(s) or linker(s) as described herein. Similarly, if more than one TLR peptide agonist is comprised by said complex, the more than one TLR peptide agonists are also covalently linked, optionally with peptidic spacer(s) or linker(s) as described herein.

Particularly preferably the nucleic acid for use according to the present invention encodes a complex which is a (recombinant) fusion protein comprising (a) a cell penetrating peptide as described above, (b) at least one, preferably at least two, more preferably at least three, even more preferably at least four, particularly preferably at least five, most preferably at least six antigens or antigenic epitopes as described above, preferably arranged in a consecutive manner as described above and (c) at least one TLR agonist as described above.

Production and Purification of the Complexes

According to a further aspect the present invention provides a vector for use in the prevention and/or treatment of colorectal cancer, in particular a recombinant vector, comprising a nucleic acid as described above.

The term "vector", as used in the context of the present invention, refers to a nucleic acid molecule, preferably to an artificial nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antibody or antibody fragment thereof according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector. Preferably, a vector in the context of the present application is an expression vector.

Cells transformed with a vector as described above for use in the prevention and/or treatment of colorectal cancer are also included within the scope of the invention. Examples of such cells include, but are not limited to, bacterial cells, e.g. E. coli, and eukaryotic cells, e.g., yeast cells, animal cells or plant cells. In one embodiment the cells are mammalian, e.g., human, CHO, HEK293T, PER.C6, NS0, myeloma or hybridoma cells. Accordingly, the present invention also relates to a cell expressing the antibody, or the antigen binding fragment thereof, for use according to the present invention; or comprising the vector for use according to the present invention.

In particular, a cell may be transfected with a vector as described above, preferably with an expression vector. The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Numerous expression systems can be used, including without limitation chromosomes, episomes, and derived viruses. More particularly, the vector as described above, in particular the recombinant vector used, can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses.

For example, such vectors, in particular recombinant vectors, can equally be cosmid or phagemid derivatives. The nucleotide sequence, in particular the nucleic acid according to the present invention, may be inserted in the recombinant expression vector by methods well known to a person skilled in the art such as, for example, those described in MOLECULAR CLONING: A LABORATORY MANUAL, Sambrook et al., 4th Ed., Cold Spring Harbor Laboratory Press, Cold Spring Harbor, N.Y., 2001.

The vector, in particular the recombinant vector, may also include nucleotide sequences that control the regulation of the expression, in particular of the nucleic acid for use according to the present invention, as well as nucleotide sequences permitting the expression, the transcription, and the translation, in particular of the nucleic acid for use according to the present invention. Typically, these sequences are selected according to the host cells used.

Thus, for example, an appropriate secretion signal can be integrated in the vector for use according to the present invention, in particular in a recombinant vector, so that the polypeptide or protein encoded by the nucleic acid for use according to the present invention, will be directed, for example towards the lumen of the endoplasmic reticulum, towards the periplasmic space, on the membrane or towards the extracellular environment. The choice of an appropriate secretion signal may facilitate subsequent protein purification.

In yet another aspect the present invention provides a host cell for use in the prevention and/or treatment of colorectal cancer, the host cell comprising a vector, in particular a recombinant vector, as described herein.

The introduction of the vector, in particular the recombinant vector, into a host cell can be carried out according to methods that are well known to a person skilled in the art, such as those described in BASIC METHODS IN MOLECULAR BIOLOGY, Davis et al., 2nd ed., McGraw-Hill Professional Publishing, 1995, and MOLECULAR CLONING: A LABORATORY MANUAL, supra, including for example transfection as described above, e.g. by calcium phosphate, by DEAE dextran, or by cationic lipids; microinjection, electroporation, transduction or infection.

The host cell can be, for example, bacterial cells such as E. coli, cells of fungi such as yeast cells and cells of Aspergillus, Streptomyces, insect cells, and/or any cell line, e.g. Chinese Hamster Ovary cells (CHO), C127 mouse cell line, BHK cell line of Syrian hamster cells, Human Embryonic Kidney 293 (HEK 293) cells. Preferably, the host cell for use according to the present invention is mammalian, e.g., human, CHO, HEK293T, PER.C6, NS0, myeloma or hybridoma cells. Dendritic cells and dendritic cell lines are particularly preferred as a host cell. Typically, the choice of a culture medium depends in particular on the choice of the cell type and/or the cell line, whereby the skilled person is aware of suitable culture media, which are appropriate for a selected cell type and/or cell line.

The host cells can be used, for example, to express a polypeptide or protein, in particular the complex for use according to the present invention, on the basis of the vector and/or the nucleic acid as described herein. After purification by standard methods, the expressed polypeptide or protein, in particular the complex for use according to the present invention, can be used as described herein.

Accordingly, the present invention also provides a method for preparing the complex as defined herein, in particular wherein the complex is a polypeptide or protein. Said method comprises the steps of:
 (i) cultivating a host cell as described above in a culture medium; and
 (ii) separating the complex as defined herein from the culture medium or separating the complex as defined herein from the host cell lysate after host cell lysis.

Thus, the complex obtained by such a method according to the present invention is preferably a complex for use according to the present invention as described herein.

For protein extraction commercially available kits and/or reagents may be used, for example BugBuster™ from Novagen.

Preferably, the method for preparing the complex as defined herein further comprises the following step:
 (iii) solubilization of the complex as defined herein, e.g. by resuspension in solutions containing urea or guanidine hydrochloride (GuHCl),
wherein step (iii) follows step (ii) as described above.

Moreover, it is preferred that the method for preparing the complex as defined herein further comprises the following step:
 (iv) purification of the complex as defined herein, preferably by one-step affinity chromatography,
wherein step (iv) follows step (ii), or, if present, step (iii) as described above.

In addition, the complex as defined herein may also be prepared by synthetic chemistry methods, for example by solid-phase peptide synthesis.

Purification of those peptides or proteins may be carried out by means of any technique known in the art for protein/peptide purification. Exemplary techniques include ion-exchange chromatography, hydrophobic interaction chromatography, and immunoaffinity methods.

Thus, the present invention also provides a method for preparing the complex as defined herein comprising the steps of:
 (i) chemically synthesizing said complex; and
 (ii) purifying said complex.

Preferably, in the method for preparing a complex as defined herein, the complex chemically synthesized in step (i) and purified in step (ii) comprises an amino acid sequences as described herein for a cell penetrating peptide, an amino acid sequence as described herein for a TLR peptide agonist, and, optionally if the at least one antigen and/or antigenic epitope is a peptide or a protein, an amino acid sequence as described herein for an antigen or antigenic epitope.

Alternatively, the present invention also provides a method for preparing the complex as defined herein, wherein
 (i) the cell penetrating peptide, the at least one antigen or antigenic fragment and/or the at least one TLR peptide agonist are synthesized separately;
 (ii) optionally, the cell penetrating peptide, the at least one antigen or antigenic fragment and/or the at least one TLR peptide agonist are purified; and (iii) the cell penetrating peptide, the at least one antigen or antigenic fragment and/or the at least one TLR peptide agonist are covalently linked as described above, optionally by a spacer or linker or by a cross-linking agent as described above.

Cells Loaded with the Complexes According to the Invention

In yet another aspect the present invention relates to a cell loaded with the complex as defined herein for use in the prevention and/or treatment of colorectal cancer. For example, the cells loaded with the complex as defined herein are cells from a subject to be treated, in particular isolated cells from a subject to be treated, i.e. cells isolated from a subject to be treated.

As used in the context of the present invention, the term "subject" refers in particular to mammals. For example, mammals contemplated by the present invention include human, primates, domesticated animals such as cattle, sheep, pigs, horses, laboratory rodents and the like. More preferably, the term "subject" refers to a human subject.

As used in the context of the present invention, "treatment" and "treating" and the like generally mean obtaining a desired pharmacological and physiological effect. The effect may be prophylactic in terms of preventing or partially preventing a disease, a symptom or a condition thereof and/or may be therapeutic in terms of a partial or complete cure of a disease, a condition, a symptom or an adverse effect attributed to the disease. The term "treatment" as used herein covers any treatment of a disease in a mammal, in particular in a human, and includes: (a) preventing the disease from occurring in a subject who may be predisposed to the disease but the outbreak of the disease has not yet occurred and/or the disease has not yet been diagnosed in this subject, for example a preventive early asymptomatic intervention; (b) inhibiting the disease, i.e., arresting or slowing down its development; or (c) relieving the disease, i.e., causing an at least partial regression of the disease and/or of at least one of its symptoms or conditions such as improvement or remediation of damage. In particular, the methods, uses, formulations and compositions according to the invention are useful in the treatment of cancers or infectious diseases and/or in the prevention of evolution of cancers into an advanced or metastatic stage in subjects with early stage cancer, thereby improving the staging of the cancer. When applied to cancers, prevention of a disease or disorder includes the prevention of the appearance or development of a cancer in an individual identified as at risk of developing said cancer, for instance due to past occurrence of said cancer in the circle of the individual's relatives, and prevention of infection with tumor promoting pathogens such as, for example, Epstein-Barr virus (EBV), Human papillomavirus (HPV), Hepatitis B virus (HBV), Hepatitis C virus (HCV), Human Herpes virus 8 (HHV8), human T-cell leukemia virus type 1 (HTLV-1), Merkel cell polyomavirus (MCV) and Helicobacter pylori. Also covered by the terms "prevention/treatment" of a cancer is the stabilization or delay of an already diagnosed cancer in an individual. By "stabilization", it is meant the prevention of evolution of cancer into advanced or metastatic stage in subjects with early stage cancer.

Preferably, the cell loaded with the complex as defined herein is an antigen-presenting cell (APC). Preferably, the antigen presenting cell is selected from the group consisting of a dendritic cell (DC), a macrophage and a B-cell. Dendritic cells, in particular dendritic cells (conventional and/or plasmacytoid) isolated from a subject to be treated, are more preferred.

Methods to isolate antigen-presenting cells, in particular dendritic cells, from a subject are known to the skilled person. They include harvesting monocytes or hematopoietic stem cells from bone marrow, cord blood, or peripheral blood. They also include the use of embryonic stem (ES) cells and induced pluripotent stem cells (iPS). Antigen presenting cells, in particular dendritic cells or their precursors, can be enriched by methods including elutriation and magnetic bead based separation, which may involve enrichment for $CD14^+$ precursor cells.

Methods to load the complex as defined herein into the cells, preferably into the above-mentioned antigen presenting cells, more preferably into dendritic cells, and further to prepare such cells before administration to a subject are known to one skilled in the art. For example, preparation of dendritic cells can include their culture or differentiation using cytokines that may include for example GM-CSF and IL-4. Dendritic cell lines may also be employed. Loading of the complex of the invention into the cells, preferably into APC, more preferably into the dendritic cells, can involve co-incubation of the complex of the invention with the cells in culture, making use of the intrinsic properties of the cell penetrating peptide comprised by the complex as defined herein (i.e. its internalization ability). Further culture of the cells, e.g. the dendritic cells, thus loaded to induce efficient maturation can include addition of cytokines including IL-1β, IL-6, TNFα, PGE2, IFNα, and adjuvants which may include poly-IC, poly-ICLC (i.e. a synthetic complex of carboxymethylcellulose, polyinosinic-polycytidylic acid, and poly-L-lysine double-stranded RNA), and further TLR agonists and NLR (nucleotide-binding oligomerization domain-like receptors) agonists.

A method for preparing cells, in particular antigen presenting cells, loaded with the complex as defined herein may comprise the steps of:
(i) transducing or transfecting said cells with the complex of the invention;
(ii) cultivating said cells in a culture medium; and
(iii) separating said cells from the culture medium.

Preferably, the cells are loaded with a complex as defined herein, wherein the complex is a polypeptide or a protein and used in the prevention and/or treatment of colorectal cancer.

Preferably, the cells loaded with a complex(es) according as defined herein and used in the prevention and/or treatment of colorectal cancer present the at least one antigen or antigenic epitope comprised by said complex at the cell surface in an MHC class I context and/or in an MHC class II context.

Compositions and Kits According to the Present Invention

According to another aspect, the invention provides a composition for use in the prevention and/or treatment of colorectal cancer, the composition comprising at least one component selected from:
(i) a complex as described above,
(ii) a nucleic acid as described above,
(iii) a vector as described above,
(iv) a host cell as described above, and
(v) a cell loaded with a complex as defined herein as described above.

Preferably, the composition according to the present invention comprises the complex as defined herein.

The composition for use according to the present invention may also comprises more than one of the above components (i) to (v). For example, the composition for use according to the present invention may comprise at least two different complexes under (i), at least two different nucleic acids under (ii), at least two different vectors under (iii), at least two different host cells under (iv), and/or at least two different cells under (v); e.g., the composition for use according to the invention may comprise at least two different complexes (i) and/or at least two different nucleic acids (ii).

For example, the different complexes (i) comprised by the composition as described above may differ in either component a), i.e. in the cell penetrating peptides, in component b), i.e. in the antigens or antigenic epitopes or in the subsets of more than one antigen or antigenic epitope, or in component c), i.e. in the TLR peptide agonist or in the subset of more than one TLR peptide agonist; or the different complexes (i) comprised by the composition as described above may differ in two out of the three components a), b), and c); or the different complexes (i) comprised by the composition as described above may differ in all three components a), b), and c) of the complex. Accordingly, the different nucleic acids (ii) comprised by the composition as described above may differ in that they encode such different complexes; the different vectors (iii) comprised by the composition as described above may differ in that they comprise such different nucleic acids; the different host cells (iv) comprised by the composition as described above may differ in that they comprise such different vectors; and the different cells loaded with a complex (v) comprised by the composition as described above may differ in that they are loaded with such different complexes.

The present invention also provides a vaccine for use in the prevention and/or treatment of colorectal cancer, the vaccine comprising at least one component selected from:
 (i) a complex as described above,
 (ii) a nucleic acid as described above,
 (iii) a vector as described above,
 (iv) a host cell as described above, and
 (v) a cell loaded with a complex as described above.

Preferably, the vaccine for use according to the present invention comprises the complex as defined herein.

Thereby, the above details described for the composition for use according to the present invention regarding more than one of the components (i) to (v), also apply for the vaccine for use according to the present invention.

As used in the context of the present invention, the term "vaccine" refers to a biological preparation that provides innate and/or adaptive immunity, typically to a particular disease, preferably cancer. Thus, a vaccine supports in particular an innate and/or an adaptive immune response of the immune system of a subject to be treated. For example, the antigen or antigenic epitope of the complex as defined herein typically leads to or supports an adaptive immune response in the patient to be treated, and the TLR peptide agonist of the complex as defined herein may lead to or support an innate immune response.

The inventive composition, in particular the inventive vaccine, may also comprise a pharmaceutically acceptable carrier, adjuvant, and/or vehicle as defined below for the inventive pharmaceutical composition. In the specific context of the inventive composition, in particular of the inventive vaccine, the choice of a pharmaceutically acceptable carrier is determined in principle by the manner in which the inventive composition, in particular the inventive vaccine, is administered. The inventive composition, in particular the inventive vaccine, can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, intranodal and sublingual injections. More preferably, inventive composition, in particular the vaccines, may be administered by an intradermal, subcutaneous, intranodal or intramuscular route. Even more preferably, the inventive composition, in particular the vaccine, may be administered by subcutaneous, intranodal or intramuscular route. Particularly preferably, the inventive composition, in particular the vaccines, may be administered by subcutaneous or intranodal route. Most preferably, the inventive composition, in particular the vaccines may be administered by subcutaneous route. Inventive composition, in particular the inventive vaccines, are therefore preferably formulated in liquid (or sometimes in solid) form.

The suitable amount of the inventive composition, in particular the inventive vaccine, to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof: The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive composition, in particular the inventive vaccine, is to be administered orally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The inventive composition, in particular the inventive vaccine, can additionally contain one or more auxiliary substances in order to further increase its immunogenicity. A synergistic action of the inventive complex as defined above and of an auxiliary substance, which may be optionally contained in the inventive vaccine as described above, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CSF, which allow an immune response produced by the immune-stimulating adjuvant according to the invention to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-so, IL-si, IL-32, IL-33, IFN-alpha, IFN-beta, IFN-gamma, GM-CSF, G-CSF, M-CSF, LT-beta or TNF-alpha, growth factors, such as hGH.

Further additives which may be included in the inventive vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive composition, in particular the inventive vaccine, can also additionally contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR 11, TLR12 or TLR13.

Another class of compounds, which may be added to an inventive composition, in particular to an inventive vaccine, in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, in particular the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

The present invention also provides a pharmaceutical composition for use in the prevention and/or treatment of colorectal cancer, in particular a vaccine composition as described above, and a method for treating a subject, preferably a mammalian subject, and most preferably a human subject, who is suffering from colorectal cancer.

In particular, the present invention provides a pharmaceutical composition for use in the prevention and/or treatment of colorectal cancer comprising at least one complex as defined herein or at least one cell loaded with a complex as defined herein, and optionally a pharmaceutically acceptable carrier and/or vehicle, or any excipient, buffer, stabilizer or other materials well known to those skilled in the art, in particular the pharmaceutical composition comprising at least one complex as defined herein or at least one cell loaded with a complex as defined herein and a pharmaceutically acceptable carrier.

As a further ingredient, the inventive pharmaceutical composition may in particular comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g phosphate, citrate etc. buffered solutions. Particularly for injection of the inventive inventive pharmaceutical composition, water or preferably a buffer, more preferably an aqueous buffer, may be used, containing a sodium salt, preferably at least 30 mM of a sodium salt, a calcium salt, preferably at least 0.05 mM of a calcium salt, and optionally a potassium salt, preferably at least 1 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2COS$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined above, may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. Typically, the salts in the injection buffer are present in a concentration of at least 30 mM sodium chloride (NaCl), at least 1 mM potassium chloride (KCl) and at least 0.05 mM calcium chloride ($CaCl_2$). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Saline (0.9% NaCl) and Ringer-Lactate solution are particularly preferred as a liquid basis.

However, one or more compatible solid or liquid fillers or diluents or encapsulating compounds may be used as well for the inventive pharmaceutical composition, which are suitable for administration to a subject to be treated. The term "compatible" as used herein means that these constituents of the inventive pharmaceutical composition are capable of being mixed with the complex as defined herein as defined above in such a manner that no interaction occurs which would substantially reduce the pharmaceutical effectiveness of the inventive pharmaceutical composition under typical use conditions. Pharmaceutically acceptable carriers, fillers and diluents must, of course, have sufficiently high purity and sufficiently low toxicity to make them suitable for administration to a subject to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, intranodal and sublingual injection or infusion techniques. Preferably, the inventive pharmaceutical composition may be administered intradermally, intramuscularly, intranodally or subcutaneously. More preferably the inventive pharmaceutical composition may be administered intramuscularly, intranodally or subcutaneously. Even more preferably the inventive pharmaceutical composition may be administered intranodally or subcutaneously. Most preferably, the inventive pharmaceutical composition may be administered subcutaneously.

Preferably, the inventive pharmaceutical composition may be administered by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, intranodal and sublingual injection or via infusion techniques. Sterile injectable forms of the inventive pharmaceutical compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1.3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation of the inventive pharmaceutical composition.

For intravenous, cutaneous or subcutaneous injection, or injection at the site of affliction, the active ingredient will preferably be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be), this being sufficient to show benefit to the individual. The actual amount administered, and rate and time-course of administration, will depend on the nature and severity of what is being treated. The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive immunostimulatory composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

In this context, prescription of treatment, e.g. decisions on dosage etc. when using the above pharmaceutical composition is typically within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980.

Accordingly, the inventive pharmaceutical composition typically comprises a "safe and effective amount" of the components of the inventive pharmaceutical composition, in particular of the complex as defined herein as defined above and/or cells loaded with said complex. As used herein, a "safe and effective amount" means an amount of the complex as defined herein that is sufficient to significantly induce a positive modification of a disease or disorder, i.e. an amount of the complex as defined herein or cells loaded with said complex, that elicits the biological or medicinal response in a tissue, system, animal or human that is being sought. An effective amount may be a "therapeutically effective amount" for the alleviation of the symptoms of the disease or condition being treated and/or a "prophylactically effective amount" for prophylaxis of the symptoms of the disease or condition being prevented. The term also includes the amount of active complex sufficient to reduce the progression of the disease, notably to reduce or inhibit the tumor growth or infection and thereby elicit the response being sought, in particular such response could be an immune response directed against the antigens or antigenic epitopes comprised in by the complex (i.e. an "inhibition effective amount"). At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of the components of the inventive pharmaceutical composition, particularly of the complex as defined herein as defined above, will furthermore vary in connection with the particular condition to be treated and also with the age and physical condition of the patient to be treated, the body weight, general health, sex, diet, time of administration, rate of excretion, drug combination, the activity of the specific components a), b), and c) of the complex as defined herein as defined above, the severity of the condition, the duration of the treatment, the nature of the accompanying therapy, of the particular pharmaceutically acceptable carrier used, and similar factors, within the knowledge and experience of the accompanying doctor. The inventive pharmaceutical composition may be used for human and also for veterinary medical purposes, preferably for human medical purposes, as a pharmaceutical composition in general or as a vaccine.

Pharmaceutical compositions, in particular vaccine compositions, or formulations according to the invention may be administered as a pharmaceutical formulation which can contain a complex as defined herein in any form described herein.

The terms "pharmaceutical formulation" and "pharmaceutical composition" as used in the context of the present invention refer in particular to preparations which are in such a form as to permit biological activity of the active ingredient(s) to be unequivocally effective and which contain no additional component which would be toxic to subjects to which the said formulation would be administered.

In the context of the present invention, an "efficacy" of a treatment can be measured based on changes in the course of a disease in response to a use or a method according to the present invention. For example, the efficacy of a treatment of cancer can be measured by a reduction of tumor volume, and/or an increase of progression free survival time, and/or a decreased risk of relapse post-resection for primary cancer. More specifically for cancer treated by immunotherapy, assessment of efficacy can be by the spectrum of clinical patterns of antitumor response for immunotherapeutic agents through novel immune-related response criteria (irRC), which are adapted from Response Evaluation Criteria in Solid Tumors (RECIST) and World Health Organization (WHO) criteria (J. Natl. Cancer Inst. 2010, 102(18): 1388-1397). The efficacy of prevention of infectious disease is ultimately assessed by epidemiological studies in human populations, which often correlates with titres of neutralizing antibodies in sera, and induction of multifunctional pathogen specific T cell responses. Preclinical assessment can include resistance to infection after challenge with infectious pathogen. Treatment of an infectious disease can be measured by inhibition of the pathogen's growth or elimination of the pathogen (and, thus, absence of detection of the pathogen), correlating with pathogen specific antibodies and/or T cell immune responses.

Pharmaceutical compositions, in particular vaccine compositions, or formulations according to the invention may also be administered as a pharmaceutical formulation which can contain antigen presenting cells loaded with a complex according to the invention in any form described herein.

The vaccine and/or the composition for use according to the present invention may also be formulated as pharmaceutical compositions and unit dosages thereof, in particular together with a conventionally employed adjuvant, immunomodulatory material, carrier, diluent or excipient as described above and below, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous and intradermal) use by injection or continuous infusion.

In the context of the present invention, in particular in the context of a pharmaceutical composition and vaccines according to the present invention, injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Examples of suitable adjuvants and/or immunomodulatory materials in the context of the present invention include MPL® (Corixa), aluminum-based minerals including aluminum compounds (generically called Alum), ASO1-4, MF59, CalciumPhosphate, Liposomes, Iscom, polyinosinic: polycytidylic acid (polyIC), including its stabilized form poly-ICLC (Hiltonol), CpG oligodeoxynucleotides, Granulocyte-macrophage colony-stimulating factor (GM-CSF), lipopolysaccharide (LPS), Montanide, polylactide co-glycolide (PLG), Flagellin, Soap Bark tree saponins (QS21), amino alkyl glucosamide compounds (e.g. RC529), two component antibacterial peptides with synthetic oligodeoxynucleotides (e.g. IC31), Imiquimod, Resiquimod, Immunostimulatory sequences (ISS), monophosphoryl lipid A (MPLA), Fibroblast-stimulating lipopeptide (FSL1), and anti-CD40 antibodies.

Compositions, in particular pharmaceutical compositions and vaccines, for use according to the present invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Compositions, in particular pharmaceutical compositions and vaccines, for use according to the present invention may also be formulated as a depot preparation, which may be administered by implantation or by intramuscular injection.

Compositions, in particular pharmaceutical compositions and vaccines, for use according to the present invention may also be solid compositions, which may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions, in particular pharmaceutical compositions and vaccines, for use according to the present invention may also be administered in sustained release forms or from sustained release drug delivery systems.

Moreover, the compositions, in particular pharmaceutical compositions and vaccines, for use according to the present invention may be adapted for delivery by repeated administration.

Further materials as well as formulation processing techniques and the like, which are useful in the context of compositions, in particular pharmaceutical compositions and vaccines, for use according to the present invention or in the context of their preparation are set out in "Part 5 of Remington's "The Science and Practice of Pharmacy", 22$^{nd}$ Edition, 2012, University of the Sciences in Philadelphia, Lippincott Williams & Wilkins".

In a further aspect, the present invention also relates to a kit-of-parts for use in the prevention and/or treatment of colorectal cancer, the kit of parts comprising at least one of:
 (i) a complex as described above,
 (ii) a nucleic acid as described above,
 (iii) a vector as described above,
 (iv) a host cell as described above, and
 (v) a cell loaded with a complex as described above.

In particular, the kit-of-parts of the invention may comprise more than one component (i) to (v). For example, the kit-of-parts according to the present invention may comprise at least two different complexes under (i), at least two different nucleic acids under (ii), at least two different vectors under (iii), at least two different host cells under (iv), and/or at least two different cells under (v); e.g., the kit-of-parts of the invention may comprise at least two different complexes (i) and/or at least two different nucleic acids (ii).

For example, the different complexes (i) comprised by the kit-of-parts as described above may differ in either component a), i.e. in the cell penetrating peptides, in component b), i.e. in the antigens or antigenic epitopes or in the subsets of more than one antigen or antigenic epitope, or in component c), i.e. in the TLR peptide agonist or in the subset of more than one TLR peptide agonist; or the different complexes (i) comprised by the kit-of-parts as described above may differ in two out of the three components a), b), and c); or the different complexes (i) comprised by the kit-of-parts as described above may differ in all three components a), b), and c) of the complex. Accordingly, the different nucleic acids (ii) comprised by the kit-of-parts as described above may differ in that they encode such different complexes; the different vectors (iii) comprised by the kit-of-parts as described above may differ in that they comprise such different nucleic acids; the different host cells (iv) comprised by the kit-of-parts as described above may differ in that they comprise such different vectors; and the different cells loaded with a complex (v) comprised by the kit-of-parts as described above may differ in that they are loaded with such different complexes.

The various components of the kit-of-parts may be packaged in one or more containers. The above components may be provided in a lyophilized or dry form or dissolved in a suitable buffer. The kit may also comprise additional reagents including, for instance, preservatives, growth media, and/or buffers for storage and/or reconstitution of the above-referenced components, washing solutions, and the like. In addition, the kit-of-parts according to the present invention may optionally contain instructions of use.

Moreover, the present invention also provides a vaccination kit for treating, preventing and/or stabilizing colorectal cancer, comprising the pharmaceutical composition as described herein or a vaccine as described herein and instructions for use of said pharmaceutical composition or of said vaccine in the prevention and/or treatment of colorectal cancer.

Thus, the present invention also provides a kit comprising the complex as described herein, the cell as described herein, the composition as described herein, the vaccine as described herein, and/or the pharmaceutical composition as described herein.

Preferably, such a kit further comprises a package insert or instruction leaflet with directions to treat colorectal cancer by using the complex for use according to the present invention as described herein, the cell as described herein, the composition as described herein, the vaccine as described herein, and/or the pharmaceutical composition as described herein.

Use and Methods According to the Invention

In another aspect, the present invention provides the use of any one of: (i) a complex as described herein, and/or (ii) cells, such as antigen-presenting cells, loaded with a complex as described herein, (for the preparation of a medicament) for the prevention, treatment or stabilization of colorectal cancer. Accordingly, the present invention provides any one of: (i) a complex as described herein, and/or (ii) cells, such as antigen-presenting cells, loaded with a complex as described herein, for use in the prevention, treatment or stabilization of colorectal cancer.

The present invention also provides a complex for use according to the present invention, which allows the transport and presentation of the at least one antigen or antigenic epitope comprised by the complex at the cell surface of antigen presenting cells in an MHC class I and/or MHC class II context, for use in vaccination and/or immunotherapy.

According to another aspect, the present invention provides a method of preventing, treating or repressing colorectal cancer, wherein said method comprises administering any one of: (i) a complex of the invention, (ii) cells, such as antigen-presenting cells, loaded with a complex of the invention, or (iii) a pharmaceutical formulation of (i) to (ii), to said subject.

Moreover, the present invention provides a method for eliciting or improving, in a subject, an immune response against one or multiple epitopes that is dependent on CD4$^+$ helper T cells and/or CD8$^+$ cytotoxic T cells, wherein said method comprises administering any one of: (i) a complex for use according to the present invention, and/or (ii) cells, such as antigen-presenting cells, loaded with said complex, or (iii) a pharmaceutical formulation of (i) to (ii), to said subject.

An immune response that is dependent on CD4$^+$ and/or CD8$^+$ response can be determined by evaluating an inflammatory response, a pro-inflammatory cytokine response, including an increase in the expression of one or more of IFN-γ, TNF-α and IL-2 mRNA or protein relative to the level before administration of the compounds of the invention. It can also be measured by an increase in the frequency or absolute number of antigen-specific T cells after administration of the compounds of the invention, measured by HLA-peptide multimer staining, ELISPOT assays, and delayed type hypersensitivity tests. It can also be indirectly measured by an increase in antigen-specific serum antibodies that are dependent on antigen-specific T helper cells.

The present invention also provides a method for eliciting or improving, in a subject, an immune response against one or multiple antigens or antigenic epitopes that is restricted by multiple MHC class I molecules and/or multiple MHC class II molecules, wherein said method comprises administering any one of: (i) a complex for use according to the present invention, and/or (ii) cells, such as antigen-presenting cells, loaded with said complex, or (iii) a pharmaceutical formulation of (i) to (ii), to said subject.

A method for eliciting or improving, in a subject, an immune response against multiple epitopes as described herein, that is restricted by multiple MHC class I molecules and/or multiple MHC class II molecules can be determined by evaluating a cytokine response, including an increase in the expression of one or more of IFN-γ, TNF-α and IL-2 mRNA or protein relative to the level before administration of the compounds of the invention, after in vitro stimulation of T cells with individual peptides binding to discrete MHC class I and class II molecules on antigen presenting cells. Restriction to different MHC molecules can also be validated by using antigen presenting cells expressing different MHC molecules, or by using MHC blocking antibodies. It can also be measured by an increase in the frequency or absolute number of antigen-specific T cells after administration of the compounds of the invention, measured by HLA-peptide multimer staining, which uses multimers assembled with discrete MHC molecules.

Preferably, in the methods for eliciting or improving an immune response against one or multiple antigens or antigenic epitopes according to the present invention, the immune response is directed against one or multiple epitopes of a tumor-associated antigen or a tumor-specific antigen as, for instance, a combination of epitopes as described herein.

Alternatively or additionally, the immune response may be directed against multiple epitopes of an antigenic protein from a pathogen.

The methods according to the present invention as described herein, may be for eliciting or improving, in a subject, an immune response against one or multiple epitopes that is restricted by MHC class I molecules and/or MHC class II molecules.

In particular, the present invention thus provides a method for preventing and/or treating colorectal cancer or initiating, enhancing or prolonging an anti-tumor-response in a subject in need thereof comprising administering to the subject a complex comprising:

a cell penetrating peptide;
at least one antigen or antigenic epitope; and
at least one TLR peptide agonist,
wherein the components a)—c) are covalently linked.

In such a method it is preferred that the complex for use according to the present invention as described herein, the cell as described herein, the composition as described herein, the vaccine as described herein, and/or the pharmaceutical composition as described herein is administered to the subject.

Preferably, the subject has colorectal cancer and/or was diagnosed with colorectal cancer. In another aspect, the present invention provides the use of any one of: (i) a complex as described herein, and/or (ii) cells, such as antigen-presenting cells, loaded with the complex as described herein, for the preparation of an imaging composition for imaging techniques in the context of (diagnosis of) colorectal cancer or for the preparation of a diagnosis composition ("diagnostic compositions") for diagnosing colorectal cancer. A diagnostic composition for diagnosing colorectal cancer according to the present invention comprises at least one component selected from:

(i) a complex as described above,
(ii) a nucleic acid as described above,
(iii) a vector as described above,
(iv) a host cell as described above, and
(v) a cell loaded with a complex as described above.

Preferably, the diagnostic composition according to the present invention comprises the complex as described above.

In particular, the complex for use according to the present invention, the cell, such as antigen-presenting cell, loaded with the complex for use according to the present invention, the inventive composition, the inventive pharmaceutical composition or the inventive vaccine or, most preferably, the inventive diagnostic composition may be utilized in diagnosis as a diagnostic tool, e.g. in (in vivo or in vitro) assays, e.g. in immunoassays, to detect, prognose, diagnose, or monitor colorectal cancer.

As an example, (in vitro) assays may be performed by delivering the complex for use according to the present invention, the cell, such as antigen-presenting cell, loaded with the complex for use according to the present invention, the inventive composition, the inventive pharmaceutical composition or the inventive vaccine or, most preferably, the inventive diagnostic composition to target cells typically selected from e.g. cultured animal cells, human cells or micro-organisms, and to monitor the cell response by biophysical methods typically known to a skilled person. The target cells typically used therein may be cultured cells (in vitro), e.g. cells isolated from human or animal body, such as blood cells isolated from human or animal body, or in vivo cells, i.e. cells composing the organs or tissues of living animals or humans, or microorganisms found in living animals or humans. Particularly preferable in this context are so called markers or labels, which may be contained in the complex for use according to the present invention and, in particular, in the diagnostic composition according to the present invention.

According to a further aspect, the invention provides a method of diagnosing colorectal cancer in a subject, wherein said method comprises administering any one of: (i) a complex of the invention, (ii) cells, such as antigen-presenting cells, loaded with the complex of the invention, or (iii) a pharmaceutical formulation of (i) to (ii), to said subject or to said subject's sample ex vivo.

Preferably, uses and methods according to the present invention comprise administration of a complex for use according to the invention.

Moreover, uses and methods according to the present invention comprise administration of more than one complex, cells, or pharmaceutical formulation according to the invention. For example, in the uses and methods according to the present invention, at least two different complexes are used or administered, wherein each complex comprises at least one antigen or antigenic epitope and said antigen or antigenic epitope or (if more than one antigen or antigenic epitope is comprised by said complex) said subset of antigens or antigenic epitopes are different between the two complexes.

For example, the different complexes (i) comprised by the composition as described above may differ in either component a), i.e. in the cell penetrating peptides, in component b), i.e. in the antigens or antigenic epitopes or in the subsets of more than one antigen or antigenic epitope, or in component c), i.e. in the TLR peptide agonist or in the subset of more than one TLR peptide agonist; or the different complexes (i) comprised by the composition as described above may differ in two out of the three components a), b), and c); or the different complexes (i) comprised by the composition as described above may differ in all three components a), b), and c) of the complex. Accordingly, the different nucleic acids (ii) comprised by the composition as described above may differ in that they encode such different complexes; the different vectors (iii) comprised by the composition as described above may differ in that they comprise such different nucleic acids; the different host cells (iv) comprised by the composition as described above may differ in that they comprise such different vectors; and the different cells loaded with a complex (v) comprised by the composition as described above may differ in that they are loaded with such different complexes.

Moreover, in the uses and methods according to the present invention, the cells according to the present invention may be antigen presenting cells, in particular dendritic cells, more preferably dendritic cells from the subject to be treated.

Mode of Administration

The complex for use according to the present invention; the cell, such as antigen-presenting cell, loaded with the complex for use according to the present invention; the inventive composition; the inventive pharmaceutical composition or the inventive vaccine may be administered in any manner as described above, including enterally, such as orally or rectally, and parenterally, such as intravenously or combinations thereof. Parenteral administration includes, but is not limited to, intravenous, intra-arterial, intra-peritoneal, subcutaneous, intradermal and intramuscular. Preferably, the complex for use according to the present invention; the cell, such as antigen-presenting cell, loaded with the complex for use according to the present invention; the inventive composition; the inventive pharmaceutical composition and/or the inventive vaccine are administered via an enteral route of administration, such as oral, sublingual and rectal. The complex for use according to the present invention; the cell, such as antigen-presenting cell, loaded with the complex for use according to the present invention; the inventive composition; the inventive pharmaceutical composition or the inventive vaccine may also be preferably administered via topical, intratumoral, intradermal, subcutaneous, intramuscular, intranasal, or intranodal route. The complex for use according to the present invention; the cell, such as antigen-presenting cell, loaded with the complex for use according to the present invention; the inventive composition; the inventive pharmaceutical composition or the inventive vaccine may also be administered in the form of an implant, which allows slow release of the compositions as well as a slow controlled i.v. infusion. For example, the complex for use according to the present invention; the cell, such as antigen-presenting cell, loaded with the complex for use according to the present invention; the inventive composition; the inventive pharmaceutical composition or the inventive vaccine may be administered subcutaneously.

The administration of complex for use according to the present invention; the cell, such as antigen-presenting cell, loaded with the complex for use according to the present invention; the inventive composition; the inventive pharmaceutical composition or the inventive vaccine may require multiple successive injections/administrations. Thus, the administration may be repeated at least two times, for example once as primary immunization injections/administration and, later, as booster injections/administration.

In particular, the complex for use according to the present invention; the cell, such as antigen-presenting cell, loaded with the complex for use according to the present invention; the inventive composition; the inventive pharmaceutical composition or the inventive vaccine may be administered repeatedly or continuously. The complex for use according to the present invention; the cell, such as antigen-presenting cell, loaded with the complex for use according to the present invention; the inventive composition; the inventive pharmaceutical composition or the inventive vaccine may be administered repeatedly or continuously for a period of at least 1, 2, 3, or 4 weeks; 2, 3, 4, 5, 6, 8, 10, or 12 months; or 2, 3, 4, or 5 years.

Moreover, the cell penetrating peptide, components a), b), and c), i.e. the at least one antigen or antigenic epitope and the at least one TLR peptide agonist, composing the complex for use according to the present invention may be contained in separate compositions which are mixed just before administration or which are administered simultaneously to the subject in need thereof. According to one approach, the complex for use according to the present invention; the cell, such as antigen-presenting cell, loaded with the complex for use according to the present invention; the inventive composition; the inventive pharmaceutical composition or the inventive vaccine may be administered directly to a patient using the administration routes as described above, in particular for pharmaceutical compositions. Alternatively, the complex for use according to the present invention; the cell, such as antigen-presenting cell, loaded with the complex for use according to the present invention; the inventive composition; the inventive pharmaceutical composition or the inventive vaccine may be administered to a patient using an ex vivo approach, e.g. by introducing the pharmaceutical composition, the vaccine or the inventive transporter cargo conjugate molecule as defined above into cells, preferably autologous cells, i.e. cells derived from the patient to be treated, and transplanting these cells into the site of the patient to be treated, optionally subsequent to storing and/or culturing these cells prior to treatment.

The dosage administered, as single or multiple doses, to an individual will vary depending upon a variety of factors, including pharmacokinetic properties, subject conditions and characteristics (sex, age, body weight, health, size), extent of symptoms, concurrent treatments, frequency of treatment and the effect desired.

Typically, for cancer treatment, the therapeutically effective dose of a complex for use according to the present invention is from about 0.01 mg to 5 mg per injection, in particular from about 0.1 mg to 2 mg per injection, or from about 0.01 nmol to 1 mmol per injection, in particular from 1 nmol to 1 mmol per injection, preferably from 1 mol to 1 mmol per injection.

Typically, for cancer treatment, the therapeutically effective dose of an antigen presenting cell loaded with a complex for use according to the present invention is from about 0.2 million cells to 2 million cells per injection.

Combination Therapy

The administration of the complex for use according to the present invention; the cell, such as antigen-presenting cell, loaded with the complex for use according to the present invention; the inventive composition; the inventive pharmaceutical composition or the inventive vaccine in the methods and uses according to the invention can be carried out alone or in combination with a co-agent useful for treating and/or stabilizing colorectal cancer.

For instance, in the case of treatment, prevention, or stabilization of a colorectal cancer, the administration of the pharmaceutical compositions in the methods and uses according to the invention can be carried out in combination with substances used in conventional chemotherapy directed against solid colorectal tumors and for control of establishment of metastases or any other molecule that act by triggering programmed cell death e.g. for example a co-agent selected from Tumor Necrosis Family Members including, but not limited, to Fas Ligand and tumor necrosis factor (TNF)-related apoptosis inducing (TRAIL) ligand. According to a further embodiment, the administration of the complex for use according to the present invention; the cell, such as antigen-presenting cell, loaded with the complex for use according to the present invention; the inventive composition; the inventive pharmaceutical composition or the inventive vaccine in the methods and uses according to the present invention can be carried out in parallel of radiotherapy.

The invention encompasses the administration of the complex for use according to the present invention; the cell, such as antigen-presenting cell, loaded with the complex for use according to the present invention; the inventive composition; the inventive pharmaceutical composition or the inventive vaccine, wherein it is administered to a subject prior to, simultaneously or sequentially with other therapeutic regimens or co-agents useful for treating, and/or stabilizing a colorectal cancer and/or preventing colorectal cancer relapsing (e.g. multiple drug regimens), in a therapeutically effective amount. Said complex, cell, composition, vaccine or pharmaceutical composition, that is administered simultaneously with said co-agents can be administered in the same or different composition(s) and by the same or different route(s) of administration.

Said other therapeutic regimens or co-agents may be selected from the group consisting of radiation therapy, chemotherapy, surgery, targeted therapy (including small molecules, peptides and monoclonal antibodies), and anti-angiogenic therapy. Anti-angiogenic therapy is defined herein as the administration of an agent that directly or indirectly targets tumor-associated vasculature.

Accordingly, the present invention also provides a combination of
(i) a complex as defined herein; and
(ii) a chemotherapeutic agent, a targeted drug and/or an immunotherapeutic agent, such as an immune checkpoint modulator,
for use in the prevention and/or treatment of colorectal cancer.

Traditional chemotherapeutic agents are cytotoxic, i.e. they act by killing cells that divide rapidly, one of the main properties of most cancer cells. Preferred chemotherapeutic agents for combination with the complex as defined herein are such chemotherapeutic agents known to the skilled person for treatment of colorectal cancer. Preferred chemotherapeutic agents for combination include 5-Fluorouracil (5-FU), Capecitabine (Xeloda®), Irinotecan (Camptosar®) and Oxaliplatin (Eloxatin®). It is also preferred that the complex as defined herein is combined with a combined chemotherapy, preferably selected from (i) FOLFOX (5-FU, leucovorin, and oxaliplatin); (ii) CapeOx (Capecitabine and oxaliplatin); (iii) 5-FU and leucovorin; (iv) FOLFOXIRI (leucovorin, 5-FU, oxaliplatin, and irinotecan); and (v) FOLFIRI (5-FU, leucovorin, and irinotecan). In non-spread cancer, a combination with (i) FOLFOX (5-FU, leucovorin, and oxaliplatin); (ii) CapeOx (Capecitabine and oxaliplatin); or (iii) 5-FU and leucovorin is preferred. For cancer that has spread, a combination with (iv) FOLFOXIRI (leucovorin, 5-FU, oxaliplatin, and irinotecan); (i) FOLFOX (5-FU, leucovorin, and oxaliplatin); or (v) FOLFIRI (5-FU, leucovorin, and irinotecan) is preferred.

Targeted drugs for combination with the complex as defined herein for treatment of colorectal cancer include VEGF-targeted drugs and EGFR-targeted drugs. Preferred examples of VEGF-targeted drugs include Bevacizumab (Avastin®), ramucirumab (Cyramza®) or ziv-aflibercept (Zaltrap®). Preferred examples of EGFR-targeted drugs include Cetuximab (Erbitux®), panitumumab (Vectibix®) or Regorafenib (Stivarga®).

Immunotherapeutic agents for combination with the complex as defined herein for treatment of colorectal cancer include vaccines, chimeric antigen receptors (CARs), checkpoint modulators and oncolytic virus therapies.

Preferred vaccines for combination with the complex as defined herein for treatment of colorectal cancer include TroVax, OncoVax, IMA910, ETBX-011, MicOryx, EP-2101, MKC1106-PP, CDX-1307, V934/V935, MelCancerVac, Imprime PGG, FANG, Tecemotide, AlloStim, DCVax, GI-6301, AVX701, OCV—CO2.

Artificial T cell receptors (also known as chimeric T cell receptors, chimeric immunoreceptors, chimeric antigen receptors (CARs)) are engineered receptors, which graft an arbitrary specificity onto an immune effector cell. Artificial T cell receptors (CARs) are preferred in the context of adoptive cell transfer. To this end, T cells are removed from a patient and modified so that they express receptors specific to colorectal cancer. The T cells, which can then recognize and kill the cancer cells, are reintroduced into the patient.

As used herein, the term "immune checkpoint modulator" (also referred to as "checkpoint modulator") refers to a molecule or to a compound that modulates (e.g., totally or partially reduces, inhibits, interferes with, activates, stimulates, increases, reinforces or supports) the function of one or more checkpoint molecules. Thus, an immune checkpoint modulator may be an "immune checkpoint inhibitor" (also referred to as "checkpoint inhibitor" or "inhibitor") or an "immune checkpoint activator" (also referred to as "checkpoint activator" or "activator"). An "immune checkpoint inhibitor" (also referred to as "checkpoint inhibitor" or "inhibitor") totally or partially reduces, inhibits, interferes with, or negatively modulates the function of one or more checkpoint molecules. An "immune checkpoint activator" (also referred to as "checkpoint activator" or "activator") totally or partially activates, stimulates, increases, reinforces, supports or positively modulates the function of one or more checkpoint molecules. Immune checkpoint modulators are typically able to modulate (i) self-tolerance and/or (ii) the amplitude and/or the duration of the immune response. Preferably, the immune checkpoint modulator used according to the present invention modulates the function of one or more human checkpoint molecules and is, thus, a "human checkpoint inhibitor".

Checkpoint molecules are molecules, such as proteins, are typically involved in immune pathways and, for example, regulate T-cell activation, T-cell proliferation and/or T-cell function. Accordingly, the function of checkpoint molecules, which is modulated (e.g., totally or partially reduced, inhibited, interfered with, activated, stimulated, increased, reinforced or supported) by checkpoint modulators, is typically the (regulation of) T-cell activation, T-cell proliferation and/or T cell function. Immune checkpoint molecules thus regulate and maintain self-tolerance and the duration and amplitude of physiological immune responses. Many of the immune checkpoint molecules belong to the B7:CD28 family or to the tumor necrosis factor receptor (TNFR) super family and, by the binding of specific ligands, activate signaling molecules that are recruited to the cytoplasmic domain (cf. Susumu Suzuki et al., 2016: Current status of immunotherapy. Japanese Journal of Clinical Oncology, 2016: doi: 10.1093/jjco/hyv201 [Epub ahead of print]; in particular Table 1).

Preferably, the immune checkpoint modulator for combination with the complex as defined herein for treatment of colorectal cancer is an activator or an inhibitor of one or more immune checkpoint point molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAMI, GARP, PS, CSF1R, CD94/NKG2A, TDO, GITR, TNFR and/or FasR/DcR3; or an activator or an inhibitor of one or more ligands thereof.

More preferably, the immune checkpoint modulator is an activator of a (co-)stimulatory checkpoint molecule or an inhibitor of an inhibitory checkpoint molecule or a combination thereof. Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAMI, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAMI, GARP, PS, CSF1R, CD94/NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the CTLA-4 pathway and/or of the PD-1 pathway. In particular, the immune checkpoint modulator is preferably a modulator of CD40, CTLA-4, PD-L1, PD-L2, PD-1 and/or IDO, more preferably the immune checkpoint modulator is an inhibitor of CTLA-4, PD-L1, PD-L2, PD-1 and/or IDO or an activator of CD40, even more preferably the immune checkpoint modulator is an inhibitor of CTLA-4, PD-L1, PD-1 and/or IDO and most preferably the immune checkpoint modulator is an inhibitor of CTLA-4 and/or PD-1.

Accordingly, the checkpoint modulator for combination with the complex as defined herein for treatment of colorectal cancer may be selected from known modulators of the CD40 pathway, the CTLA-4 pathway or the PD-1 pathway. Preferred inhibitors of the CTLA-4 pathway and of the PD-1 pathway include the monoclonal antibodies Yervoy© (Ipilimumab; Bristol Myers Squibb) and Tremelimumab (Pfizer/MedImmune) as well as Opdivo® (Nivolumab; Bristol Myers Squibb), Keytrudao (Pembrolizumab; Merck), Durvalumab (MedImmune/AstraZeneca), MEDI4736 (AstraZeneca; cf. WO 2011/066389 A1), MPDL3280A (Roche/Genentech; cf. U.S. Pat. No. 8,217,149 B2), Pidilizumab (CT-011; CureTech), MEDIo680 (AMP-514; AstraZeneca), MSB-0010718C (Merck), MIH1 (Affymetrix) and Lambrolizumab (e.g. disclosed as hPD109A and its humanized derivatives h409All, h409A16 and h409A17 in WO2008/156712; Hamid et al., 2013; N. Engl. J. Med. 369: 134-144). More preferred checkpoint inhibitors include the CTLA-4 inhibitors Yervoy© (Ipilimumab; Bristol Myers Squibb) and Tremelimumab (Pfizer/MedImmune) as well as the PD-1 inhibitors Opdivoo (Nivolumab; Bristol Myers Squibb), Keytruda© (Pembrolizumab; Merck), Pidilizumab (CT-011; CureTech), MEDIo680 (AMP-514; AstraZeneca), AMP-224 and Lambrolizumab (e.g. disclosed as hPD 109A and its humanized derivatives h409All, h409A16 and h409A17 in WO2008/156712; Hamid O. et al., 2013; N. Engl. J. Med. 369: 134-144).

It is also preferred that the immune checkpoint modulator for combination with the complex as defined herein for treatment of colorectal cancer is selected from the group consisting of Pembrolizumab, Ipilimumab, Nivolumab, MPDL3280A, MEDI4736, Tremelimumab, Avelumab, PDRooi, LAG525, INCB24360, Varlilumab, Urelumab, AMP-224 and CM-24.

Oncolytic viruses are engineered to cause cell lysis by replicating in tumors, thus activating an antitumor immune response. An oncolytic virus therapy for combination with the complex as defined herein for treatment of colorectal cancer is preferably selected from the group consisting of JX594 (Thymidine Kinase-Deactivated Vaccinia Virus), ColoAd1 (adenovirus), NV1020 (HSV-derived), ADXS 11-001 (attenuated Listeria vaccine), Reolysin® (special formulation of the human reovirus), PANVAC (recombinant vaccinia-virus CEA-MUC-I-TRICOM), Ad5-hGCC-PA-DRE (recombinant adenovirus vaccine) and vvDD-CDSR (vaccinia virus).

Preferably, (i) the complex and (ii) the chemotherapeutic agent, the targeted drug and/or the immunotherapeutic agent, such as an immune checkpoint modulator, are administered at about the same time.

"At about the same time", as used herein, means in particular simultaneous administration or that directly after administration of (i) the chemotherapeutic agent, the targeted drug and/or the immunotherapeutic agent, such as an immune checkpoint modulator, (ii) the complex is administered or directly after administration of (i) the complex (ii) the chemotherapeutic agent, the targeted drug and/or the immunotherapeutic agent, such as an immune checkpoint modulator, is administered. The skilled person understands that "directly after" includes the time necessary to prepare the second administration—in particular the time necessary for exposing and disinfecting the location for the second administration as well as appropriate preparation of the "administration device" (e.g., syringe, pump, etc.). Simultaneous administration also includes if the periods of administration of (i) the complex and of (ii) the chemotherapeutic agent, the targeted drug and/or the immunotherapeutic agent, such as an immune checkpoint modulator, overlap or if, for example, one component is administered over a longer period of time, such as 30 min, 1 h, 2 h or even more, e.g. by infusion, and the other component is administered at some time during such a long period. Administration of(i) the complex and of(ii) the chemotherapeutic agent, the targeted drug and/or the immunotherapeutic agent, such as an immune checkpoint modulator, at about the same time is in particular preferred if different routes of administration and/or different administration sites are used.

It is also preferred that (i) the complex and (ii) the chemotherapeutic agent, the targeted drug and/or the immunotherapeutic agent, such as an immune checkpoint modulator, are administered consecutively. This means that (i) the complex is administered before or after (ii) the chemotherapeutic agent, the targeted drug and/or the immunotherapeutic agent, such as an immune checkpoint modulator. In consecutive administration, the time between administration of the first component and administration of the second component is preferably no more than one week, more preferably no more than 3 days, even more preferably no more than 2 days and most preferably no more than 24 h. It is particularly preferred that (i) the complex and (ii) the chemotherapeutic agent, the targeted drug and/or the immunotherapeutic agent, such as an immune checkpoint modulator, are administered at the same day with the time between administration of the first component (the checkpoint modulator of the complex) and administration of the second component (the other of the checkpoint modulator and the complex) being preferably no more than 6 hours, more preferably no more than 3 hours, even more preferably no more than 2 hours and most preferably no more than 1 h. Preferably, (i) the complex and (ii) the chemotherapeutic agent, the targeted drug and/or the immunotherapeutic agent, such as an immune checkpoint modulator, are administered via the same route of administration. It is also preferred that (i) the complex and (ii) the chemotherapeutic agent, the targeted drug and/or the immunotherapeutic agent, such as an immune checkpoint modulator, are administered via distinct routes of administration.

Moreover, (i) the complex and (ii) the chemotherapeutic agent, the targeted drug and/or the immunotherapeutic agent, such as an immune checkpoint modulator, are preferably provided in distinct compositions. Alternatively, (i) the complex and (ii) the chemotherapeutic agent, the targeted drug and/or the immunotherapeutic agent, such as an immune checkpoint modulator, are preferably provided in the same composition.

Accordingly, the present invention provides a pharmaceutical formulation comprising a complex for use according to the invention or a cell for use according to the invention, in particular an antigen-presenting cell for use according to the invention, combined with at least one co-agent useful for treating and/or stabilizing a cancer and/or preventing colorectal cancer relapsing, and at least one pharmaceutically acceptable carrier.

Moreover, the complex for use according to the present invention; the cell, such as antigen-presenting cell, loaded with the complex for use according to the present invention; the inventive composition; the inventive pharmaceutical composition or the inventive vaccine can be administered after surgery where solid tumors have been removed as a prophylaxis against relapsing and/or metastases.

Moreover, the administration of the imaging or diagnosis composition in the methods and uses according to the invention can be carried out alone or in combination with a co-agent useful for imaging and/or diagnosing colorectal cancer.

Subjects

The present invention can be applied to any subject suffering from colorectal cancer or at risk to develop colorectal cancer. In particular, the therapeutic effect of said complex may be to elicit an immune response directed against said antigens or antigenic epitopes, in particular a response that is dependent on $CD4^+$ helper T cells and/or $CD8^+$ cytotoxic T cells and/or that is restricted by MIC class I molecules and/or MHC class II molecules.

It is also preferred that subjects according to the invention have been subjected to a surgical removal of a tumor.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

All references cited herein are herewith incorporated by reference.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

EXAMPLES

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: In Vitro Human Dendritic Cell Maturation

The goal of this study was to investigate the capacity of a complex for use according to the present invention to induce maturation of dendritic cells. In the present study, the complex for use according to the present invention is a fusion protein, comprising the cell-penetrating peptide "Z13", a protein "MAD5", which consists of different $CD8^+$ and $CD4^+$ epitopes from various antigens, and the TLR4 peptide agonist "EDA". Accordingly, a fused protein with the EDA peptide at the N-terminal position and different control conjugated proteins without Z13 or EDA or both were designed.

Namely, the following constructs were designed, whereby in the amino acid sequence the cell-penetrating peptide "Z1" is shown underlined and the TLR peptide agonist "EDA" is shown in italics:

```
EDAZ13Mad5
Sequence:
                                      [SEQ ID NO: 26]
MHHHHHHNID RPKGLAFTDV DVDSIKIAWE SPQGQVSRYR
```

```
-continued
VTYSSPEDGI RELFPAPDGEDDTAELQGLR PGSEYTVSVV

ALHDDMESQP LIGIQSTKRY KNRVASRKSR AKFKQLLQHY

REVAAAKSSE NDRLRLLLKE SLKISQAVHA AHAEINEAGR

EVVGVGALKV PRNQDWLGVP RFAKFASFEA QGALANIAVD

KANLDVEQLE SIINFEKLTE WTGS
```

Molecular weight: 25'057 Da
Characteristics:
Mad5 cargo contains OVACD4, gp100CD8, EalphaCD4 and OVACD8 epitopes
Contains EDA TLR agonist (Lasarte, J. J., et al., The extra domain A from fibronectin targets antigens to TLR4-expressing cells and induces cytotoxic T cell responses in vivo. J Immunol, 2007. 178(2): p. 748-56)
Storage buffer: 50 mM Tris-HCl, 150 mM NaCl, 10% Glycerol, 2 mM DTT, 1 M L-Arginine, pH 8
Endotoxin level: <0.01 EU/ug

```
Z13Mad5
Sequence:
                                    [SEQ ID NO: 29]
MHHHHHHKRY KNRVASRKSR AKFKQLLQHY REVAAAKSSE

NDRLRLLLKE SLKISQAVHA AHAEINEAGR EVVGVGALKV

PRNQDWLGVP RFAKFASFEA QGALANIAVD KANLDVEQLE

SIINFEKLTE WTGS
```

Molecular weight: 15'196 Da
Characteristics:
Mad5 cargo contains OVACD4, gp100CD8, EalphaCD4 and OVACD8 epitopes
Storage buffer: 50 mM Tris-HCl, 150 mM NaCl, 10% Glycerol, 2 mM DTT, 1 M L-Arginine, pH 9
Endotoxin level:
  Batch 1: 0.32 EU/mg
  Batch 2: 0.44 EU/mg

```
Mad5
Sequence:
                                    [SEQ ID NO: 30]
MHHHHHHE SLKISQAVHA AHAEINEAGR EVVGVGALKV

PRNQDWLGVP RFAKFASFEA QGALANIAVD KANLDVEQLE

SIINFEKLTE WTGS
```

Molecular weight: 10'154.6 Da
Characteristics:
Mad5 cargo contains OVACD4, gp100CD8, EalphaCD4 and OVACD8 epitopes
Storage buffer: 50 mM Tris-HCl, 150 mM NaCl, 10% Glycerol, 2 mM DTT, 0.5 M L-Arginine, pH 8
Endotoxin level: 0.069 EU/mg The EDAZ13Mad5, Z13Mad5 and Mad5 proteins were investigated for their capacity to induce human dendritic cell (DC) maturation. After incubation during 48 h with 300 nM of protein, activation markers expression (CD86, CD40, CD83 and HLA-DR) was assessed on the human DCs by FACS (FIGS. 1-4). Specific buffers of each protein were used as negative controls.

Figure 1:
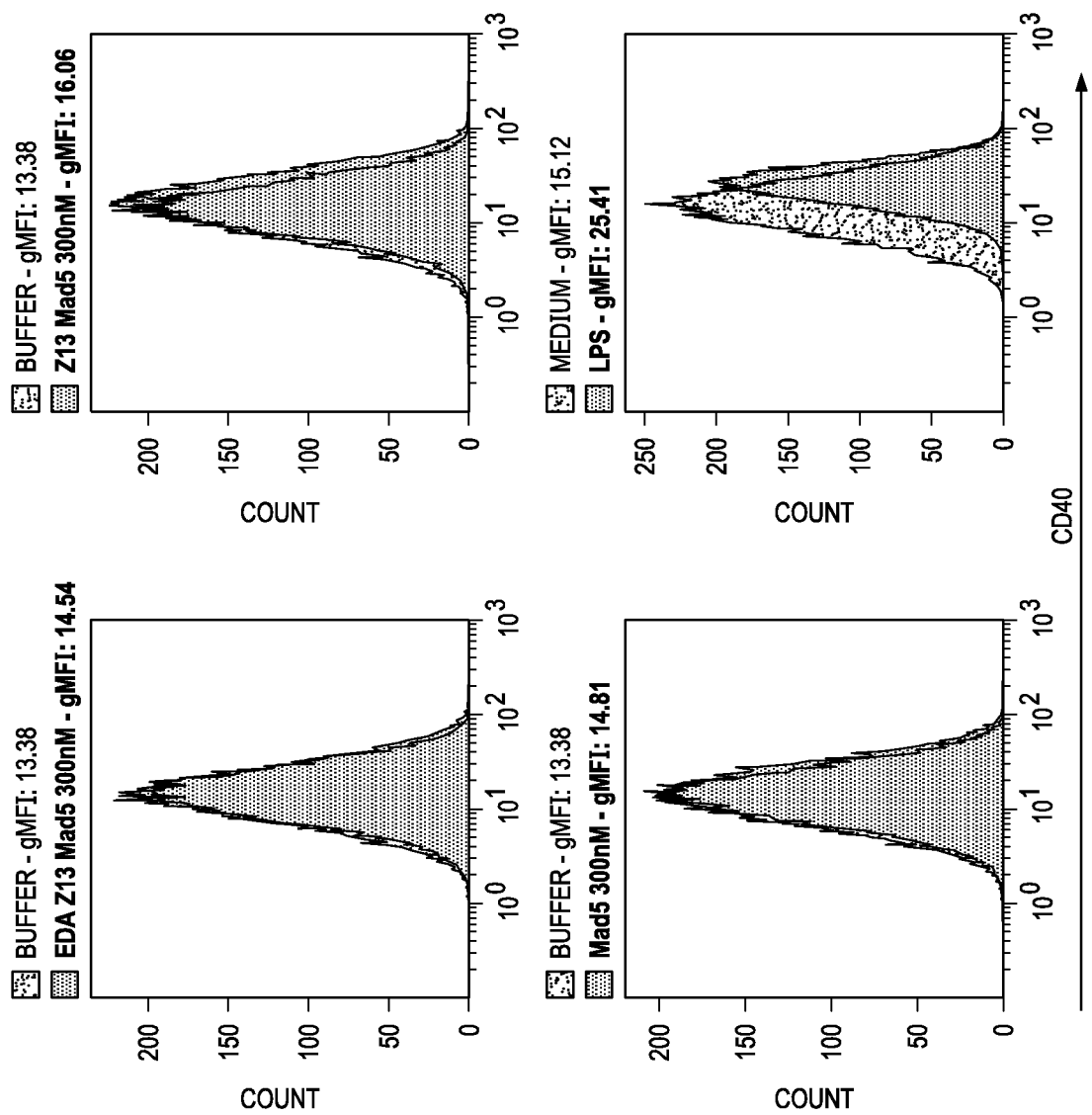
FIG. 1 shows for Example 1 expression of activation marker CD40 by human blood monocyte-derived dendritic cells (DCs) from one single buffy. The DCs were stimulated with 300 nM of EDAZ13Mad5, Z13Mad5, Mad5 or 25 ng/ml of LPS during 48 h. Isotype staining for each condition was also performed (isotype is not shown in the FIG. 1) (one experiment).
Figure 2:
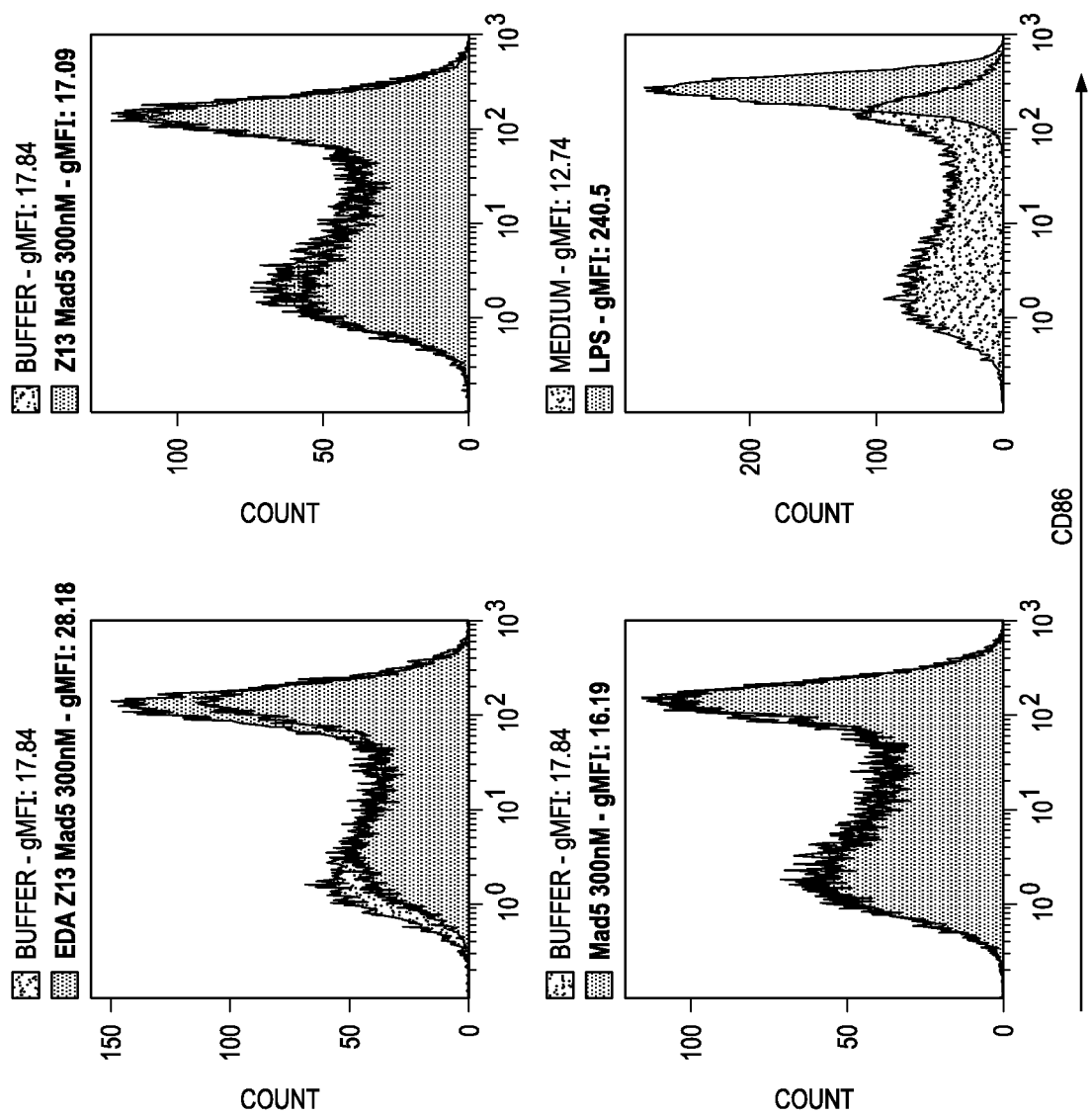
FIG. 2 shows for Example 1 expression of activation marker CD86 by human blood monocyte-derived dendritic cells (DCs) from one single buffy. The DCs were stimulated with 300 nM of EDAZ13Mad5, Z13Mad5, Mad5 or 25 ng/ml of LPS during 48 h. Isotype staining for each condition was also performed (isotype is not shown in the FIG. 2) (one experiment).
Figure 3:
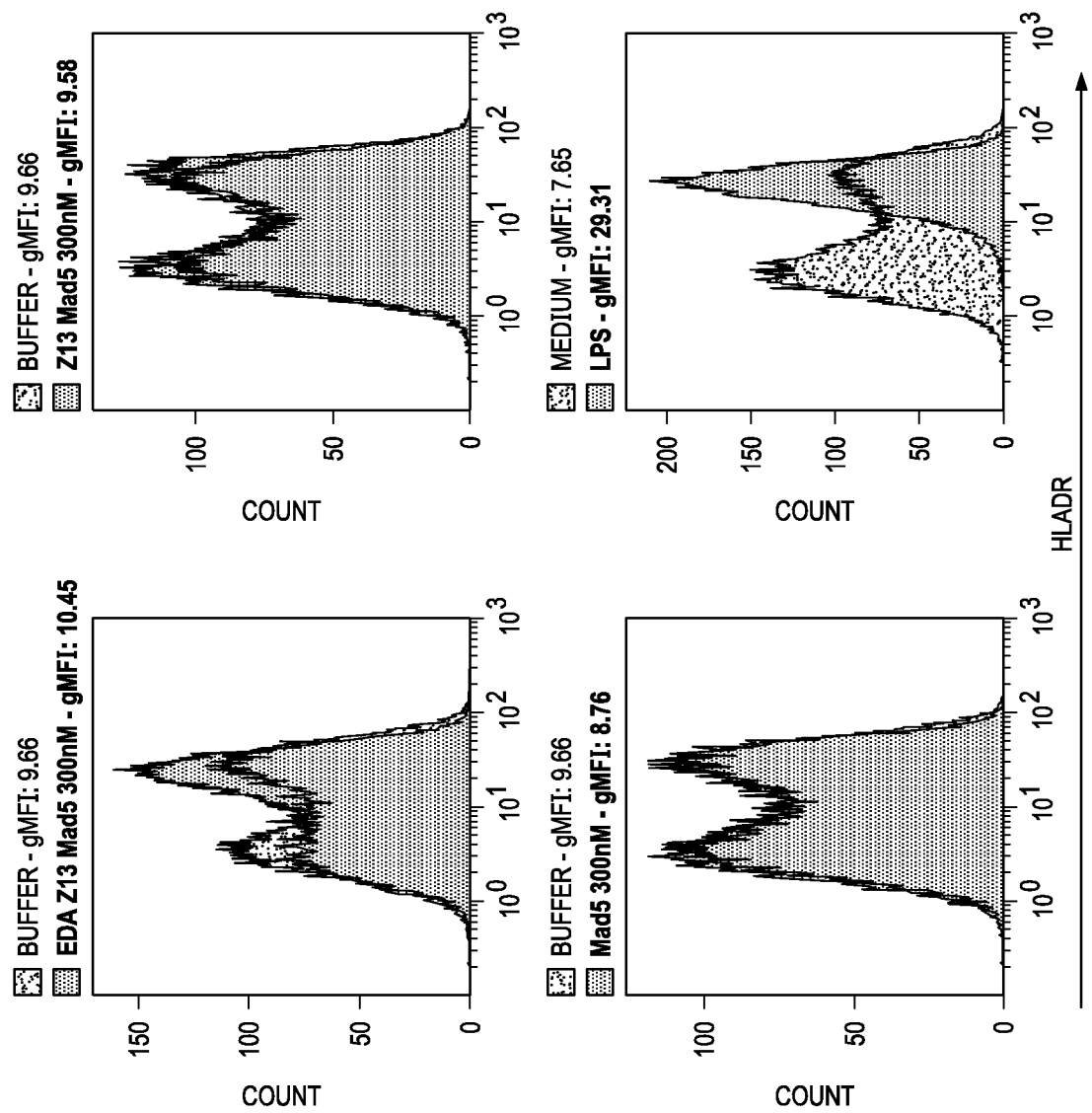
FIG. 3 shows for Example 1 expression of activation marker HLADR by human blood monocyte-derived dendritic cells (DCs) from one single buffy. The DCs were stimulated with 300 nM of EDAZ13Mad5, Z13Mad5, Mad5 or 25 ng/ml of LPS during 48 h. Isotype staining for each condition was also performed (isotype is not shown in the FIG. 3) (one experiment).
Figure 4:
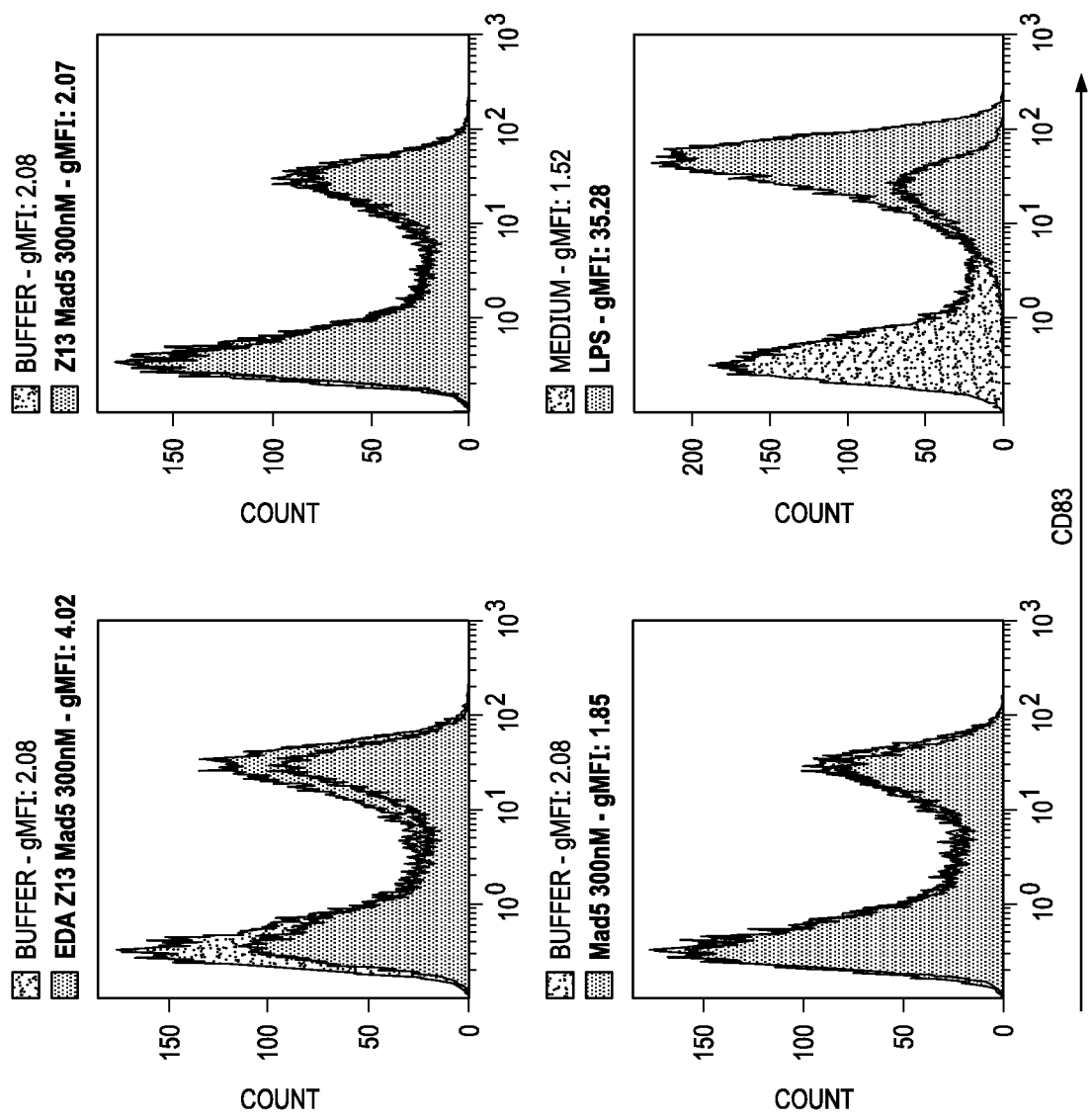
FIG. 4 shows for Example 1 expression of activation marker CD83 by human blood monocyte-derived dendritic cells (DCs) from one single buffy. The DCs were stimulated with 300 nM of EDAZ13Mad5, Z13Mad5, Mad5 or 25 ng/ml of LPS during 48 h. Isotype staining for each condition was also performed (isotype is not shown in the FIG. 4) (one experiment).

Results are shown for CD40 in FIG. 1, for CD86 in FIG. 2, for HLADR in FIG. 3, and for CD83 in FIG. 4. Whereas EDAZ13Mad5 induced maturation of human DCs, shown by the up-regulation of CD86, HLADR and CD83, Z13Mad5 and Mad5 proteins were not able to activate human DCs. These results indicate that the EDA portion of the protein is responsible for the up-regulation of the activation markers on the human DCs.

Example 2: In Vitro Epitope Presentation (MHC I)

The goal of this study was to assess functional MHC class I-restricted cross-presentation in a murine in an vitro system using bone marrow derived dendritic cells (BMDCs) and splenocytes from different TCR transgenic mice. To this end, the constructs EDAZ13Mad5 and Mad5 (described above in Example 1) and the construct EDAMad5 were used:

```
EDAMad5
Sequence
                                    [SEQ ID NO: 31]
MHHHHHHNID RPKGLAFTDV DVDSIKIAWE SPQGQVSRYR

VTYSSPEDGI RELFPAPDGEDDTAELQGLR PGSEYTVSVV

ALHDDMESQP LIGIQSTE SLKISQAVHA AHAEINEAGR

EVVGVGALKV PRNQDWLGVP RFAKFASFEA QGALANIAVD

KANLDVEQLE SIINFEKLTE WTGS
```

Molecular weight: 20'017 Da
Characteristics:
Mad5 cargo contains OVACD4, gp100CD8, EalphaCD4 and OVACD8 epitopes
Contains EDA TLR agonist
Storage buffer: 50 mM Tris-HCl, 150 mM NaCl, 10% Glycerol, 2 mM DTT, 0.5 M L-Arginine, pH 8
Endotoxin level: 1.8 EU/mg BMDCs were loaded overnight with 300 nM of with the EDAMad5, EDAZ13Mad5 and Mad5 proteins containing OVACD8, OVACD4 and gp100 epitopes. Processing and presentation of these MHC I-restricted OVACD8 and gp100 epitopes were monitored by measuring the in vitro proliferation of naïve $OVA_{257-264}$ specific CD8$^+$ T cells from OT-1 T cell receptor (TCR) transgenic mice and gp100-specific CD8$^+$ T cells from P-mel T cell TCR transgenic mice respectively. Accordingly, efficient MHC class I-restricted presentation of OVACD8 epitope and gp100 epitope was monitored after 4 days with CFSE-labeled OT1 cells and P-Mel cells respectively. Processing and presentation of MHC II-restricted OVACD4 epitope was monitored by measuring the in vitro proliferation of naïve $OVA_{323-339}$-specific CD4$^+$ T cells from OT-2 T cell receptor (TCR) transgenic mice. Accordingly, efficient MHC class II-restricted presentation of OVACD4 epitope was monitored after 4 days with CFSE-labeled OT2 cells. As control, BMDCs were pulsed for 1 h with SuM peptide (one experiment representative of 2 individual experiments).

Figure 5A:
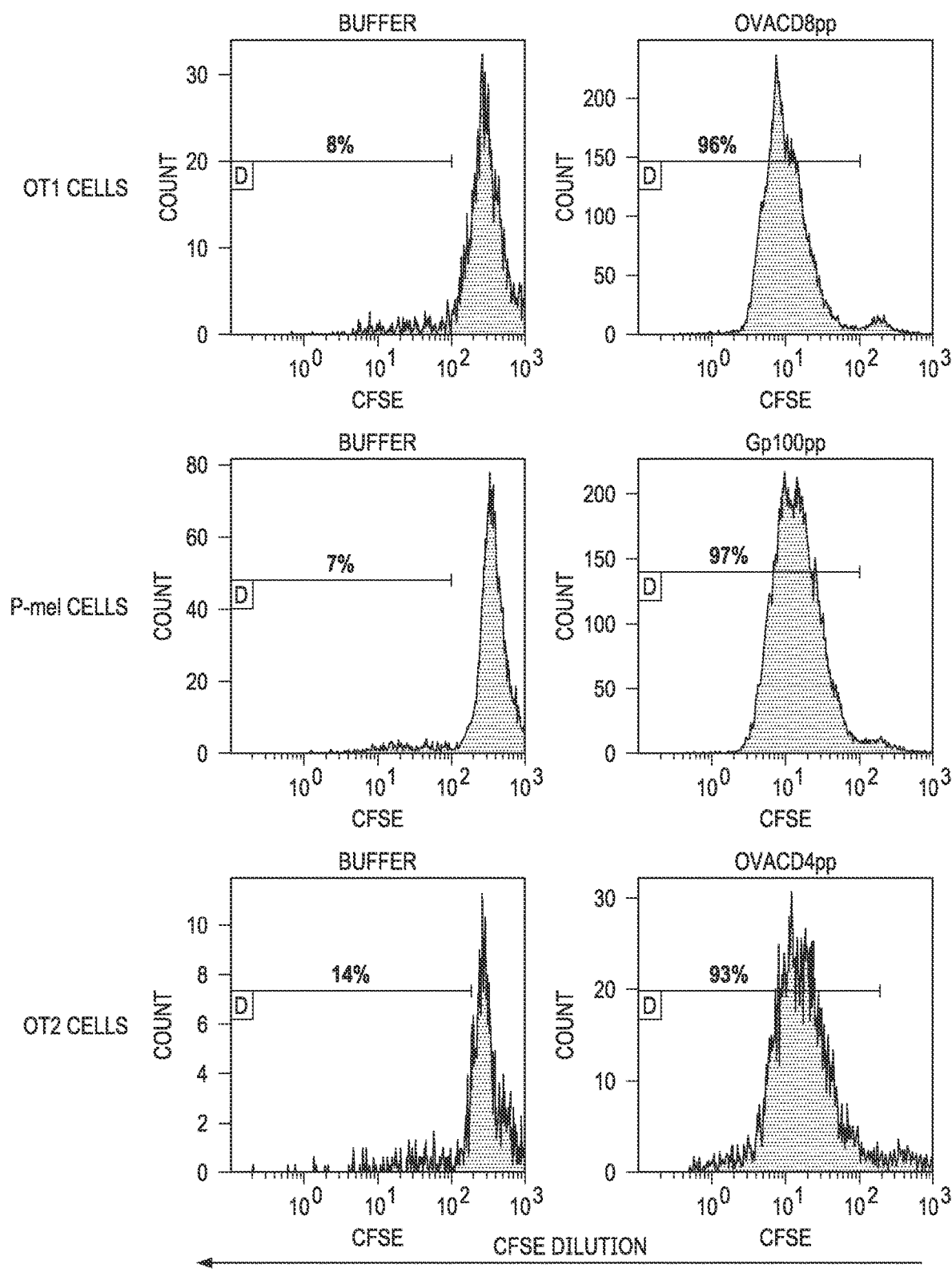
FIG. 5A-C shows for Example 2 functional MHC class I-restricted cross-presentation in a murine in an vitro system using bone marrow derived dendritic cells (BMDCs) and splenocytes from different TCR transgenic mice. To this end, BMDCs were loaded overnight with 300 nM of EDAZ13Mad5, EDAMad5 or Mad5. Efficient MHC class I-restricted presentation of OVACD8 epitope and gp100 epitope was monitored after 4 days with CFSE-labeled OT1 cells and P-Mel cells respectively. Efficient MHC class II-restricted presentation of OVACD4 epitope was monitored after 4 days with CFSE-labeled OT2 cells. As control, BMDCs were pulsed for ih with 5 µM peptide (one experiment representative of 2 individual experiments).
Figure 5B:
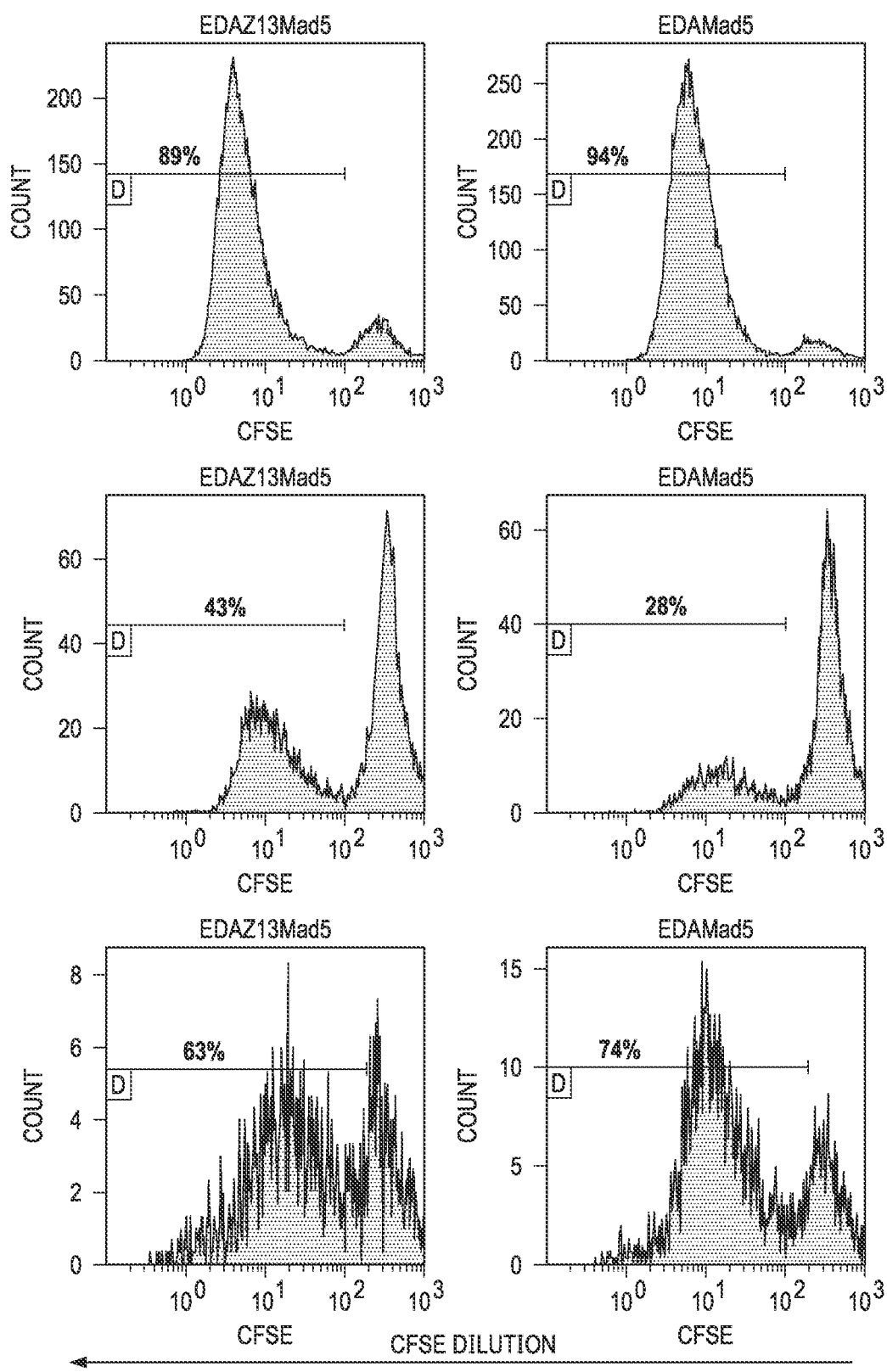
Figure 5C:
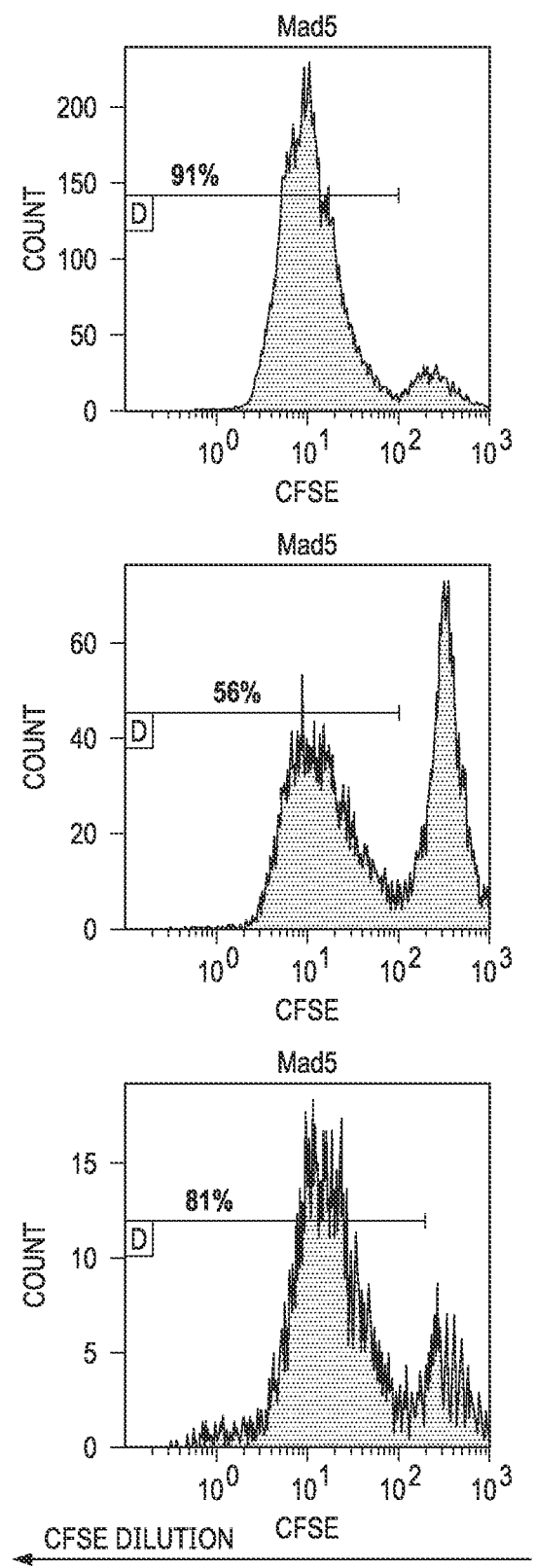

Results are shown in FIG. 5. Similar cross-presentation and processing capacity of all assessed Mad5-based proteins were observed.

Example 3: CD8 T Cell Immune Response

Figure 6A:
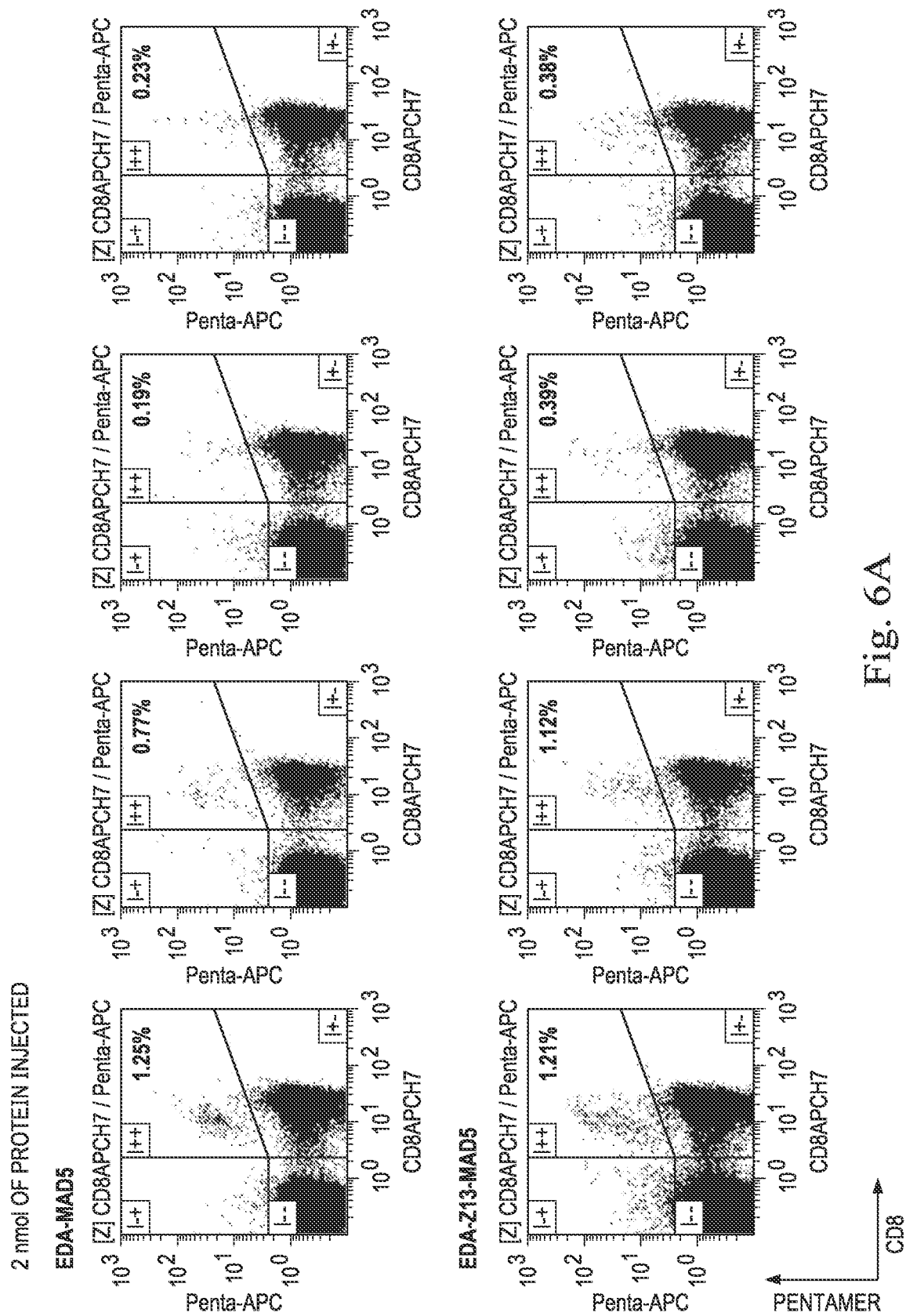
FIG. 6A-B shows the results for the 2 nmol groups for Example 3. C57BL/6 mice were vaccinated twice (Wk0 and Wk2) with 2 nmol of EDAMad5 or EDAZ13Mad5. Positive control group was vaccinated with Mad5 and MPLA (equimolar to EDA). Mice were bled 7 days after last vaccination and pentamer staining was performed (3-4 mice per group, one experiment).
Figure 6B:
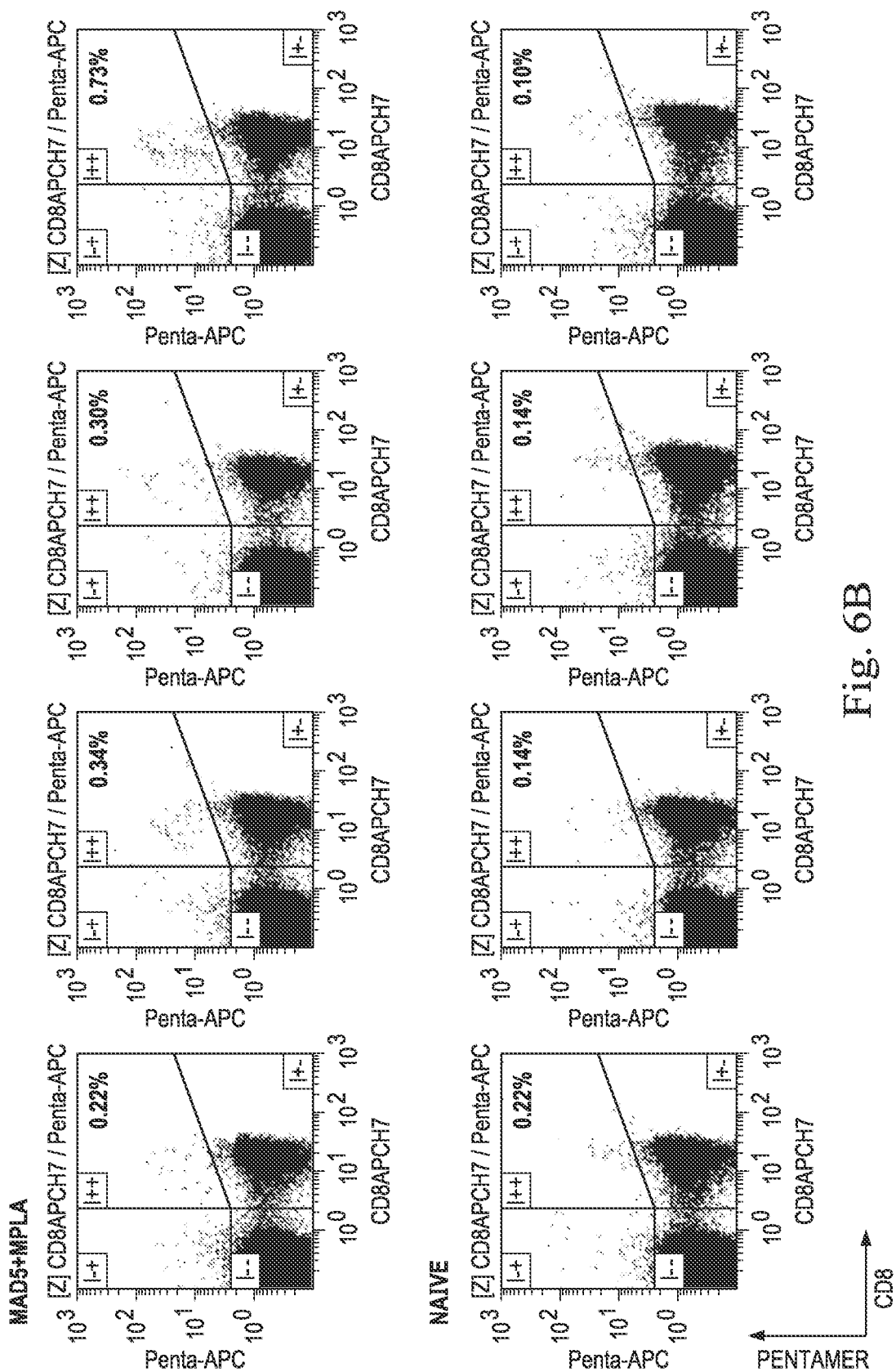
Figure 7A:
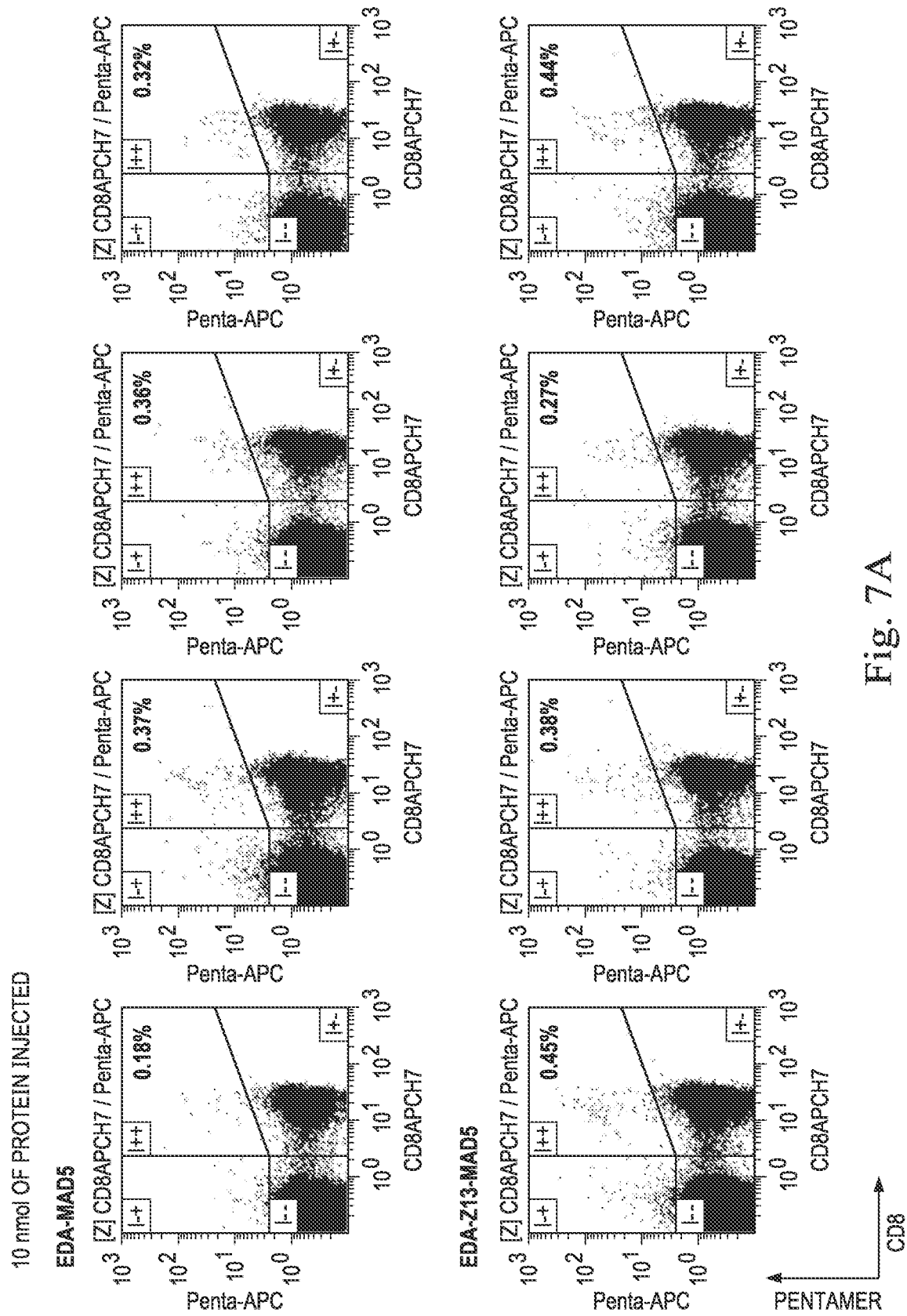
FIG. 7A-B shows the results for the 10 nmol groups for Example 3. C57BL/6 mice were vaccinated twice (Wk0 and Wk2) with 10 nmol of EDAMad5 or EDAZ13Mad5. Positive control group was vaccinated with Mad5 and MPLA (equimolar to EDA). Mice were bled 7 days after last vaccination and pentamer staining was performed (3-4 mice per group, one experiment).
Figure 7B:
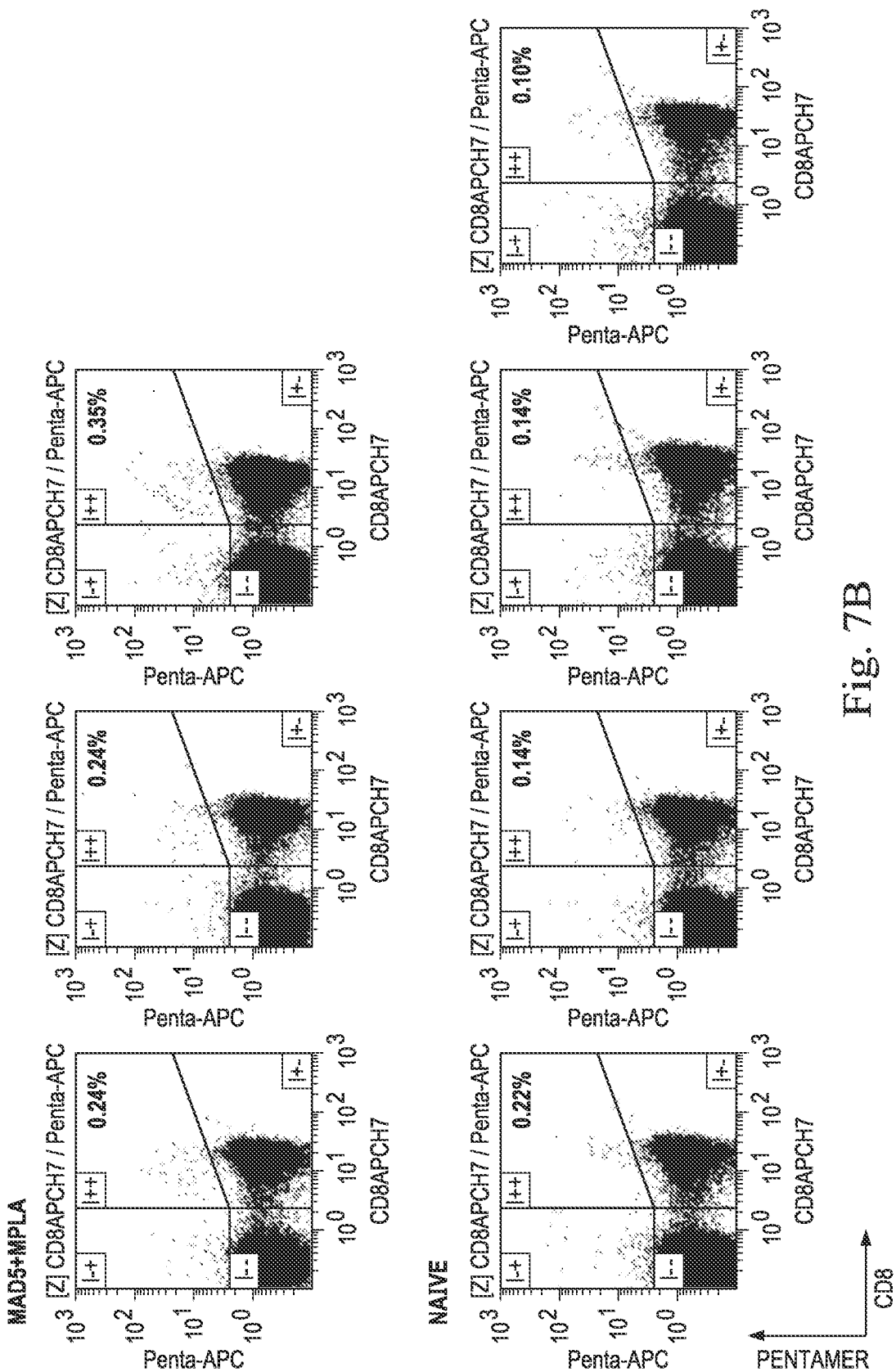

To investigate the efficacy of EDA-conjugated proteins in inducing polyclonal CD8$^+$ T cell response, C57BL/6 mice were vaccinated twice (Wk0 and Wk2), by subcutaneous injection of either 2 nmol or 10 nmol of the constructs EDAZ13Mad5 or EDAMad5 (described in Examples 1 and 2). Positive control group was vaccinated with Mad5 and the TLR4 agonist MPLA (equimolar to EDA). Two doses were assessed 2 nmol of the construct (FIG. 6) and 10 nmol of the construct (FIG. 7). 3-4 mice were used per group.

Figure 8:
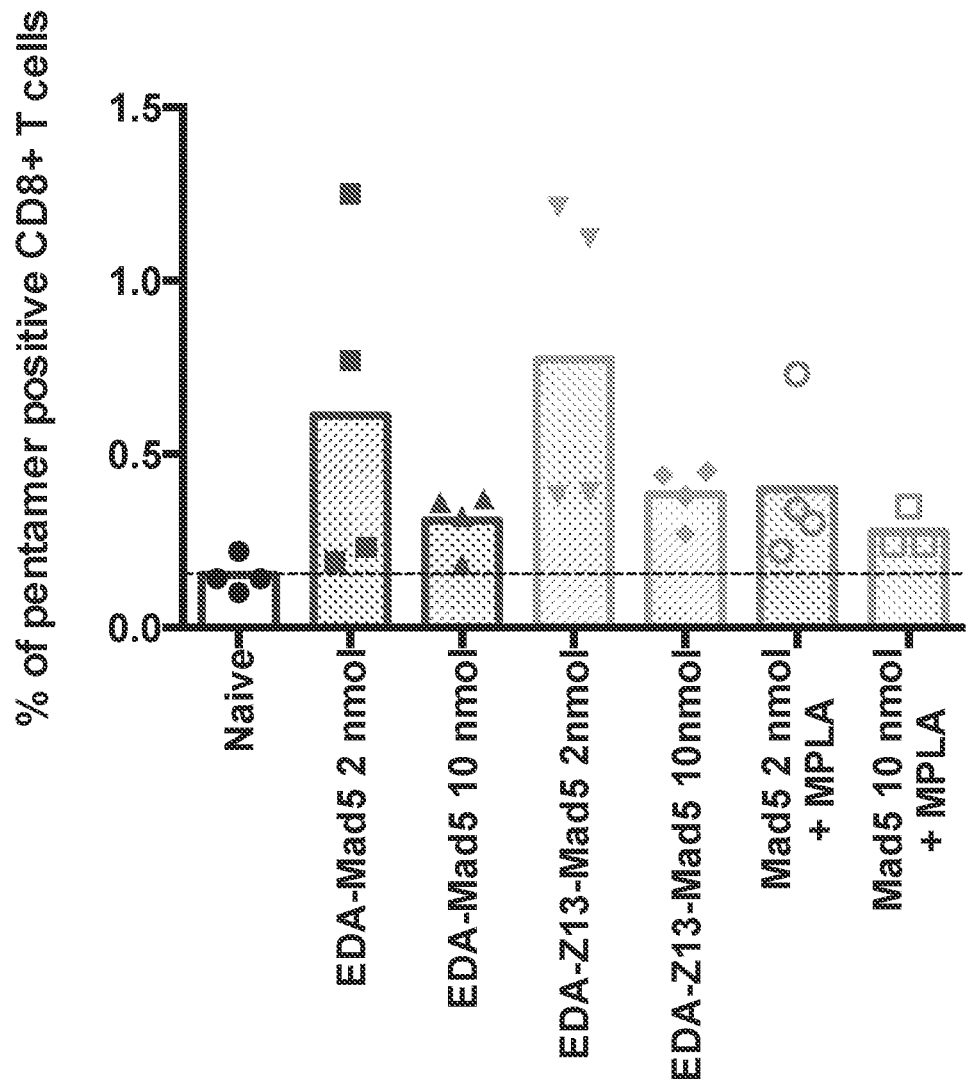
FIG. 8 shows for Example 3 the percentage of pentamer positive CD8$^+$T cells for all groups tested. C57BL/6 mice were vaccinated twice (Wk0 and Wk2) with 2 nmol or 10 nmol of EDAMad5 or EDAZ13Mad5. Positive control group was vaccinated with Mad5 and MPLA (equimolar to EDA). Mice were bled 7 days after last vaccination and pentamer staining was performed (one experiment with 3-4 mice per group).

Seven days after the last vaccination, mice were bled and pentamer staining was performed to monitor the OVA-specific immune response in the blood. In FIG. 8, the percentage of pentamer positive CD8+ T cells is shown for all groups and both doses tested.

These data show that interestingly the immune response is lower at 10 nmol compared to 2 nmol. At both doses, 2 nmol and 10 nmol, the vaccine mediated immune response was observed more consistently in the EDAZ13Mad5 group in contrast to the EDAMad5 group. Moreover, there is an increased immune response when the TLR4 agonist is conjugated with the vaccine.

Example 4: Vaccine Efficacy on Tumor Growth in a Benchmark EG.7-OVA Tumor Model

To evaluate the effect of EDA construct proteins on tumor growth control, the s.c. model of EG.7-OVA thymoma cells was chosen. C57BL/6 mice were implanted s.c. with $3 \times 10^5$ EG7-OVA tumor cells in the left flank. After tumor implantation, mice were vaccinated at day 5 and 13 with 10 nmol of one of the following constructs (cf. Examples 1 and 2 for construct description): EDAZ13Mad5, EDAMad5, Mad5, or Mad5 and MPLA (equimolar to EDA) s.c. in the right flank. Tumor size was measured with a caliper.

Figure 9:
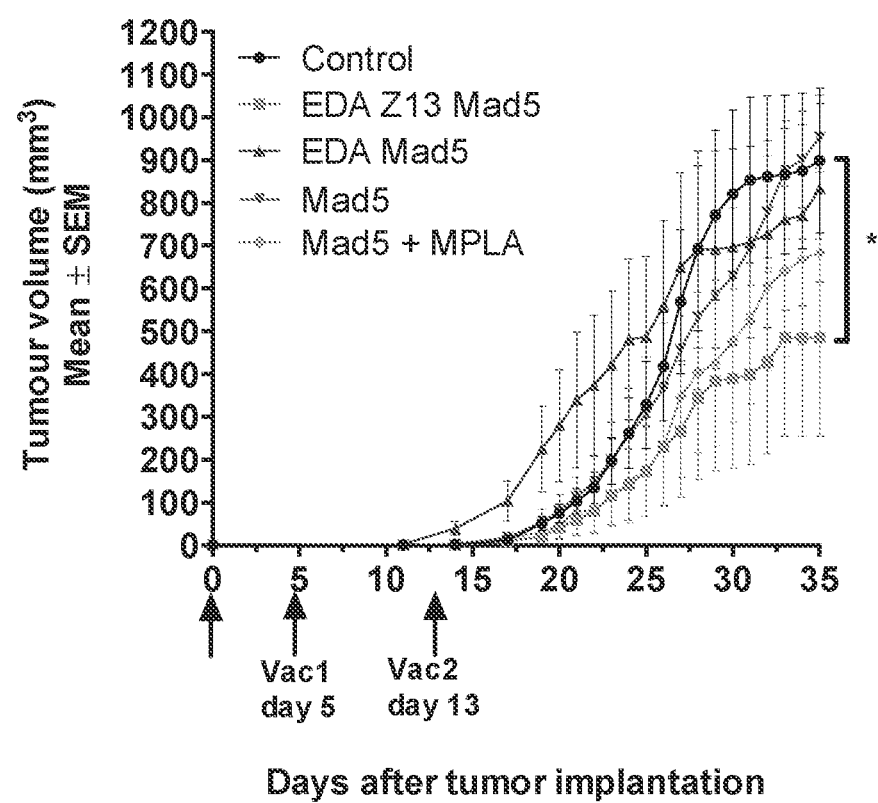
FIG. 9 shows for Example 4 the tumor growth of 7 mice per group (mean±SEM); *, $p<0.05$ EDAZ13Mad5 versus control group (2-way Anova test). C57BL/6 mice were implanted s.c. with $3\times10^5$ EG7-OVA tumor cells in the left flank and vaccinated twice (d5 and d13) by subcutaneous injection of 10 nmol of EDAZ13Mad5, EDAMad5, Mad5 or Mad5 and MPLA (equimolar to EDA) s.c. in the right flank. Tumor size was measured with a caliper.
Figure 10:
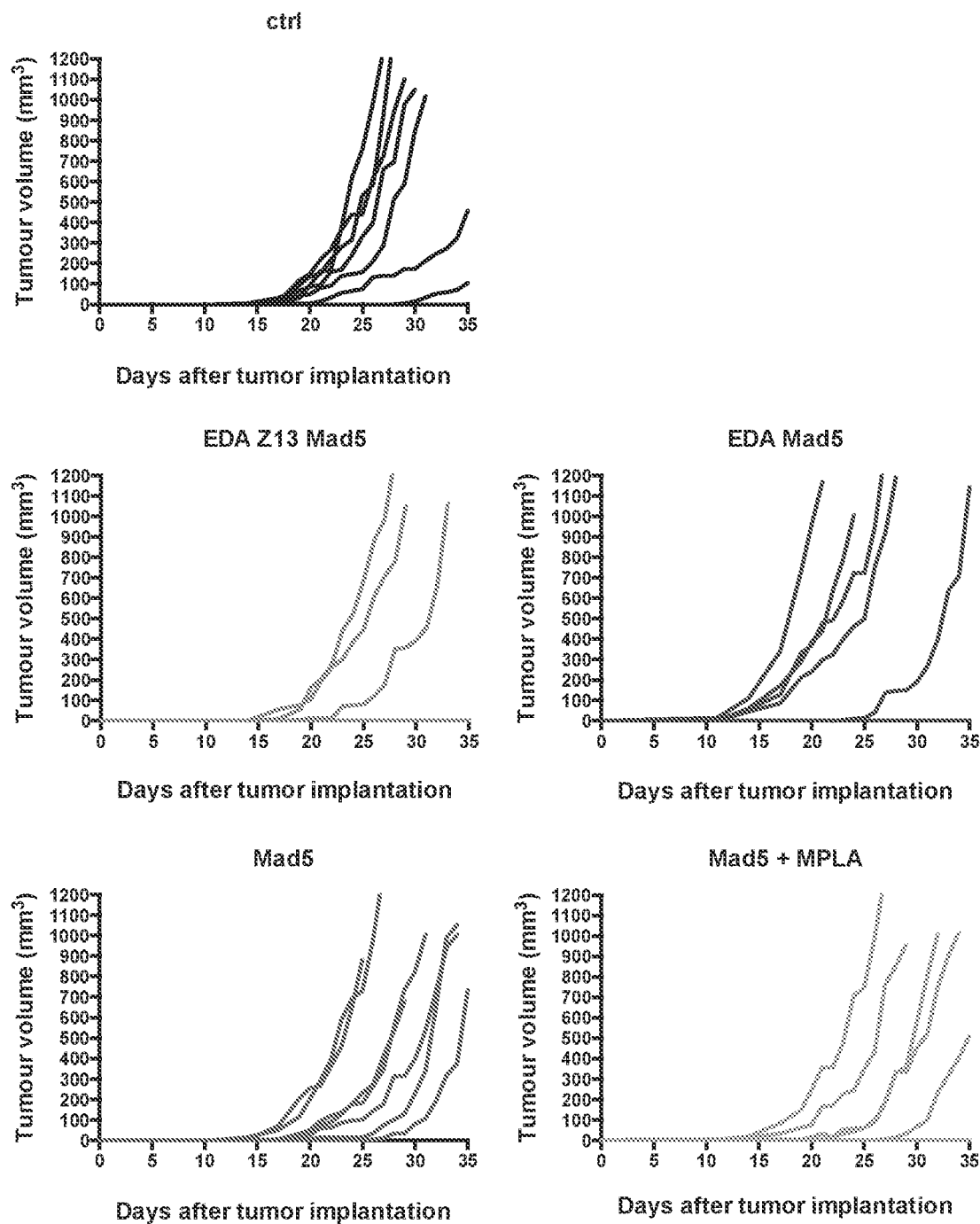
FIG. 10 shows for Example 4 individual tumor growth curves (7 individual mice per group). C57BL/6 mice were implanted s.c. with 3×10 EG7-OVA tumor cells in the left flank and vaccinated twice (d5 and d13) by subcutaneous injection of 10 nmol of EDAZ13Mad5, EDAMad5, Mad5 or Mad5 and MPLA (equimolar to EDA) s.c. in the right flank. Tumor size was measured with a caliper.
Figure 11A:
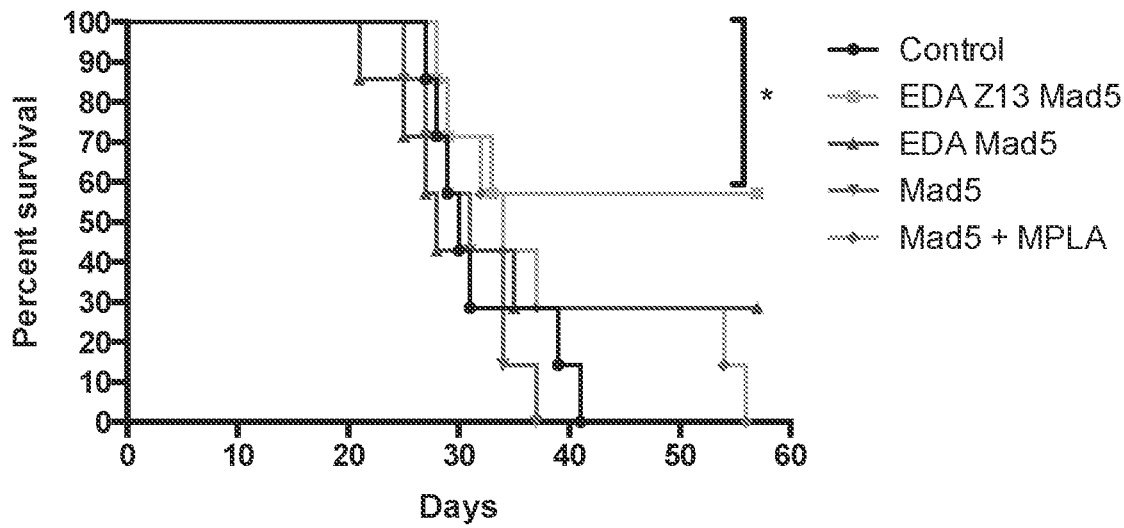
FIG. 11A-B shows for Example 4 (A) the survival curve of 7 mice per group; *, $p<0.05$ EDAZ13Mad5 versus control group (Log-rank test) and (B) the tumor-free progression curve of 7 mice per group; *, $p<0.05$ EDAZ13Mad5 versus control group (Log-rank test).
Figure 11B:
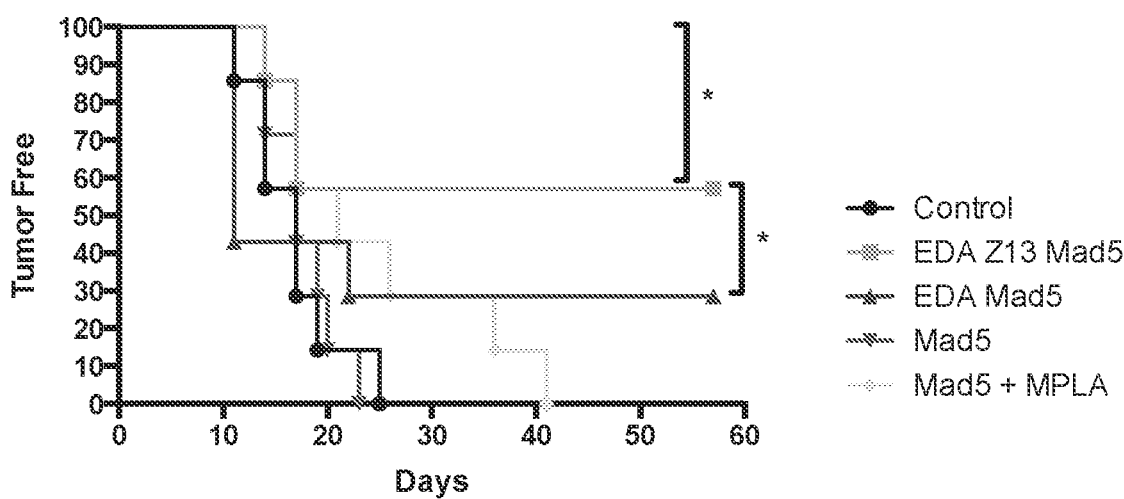

FIG. 9 shows the tumor growth of 7 mice per group (mean±SEM); *, p<0.05 EDAZ13Mad5 versus control group (2-way Anova test). FIG. 10 shows individual tumor growth curves (7 individual mice per group). FIG. 11 A shows the survival curve of 7 mice per group; *, p<0.05 EDAZ13Mad5 versus control group (Log-rank test). FIG. 11 B shows the tumor-free progression curve of 7 mice per group; *, p<0.05 EDAZ13Mad5 versus control group (Log-rank test).

The results show that in a therapeutic setting, EDAZ13Mad5 was the only protein vaccine to significantly control the tumor growth compared to the control group with a significant better tumor free progression curve and survival curve.

The results therefore suggest that the construct protein EDAZ13Mad5 is a highly potent vaccine for controlling the tumor growth in a therapeutic setting.

Example 5: Vaccine Efficacy on Tumor Growth in a Melanoma Metastasis Model

Figure 12:
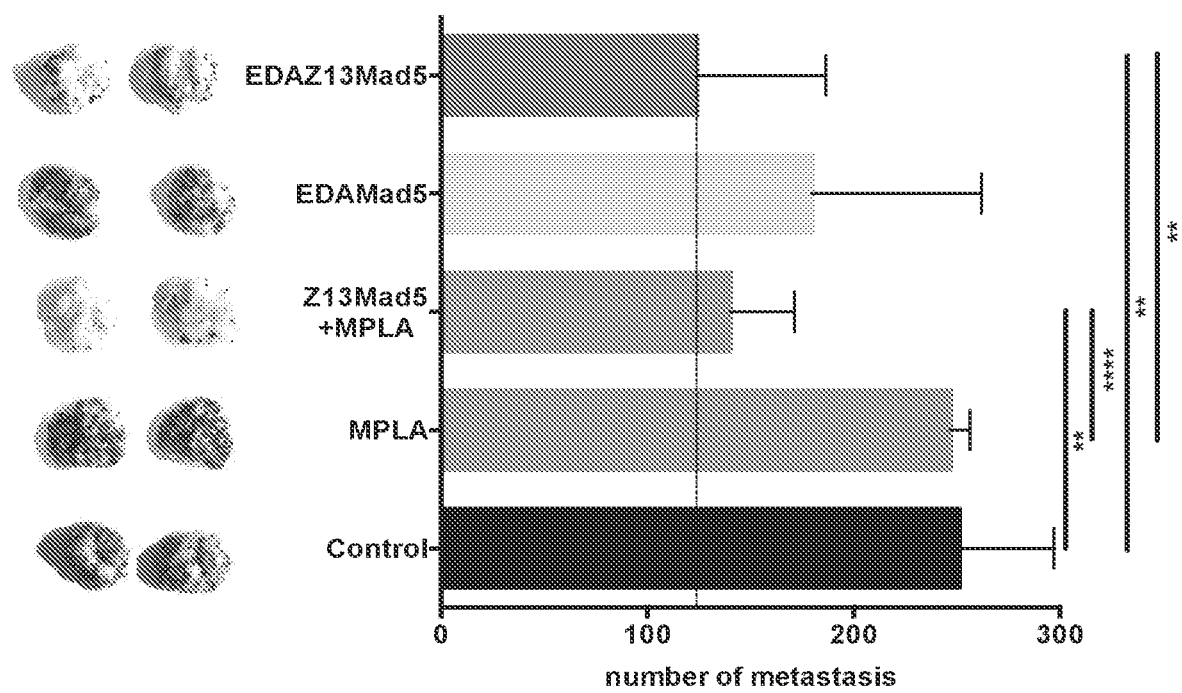
FIG. 12 shows for Example 5 the number of metastasis for every experimental group. C57BL/6 mice were implanted i.v. with $1\times10^5$ B16-OVA melanoma tumor cells and vaccinated twice (do and d9) by subcutaneous injection of 2 nmol of EDAZ13Mad5, EDAMad5 or Z13Mad5+MPLA (equimolar to EDA) or MPLA alone s.c. in the right flank. Mice were euthanized at day i3 and lung recovered. Number of metastasis foci was counted for each lung. *, $p<0.01$; ***, $p<0.0001$ (Unpaired T test).

To assess the efficacy in a lung metastasis model using B16-OVA tumor cells in a semi-therapeutic setting, different construct proteins were used: EDAMad5, EDAZ13Mad5, Z13Mad5+MPLA (cf. Examples 1 and 2 for design of the constructs), and MPLA alone. C57BL/6 mice were implanted i.v. with $1 \times 10^5$ B16-OVA melanoma tumor cells and at the same time (d0) 2 nmol of the vaccine (EDAMad5, EDAZ13Mad5, Z13Mad5+MPLA, MPLA alone) was administered by subcutaneous injection in the right flank. Nine days later, mice were vaccinated a second time with the same dose. Further control groups were vaccinated with 2 nmol of Z13Mad5 and the TLR4 agonist MPLA (equimolar to EDA) or MPLA alone. Mice were euthanized at day 13 and lung recovered. Number of metastasis foci was counted for each lung. The results are shown in FIG. 12.

The results show that the conjugate EDAZ13Mad5 is as potent as Z13Mad5+MPLA to inhibit tumor metastasis in the lung. Furthermore, EDA-Mad5 is less potent than EDAZ13Mad5, indicating a crucial role of Z13 in vaccine efficacy.

Figure 13:
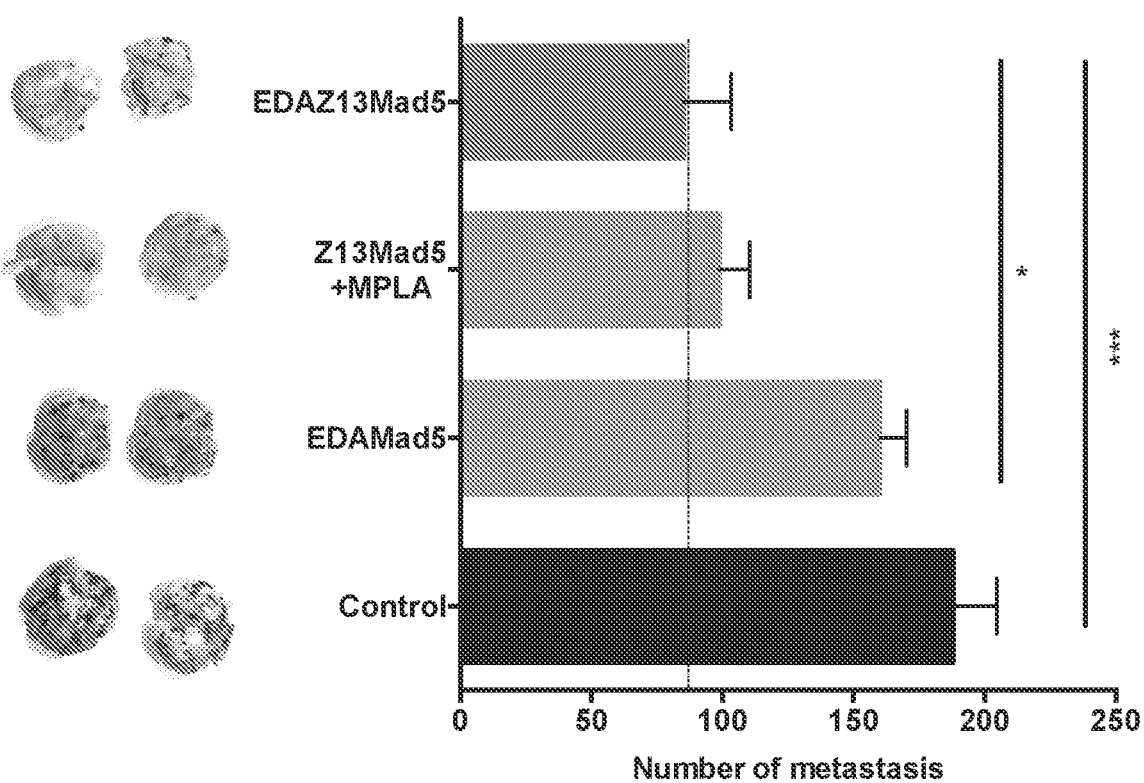
FIG. 13 shows for Example 6 the number of metastasis for every experimental group. C57BL/6 mice were vaccinated twice (d-21 and d-7) by subcutaneous injection of 2 nmoles of EDAZ13Mad5, EDAMad5 or Z13Mad5+MPLA (equimolar to EDA) s.c. in the right flank. At day 0, mice were implanted i.v. with $1\times10^5$ B16-OVA melanoma tumor cells. Mice were euthanized at day 14 and lung recovered. Number of metastasis foci was counted for each lung. *, $p<0.05$. ***, $p<0.001$ (Unpaired T test).

Example 6: Vaccine Efficacy on Tumor Growth in a Melanoma Metastasis Model—Prophylactic Setting Furthermore, the efficacy of the different construct proteins EDAMad5, EDAZ13Mad5, and Z13Mad5+MPLA (cf. Examples 1 and 2 for design of the constructs) was assessed in a lung metastasis model in a prophylactic setting. C57BL/6 mice were vaccinated 21 and 7 days before implantation of tumor cells (d-21 and d-7) by subcutaneous injection of 2 nmol of EDAZ13Mad5, EDAMad5 or Z13Mad5+ MPLA (equimolar to EDA) s.c. in the right flank. At day 0, mice were implanted i.v. with $1 \times 10^5$ B16-OVA melanoma tumor cells. Mice were euthanized at day 14 and lung recovered. Results are shown in FIG. 13.

Example 7: Design of Further Constructs Comprising a TLR2 Peptide Agonist

Herein, the complex for use according to the present invention is again a fusion protein, comprising the cell-penetrating peptide "Z13", the protein "MAD5", which consists of different CD8+ and CD4+ epitopes from various antigens, and the TLR2 peptide agonist "Anaxa". Accordingly, fused proteins with the Anaxa peptide at the C-terminal or N-terminal position were designed.

Namely, the following constructs were designed, whereby in the amino acid sequence the cell-penetrating peptide "Z13" is shown underlined and the TLR peptide agonist "Anaxa" is shown in italics:

```
AnaxaZ13Mad5
Sequence:
                                     [SEQ ID NO: 27]
MHHHHHHSTV HEILCKLSLE GDHSTPPSAY GSVKPYTNFD

AEKRYKNRVA SRKSRAKFKQ LLQHYREVAA AKSSENDRLR

LLLKESLKIS QAVHAAHAEI NEAGREVVGV GALKVPRNQD

WLGVPRFAKF ASFEAQGALA NIAVDKANLD VEQLESIINF

EKLTEWTGS
```

Molecular weight: 18973 Da
  Characteristics:
  Mad5 cargo contains OVACD4, gp100CD8, EalphaCD4 and OVACD8 epitopes
  Contains the 35-mer peptide of Annexin
  Storage buffer: 50 mM Tris-HCl, 150 mM NaCl, 10% Glycerol, 2 mM DTT, 0.5 M L-Arginine, pH 8
  Endotoxin level: 5.17 EU/mg

```
Z13Mad5Anaxa
Sequence:
                                     [SEQ ID NO: 28]
MHHHHHHKRYKNRVA SRKSRAKFKQ LLQHYREVAA

AKSSENDRLR LLLKESLKIS QAVHAAHAEI NEAGREVVGV

GALKVPRNQD WLGVPRFAKF ASFEAQGALA NIAVDKANLD

VEQLESIINF EKLTEWTGSS TVHEILCKLS LEGDHSTPPS

AYGSVKPYTN FDAE
```

Molecular weight: 18973 Da
 Characteristics:
  Mad5 cargo contains OVACD4, gp100CD8, EalphaCD4 and OVACD8 epitopes
  Contains the 35-mer peptide of Annexin
  Storage buffer: 50 mM Tris-HCl, 150 mM NaCl, 10% Glycerol, 2 mM DTT, 0.5 M L-Arginine, pH 8
Endotoxin level: 3.1 EU/mg

Example 8: TLR2 Binding (HEK-hTLR2 Cell Lines)

The goal of this study was to assess whether the Z13Mad5Anaxa and AnaxaZ13Mad5 construct proteins (cf. Example 7 for design of these construct proteins) were able to bind TLR2 as an agonist. HEK-Blue™ hTLR2 were seeded in flat 96-well plate in culture medium, stimulated with 0.3 µM, 1 µM or 3 µM of AnaxaZ13Mad5 or Z13Mad5Anaxa and incubated at 37° C. for 24 h. Positive control was performed with 500 ng/ml of PamsCSK4, a TLR2 agonist.

Figure 14A:
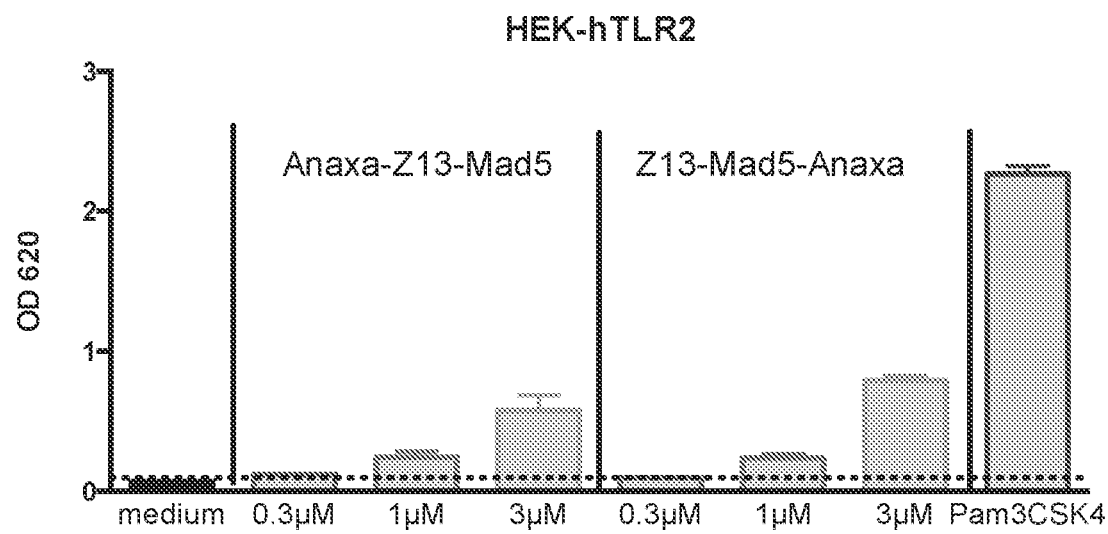
FIG. 14A-B shows the results for Example 8. HEK-hTLR2 cell lines were seeded in flat 96-well plate in culture medium, stimulated with 0.3 μM, 1 μM or 3 μM of AnaxaZ13Mad5 or Z13Mad5Anaxa and incubated at 37° C. for 24 h. Positive control was performed with 500 ng/ml of PamsCSK4. (A) Twenty microliters of supernatant were added to QuantiBlue® detection medium and incubated at 37° C. for 1 h before OD reading (620 nm). (B) Quantification of IL-8 secretion (by ELISA) in the supernatant.
Figure 14B:
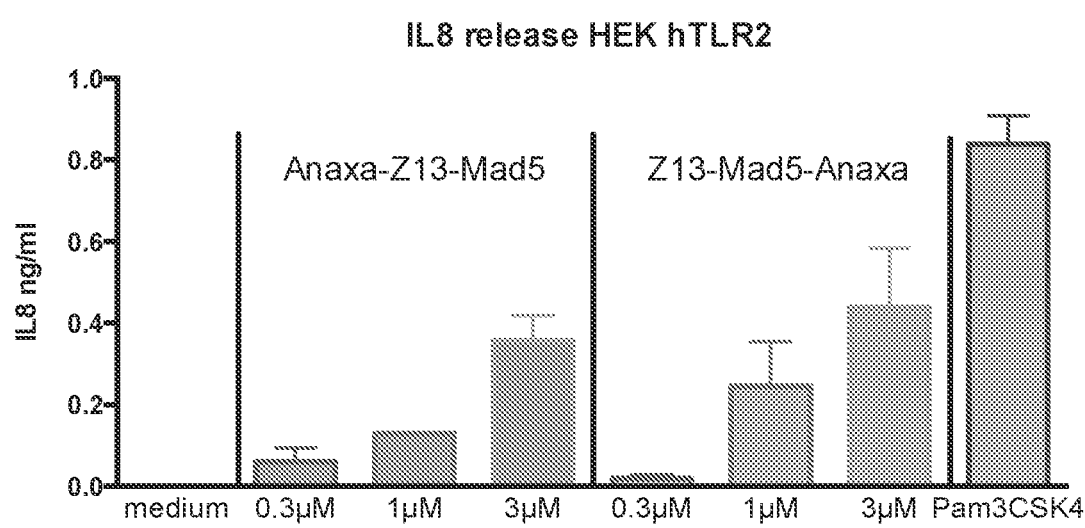

To monitor the activation of NF-κB/API, twenty microliters of the supernatant were added to QuantiBlue® detection medium and incubated at 37° C. for 1 h before OD reading (620 nm). Results are shown in FIG. 14 A.

The secretion of IL-8 in the supernatant was quantified by ELISA. Results are shown in FIG. 14 B.

Results (FIG. 14 A, B) showed that Z13Mad5Anaxa and AnaxaZ13Mad5 are similarly able to bind to TLR2 in a dose dependent manner.

Example 9: In Vivo Induction of Specific CD8+ T Cells

Figure 15:
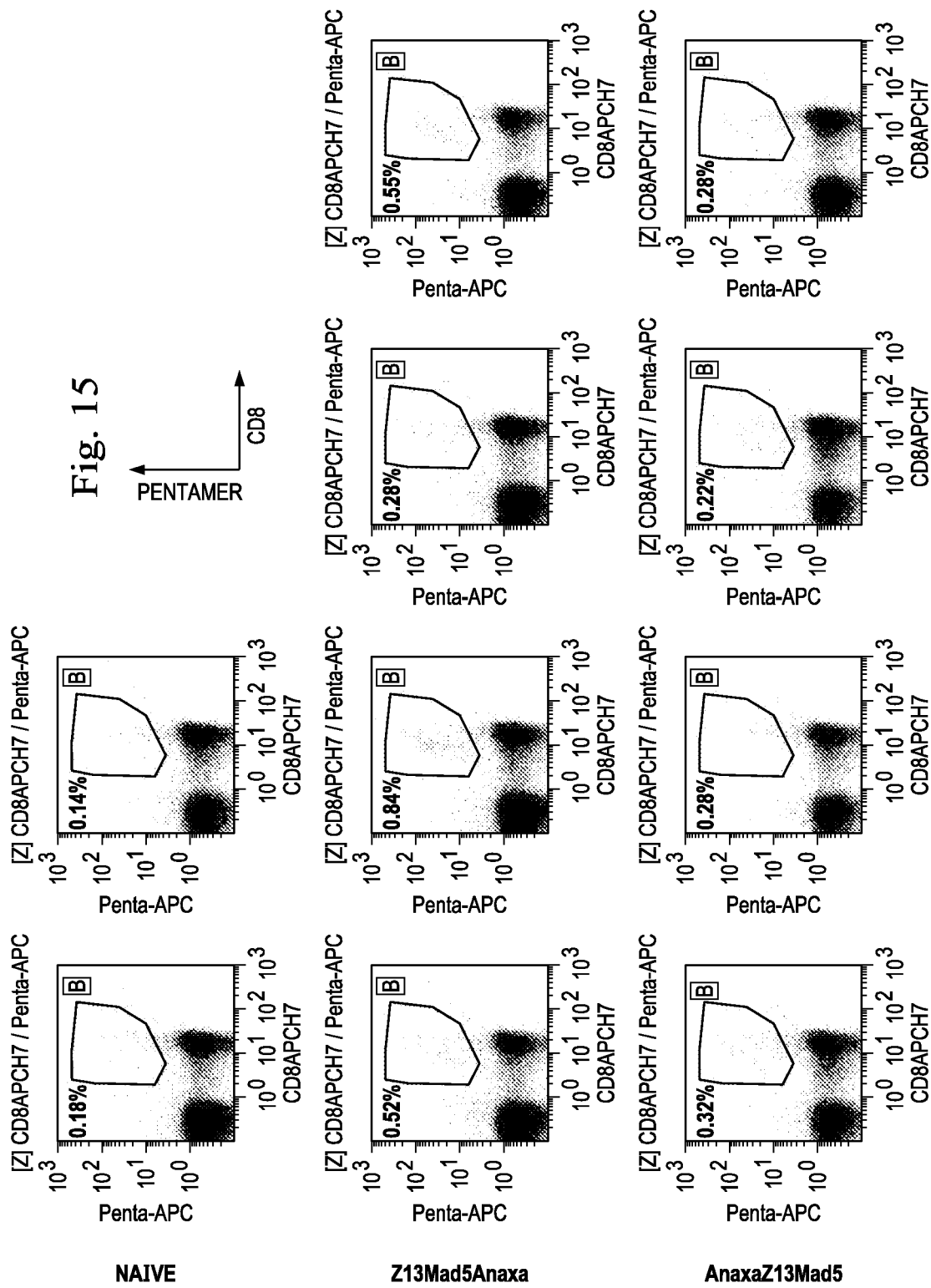
FIG. 15 shows the results for Example 9. C57BL/6 mice were vaccinated twice (Wk0 and Wk2) with 2 nmoles of Z13Mad5Anaxa or AnaxaZ13Mad5. Mice were bled 7 days after last vaccination and pentamer staining was performed (one experiment).
Figure 16:
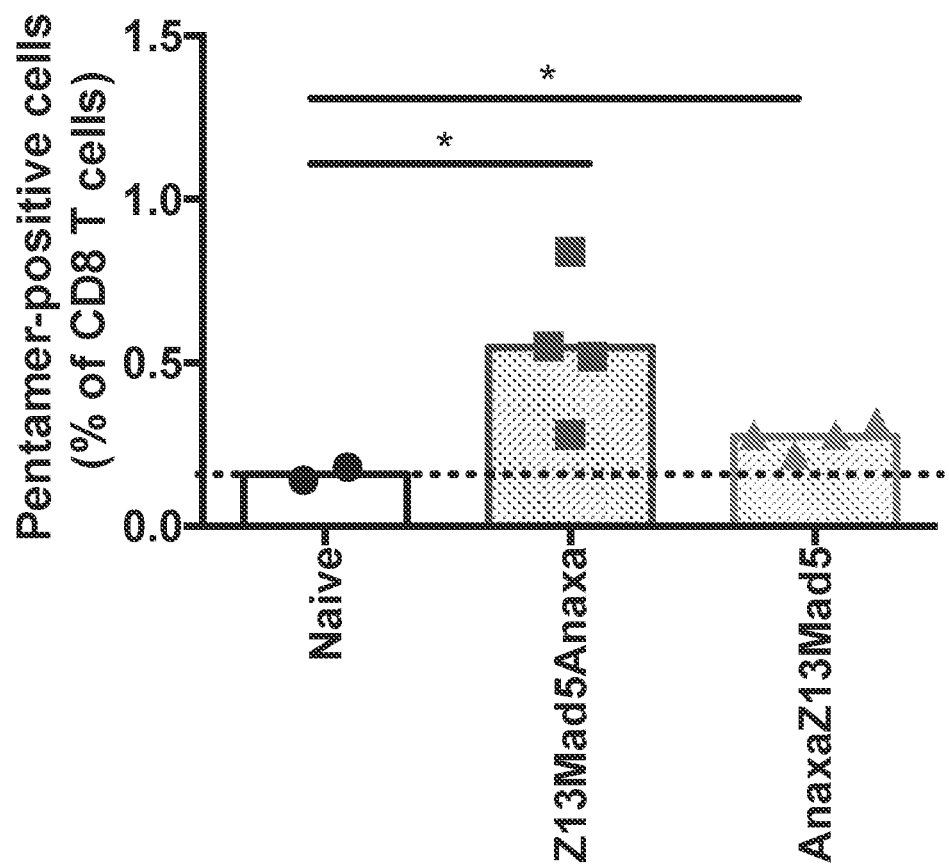
FIG. 16 shows the results for Example 9. C57BL/6 mice were vaccinated twice (Wk0 and Wk2) with 2 nmoles Z13Mad5Anaxa or AnaxaZ13Mad5. Mice were bled 7 days after last vaccination and pentamer staining was performed (one experiment with 4 mice per group). *, $p<0.05$.

To investigate the efficacy of the Anaxa-conjugated proteins of Example 7 in the induction of CD8+ T cell responses, C57BL/6 mice were vaccinated twice (Wk0 and Wk2), by subcutaneous injection of 2 nmol of AnaxaZ13Mad5 or 2 nmol of Z13Mad5Anaxa. Seven days after the last vaccination, mice were bled and to monitor the OVA-specific immune response in the blood, pentamer staining was performed (one experiment with 4 mice per group). Results are shown in FIGS. 15 and 16.

These data indicate that both, the Z13Mad5Anaxa vaccine and the AnaxaZ13Mad5 construct, elicit a strong immune response.

Example 10: Therapeutic Effect on Tumor Growth

To evaluate the effect of the Anaxa-conjugated construct proteins designed in Example 7 on tumor growth control, a benchmark tumor model was used, namely the s.c. implantation of EG.7-OVA thymoma cells.

Figure 17:
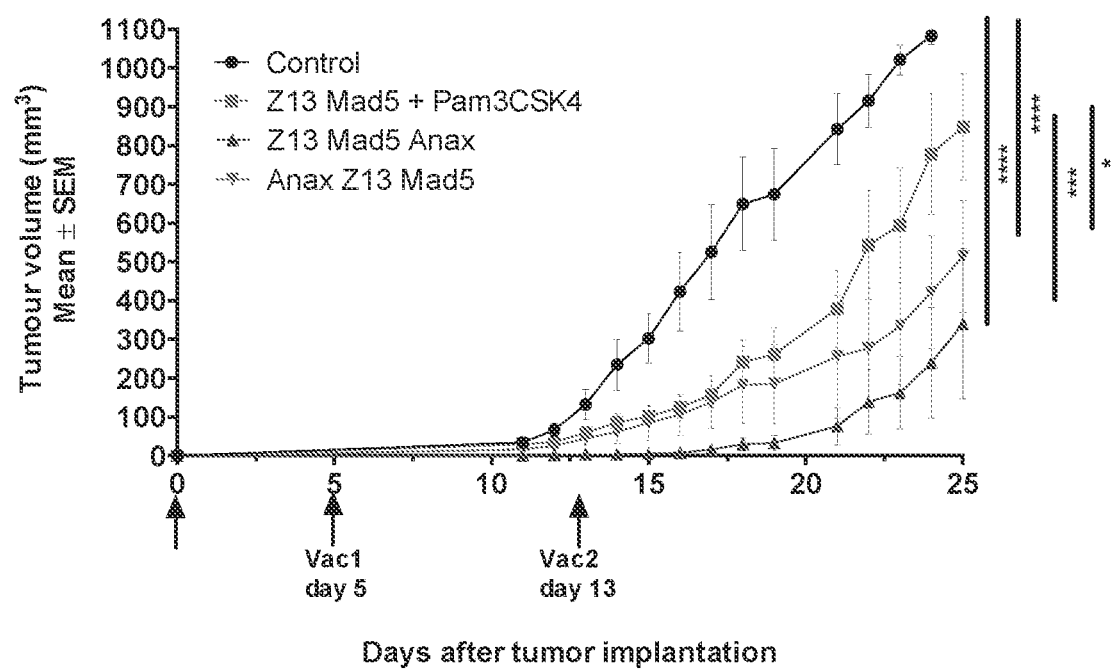
FIG. 17 shows for Example 10 the tumor growth of 7 mice per group (mean±SEM). C57BL/6 mice were implanted s.c. with $3\times10^5$ EG7-OVA tumor cells in the left flank and vaccinated twice (d5 and dis) by subcutaneous injection of 10 nmol of either AnaxZ13Mad5, Z13Mad5Anaxa or co-injection of Z13Mad5+PamsCSK4 (equimolar to Anaxa) in the right flank. Tumor size was measured with a caliper. *, $p<0.05$; *, $p<0.0001$, **, $p<0.0001$.
Figure 18:
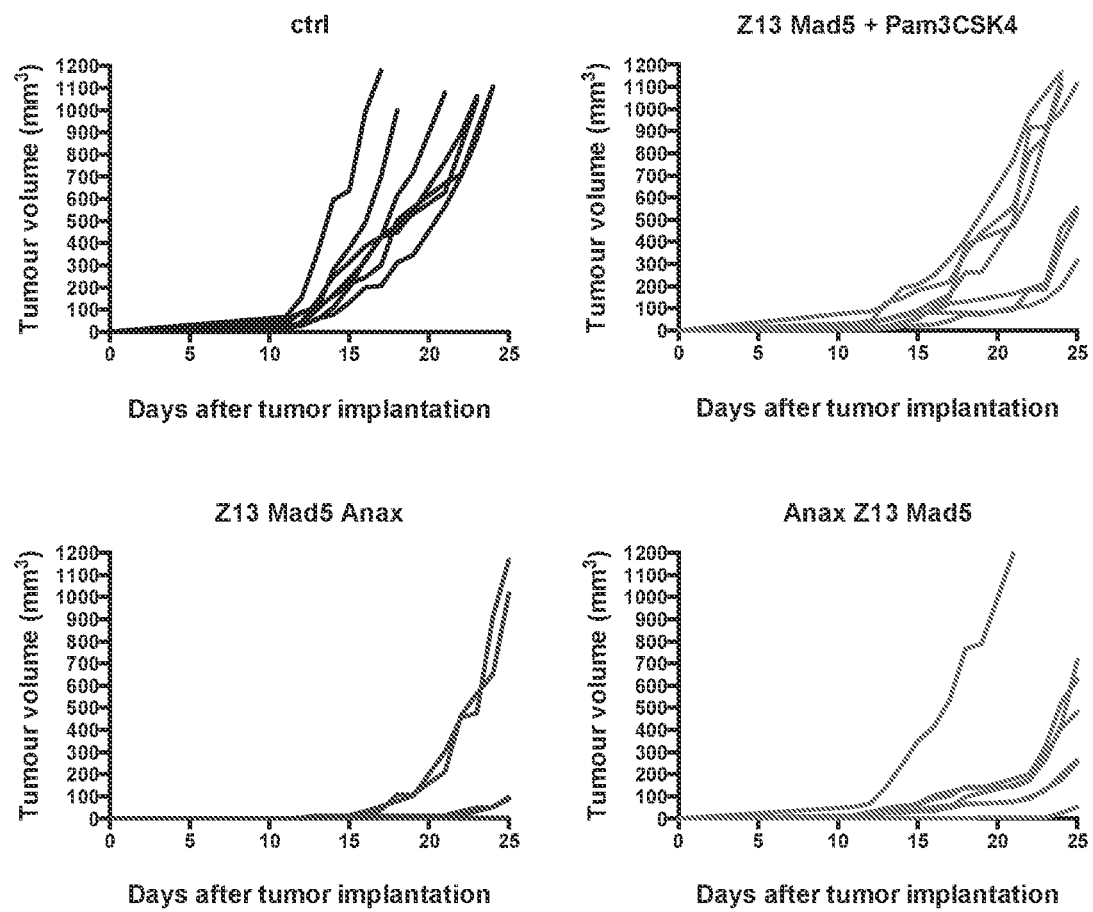
FIG. 18 shows for Example 10 the individual tumor growth curves (7 individual mice per group). C57BL/6 mice were implanted s.c. with $3\times10^5$ EG7-OVA tumor cells in the left flank and vaccinated twice (d5 and dis) by subcutaneous injection of 10 nmol of either AnaxZ13Mad5, Z13Mad5Anaxa or co-injection of Z13Mad5+Pam3CSK4 (equimolar to Anaxa) s.c. in the right flank. Tumor size was measured with a caliper.
Figure 19:
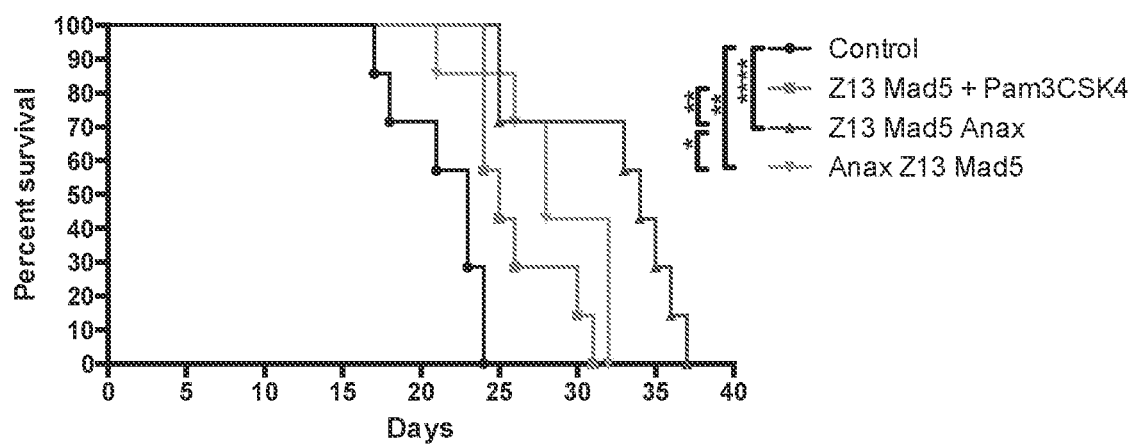
FIG. 19 shows for Example 10 the survival curve of 7 mice per group. C57BL/6 mice were implanted s.c. with $3\times10^5$ EG7-OVA tumor cells in the left flank and vaccinated twice (d5 and dis) by subcutaneous injection of 10 nmol of either AnaxZ13Mad5, Z13Mad5Anaxa or co-injection of Z13Mad5+Pam3CSK4 (equimolar to Anaxa) in the right flank. Tumor size was measured with a caliper. *, $p<0.05$, *, $p<0.01$, ****, $p<0.0001$ (Log-rank test).

C57BL/6 mice were implanted s.c. with $3 \times 10^5$ EG7-OVA tumor cells in the left flank. After tumor implantation, the three groups of 7 mice each were vaccinated s.c. in the right flank at day 5 and 13 by subcutaneous injection of 10 nmol of either AnaxZ13Mad5 (group 1), Z13Mad5Anaxa (group 2) or Z13Mad5 and PamsCSK4 (equimolar to Anaxa; group 3). In order to compare the effect to a protein mixed with an external adjuvant, a control group was vaccinated with Z13Mad5 and Pam3CSK4 (equimolar to Anaxa). Tumor size was measured with a caliper. Results are shown in FIG. 17-19.

In a therapeutic schedule, Z13Mad5Anaxa and AnaxaZ13Mad5 are better protein vaccines for controlling tumor growth compared to the control group, i.e. co-injection of Z13Mad5 and PamsCSK showing a significant better survival curve. In particular, Z13Mad5Anaxa and AnaxaZ13Mad5 demonstrate significantly higher efficacy than Z13Mad5 administrated separately with Pam3CSK4. The results therefore suggest that the construct proteins Z13Mad5Anaxa and AnaxaZ13Mad5 are promising conjugate-vaccines for controlling the tumor growth in a therapeutic setting.

Example 11: Therapeutic Effect on Tumor Growth—Comparison of Constructs with Different TLR Agonists The goal of this study was to compare the efficacy of the different construct protein vaccines conjugated to different TLR agonist, namely EDAZ13Mad5 and Z13Mad5Anaxa of Example 1 and 7, on tumor growth control. To this end, C57BL/6 mice were implanted s.c. with $3 \times 10^5$ EG.7-OVA thymoma cells in the left flank as described previously in Example 10. Mice (7 individual mice per group) were vaccinated s.c. in the right flank at day 5 and 13 with 2 nmol of either EDAZ13Mad5, Z13Mad5Anaxa or co-injection of Z13Mad5+ MPLA (equimolar to EDA).

Figure 20:
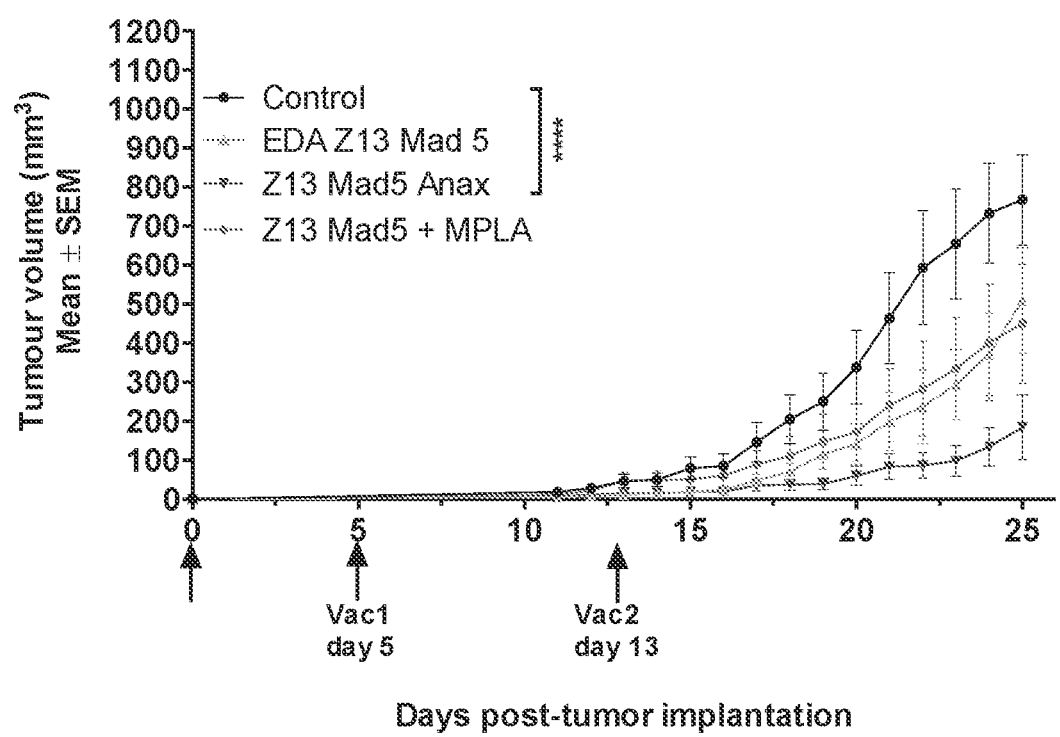
FIG. 20 shows for Example 11 the tumor growth of 7 mice per group (mean±SEM). C57BL/6 mice were implanted s.c. with $3\times10^5$ EG7-OVA tumor cells in the left flank and vaccinated twice (d5 and d13) by subcutaneous injection of 2 nmoles of Hp91Z13Mad5, EDAZ13Mad5, Z13Mad5Anaxa, Z13Mad5EDA or Z13Mad5 and MPLA (equimolar to EDA) in the right flank. *, $p<0.05$; , $p<0.01$; *, $p<0.001$; **, $p<0.0001$ (2-way Anova test at day 23).
Figure 21:
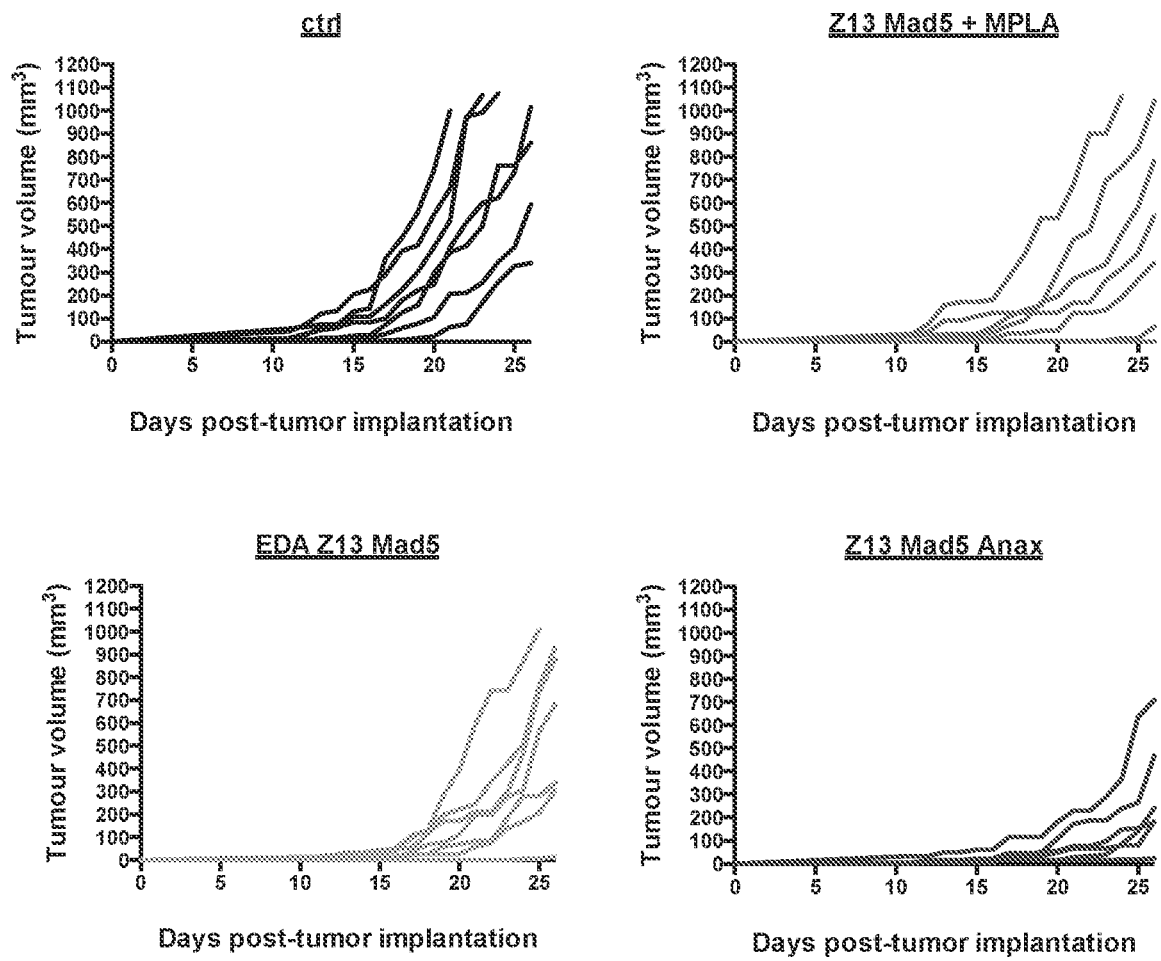
FIG. 21 shows for Example 11 the individual tumor growth curves (7 individual mice per group). C57BL/6 mice were implanted s.c. with $3\times10^5$ EG7-OVA tumor cells in the left flank and vaccinated twice (d5 and d13) by subcutaneous injection of 2 nmoles of Hp91Z13Mad5, EDAZ13Mad5, Z13Mad5Anaxa, Z13Mad5EDA or Z13Mad5 and MPLA (equimolar to EDA) s.c. in the right flank.
Figure 22:
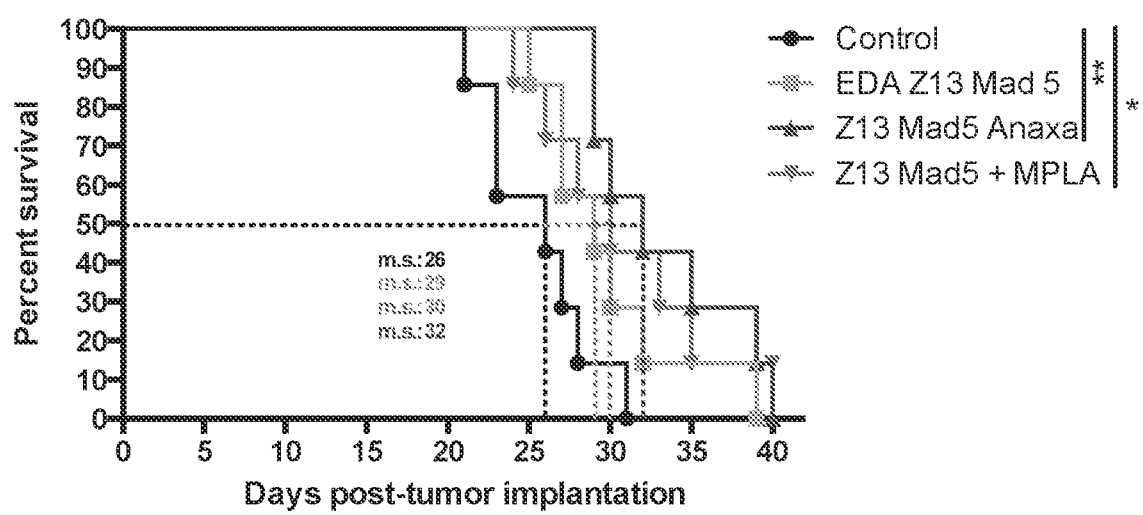
FIG. 22 shows for Example 11 the survival curves of all 7 mice per group. Median survival is indicated on the graph (m.s.). *, $p<0.05$; *, $p<0.01$ (Log-rank test).

Results are shown in FIGS. 20, 21 and 22. In this experimental setting, Z13Mad5Anaxa, EDAZ13Mad5, and Z13Mad5+ MPLA were similarly able to significantly control tumor growth. Moreover, these data indicate that Z13Mad5Anaxa is the best construct to significantly control tumor growth and EDAZ13Mad5 was slightly better than Z13Mad5+ MPLA in this experimental setting.

Example 12: Dose Effect of Z13Mad5Anaxa on Tumor Growth Control

To identify the optimal dose of the conjugate vaccine, three different doses (0.5 nmol, 2 nmol and nmol) of Z13Mad5Anaxa (cf. Example 7) were assessed for their ability to control tumor growth. The dose effect of Z13Mad5Anaxa construct was evaluated in the s.c. model of EG.7-OVA thymoma cells as described previously in Example 10. After tumor implantation, mice were vaccinated twice (at day 5 and at day 13 after tumor implantation) in a therapeutic setting at 0.5, 2 or 10 nmol of Z13Mad5Anaxa.

C57BL/6 mice were implanted s.c. with $3 \times 10^5$ EG7-OVA tumor cells in the left flank and vaccinated twice (d5 and d is) by subcutaneous injection of either 0.5 nmol, 2 nmol or 10 nmol of Z13Mad5Anaxa in the right flank. Tumor size was measured with a caliper.

Figure 23:
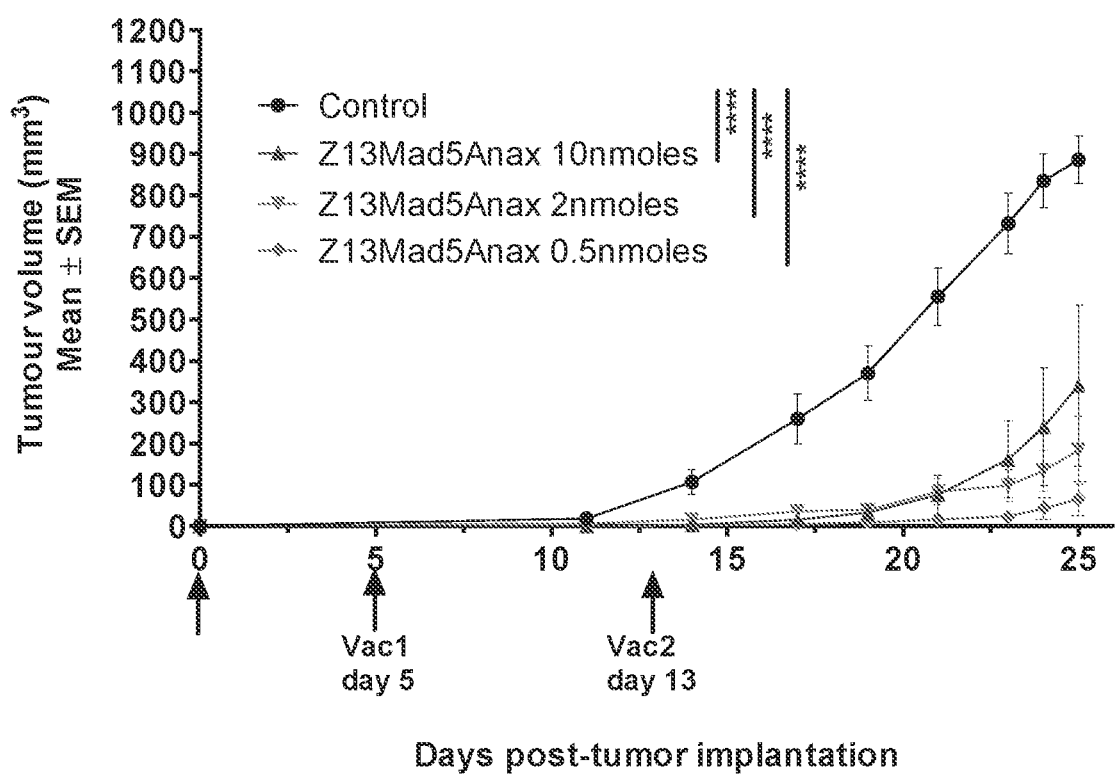
FIG. 23 shows for Example 12 the tumor growth of 7 mice per group (mean±SEM); ****, $p<0.0001$ (Log-rank test). C57BL/6 mice were implanted s.c. with $3\times10^5$ EG7-OVA tumor cells in the left flank and vaccinated twice (once at d5 and once at d i3) by subcutaneous injection of either 0.5 nmol, 2 nmol or 10 nmol of Z13Mad5Anaxa in the right flank. Tumor size was measured with a caliper.

The tumor growth of 7 mice per group is depicted in FIG. 23. Those data show that the doses of 0.5 and 2 nmol are at least as efficacious as 10 nmol for controlling tumor growth.

Example 13: Effect of Different Routes of Administration of Z13Mad5Anaxa

This study was based on the previous Examples demonstrating the efficacy of Z13Mad5Anaxa conjugate vaccine (cf. Example 7), which is able to elicit specific immune responses and is efficacious for controlling tumor growth in the subcutaneous tumor model EG7 as shown above.

To investigate the effect of subcutaneous, intramuscular and intradermal routes of administration, immune responses elicited by subcutaneous, intramuscular and intradermal injection were compared. Intradermal injections were performed using the PLEASE® device from Pantec Biosolutions.

Figure 24A:
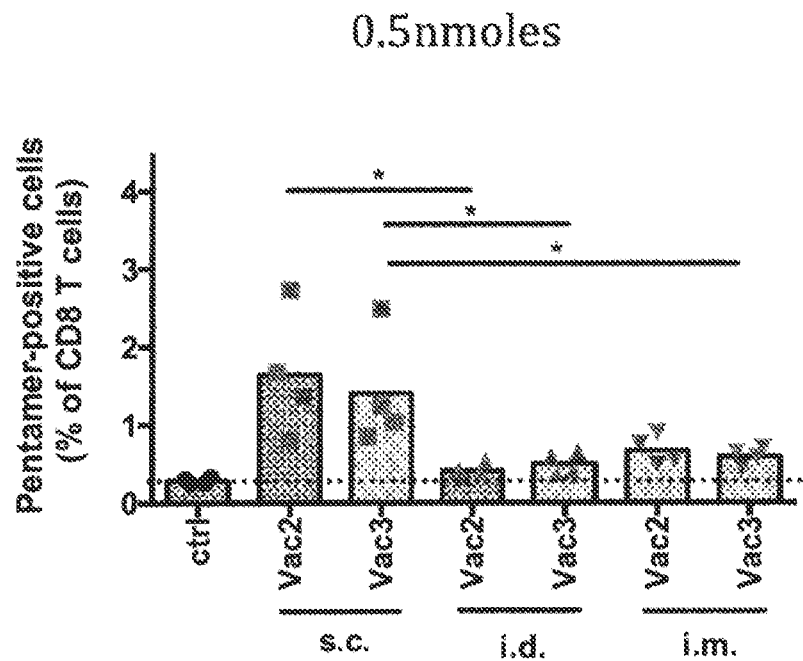
FIG. 24A-B shows for Example 13 the SIINFEKL-specific CD8 T cell responses detected in the blood of C57BL/6 mice vaccinated three times (once at Wk0, once at Wk2 and once at Wk4) s.c., id. or i.m. with 0.5 nmol (A) or 2 nmol (B) of Z13Mad5Anaxa. Blood was obtained from mice 7 days after the 2nd and the 3rd vaccination and multimer staining was performed (one experiment with 4 mice per group). *, p<0.05.
Figure 24B:
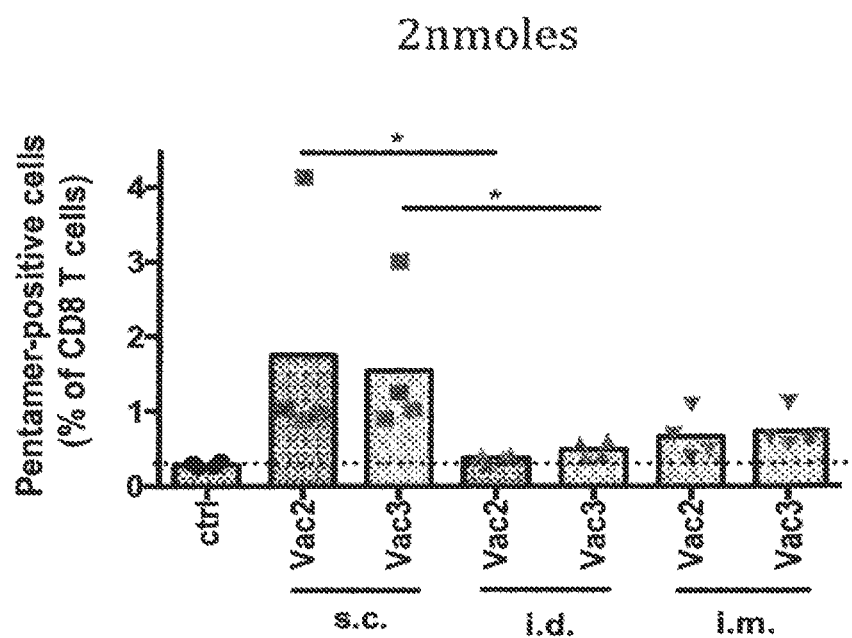

Mice were vaccinated three times every two weeks (Wk0, Wk2 and Wk4) with 0.5 or 2 nmol of Z13Mad5Anaxa (cf. Example 7). In order to target several lymph nodes, the 1st and the 3rd vaccinations were performed in the right flank whereas the 2nd was done in the left flank. SIINFEKL-specific CD8+ T cell response was analyzed 1 week after the 2nd and the 3rd vaccination in the blood. FIG. 24 shows the SIINFEKL-specific CD8 T cell responses after each vaccination detected in the blood of C57BL/6 mice vaccinated three times (Wk0, Wk2 and Wk4) s.c., i.d. or i.m. with 0.5 nmol (FIG. 24 A) or 2 nmol (FIG. 24 B) of Z13Mad5Anaxa. Blood was obtained from mice 7 days after the 2nd and the 3rd vaccination and multimer staining was performed (one experiment with 4 mice per group).

The results indicate that at the two doses assessed (0.5 and 2 nmol), (i) all routes of administration tested elicited a SIINFEKL-specific CD8 immune response and (ii) the subcutaneous vaccination elicited the strongest SIINFEKL-specific CD8 immune response. For subcutaneous administration, the maximum response was reached after the Snd vaccination and still maintained after the 3rd vaccination. The SIINFEKL-specific CD8 immune response after the 2nd vaccination elicited by intradermal and intramuscular vaccinations is lower compared to subcutaneous vaccination and is not enhanced after the 3rd vaccination.

Next, the effector function and the exhaustion status of SIINFEKL-specific CD8 T cells was evaluated by analyzing KLRG 1 (Killer cell lectin-like receptor subfamily G member 1) and PD-1 respectively.

To this end, C57BL/6 mice were vaccinated three times (Wk0, Wk2 and Wk4) s.c., i.d. or i.m. with 2 nmol of Z13Mad5Anaxa (cf. Example 7). Blood was obtained from mice 7 days after the 2nd and the 3rd vaccination and FACS staining was performed. KLRG1 and PD-1 expression were analyzed on multimer-positive CD8 T cells (one experiment with 4 mice per group). Results are shown in FIG. 25.

These data indicate that the expression of KLRG 1 is strongly increasing on SIINFEKL-specific CD8 T cells after subcutaneous vaccination. After i.d. or i.m. vaccination, the observed effects were lower. The percentage of KLRG 1-positive cells among SIINFEKL-specific CD8 T cells is also enhanced after s.c. vaccination (data not shown).

In contrast to KLRG 1, PD-1 expression is decreasing with the time and the vaccinations, for subcutaneous and intramuscular vaccination routes. This suggests that SIINFEKL-specific CD8 T cells are not exhausted. The percentage of PD1-positive cells among SIINFEKL-specific CD8 T cells is also reduced after s.c. and i.m. vaccination (data not shown). It is important to note that PD-1 expression is higher after the 2nd vaccination when mice were vaccinated subcutaneously, reflecting the early activation status of specific T cells (Keir, M. E., et al., PD-1 and its ligands in tolerance and immunity. Annu Rev Immunol, 2008. 26: p. 677-704).

The expression of the late exhaustion marker Tim-3 was also analyzed. A very low expression as observed for all groups.

Taken together, results indicate that subcutaneous vaccination elicits the best specific CD8 immune response compared to intramuscular or intradermal injections.

Example 14: Intranodal Route of Administration

Based on the previous experiments (Example 1i), the intranodal route of administration was additionally investigated. To this end, the immune response elicited by intranodal injection of Z13Mad5Anaxa (cf. Example 7) was investigated.

For this purpose, mice were first injected with Evans Blue subcutaneously in order to allow easily visualizing the lymph nodes for injection and inject intranodally without invasive surgery, for example as described in Jewell, C.M., S.C. Lopez, and D.J. Irvine, In situ engineering of the lymph node microenvironment via intranodal injection of adjuvant-releasing polymer particles. Proc Natl Acad Sci USA, 2011. 108(38): p. 15745-50.

C57BL/6 mice were vaccinated two times every two weeks (Wk0 and Wk2) intranodally with 0.5 nmol of Z13Mad5Anaxa (cf. Example 7). The 1st vaccination was performed in the right inguinal lymph node, whereas the second vaccination was done in the left inguinal lymph node. Blood was obtained from mice 7 days after the 2nd vaccination and multimer staining was performed (3 mice per group). In other words, SIINFEKL-specific CD8$^+$ T cell response was analyzed one week after the 2nd vaccination in the blood. FIG. 26 shows the SIINFEKL-specific CD8 T cell responses. Those data indicate that also intranodal injection was able to elicit SIINFEKL-specific CD8 T cells.

Example 15: Vaccination Schedule

The vaccination schedule evaluation work was initiated with the objective to identify the impact of the third vaccination using the same Z13Mad5Anaxa construct as described above (cf. Example 7). The subcutaneous route was chosen given the previous results.

Figure 27A:
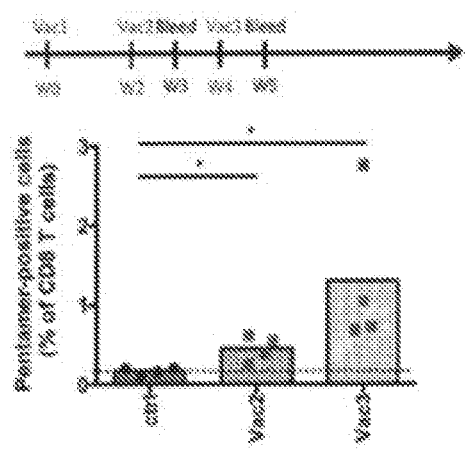
Figure 27B:
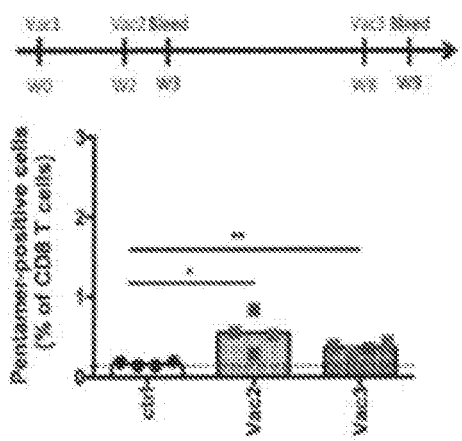
Figure 27C:
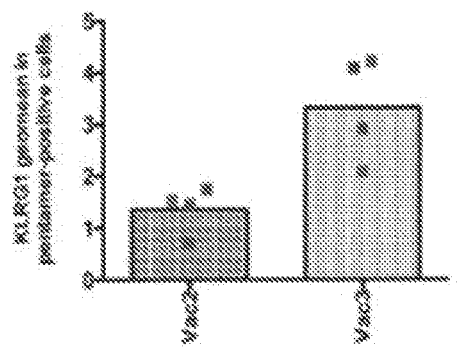
Figure 27D:
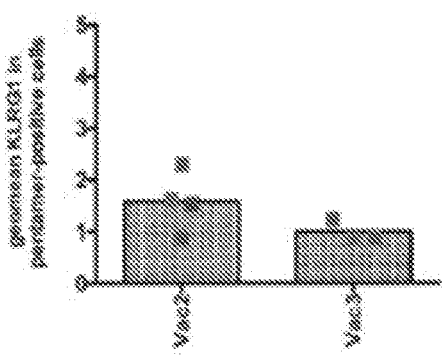

In the experiment first two vaccinations were performed at wk0 and wk2 with a 3rd vaccination either at wk4 (FIG. 27 A) or at wk8 (FIG. 27B). Thus, C57BL/6 mice were vaccinated three times (FIGS. 27 A and C: Wk0, Wk2 and Wk4 and FIGS. 27 B and D: Wk0, Wk2 and Wk8) s.c. with 2 nmol of Z13Mad5Anaxa. Blood was obtained from mice 7 days after last vaccination and pentamer staining was performed (one experiment with 4 mice per group). Accordingly, SIINFEKL-specific CD8$^+$ T cell response was analyzed 1 week after the 2nd and the 3rd vaccination (FIGS. 27 A and B). Additionally, the effector function of SIINFEKL-specific T cells was evaluated by analyzing the expression of KLRG 1 on specific CD8 T cells (FIGS. 27C and D).

The data indicate that compared to control the percentage of SIINFEKL-specific CD8 T cells was significantly increased at all time points tested (Vac2 and Vac) as well as in both vaccination schedules (FIGS. 27 A and B).

Interestingly, the third vaccination at Wk4 allowed to most prominently increasing the percentage of SIINFEKL-specific CD8 T cells (FIG. 27 A). The same cells also demonstrate an improved effector function through higher KLRG 1 expression (FIG. 27 C). In contrast, with a third vaccination performed at Wk8 no improvement from the second to the third vaccination could be observed in the SIINFEKL-specific immune response and in the KLRG 1 expression.

Taken together, these results indicate that the CD8 immune response could be increased by shorten the delay between the second and the third vaccination.

Given that an earlier third vaccination seems to increase immune response, in the next study two short schedules of vaccination were investigated:
  i) three vaccinations at day 0, day 3 and day 7 and
  ii) three vaccinations at day 0, day 7 and day 14.

Again, C57BL/6 mice were used and vaccination was performed s.c. with 0.5 nmol of Z13Mad5Anaxa (cf. Example 7). Multimer staining was performed on blood samples obtained one week after the 2nd and the 3rd vaccination (one experiment with 4 mice per group).

Figure 28A:
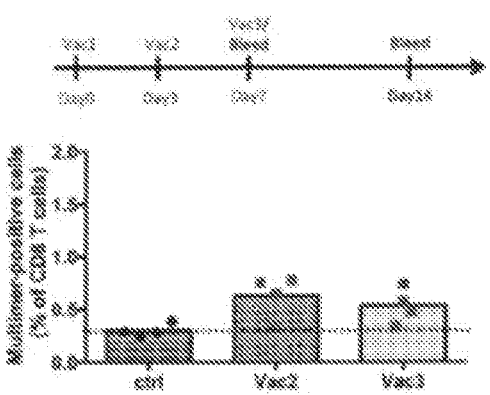
Figure 28D:
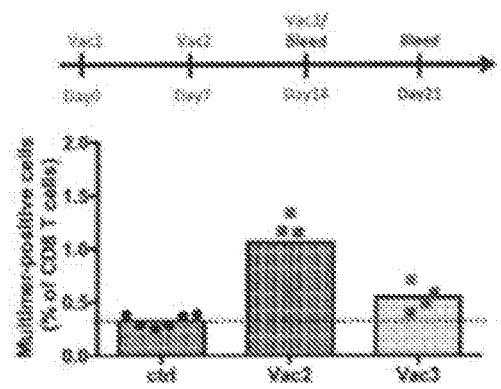
Figure 28B:
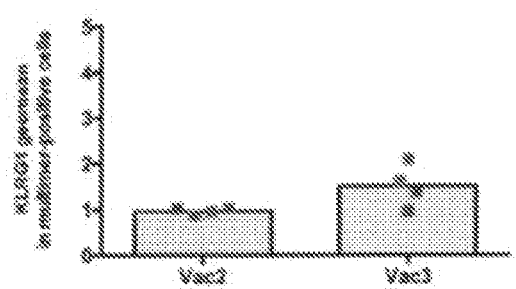
Figure 28E:
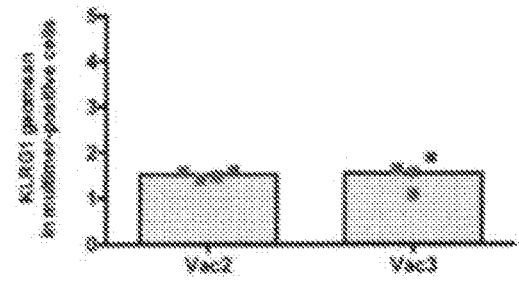
Figure 28C:
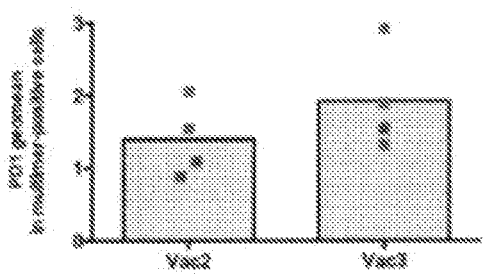
Figure 28F:
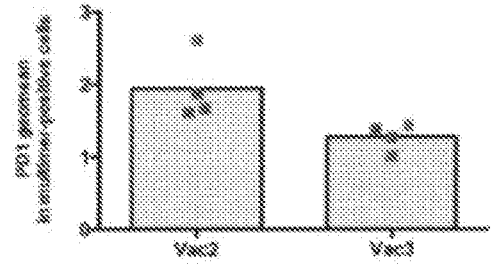

Thus, SIINFEKL-specific CD8+ T cell response was analyzed one week after the 2nd and the 3rd vaccination (FIGS. 28A and D). Additionally, the effector function of SIINFEKL-specific T cells was evaluated by analyzing the expression of KLRG 1 on specific CD8 T cells (FIGS. 28B and 28E) and the exhaustion status by analyzing the PD-1 expression of specific T cells (FIGS. 28C and 28F).

The data indicate that—similarly to the first study regarding the vaccination schedule described above—compared to control the percentage of SIINFEKL-specific CD8 T cells was increased at all time points tested (Vac2 and Vac3) as well as in both vaccination schedules (FIGS. 28 A and B).

However, compared to the schedule wko-wk2-wk4, a schedule with vaccinations at Day0, Day3 and Day7 did not elicit such a high SIINFEKL-specific CD8 T cell immune response. Concerning the schedule with vaccinations at Day0, Day7 and Day14, the SIINFEKL-specific CD8 T cell immune response elicited is better compared to the previous schedule (do-d3-d7) but is not maintained after the 3rd vaccination.

Taken together, vaccination schedule data set indicates that the Wk0-Wk2-Wk4 vaccination schedule is the best vaccination schedule for inducing potent OVA-specific CD8 immune response with high effector function.

Example 16: Capacity of TLR Agonist-CPP Conjugate Constructs to Activate Murine Antigen-Presenting Cells (APCs)

To investigate the effect of both, the CPP component and the TLR agonist component in a complex for use according to the present invention, again the fusion proteins as described above (cf. Examples 1, 2 and 7) were used.

In addition, a further "control peptide" was designed, which is also a fusion protein and which comprises the protein "MAD5", which consists of different CD8+ and CD4+ epitopes from various antigens, and the TLR2 peptide agonist "Anaxa" (i.e. without cell penetrating peptide). Accordingly, the following control construct was additionally designed:

```
Mad5Anaxa
Sequence:
                                      [SEQ ID NO: 32]
MHHHHHHESL KISQAVHAAH AEINEAGREV VGVGALKVPR

NQDWLGVPRF AKFASFEAQG ALANIAVDKA NLDVEQLESI

INFEKLTEWT GSSTVHEILC KLSLEGDHST PPSAYGSVKP

YTNFDAE
```

Molecular weight: 13933 Da
Characteristics:
  Mad5 cargo contains OVACD4, gp100CD8, EalphaCD4 and OVACD8 epitopes
  Contains the 35-mer peptide of Annexin in C-terminal position
  Storage buffer: 50 mM Tris-HCl, 150 mM NaCl, 10% Glycerol, 2 mM DTT, 0.5 M L-Arginine, pH 8
  Endotoxin level: Batch 1-12.15 EU/mg The aim of this study was to evaluate the capacity of two exemplary complexes according to the present invention, namely EDAZ13Mad5 (cf. Example 1) and Z13Mad5Anaxa (cf. Example 7), to promote antigen-presenting cells activation in comparison to reference complexes lacking either the cell penetrating peptide component Z13 (Mad5Anaxa, cf. above; EDAMad5, cf. Example 2) or the TLR agonist (Z13Mad5, cf. Example 1).

To this end, the capacity of the above mentioned constructs to promote antigen-presenting cells (APC) activation was assessed in bone marrow-derived dendritic cells (BMDCs), which express all TLRs except TLR7.

BMDCs were seeded in flat 96-well plate in culture medium, stimulated with 1 µM of either Z13Mad5Anaxa (cf. Example 7), Mad5Anaxa (cf. above), Z13Mad5 (cf Example 1), EDAZ13Mad5 (cf. Example 1) or EDAMad5 (cf. Example 2) and incubated for 24 h at 37° C.

The APC activation was investigated by monitoring the secretion of IL-6 in the culture supernatant of BMDCs. IL-6 secretion was quantified by ELISA in the supernatant.

The results are shown in FIG. 29. These data clearly show that Z13Mad5Anaxa was able to activate BMDCs, whereas no such activation was observed when the cells were cultured in presence of Z13Mad5 or Mad5Anaxa. This suggests that not only the TLR agonist (Anaxa or EDA) is critical for the activation of macrophages and dendritic cells, but that the CPP is also needed. Also the presence of the CPP without the TLR agonist is not sufficient, but indeed both, CPP and TLR agonist are critical for the activation of macrophages and dendritic cells.

Those results were confirmed by using another cell line, namely in the Raw 264.7 mouse macrophage cell line, which expresses all TLRs except TLR5 (Applequist, S.E., R.P. Wallin, and H.G. Ljunggren, Variable expression of Toll-like receptor in murine innate and adaptive immune cell lines. Int Immunol, 2002. 14(9): p. 1065-74).

Raw 264.7 cells were seeded in flat 96-well plate in culture medium, stimulated with 1 µM of either Z13Mad5Anaxa (cf. Example 7), Mad5Anaxa (cf above) or Z13Mad5 (cf. Example 1) and incubated for 24 h at 37° C.

In Raw 264.7 cells the APC activation was investigated by monitoring the secretion of TNF-α in the culture supernatant of Raw 264.7. TNF-α secretion was quantified by ELISA in the supernatant. The results are shown in Figure so.

It is thought that the CPP may facilitate the entry of the molecule into the cells, allowing a better targeting of intracellular TLR.

Taken together, the data reveal the critical role of both, CPP and TLR agonist, within the conjugate constructs to activate APC. This effect may be due to helping the entry of the construct into the cells, therefore resulting in an optimal targeting of the intracellular TLR.

Example 17: Ability of the Conjugate Constructs to Bind to Human TLR4

It was recently shown that the Anaxa peptide owns an adjuvant activity by signaling through TLR2 (WO 2012/048190 A1), whereas the EDA peptide is a natural ligand for TLR4 (Okamura, Y., et al., The extra domain A of fibronectin activates Toll-like receptor 4. J Biol Chem, 2001. 276(13): p. 10229-83).

Moreover, as shown above in Example 8 and FIG. 14, a complex for use according to the present invention comprising the Anaxa peptide as TLR agonist, for example Z13Mad5Anaxa, is able to bind to human TLR2 and to promote the secretion of IL-8 by HEK-hTLR2 cells (cf. Example 8, FIG. 14).

In the present study, the ability of complexes according to the present invention comprising either the Anaxa peptide as TLR agonist or the EDA peptide as TLR agonist to bind to human TLR4 was evaluated. To this end, HEK cells transfected with human TLR4 (HEK-hTLR4) were seeded in flat 96-well plate in culture medium, stimulated with 1 µM of either Z13Mad5Anaxa (cf. Example 7), Mad5Anaxa (cf. above), Z13Mad5 (cf. Example 1), EDAZ13Mad5 (cf. Example 1) or EDAMad5 (cf. Example 2) and incubated for 24 h at 37° C. IL-8 secretion was quantified by ELISA in the supernatant.

Results are shown in FIG. 31. As expected, incubation of HEK-hTLR4 with EDAZ13Mad5 resulted in remarkable IL-8 secretion, indicating binding of EDAZ13Mad5 to TLR4. In line with the results obtained in Example 16, the IL-8 secretion of EDAMad5 (without the CPP) was remarkably lower as compared to EDAZ13Mad5, showing the effect of the presence of a CPP. The Z13Mad5 construct, which does not comprise a TLR agonist, showed no IL-8 secretion, indicating—as expected—a lack of binding to TLR4.

Interestingly, incubation of HEK-hTLR4 with the construct Z13Mad5Anaxa resulted in the most pronounced IL-8 secretion, indicating binding of Z13Mad5Anaxa to TLR4. This is astonishing, since Anaxa was previously hypothesized to be a TLR2 agonist. Again, the same construct but without the CPP (Mad5Anaxa) resulted in remarkably lower IL-8 secretion, confirming the results obtained in Example 16.

Taken together, these data (i) confirm the results obtained in Example 16, (ii) confirm that EDA is indeed a TLR4 agonist, and (iii) show surprisingly that the Anaxa peptide is also a TLR4 agonist (in addition to being a TLR2 agonist, cf. Example 8 and FIG. 14).

Example 18: Vaccine Efficacy on Tumor Growth in a Lung Metastasis Model—Semi-Therapeutic Setting: TLR Agonist EDA This study is based on Example 6, showing the efficacy of a complex for use according to the present invention, namely EDAZ13Mad5, in a melanoma lung metastasis model in a prophylactic setting (cf. FIG. 13).

In the present study the same lung metastasis model was used as well as the construct proteins EDAZ13Mad5 and Z13Mad5+MPLA (cf. Examples 1 and 2 for design of the constructs). However, in the semi-therapeutic setting, C57BL/6 mice were vaccinated at the same time as tumor cells were implanted (d0) and, for a second time, at nine days after implantation (d9). Vaccination was performed by subcutaneous injection of 2 nmol of EDAZ13Mad5, Z13Mad5+MPLA (equimolar to EDA) or MPLA s.c. in the right flank. At day 0, mice were implanted i.v. with 1×10$^5$ B16-OVA melanoma tumor cells and vaccinated twice (d0 and d9) by subcutaneous injection of 2 nmol of EDAZ13Mad5, Z13Mad5$^+$ MPLA (equimolar to EDA) or MPLA alone s.c. in the right flank. Mice were euthanized at day 13 and lung recovered. Results are shown in FIG. 32.

The results show that EDAZ13Mad5 is slightly more potent than Z13Mad5$^+$ MPLA to inhibit the growth of melanoma metastasis. In addition, no adjuvant effect was observed in mice injected with MPLA only.

Both, EDAZ13Mad5 and Z13Mad5$^+$ MPLA, significantly inhibit the growth of melanoma metastasis in the lung in prophylactic and semitherapeutic settings.

Example 19: Vaccine Efficacy on Tumor Growth in a Lung Metastasis Model—Semi-Therapeutic Setting: TLR Agonist Anaxa This study is based on Example 18 with the same model (semitherapeutic settings) and experimental schedule. However, the effect of complexes according to the present invention comprising the "Anaxa" peptide as TLR agonist were investigated—instead of the EDA TLR agonist as in Example 18.

To this end, C57BL/6 mice were implanted i.v. with 1×10$^5$ B16-OVA melanoma tumor cells and vaccinated twice (d0 and d9) by subcutaneous injection of 0.5 nmol of Z13Mad5Anaxa, Mad5Anaxa or Z13Mad5$^+$ Pam3CSK4 (equimolar to Anaxa) s.c. in the right flank. Mice were euthanized at day 21 and the lung was recovered. Number of metastasis foci was counted for each lung. The results are shown in FIG. 33.

The results show that Z13Mad5Anaxa is sensibly more potent than Z13Mad5$^+$ Pam3CSK4 to inhibit the growth of melanoma metastasis. In contrast, Mad5Anaxa was not able to control metastasis growth in the lung, underlining again the importance of CPP.

Altogether, the B16-OVA lung metastasis experiment showed that Z3i Mad5Anaxa was highly efficacious in inhibiting the growth of melanoma metastasis in the lung.

Example 20: Vaccine Efficacy in a Glioblastoma Model

In this study, another cancer model was used, namely a glioblastoma model. Glioma is the most frequent form of primary brain tumors in adults, with glioblastoma multiforme (GBM) being the most lethal. This tumor is notorious for its highly invasive and aggressive behavior. Currently, the best treatment against GBM is a regimen involving a combination of surgery, chemotherapy and radiotherapy, which has a median survival period of only 14.6 months. There is an urgent, unmet medical need for new treatment modalities that improve the prognosis of glioma patients. T-cell mediated immunotherapy is a conceptually attractive treatment option to use in conjunction with existing modalities for glioma, in particular highly invasive GBM.

The Gl261 glioma is a carcinogen-induced mouse glioma model. This model represents one of the very few brain tumor models developed in immunocompetent animals, that has growth characteristics similar to human GBM (Newcomb, E. and D. Zagzag, The murine GL261 glioma experimental model to assess novel brain tumor treatments, in *CNS Cancer Models, Markers, Prognostic, Factors, Targets, and Therapeutic Approaches*, E.G. Van Meir, Editor. 2009, Humana Press: Atlanta. p. 227-241; Jacobs, V. L., et al., Current review of in vivo GBM rodent models: emphasis on the CNS-1 tumour model. ASN Neuro, 2011. 3(3): p. e00063). Low numbers of intracranially transplanted Gl261 cells formed intracranial tumors in C57BL/6 mice (Zhu, X., et al., Poly-/CLCpromotes the infiltration ofeoffector T cells into intracranial gliomas via induction of CXCLIO in IFN-alpha and IFN-gamma dependent manners. Cancer Immunol lmmunother, 2010. 59(9): p. 1401-9; Zhu, X., et al., Toll like receptor-3 ligand poly-/CLC promotes the efficacy of peripheral vaccinations with tumor antigen-derived peptide epitopes in murine CNS tumor models. J Transl Med, 2007. 5: p. 10). The cells are moderately immunogenic: they are able to elicit tumor-specific immune response at the tumor site. However, the tumor-specific immune cells are not capable of complete tumor clearance.

Recently, M. Ollin generated a new Gl261 model (Ohlfest, J. R., et al., Vaccine injection site matters: qualitative and quantitative defects in CDB T cells primed as a function of proximity to the tumor in a murine glioma model. J Immunol, 2013. 190(2): p. 613-20) by transfecting Gl261 cell line with the "Quad Cassette" expressing four peptides presented by H-2b class I or II molecules: human gp100$_{25-33}$, chicken OVA$_{257-264}$, chicken OVA$_{323-359}$, and mouse I-Eα$_{52-68}$. The Quad-Gl261 cell line also stably expresses luciferase, which allows the follow-up of tumor growth by bioluminescence. The goal of this study was to assess the efficacy of a complex for use according to the present invention in the Quad-Gl261 glioblastoma model.

The effect of a complex for use according to the present invention, namely Z13Mad5Anaxa (cf. Example 7) was evaluated in the above described glioblastoma model. T cell homing at the tumor site was therefore analyzed in Gl261-Quad tumor-bearing mice vaccinated twice (Wk1 and Wk3) with Z13Mad5Anaxa vaccine. A group vaccinated with Z13Mad5 and Anaxa (equimolar to Z13Mad5Anaxa) administered separately was used as control. Briefly, C57BL/6 mice were implanted i.e. (intracranially) with 5×10$^5$ Gl261-Quad tumor cells and vaccinated twice (at d7 and d21 following implantation) by s.c. injection of 2 nmol of Z13Mad5Anaxa (group 1) or 2 nmol of Z13Mad5 and 2 nmol of Anaxa (group 2). At Wk4, the blood and the brain infiltrating leukocytes (BILs) were analyzed, whereby SIINFEKL-specific CD8 T cells were quantified in blood and in BILs at d28 by multimer staining (5-8 mice per group). Results are shown in FIG. 34.

In general, low frequency of SIINFEKL-specific CD8 T cells was quantified in the blood. However, a higher percentage of SIINFEKL-specific CD8 T cells was observed in the blood of Z13Mad5Anaxa-vaccinated mice. In all groups, there was a sensibly stronger accumulation of SIINFEKL-specific CD8 T cells in the BILs.

After two vaccinations with Z13Mad5Anaxa, the frequency of SIINFEKL-specific cells CD8$^+$ T cells in the BILs was 2-fold higher (24%) than with Z13Mad5$^+$ Anaxa (12%).

Next, cytokine secretion was assessed. To this end, C57BL/6 mice were implanted i.e. with 5×10$^5$ Gl261-Quad tumor cells and vaccinated twice (d7 and 21) by s.c. injection of 2 nmol of Z13Mad5Anaxa or 2 nmol of Z13Mad5 and 2 nmol of Anaxa. BILs were isolated and cultured during 6 h with matured BMDCs loaded or not with SIINFEKL peptide in presence of BrefeldinA before intracellular staining for cytokines. Results are shown in FIG. 35.

Despite heterogeneity, a high level of cytokine secretion was observed for brain-infiltrating CD8 T cells from mice vaccinated with Z13Mad5Anaxa. These results demonstrate that Z13Mad5Anaxa vaccine was able to elicit a stronger SIINFEKL specific CD8 T cell immune response in the brain of tumor-bearing mice with potent effector function.

The results obtained are indicating that Z13Mad5Anaxa is efficacious for eliciting high brain infiltrating SIINFEKL-specific CD8 immune response. Z13Mad5Anaxa is able to promote the secretion of cytokine by antigen-specific CD8 T cells in the brain.

Example 21: Vaccine Efficacy on Survival in the Gl261-Quad Glioblastoma Model

In an independent experiment, the survival of control and Z13Mad5Anaxa-vaccinated mice was monitored. The therapeutic settings were three consecutive vaccinations with 2 nmol of Z13Mad5Anaxa at day 7, 21 and 35, post i.e. tumor implantation.

C57BL/6 mice were implanted i.e. with 5×10$^1$ Gl261-Quad tumor cells and vaccinated three times (d7, d21 and d35) by s.c. injection of 2 nmol of Z13Mad5Anaxa. Mice were weight daily and euthanized when weight loss reached more than 15%. Results are shown in FIG. 36.

The results show that Z13Mad5Anaxa therapeutic vaccination is more efficacious than the control group with a median survival prolonged by 10 days.

Example 22: Vaccine Efficacy in a Subcutaneous Tumor Model—Prophylactic Setting

This study is based on the results obtained in Example 10 as shown in FIGS. 17-19.

To evaluate the effect of the Anaxa-conjugated construct proteins designed in Example 7 on tumor growth control, a benchmark tumor model was used, namely the s.c. implantation of EG.7-OVA thymoma cells. In contrast to Example 10, wherein vaccination was performed on days 5 and 13, in the present study a prophylactic setting was evaluated, wherein mice were vaccinated 21 and 7 days before tumor implantation.

C57BL/6 mice were vaccinated twice (d-21 and d-7) by s.c. injection of 0.5 nmol of Z13Mad5Anaxa in the right flank and then implanted at day0 s.c. with 3×10$^5$ EG7-OVA tumor cells in the left flank and. Tumor size was measured with a caliper.

The results are shown in FIG. 37 with tumor volume (FIG. 37A) and survival rate (FIG. 37B). The data is showing that prophylactic vaccination with Z13Mad5Anaxa is highly efficacious for controlling tumor growth and survival rate. The volume of the tumor is highly significantly decreased in mice treated with Z13Mad5Anaxa as compared to control mice. The survival rate is highly significantly increased in mice treated with Z13Mad5Anaxa as compared to control mice.

Example 23: Vaccine Efficacy in a Subcutaneous Tumor Model—Therapeutic Setting with Established Tumor This study is based on the results obtained in Example 10 as shown in FIGS. 17-19 and on the results obtained in Example 22 shown in FIG. 37. It was the goal of this study to evaluate the effect of Z13Mad5Anaxa (cf. Example 7) on an established tumor.

For this purpose, the s.c. model of B16-OVA melanoma cells was used. In this model tumor cells are spreading slowly, therefore allowing a bigger vaccination time window.

The first vaccination with the low dose of 0.5 nmol of Z13Mad5Anaxa was performed once the tumor was established and visible i.e. at day 14 after tumor cell implantation. A second vaccination was done at day 21.

Thus, C57BL/6 mice were implanted s.c. with 1×10$^5$ B16-OVA tumor cells in the left flank and vaccinated twice (d 14 and d21) by s.c. injection of 0.5 nmol of Z13Mad5Anaxa in the right flank. Tumor growth and survival curves were monitored. Results are shown in FIG. 38.

The results indicate that Z13Mad5Anaxa efficaciously controls the growth of an established and visible tumor. Moreover, despite an established and visible tumor survival rates increased in mice treated with Z13Mad5Anaxa as compared to controls.

Example 24: Vaccine Efficacy in a Subcutaneous Tumor Model—Therapeutic Setting: Effect of the CPP The protocol of this study corresponds to the study described in Example 10, with the difference that an additional group "Mad5Anaxa" (cf. Example 16) was evaluated.

Briefly, a benchmark tumor model was used, namely the s.c. implantation of EG.7-OVA thymoma cells. C57BL/6 mice were implanted s.c. with 3×10⁵ EG7-OVA tumor cells in the left flank. After tumor implantation, groups of 7 mice each were vaccinated s.c. in the right flank at day 5 and 13 by subcutaneous injection of 0.5 nmol of either Z13Mad5Anaxa (group 1) or Mad5Anaxa (group 2) and compared to a control group. Tumor size was measured with a caliper. Results are shown in FIG. 39.

The results show that the mice treated with Z13Mad5Anaxa show a significantly decreased tumor volume and a significantly increased survival rate compared to both, control mice and mice treated with Mad5Anaxa, i.e. a construct without CPP. These results indicate that the presence of a CPP results in significantly decreased tumor volume and a significantly increased survival rate, i.e. in increased efficiency of vaccination. Therefore, the results indicate—together with the results obtained in Example 10—that the presence of a CPP and the TLR agonist exert a synergic effect on tumor growth and survival rate.

Example 25: Comparison of the Kinetic of Immune Responses with Complexes Having Different Cell Penetrating Peptides To investigate the effect of different CPPs in the complex for use according to the present invention the fusion protein Z13Mad5Anaxa as described above (cf. Example 7) was used.

In addition, further fusion proteins were designed, which comprise CPPs other than Z13—namely Z14 (SEQ ID NO: 7) or Z18 (SEQ ID NO: 11). Those fusion proteins also comprise the protein "MAD5", which consists of different CD8⁺ and CD4⁺ epitopes from various antigens, and the TLR2 peptide agonist "Anaxa". Accordingly, the following constructs were additionally designed:

```
Z14Mad5Anaxa
Sequence:
                                         (SEQ ID NO: 33)
MHHHHHHKRY KNRVASRKSR AKFKQLLQHY REVAAAKESL

KISQAVHAAH AEINEAGREV VGVGALKVPR NQDWLGVPRF

AKFASFEAQG ALANIAVDKA NLDVEQLESI INFEKLTEWT

GSSTVHEILC KLSLEGDHST PPSAYGSVKP YTNFDAE

Z18Mad5Anaxa
Sequence:
                                         (SEQ ID NO: 34)
MHHHHHHREV AAAKSSENDR LRLLLKESLK ISQAVHAAHA

EINEAGREVV GVGALKVPRN QDWLGVPRFA KFASFEAQGA

LANIAVDKAN LDVEQLESII NFEKLTEWTG SSTVHEILCK

LSLEGDHSTP PSAYGSVKPY TNFDAE
```

C57BL/6 mice were assigned to eight different groups (4 mice per group): three groups receiving 2 nmol of either Z13Mad5Anaxa, Z14Mad5Anaxa or Z18Mad5Anaxa and a respective control and three groups receiving 0.5 nmol of Z13Mad5Anaxa, Z14Mad5Anaxa or Z18Mad5Anaxa and a respective control. The mice were vaccinated five times (Week0, Week2, Week4, Week6 and Week8) s.c. Mice were bled 7 days after the 2$^{nd}$, 3$^{rd}$, 4$^{th}$ and 5$^{th}$ vaccination and multimer staining was performed (one experiment with 4 mice per group).

The results are shown in FIG. 40. All groups vaccinated with Z13Mad5Anaxa, Z14Mad5Anaxa or Z18Mad5Anaxa showed an increased percentage of multimer-positive cells compared to the control group (except for the second vaccination of Z18Mad5Anaxa). These results indicate that complexes according to the present invention having different cell penetrating peptides are able to elicit an immune response at different doses.

Example 26: Comparison of T Cell Immune Responses with Complexes Having Different Cell Penetrating Peptides To investigate the CD8 T cell immune responses in more detail, C57BL/6 mice were assigned to three different groups (3-4 mice per group): naïve, Z13Mad5Anaxa or Z14Mad5Anaxa.

C57BL/6 mice of the Z13Mad5Anaxa group and of the Z14Mad5Anaxa group were vaccinated five times (Week0, Week2, Week4, Week6 and Week8) s.c. with 2 nmol of either Z13Mad5Anaxa (cf. Example 7) or Z14Mad5Anaxa (cf. Example 25). Nine days after the 5$^{th}$ vaccination, mice were euthanized, organs recovered and multimer staining was performed to identify the percentage of SIINFEKL-specific CD8 T cells in the spleen, bone marrow and draining lymph nodes (inguinal and axillary).

The results are shown in FIG. 41. Mice vaccinated with Z13Mad5Anaxa or with Z14Mad5Anaxa showed a similar increase in multimer-positive cells, in particular in the spleen and bone marrow as well as a slight increase in draining lymph nodes.

To further investigate the CD8 T cell effector function after vaccination with complexes with different CPPs, in the same groups of mice as described above Elispot assay was performed on spleen cells stimulated with SIINFEKL OVACD8 peptide (SEQ ID NO: 35) nine days after the 5$^{th}$ vaccination in order to quantify IFN-γ producing cells.

The results are shown in FIG. 42A. Mice vaccinated with Z13Mad5Anaxa showed a significant increase in IFN-γ producing cells compared to naïve mice. Mice vaccinated with Z14Mad5Anaxa showed also an increase in IFN-γ producing cells compared to naïve mice, however, the increase was not significant, which may be due to the low number of mice (3 mice in Z14Mad5Anaxa group).

To investigate the CD4 T cell responses after vaccination with complexes with different CPPs, in the same groups of mice as described above Elispot assay was performed on spleen cells stimulated with OVACD4 peptide (SEQ ID NO: 36) nine days after the 5$^{th}$ vaccination in order to quantify IFN-γ producing cells.

The results are shown in FIG. 42B. Mice vaccinated with Z13Mad5Anaxa showed a highly significant increase in IFN-γ producing cells compared to naïve mice. Mice vaccinated with Z14Mad5Anaxa showed also an increase in IFN-γ producing cells compared to naïve mice, however, the increase was not significant, which may be due to the low number of mice (3 mice in Z14Mad5Anaxa group).

In addition, in the above described groups of mice, intracellular staining was performed on spleen cells stimulated with SIINFEKL OVACD8 peptide (SEQ ID NO: 35) to identify CD107a⁺IFN-γ⁺TNF-α⁺ cells. Results are shown in FIG. 43. Mice vaccinated with Z13Mad5Anaxa or with Z14Mad5Anaxa showed a similar increase in CD107a⁺IFN-γ⁺ TNF-α⁺ cells.

Example 27: Comparison of the Effect of Complexes Having Different Cell Penetrating Peptides on Tumor Growth and Survival in the EG.7-OVA s.c. Model To investigate the effects of complexes having different cell penetrating peptides on tumor growth and survival the EG.7-OVA s.c. model was used. On do C57BL/6 mice were implanted s.c. with $3 \times 10^5$ EG7-OVA tumor cells in the left flank and assigned to three different groups (naïve, Z13Mad5Anaxa and Z14Mad5Anaxa). Mice were vaccinated twice at d5 and d13 after tumor implantation by s.c. injection of either 0.5 nmol of Z13Mad5Anaxa or Z14Mad5Anaxa in the right flank.

Results are shown in FIG. 44. Vaccination with Z13Mad5Anaxa or with Z14Mad5Anaxa resulted in significantly decreased tumor volumes compared to control mice (FIG. 44 A) as well as to significantly increased survival rates compared to control mice (FIG. 44 B). Those results indicate that both complexes, Z13Mad5Anaxa and Z14Mad5Anaxa, are able to significantly decrease tumor growth and to significantly prolong survival.

Example 28: Comparison of the Immune Responses after Vaccination with Complexes Having Different Cell Penetrating Peptides In this experiment the effect of different CPPs in the complex for use according to the present invention was investigated by using a complex with the TLR agonist "EDA". Therefore, the fusion protein EDAZ 13Mad5 as described above (cf. Example 1) was used.

In addition, further fusion proteins were designed, which comprise CPPs other than Z13—namely Z14 (SEQ ID NO: 7) or Z18 (SEQ ID NO: 11). Those fusion proteins also comprise the protein "MAD5", which consists of different $CD8^+$ and $CD4^+$ epitopes from various antigens, and the TLR4 peptide agonist "EDA". Accordingly, the following constructs were additionally designed:

```
EDAZ14Mad5
Sequence:
                                         (SEQ ID NO: 37)
MHHHHHHNID RPKGLAFTDV DVDSIKIAWE SPQGQVSRYR

VTYSSPEDGI RELFPAPDGE DDTAELQGLR PGSEYTVSVV

ALHDDMESQP LIGIQSTKRY KNRVASRKSR AKFKQLLQHY

REVAAAKESL KISQAVHAAH AEINEAGREV VGVGALKVPR

NQDWLGVPRF AKFASFEAQG ALANIAVDKA NLDVEQLESI

INFEKLTEWT GS

EDAZ18Mad5
Sequence:
                                         (SEQ ID NO: 38)
MHHHHHHNID RPKGLAFTDV DVDSIKIAWE SPQGQVSRYR

VTYSSPEDGI RELFPAPDGE DDTAELQGLR PGSEYTVSVV

ALHDDMESQP LIGIQSTREV AAAKSSENDR LRLLLKESLK

ISQAVHAAHA EINEAGREVV GVGALKVPRN QDWLGVPRFA

KFASFEAQGA LANIAVDKAN LDVEQLESII NFEKLTEWTG

S
```

C57BL/6 mice were assigned to eight different groups (4 mice per group): three groups receiving 2 nmol of either EDAZ13Mad5, EDAZ14Mad5 or EDAZ18Mad5 and a respective control and three groups receiving 0.5 nmol of either EDAZ13Mad5, EDAZ14Mad5 or EDAZ18Mad5 and a respective control group. The mice were vaccinated three times (Week0, Week2 and Week4) s.c. Mice were bled 7 days after the $2^{nd}$ and $3^{rd}$ vaccination and multimer staining was performed (one experiment with 4 mice per group).

The results are shown in FIG. 45. All groups vaccinated with EDAZ13Mad5, EDAZ14Mad5 or EDAZ18Mad5 showed an increased percentage of multimer-positive cells compared to the control group. These results indicate that complexes according to the present invention having different cell penetrating peptides are able to elicit an immune response at different doses.

Example 29: Effect of EDAZ14Mad5 on Tumor Growth and Survival in the EG.7-OVA s.c. Model To investigate the effect of EDAZ 14Mad5 on tumor growth and survival the EG.7-OVA s.c. model was used (cf. Example 4 and FIGS. 9-11 for the effect of EDAZ13Mad5 in the same model).

On do C57BL/6 mice were implanted s.c. with $3 \times 10^5$ EG7-OVA tumor cells in the left flank and assigned to two different groups (naïve and EDAZ14Mad5). Mice were vaccinated twice at d5 and d13 after tumor implantation by s.c. injection of 0.5 nmol of EDAZ14Mad5 in the right flank.

Results are shown in FIG. 46. Similarly to EDAZ13Mad5 (cf. Example 4, FIGS. 9-11) vaccination with EDAZ14Mad5 resulted in significantly decreased tumor volumes compared to control mice (FIG. 46 A) as well as to significantly increased survival rates compared to control mice (FIG. 46 B). Those results indicate that EDAZ14Mad5 is able to significantly decrease tumor growth and to significantly prolong survival—similarly to EDAZ13Mad5 (cf. Example 4, FIGS. 9-11).

Example 30: Superior Efficacy of Z13Mad5Anaxa Fusion Construct Compared to Z13Mad5 and Anaxa in a Glioblastoma Model To investigate the efficacy of a complex according to the present invention the glioblastoma model was chosen (cf. Example 20). Namely, Z13Mad5Anaxa (cf. Example 7; SEQ ID NO: 28) was administered to one group of mice, whereas Z13Mad5 (SEQ ID NO: 29) and Anaxa (SEQ ID NO: 15) were administered (both together) to another group of mice.

T cell homing at the tumor site was analyzed in Gl261-Quad tumor-bearing mice (7-16 mice per group) vaccinated twice, namely at day 7 and at day 21 after tumor implantation (day 0), with 2 nmol Z13Mad5Anaxa vaccine. A group vaccinated with both, Z13Mad5 and Anaxa (equimolar to Z13Mad5Anaxa), was used as control. Briefly, C57BL/6 mice were implanted i.e. (intracranially) with $5 \times 10^5$ Gl261-Quad tumor cells and vaccinated twice (at d7 and d21 following implantation) by s.c. injection of 2 nmol of Z13Mad5Anaxa (group 1) or 2 nmol of Z13Mad5 and 2 nmol of Anaxa (group 2). At day 28, the blood and the brain infiltrating leukocytes (BILs) were analyzed, whereby SIIN-FEKL-specific CD8 T cells were quantified in blood and in BILs at d28 by multimer staining (7-16 mice per group).

Results are shown in FIG. 47. A significantly higher percentage of SIINFEKL-specific CD8 T cells was observed in the blood of Z13Mad5Anaxa-vaccinated mice as compared to mice vaccinated with both, Z13Mad5 and Anaxa (FIG. 47A). Similarly, a stronger accumulation of SIIN- FEKL-specific CD8 T cells was observed in the BILs of Z13Mad5Anaxa-vaccinated mice as compared to mice vaccinated with Z13Mad5 and Anaxa separately (FIG. 47B, p=a.o539).

Next, cytokine secretion was assessed. To this end, C57BL/6 mice were implanted i.e. with 5×10⁵ Gl261-Quad tumor cells and vaccinated twice (d7 and 21) by s.c. injection of 2 nmol of Z13Mad5Anaxa or 2 nmol of Z13Mad5 and 2 nmol of Anaxa. BILs were isolated and cultured during 6 h with matured BMDCs loaded or not with SIINFEKL peptide (SEQ ID NO: 35) in presence of BrefeldinA before intracellular staining for cytokines.

Results are shown in FIG. 48. In general, a high level of cytokine secretion was observed for brain-infiltrating CD8 T cells from mice vaccinated with Z13Mad5Anaxa. In particular, a significantly higher secretion of total IFN-γ and of IFN-γ and TNF-α together was observed for brain-infiltrating CD8 T cells from mice vaccinated with Z13Mad5Anaxa as compared to mice vaccinated with Z13Mad5 and Anaxa separately.

Taken together, these results demonstrate that Z13Mad5Anaxa vaccine (as compared to Z13Mad5 and Anaxa administered separately) was able to elicit a stronger SIINFEKL specific CD8 T cell immune response in the brain of tumor-bearing mice with potent effector function.

The results obtained are indicating that Z13Mad5Anaxa is efficacious for eliciting high brain infiltrating SIINFEKL-specific CD8 immune response. Z13Mad5Anaxa is able to promote the secretion of cytokine by antigen-specific CD8 T cells in the brain.

Example 31: Effect of Another Antigenic Cargo in the Complex According to the Present Invention To investigate the effect of a different antigenic cargo ("Mad8"), another complex comprising a cell penetrating peptide, different antigens and a TLR peptide agonist was designed ("Z13Mad8Anaxa"). Z13Mad8Anaxa differs from Z13Mad5Anaxa (described in Example 7) in the antigenic cargoes. In particular, "Z13Mad8Anaxa" is a fusion protein comprising the cell-penetrating peptide "Z13", the antigenic cargo "MAD8" comprising CD8 and CD4 epitopes of glycoprotein 70, and the TLR peptide agonist "Anaxa". In the following, the amino acid sequence of Z13Mad8Anaxa is shown with the cell-penetrating peptide "Z13" shown underlined and the TLR peptide agonist "Anaxa" shown in italics:

```
                                  (SEQ ID NO: 39)
KRYKNRVASR KSRAKFKQLL QHYREVAAAK SSENDRLRLLLK

VTYHSPSYAY HQFERRAILN RLVQFIKDRI SVVQALVLTS

TVHEILCKLS LEGDHSTPPS AYGSVKPYTN FDAE
```

Naïve Balb/c mice (4 mice per group) were vaccinated four times s.c. (week0, week2, week4 and week6 with 2 nmol of Z13Mad8Anaxa.

To investigate the CD4 T cell responses after vaccination, one week after the 4th vaccination, mice were euthanized; organs recovered and ex vivo Elispot assay was performed on spleen cells stimulated with gp70CD4 peptide (SEQ ID NO: 64) or gp70CD8 peptide (SEQ ID NO: 65) in order to quantify IFN-γ-producing epitope-specific CD4 and CD8 T cells.

The results are shown in FIG. 49. Mice vaccinated with Z13Mad8Anaxa showed a significant increase in IFN-γ-producing cells compared to naïve mice. These data show that Z13Mad8Anaxa vaccine was able to elicit potent epitope-specific CD8 and CD4 T cell immune response and thus that the complex according to the present invention is able to elicit self-antigen immune response.

Example 32: Effect of Another Antigenic Cargo in the Complex According to the Present Invention To investigate the effect of a further different antigenic cargo ("Mad11"), another complex comprising a cell penetrating peptide, different antigens and a TLR peptide agonist was designed ("Z13Mad11Anaxa"). Z13Mad11Anaxa differs from Z13Mad5Anaxa (described in Example 7) in the antigenic cargoes. In particular, "Z13Mad11Anaxa" is a fusion protein comprising the cell-penetrating peptide "Z13", the antigenic cargo "MAD11" comprising two CD8 epitopes of surviving as described in Derouazi M, Wang Y, Marlu R, et al. Optimal epitope composition after antigen screening using a live bacterial delivery vector: Application to TRP-2. Bioengineered Bugs. 2010; 1(1):51-60. doi: 10.4161/bbug.1.1.9482, and the TLR peptide agonist "Anaxa". In the following, the amino acid sequence of Z13Mad11Anaxa is shown:

```
                                  (SEQ ID NO: 40)
KRYKNRVASRKSRAKFKQLLQHYREVAAAKSSENDRLRLLLKNYRIAT

FKNWPFLEDCAMEELTVSEFLKLDRQRSTVHEILCKLSLEGDHSTPPS

AYGSVKPYTNFDAE
```

Naïve C57BL/6 mice (5 mice per group) were implanted i.v. with 1×10 B16 melanoma tumor cells and vaccinated twice (d0 and d10) by subcutaneous injection of 1 nmol of Z13Mad11Anaxa.

On day18 mice were euthanized, organs recovered and ex vivo Elispot assay was performed on spleen cells stimulated with survivin peptides survivin20-28 (SEQ ID NO: 67) and survivin97-104: (SEQ ID NO: 68) in order to quantify IFN-γ producing survivin-specific T cells.

The results are shown in FIG. 50. Mice vaccinated with Z13Mad 11Anaxa showed less metastasis compared to naïve mice (FIG. 50A). Moreover, in the spleen of mice vaccinated with Z13Mad11Anaxa significantly higher numbers of IFN-γ producing survivin-specific T cells were observed (FIG. 49B).

The results obtained show that Z13Mad11Anaxa is efficacious for reducing the number of metastasis and Z13Mad I 1Anaxa is able to promote the secretion of cytokines by antigen-specific CD8 T cells in the spleen.

Example 33: Effect of Another Antigenic Cargo in the Complex According to the Present Invention To investigate the effect of a further different antigenic cargo ("Mad9"), another complex comprising a cell penetrating peptide, a different antigen and a TLR peptide agonist was designed ("Z13Mad9Anaxa"). Z13Mad9Anaxa differs from Z13Mad5Anaxa (described in Example 7) in the antigenic cargo. In particular, "Z13Mad9Anaxa" is a fusion protein comprising the cell-penetrating peptide "Z13", the antigenic cargo "Mad9" comprising the neoantigen as identified by Yadav et al. Nature. 2014 Nov. 27; 515(7528):572-6 from MC-38 tumor cell line, and the TLR peptide agonist "Anaxa". In the following, the amino acid sequence of Z13Mad9Anaxa is shown with the cell-penetrating peptide "Z13" shown underlined and the TLR peptide agonist "Anaxa" shown in italics:

```
                                                    (SEQ ID NO: 41)
KRYKNRVASRKSRAKFKQLLQHYREVAAAKSSENDRLRLLLKHLELAS

MTNMELMSSIVSTVHEILCKLSLEGDHSTPPSAYGSVKPYTNFDAE
```

Naïve C57BL/6 mice (4 mice per group) were vaccinated four times s.c. (week0, week2, week4 and week6 with 2 nmol of Z13Mad9Anaxa. To investigate the CD8 T cell responses after vaccination, one week after the 4$^{th}$ vaccination, mice were euthanized, organs recovered and Elispot assay was performed on spleen cells after a 7-day in vitro restimulation with stimulated with adpgk peptide (SEQ ID NO: 66) in order to quantify to quantify IFN-γ-producing epitope-specific CD8 T cells.

The results are shown in FIG. 51. Mice vaccinated with Z13Mad9Anaxa showed a significant increase in effector neoantigen-specific CD8 T cells compared to naïve mice.

Example 34: Comparison of the Immune Responses after Vaccination with Complexes Having Different Cell Penetrating Peptides In this experiment the effect of a further different CPP in the complex according to the present invention was investigated by using a complex with the TLR agonist "Anaxa". Therefore, the fusion protein Z13Mad5Anaxa as described above (cf. Example 7, SEQ ID NO: 28) was used.

In addition, a further fusion protein was designed, which comprise the TAT CPP combined to furin linkers as described in Lu et al., Multiepitope trojan antigen peptide vaccines for the induction of antitumor CTL and Th immune responses J. Immunol., 172 (2004), pp. 4575-4582. That fusion protein also comprises the protein "MAD5", which consists of different CD8$^+$ and CD4$^+$ epitopes from various antigens, and the TLR4 peptide agonist "Anaxa". Accordingly, the following construct was additionally designed:

```
TatFMad5Anaxa
Sequence:
                                                    (SEQ ID NO: 46)
RKKRRQRRRRVKRISQAVHAAHAEINEAGRRVKRKVPRNQDWLRVKRA

SFEAQGALANIAVDKARVKRSIINFEKLRVKRSTVHEILCKLSLEGDH

STPPSAYGSVKPYTNFDAE
```

C57BL/6 mice were assigned to three different groups (8 mice per group): one group receiving 2 nmol of Z13Mad5Anaxa, one group receiving 2 nmol of TatFMad5Anaxa and a respective control. The mice were vaccinated two times (Week0 and Week2) s.c. with either 2 nmol of Z13Mad5Anaxa or 2 nmol of TatFMad5Anaxa. Mice were bled 7 days after the 2$^{nd}$ vaccination and multimer staining was performed (8 mice per group).

The results are shown in FIG. 52. Mice vaccinated with Z13Mad5Anaxa or TatFMad5Anaxa showed an increased percentage of multimer-positive cells compared to the control group. These results indicate that complexes according to the present invention having different cell penetrating peptides are able to elicit an immune response at different doses. However, the CPP derived from ZEBRA (Z13) was better than the TAT CPP.

Example 35: Superior Efficacy of Z13Mad5Anaxa Fusion Construct Compared to Z13Mad5 and Anaxa in Naïve Mice Next, the efficacy of a complex according to the present invention was investigated in naïve mice. Namely, Z13Mad5Anaxa (cf. Example 7; SEQ ID NO: 28) was administered to one group of mice, whereas Z13Mad5 (SEQ ID NO: 29) and Anaxa (SEQ ID NO: 15) were administered (both together) to another group of mice.

C57BL/6 mice of the Z13Mad5Anaxa group and of the Z13Mad5+Anaxa group were vaccinated once (Week0) by s.c. injection of 2 nmol of Z13Mad5Anaxa (group 1) or 2 nmol of Z13Mad5 and 2 nmol of Anaxa (group 2). At day 14, the blood was analyzed, whereby SIINFEKL-specific CD8 T cells were quantified in blood by multimer staining (4-8 mice per group).

Results are shown in FIG. 53. A significantly higher percentage of SIINFEKL-specific CD8 T cells was observed in the blood of Z13Mad5Anaxa-vaccinated mice as compared to mice vaccinated with Z13Mad5 and Anaxa separately (FIG. 53).

Taken together, these results demonstrate that Z13Mad5Anaxa vaccine (as compared to Z13Mad5 and Anaxa administered separately) was able to elicit a stronger SIINFEKL specific CD8 T cell immune response in the periphery.

Example 36: Effect of Another Antigenic Cargo in the Complex According to the Present Invention To investigate the effect of a further different antigenic cargo ("Mad12"), another complex comprising a cell penetrating peptide, a different antigen and a TLR peptide agonist was designed ("Z13Mad12Anaxa"). Z13Mad12Anaxa differs from Z13Mad5Anaxa (described in Example 7) in the antigenic cargo. In particular, "Z13Mad12Anaxa" is a fusion protein comprising the cell-penetrating peptide "Z13", the antigenic cargo "MAD12" comprising three neoantigens as identified by Yadav et al. Nature. 2014 Nov. 27; 515(7528):572-6 from MC-38 tumor cell line, and the TLR peptide agonist "Anaxa". In the following, the amino acid sequence of Z13Mad12Anaxa is shown:

```
                                                    (SEQ ID NO: 69)
KRYKNRVASRKSRAKFKQLLQHYREVAAAKSSENDRLRLLLKLFRAAQ

LANDVVLQIMEHLELASMTNMELMSSIVVISASIIVFNLLELEGSTVH

EILCKLSLEGDHSTPPSAYGSVKPYTNFDAE
```

Naïve C57BL/6 mice (4 mice per group) were vaccinated twice s.c. (week0, week2) with 2 nmol of Z13Mad12Anaxa. To investigate the CD8 T cell responses after vaccination, one week after the 2$^{nd}$ vaccination, the blood was analyzed, whereby neoantigen reps1-specific CD8 T cells were quantified in blood by multimer staining (4 mice per group).

The results are shown in FIG. 54. Mice vaccinated with Z13Mad12Anaxa showed a significant increase in effector neoantigen-specific CD8 T cells compared to naïve mice.

Example 37: In Vitro Human Dendritic Cell Maturation

The goal of this study was to investigate the capacity of a complex for use according to the present invention ("Z13Mad5Anaxa", SEQ ID NO: 28, cf. Example 7) to induce maturation of dendritic cells in comparison to a complex lacking a TLR peptide agonist ("Z13Mad5", SEQ ID NO: 29, cf. Example 1).

The Z13Mad5Anaxa polypeptide and the Z13Mad5 polypeptide were investigated for their capacity to induce human dendritic cell (DC) maturation. After incubation over night with 300 nM of protein, activation markers expression (CD86, CD80, CD83 and HLA-DR) was assessed on the human DCs by FACS (FIG. 55). Same buffer volumes of each protein were used as negative controls.

Results are shown in FIG. 55. Whereas Z13Mad5Anaxa induced maturation of human DCs, shown by the up-regulation of CD86, HLADR and CD83, Z13Mad5 was not able to activate human DCs. These results indicate that the Anaxa portion of the protein is responsible for the up-regulation of the activation markers on the human DCs.

| TABLE OF SEQUENCES AND SEQ ID NUMBERS (SEQUENCE LISTING): | | |
|---|---|---|
| SEQ ID NO | Sequence | Remarks |
| SEQ ID NO: 1 | RQIKIYFQNRRMKWKK | CPP: Penetratin |
| SEQ ID NO: 2 | YGRKKRRQRRR | CPP: TAT minimal |
| SEQ ID NO: 3 | MMDPNSTSEDVKFTPDPYQVPFVQAFDQAT RVYQDLGGPSQAPLPCVLWPVLPEPLPQGQL TAYHVSTAPTGSWFSAPQPAPENAYQAYAA PQLFPVSDITQNQQTNQAGGEAPQPGDNST VQTAAAVVFACPGANQGQQLADIGVPQPAP VAAPARRTRKPQQPESLEECDSELEIKRYKN RVASRKCRAKFKQLLQHYREVAAAKSSENDR LRLLLKQMCPSLDVDSIIPRTPDVLHEDLLNF | ZEBRA amino acid sequence (natural sequence from Epstein-Barr virus (EBV)) (YP_401673) |
| SEQ ID NO: 4 | KRYKNRVASRKCRAKFKQLLQHYREVAAAK SSENDRLRLLLKQMC | CPP1 (Z11) |
| SEQ ID NO: 5 | KRYKNRVASRKCRAKFKQLLQHYREVAAAK SSENDRLRLLLK | CPP2 (Z12) |
| SEQ ID NO: 6 | KRYKNRVASRKSRAKFKQLLQHYREVAAAKS SENDRLRLLLK | CPP3 (Z13) |
| SEQ ID NO: 7 | KRYKNRVASRKSRAKFKQLLQHYREVAAAK | CPP4 (Z14) |
| SEQ ID NO: 8 | KRYKNRVASRKSRAKFK | CPP5 (Z15) |
| SEQ ID NO: 9 | QHYREVAAAKSSEND | CPP6 (Z16) |
| SEQ ID NO: 10 | QLLQHYREVAAAK | CPP7 (Z17) |
| SEQ ID NO: 11 | REVAAAKSSENDRLRLLLK | CPP8 (Z18) |
| SEQ ID NO: 12 | KRYKNRVA | CPP9 (Z19) |
| SEQ ID NO: 13 | VASRKSRAKFK | CPP10 (Z20) |
| SEQ ID NO: 14 | ESLKISQAVHAAHAEINEAGREVVGVG ALKVPRNQDWLGVPRFAKFASFEAQG ALANIAVDKANLDVEQLESIINFEKLT | MAD5 cargo |
| SEQ ID NO: 15 | STVHEILCKLSLEGDHSTPPSAYGSVKPYTNF DAE | TLR2 peptide agonist Anaxa |
| SEQ ID NO: 16 | DDDK | enterokinase target site |
| SEQ ID NO: 17 | IEDGR | factor Xa target site |
| SEQ ID NO: 18 | LVPRGS | thrombin target site |
| SEQ ID NO: 19 | ENLYFQG | protease TEV target site |
| SEQ ID NO: 20 | LEVLFQGP | PreScission protease target site |
| SEQ ID NO: 21 | RX(R/K)R | furin target site |
| SEQ ID NO: 22 | GGGGG | peptidic linker |
| SEQ ID NO: 23 | GGGG | peptidic linker |
| SEQ ID NO: 24 | EQLE | peptidic linker |
| SEQ ID NO: 25 | TEWT | peptidic linker |
| SEQ ID NO: 26 | MHHHHHHNIDRPKGLAFTDVDVDSIK | EDAZ13Mad5 |

TABLE OF SEQUENCES AND SEQ ID NUMBERS (SEQUENCE LISTING):

| SEQ ID NO | Sequence | Remarks |
|---|---|---|
| | IAWESPQGQVSRYRVTYSSPEDGIREL FPAPDGEDDTAELQGLRPGSEYTVSVV ALHDDMESQPLIGIQSTKRYKNRVASR KSRAKFKQLLQHYREVAAAKSSENDRL RLLLKESLKISQAVHAAHAEINEAGREV VGVGALKVPRNQDWLGVPRFAKFASF EAQGALANIAVDKANLDVEQLESIINFE KLTEWTGS | |
| SEQ ID NO: 27 | MHHHHHHSTVHEILCKLSLEGDHSTPP SAYGSVKPYTNFDAEKRYKNRVASRKS RAKFKQLLQHYREVAAAKSSENDRLRL LLKESLKISQAVHAAHAEINEAGREVVG VGALKVPRNQDWLGVPRFAKFASFEA QGALANIAVDKANLDVEQLESIINFEKL TEWTGS | AnaxaZ13Mad5 |
| SEQ ID NO: 28 | MHHHHHHKRYKNRVASRKSRAKFQLL QHYREVAAAKSSENDRLRLLLKESLKISQ AVHAAHAEINEAGREVVGVGALKVPRNQ DWLGVPRFAKFASFEAQGALANIAVDKA NLDVEQLESIINFEKLTEWTGSSTVHEIL CKLSLEGDHSTPPSAYGSVKPYTNFDAE | Z13Mad5Anaxa |
| SEQ ID NO: 29 | MHHHHHHKRYKNRVASRKSRAKFQL LQHYREVAAAKSSENDRLRLLLKESLKI SQAVHAAHAEINEAGREVVGVGALKVP RNQDWLGVPRFAKFASFEAQGALANIA VDKANLDVEQLESIINFEKLTEWTGS | Z13Mad5 |
| SEQ ID NO: 30 | MHHHHHHESLKISQAVHAAHAEINEAGR EVVGVGALKVPRNQDWLGVPRFAKFASF EAQGALANIAVDKANLDVEQLESIINFEKL TEWTGS | Mad5 |
| SEQ ID NO: 31 | MHHHHHHNIDRPKGLAFTDVDVDSIK IAWESPQGQVSRYRVTYSSPEDGIRELF PAPDGEDDTAELQGLRPGSEYTVSVVA LHDDMESQPLIGIQSTESLKISQAVHAA HAEINEAGREVVGVGALKVPRNQDWL GVPRFAKFASFEAQGALANIAVDKANL DVEQLESIINFEKLTEWTGS | EdaMad5 |
| SEQ ID NO: 32 | MHHHHHHESLKISQAVHAAHAEINEA GREVVGVGALKVPRNQDWLGVPRFA KFASFEAQGALANIAVDKANLDVEQLE SIINFEKLTEWTGSSTVHEILCKLSLEG DHSTPPSAYGSVKPYTNFDAE | Mad5Anaxa |
| SEQ ID NO: 33 | MHHHHHHKRYKNRVASRKSRAKFQ LLQHYREVAAAKESLKISQAVHAAHAE INEAGREVVGVGALKVPRNQDWLGV PRFAKFASFEAQGALANIAVDKANLD VEQLESIINFEKLTEWTGSSTVHEILC KLSLEGDHSTPPSAYGSVKPYTNFDAE | Z14 Mad5Anaxa |
| SEQ ID NO: 34 | MHHHHHHREVAAAKSSENDRLRLLLK ESLKISQAVHAAHAEINEAGREVVGVG ALKVPRNQDWLGVPRFAKFASFEAQG ALANIAVDKANLDVEQLESIINFEKLTE WTGSSTVHEILCKLSLEGDHSTPPSAY GSVKPYTNFDAE | Z18 Mad5Anaxa |
| SEQ ID NO: 35 | SIINFEKL | SIINFEKL OVACD8 |
| SEQ ID NO: 36 | ISQAVHAAHAEINEAGR | OVACD4 peptide |
| SEQ ID NO: 37 | MHHHHHHNIDRPKGLAFTDVDVDSIK IAWESPQGQVSRYRVTYSSPEDGIREL FPAPDGEDDTAELQGLRPGSEYTVSV VALHDDMESQPLIGIQSTKRYKNRVAS RKSRAKFKQLLQHYREVAAAKESLKISQ AVHAAHAEINEAGREVVGVGALKVPR NQDWLGVPRFAKFASFEAQGALANIA VDKANLDVEQLESIINFEKLTEWTGS | EDAZ14Mad5 |

TABLE OF SEQUENCES AND SEQ ID NUMBERS (SEQUENCE LISTING):

| SEQ ID NO | Sequence | Remarks |
|---|---|---|
| SEQ ID NO: 38 | MHHHHHHNIDRPKGLAFTDVDVDSIKI AWESPQGQVSRYRVTYSSPEDGIRELFP APDGEDDTAELQGLRPGSEYTVSVVAL HDDMESQPLIGIQSTREVAAAKSSENDR LRLLLKESLKISQAVHAAHAEINEAGREV VGVGALKVPRNQDWLGVPRFAKFASFE AQGALANIAVDKANLDVEQLESIINFEKL TEWTGS | EDAZ18Mad5 |
| SEQ ID NO: 39 | KRYKNRVASRKSRAKFKQLLQHYREVAA AKSSENDRLRLLLKVTYHSPSYAYHQFE RRAILNRLVQFIKDRISVVQALVLTSTVH EILCKLSLEGDHSTPPSAYGSVKPYTN FDAE | Z13Mad8Anaxa |
| SEQ ID NO: 40 | KRYKNRVASRKSRAKFKQLLQHYREVA AAKSSENDRLRLLLKNYRIATFKNWPF LEDCAMEELTVSEFLKLDRQRSTVHEI LCKLSLEGDHSTPPSAYGSVKPYTNFD | Z13Mad11Anaxa |
| SEQ ID NO: 41 | KRYKNRVASRKSRAKFKQLLQHYREVAAAKS SENDRLRLLLKHLELASMTNMELMSSIVSTV HEILCKLSLEGDHSTPPSAYGSVKPYTNFDAE | Z13Mad9Anaxa |
| SEQ ID NO: 42 | HLELASMTNMELMSSIV | Mad9 |
| SEQ ID NO: 43 | VTYHSPSYAYHQFERRAILN RLVQFIKDRISVVQALVLT | Mad8 |
| SEQ ID NO: 44 | NYRIATFKNWPFLEDCAMEELTVSEF | Mad11 |
| SEQ ID NO: 45 | NIDRPKGLAFTDVDVDSIKIAWESPQGQVSR YRVTYSSPEDGIRELFPAPDGEDDTAELQGL RPGSEYTVSVVALHDDMESQPLIGIQST | EDA |
| SEQ ID NO: 46 | RKKRRQRRRRVKRISQAVHAAHAEINEAGRR VKRKVPRNQDWLRVKRASFEAQGALANIAV DKARVKRSIINFEKLRVKRSTVHEILCKLSLEG DHSTPPSAYGSVKPYTNFDAE | TatFMad5Anaxa |
| SEQ ID NO: 47 | MAPPQVLAFGLLLAAATATFAAAQEECVCEN YKLAVNCFVNNNRQCQCTSVGAQNTVICSKL AAKCLVMKAEMNGSKLGRRAKPEGALQNND GLYDPDCDESGLFKAKQCNGTSMCWCVNTA GVRRTDKDTEITCSERVRTYWIIIELKHKARE KPYDSKSLRTALQKEITTRYQLDPKFITSILYE NNVITIDLVQNSSQKTQNDVDIADVAYYFEK DVKGESLFHSKKMDLTVNGEQLDLDPGQTLI YYVDEKAPEFSMQGLKAGVIAVIVVVVIAVVA GIVVLVISRKKRMAKYEKAEIKEMGEMHREL NA | EpCAM |
| SEQ ID NO: 48 | GLKAGVIAV | EpCAM epitope |
| SEQ ID NO: 49 | MTPGTQSPFFLLLLLTVLTVVTGSGHASSTP GGEKETSATQRSSVPSSTEKNAVSMTSSVLSS HSPGSGSSTTQGQDVTLAPATEPASGSAATW GQDVTSVPVTRPALGSTTPPAHDVTSAPDNK PAPGSTAPPAHGVTSAPDTRPAPGSTAPPAH GVTSAPDTRPAPGSTAPPAHGVTSAPDTRPA PGSTAPPAHGVTSAPDTRPAPGSTAPPAHGV TSAPDTRPAPGSTAPPAHGVTSAPDTRPAPG STAPPAHGVTSAPDTRPAPGSTAPPAHGVTS APDTRPAPGSTAPPAHGVTSAPDTRPAPGST APPAHGVTSAPDTRPAPGSTAPPAHGVTSAP DTRPAPGSTAPPAHGVTSAPDTRPAPGSTAP PAHGVTSAPDTRPAPGSTAPPAHGVTSAPDT RPAPGSTAPPAHGVTSAPDTRPAPGSTAPPA HGVTSAPDTRPAPGSTAPPAHGVTSAPDTRP APGSTAPPAHGVTSAPDTRPAPGSTAPPAHG VTSAPDTRPAPGSTAPPAHGVTSAPDTRPAP GSTAPPAHGVTSAPDTRPAPGSTAPPAHGVT SAPDTRPAPGSTAPPAHGVTSAPDTRPAPGS TAPPAHGVTSAPDTRPAPGSTAPPAHGVTSA | MUC-1 |

-continued

| SEQ ID NO | Sequence | Remarks |
|---|---|---|
| | PDTRPAPGSTAPPAHGVTSAPDTRPAPGSTA<br>PPAHGVTSAPDTRPAPGSTAPPAHGVTSAPD<br>TRPAPGSTAPPAHGVTSAPDTRPAPGSTAPP<br>AHGVTSAPDTRPAPGSTAPPAHGVTSAPDTR<br>PAPGSTAPPAHGVTSAPDTRPAPGSTAPPAH<br>GVTSAPDTRPAPGSTAPPAHGVTSAPDTRPA<br>PGSTAPPAHGVTSAPDTRPAPGSTAPPAHGV<br>TSAPDTRPAPGSTAPPAHGVTSAPDTRPAPG<br>STAPPAHGVTSAPDTRPAPGSTAPPAHGVTS<br>APDTRPAPGSTAPPAHGVTSAPDTRPAPGST<br>APPAHGVTSAPDNRPALGSTAPPVHNVTSAS<br>GSASGSASTLVHNGTSARATTTPASKSTPFSI<br>PSHHSDTPTTLASHSTKTDASSTHHSSVPPLT<br>SSNHSTSPQLSTGVSFFFLSFHISNLQFNSSLE<br>DPSTDYYQELQRDISEMFLQIYKQGGFLGLS<br>NIKFRPGSVVVQLTLAFREGTINVHDVETQF<br>NQYKTEAASRYNLTISDVSVSDVPFPFSAQSG<br>AGVPGWGIALLVLVCVLVALAIVYLIALAVCQ<br>CRRKNYGQLDIFPARDTYHPMSEYPTYHTH<br>GRYVPPSSTDRSPYEKVSAGNGGSSLSYTNPA<br>VAATSANL | |
| SEQ ID NO: 50 | GSTAPPVHN | MUC-1 epitope |
| SEQ ID NO: 51 | TAPPAHGVTS | MUC-1 epitope |
| SEQ ID NO: 52 | MGAPTLPPAWQPFLKDHRISTFKNWPFLEG<br>CACTPERMAEAGFIHCPTENEPDLAQCFFCF<br>KELEGWEPDDDPIEEHKKHSSGCAFLSVKKQ<br>FEELTLGEFLKLDRERAKNKIAKETNNKKKE<br>FEETAKKVRRAIEQLAAMD | survivin |
| SEQ ID NO: 53 | RISTFKNWPF | survivin epitope |
| SEQ ID NO: 54 | MESPSAPPHRWCIPWQRLLLTASLLTFWNPPT<br>TAKLTIESTPFNVAEGKEVLLLVHNLPQHLFG<br>YSWYKGERVDGNRQIIGYVIGTQQATPGPAYS<br>GREIIYPNASLLIQNIIQNDTGFYTLHVIKSDLV<br>NEEATGQFRVYPELPKPSISSNNSKVEDKDAV<br>AFTCEPETQDATYLWWVNNQSLPVSPRLQLS<br>NGNRTLTLFNVTRNDTASYKCETQNPVSARRS<br>DSVILNVLYGPDAPTISPLNTSYRSGENLNLSC<br>HAASNPPAQYSWFVNGTFQQSTQELFIPNITV<br>NNSGSYTCQAHNSDTGLNRTTVTTITVYAEPP<br>KPFITSNNSNPVEDEDAVALTCEPEIQNTTYL<br>WWVNNQSLPVSPRLQLSNDNRTLTLLSVTRN<br>DVGPYECGIQNKLSVDHSDPVILNVLYGPDDP<br>TISPSYTYYRPGVNLSLSCHAASNPPAQYSWLI<br>DGNIQQHTQELFISNITEKNSGLYTCQANNSAS<br>GHSRTTVKTITVSAELPKPSISSNNSKPVEDKDA<br>VAFTCEPEAQNTTYLWWVNGQSLPVSPRLQLS<br>NGNRTLTLFNVTRNDARAYVCGIQNSVSANRS<br>DPVTLDVLYGPDTPIISPPDSSYLSGANLNLSCH<br>SASNPSPQYSWRINGIPQQHTQVLFIAKITPNN<br>NGTYACFVSNLATGRNNSIVKSITVSASGTSPG<br>LSAGATVGIMIGVLVGVAL | CEA |
| SEQ ID NO: 55 | YLSGANLNLS | CEA epitope |
| SEQ ID NO: 56 | SWRINGIPQQ | CEA epitope |
| SEQ ID NO: 57 | MTEYKLVVVGAGGVGKSALTIQLIQNHFVDE<br>YDPTIEDSYRKQVVIDGETCLLDILDTAGQEE<br>YSAMRDQYMRTGEGFLCVFAINNTKSFEDIH<br>HYREQIKRVKDSEDVPMVLVGNKCDLPSRTV<br>DTKQAQDLARSYGIPFIETSAKTRQRVEDAF<br>YTLVREIRQYRLKKISKEEKTPGCVKIKKCIIM | Kirsten Ras |
| SEQ ID NO: 58 | VVVGAGGVG | Kirsten Ras epitope |
| SEQ ID NO: 59 | MPLEQRSQHCKPEEGLEARGEALGLVGAQA<br>PATEEQEAASSSSTLVEVTLGEVPAAESPDPP<br>QSPQGASSLPTTMNYPLWSQSYEDSSNQEEE<br>GPSTFPDLESEFQAALSRKVAELVHFLLLKYR<br>AREPVTKAEMLGSVVGNWQYFFPVIFSKAFS | MAGE-A3 |

TABLE OF SEQUENCES AND SEQ ID NUMBERS (SEQUENCE LISTING):

| SEQ ID NO | Sequence | Remarks |
|---|---|---|
| | SLQLVFGIELMEVDPIGHLYIFATCLGLSYDG<br>LLGDNQIMPKAGLLIIVLAIIAREGDCAPEEKI<br>WEELSVLEVFEGREDSILGDPKKLLTQHFVQ<br>ENYLEYRQVPGSDPACYEFLWGPRALVETSY<br>VKVLHHMVKISGGPHISYPPLHEWVLREGEE | |
| SEQ ID NO: 60 | KVAELVHFL | MAGE-A3 epitope |
| SEQ ID NO: 61 | MAFVCLAIGCLYTFLISTTFGCTSSSDTEIKV<br>NPPQDFEIVDPGYLGYLYLQWQPPLSLDHFK<br>ECTVEYELKYRNIGSETWKTIITKNLHYKDG<br>FDLNKGIEAKIHTLLPWQCTNGSEVQSSWAE<br>TTYWISPQGIPETKVQDMDCVYYNWQYLLC<br>SWKPGIGVLLDTNYNLFYWYEGLDHALQCV<br>DYIKADGQNIGCRFPYLEASDYKDFYICVNGS<br>SENKPIRSSYFTFQLQNIVKPLPPVYLTFTRES<br>SCEIKLKWSIPLGPIPARCFDYEIEIREDDTTL<br>VTATVENETYTLKTTNETRQLCFVVRSKVNI<br>YCSDDGIWSEWSDKQCWEGEDLSKKTLLRF<br>WLPFGFILILVIFVTGLLLRKPNTYPKMIPEF<br>FCDT | IL13Ralpha2 |
| SEQ ID NO: 62 | LPFGFIL | IL13Ralpha2 epitope |
| SEQ ID NO: 63 | LFRAAQLANDVVLQIMEHLELASMTNMELM<br>SSIVVISASIIVFNLLELEG | Mad12 |
| SEQ ID NO: 64 | LVQFIKDRISVVQA | gp70CD4 peptide |
| SEQ ID NO: 65 | SPSYVYHQF | gp70CD8 peptide |
| SEQ ID NO: 66 | ASMTNMELM | adpgk peptide |
| SEQ ID NO: 67 | ATKNWPFL | survivin20-28 |
| SEQ ID NO: 68 | TVSEFLKL | survivin97-104 |
| SEQ ID NO: 69 | KRYKNRVASRKSRAKFKQLLQHYREVAAAKS<br>SENDRLRLLLKLFRAAQLANDVVLQIMEHLE<br>LASMTNMELMSSIVVISASIIVFNLLELEGSTV<br>HEILCKLSLEGDHSTPPSAYGSVKPYTNFDAE | Z13Mad12Anaxa |
| SEQ ID NO: 70 | MELAALCRWGLLLALLPPGAASTQVCTGTD<br>MKLRLPASPETHLDMLRHLYQGCQVVQGNL<br>ELTYLPTNASLSFLQDIQEVQGYVLIAHNQVR<br>QVPLQRLRIVRGTQLFEDNYALAVLDNGDPL<br>NNTTPVTGASPGGLRELQLRSLTEILKGGVLI<br>QRNPQLCYQDTILWKDIFHKNNQLALTLIDT<br>NRSRACHPCSPMCKGSRCWGESSEDCQSLTR<br>TVCAGGCARCKGPLPTDCCHEQCAAGCTGP<br>KHSDCLACLHFNHSGICELHCPALVTYNTDT<br>FESMPNPEGRYTFGASCVTACPYNYLSTDVG<br>SCTLVCPLHNQEVTAEDGTQRCEKCSKPCAR<br>VCYGLGMEHLREVRAVTSANIQEFAGCKKIF<br>GSLAFLPESFDGDPASNTAPLQPEQLQVFETL<br>EEITGYLYISAWPDSLPDLSVFQNLQVIRGRIL<br>HNGAYSLTLQGLGISWLGLRSLRELGSGLALI<br>HHNTHLCFVHTVPWDQLFRNPHQALLHTA<br>NRPEDECVGEGLACHQLCARGHCWGPGPTQ<br>CVNCSQFLRGQECVEECRVLQGLPREYVNAR<br>HCLPCHPECQPQNGSVTCFGPEADQCVACAH<br>YKDPPFCVARCPSGVKPDLSYMPIWKFPDEE<br>GACQPCPINCTHSCVDLDDKGCPAEQRASPL<br>TSIISAVVGILLVVVLGVVFGILIKRRQQKIRKY<br>TMRRLLQETELVEPLTPSGAMPNQAQMRIL<br>KETELRKVKVLGSGAFGTVYKGIWIPDGENV<br>KIPVAIKVLRENTSPKANKEILDEAYVMAGVG<br>SPYVSRLLGICLTSTVQLVTQLMPYGCLLDH<br>VRENRGRLGSQDLLNWCMQIAKGMSYLEDV<br>RLVHRDLAARNVLVKSPNHVKITDFGLARLL<br>DIDETEYHADGGKVPIKWMALESILRRRFTH<br>QSDVWSYGVTVWELMTFGAKPYDGIPAREI<br>PDLLEKGERLPQPPICTIDVYMIMVKCWMID<br>SECRPRFRELVSEFSRMARDPQRFVVIQNEDL<br>GPASPLDSTFYRSLLEDDDMGDLVDAEEYLV | Her2/neu |

-continued

| TABLE OF SEQUENCES AND SEQ ID NUMBERS (SEQUENCE LISTING): | | |
|---|---|---|
| SEQ ID NO | Sequence | Remarks |
| | PQQGFFCPDPAPGAGGMVHHRHRSSSTRSG GGDLTLGLEPSEEEAPRSPLAPSEGAGSDVF DGDLGMGAAKGLQSLPTHDPSPLQRYSEDP TVPLPSETDGYVAPLTCSPQPEYVNQPDVRP QPPSPREGPLPAARPAGATLERPKTLSPGKN GVVKDVFAFGGAVENPEYLTPQGGAAPQPH PPPAFSPAFDNLYYWDQDPPERGAPPSTFKG TPTAENPEYLGLDVPV | |

The invention claimed is:

1. A method for treating colorectal cancer or initiating, enhancing or prolonging an anti-tumor-response in a subject in need thereof comprising administering to the subject a complex comprising:
   a) a cell penetrating peptide;
   b) at least one antigen or antigenic epitope; and
   c) at least one toll-like receptor (TLR) peptide agonist, wherein the at least one TLR peptide agonist is a TLR2 and/or TLR4 peptide agonist; and
   wherein the components a)—c) are covalently linked.

2. The method according to claim 1, wherein the complex is a recombinant polypeptide or a recombinant protein.

3. The method according to claim 2, wherein the components a) to c) are positioned in N-terminal→C-terminal direction in the order:
   (α) component a)—component b)—component c); or
   (β) component c)—component a)—component b).

4. The method according to claim 3, wherein the components are linked by a further component.

5. The method according to claim 4, wherein the components are linked by a linker or a spacer.

6. The method according to claim 1, wherein the cell penetrating peptide:
   (i) has an amino acid length of 5 to 50 amino acids in total; and/or
   (ii) has an amino acid sequence comprising a fragment of the minimal domain of ZEBRA, said minimal domain extending from residue 170 to residue 220 of the ZEBRA amino acid sequence according to SEQ ID NO: 3, wherein, optionally, 1, 2, 3, 4, or 5 amino acids have been substituted, deleted, and/or added without abrogating said peptide's cell penetrating ability.

7. The method according to claim 6, wherein the length of the amino acid sequence of said cell penetrating peptide is 10 to 45 amino acids in total.

8. The method according to claim 7, wherein the length of the amino acid sequence of said cell penetrating peptide is 15 to 45 amino acids in total.

9. The method according to claim 1, wherein the cell penetrating peptide has an amino acid sequence comprising or consisting of an amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18), or a variant thereof sharing at least 90% sequence identity to SEQ ID NOs 6, 7, 8 or 11 without abrogating said peptide's cell penetrating ability.

10. The method according to claim 1, wherein the at least one antigen or antigenic epitope comprises at least one tumor epitope.

11. The method according to claim 10, wherein the at least one tumor epitope is an epitope of an antigen selected from the group consisting of EpCAM, HER-2, MUC-1, TOMM34, RNF 43, KOC1, VEGFR, βhCG, survivin, CEA, TGFβR2, p53, OGT, CASP5, COA-1, MAGE, MAGE-A3, SART and IL13Ralpha2.

12. The method according to claim 11, wherein the complex comprises
   a) one or more epitopes of EpCAM or a functional variant thereof;
   b) one or more epitopes of MUC-1 or a functional variant thereof;
   c) one or more epitopes of survivin or a functional variant thereof;
   d) one or more epitopes of CEA or a functional variant thereof; and/or
   e) one or more epitopes of MAGE-A3 or a functional variant thereof.

13. The method according to claim 12, wherein the complex comprises a) a fragment of EpCAM comprising one or more epitopes or a functional variant thereof;
b) a fragment of MUC-1 comprising one or more epitopes or a functional variant thereof;
c) a fragment of survivin comprising one or more epitopes or a functional variant thereof;
d) a fragment of CEA comprising one or more epitopes or a functional variant thereof; and/or
e) a fragment of MAGE-A3 comprising one or more epitopes or a functional variant thereof.

14. The method according to claim 10, wherein the at least one tumor epitope is an epitope of a neoantigen.

15. The method according to claim 14, wherein the at least one tumor epitope is a colorectal cancer specific neoantigen.

16. The method according to claim 1, wherein the complex comprises more than one antigen or antigenic epitope.

17. The method according to claim 1, wherein the at least one TLR peptide agonist comprises an amino acid sequence according to SEQ ID NO: 15 or a variant thereof sharing at least 90% sequence identity to SEQ ID NO:_15 without abrogating said peptide's TLR ability.

18. The method according to claim 1, wherein the at least one antigen or antigenic epitope comprises at least one colorectal cancer epitope.

19. The method according to claim 18, wherein the complex comprises 3, 4, 5, 6, 7, 8, 9, 10 or more antigen or antigenic epitopes.

20. The method according to claim 1, wherein the at least one antigen or antigenic epitope consists of one tumor epitope.

21. The method according to claim 1, wherein the at least one TLR peptide agonist consists of the amino acid sequence according to SEQ ID NO: 15.

22. The method according to claim 1, wherein the at least one antigen or antigenic epitope consists of one colorectal cancer epitope.

23. A method for treating colorectal cancer or initiating, enhancing or prolonging an anti-tumor-response in a subject in need thereof comprising administering to the subject a vaccine comprising at least one of:
(i) a complex comprising
 a) a cell penetrating peptide;
 b) at least one antigen or antigenic epitope; and
 c) at least one TLR2 peptide agonist and/or TLR4 peptide agonist; wherein the components a)—c) are covalently linked;
(ii) a nucleic acid encoding the complex as defined (i);
(iii) a vector comprising the nucleic acid as defined in (ii);
(iv) a host cell comprising the vector as defined in (iii); or
(v) a cell loaded with a complex as defined in (i).

24. A method for treating colorectal cancer or initiating, enhancing or prolonging an anti-tumor-response in a subject in need thereof comprising administering to the subject a pharmaceutical composition comprising at least one complex comprising
a) a cell penetrating peptide;
b) at least one antigen or antigenic epitope; and
c) at least one TLR2 peptide agonist and/or TLR4 peptide agonist; wherein the components a)—c) are covalently linked;
and a pharmaceutically acceptable carrier.

25. A method for treating colorectal cancer or initiating, enhancing or prolonging an anti-tumor-response in a subject in need thereof comprising administering to the subject a combination of
(i) a complex comprising
 a) a cell penetrating peptide;
 b) at least one antigen or antigenic epitope; and
 c) at least one TLR2 peptide agonist and/or TLR4 peptide agonist; wherein the components a)—c) are covalently linked; and
(ii) a chemotherapeutic agent, a targeted drug and/or an immunotherapeutic agent.

26. The method according to claim 25, wherein the chemotherapeutic agent, the targeted drug and/or the immunotherapeutic agent is an immune checkpoint modulator.

* * * * *